United States Patent
Poirier et al.

(10) Patent No.: US 11,713,356 B2
(45) Date of Patent: Aug. 1, 2023

(54) MODIFIED BIFUNCTIONAL ANTI-HUMAN SIGNAL REGULATORY PROTEIN ALPHA (SIRPA) ANTIBODY AND METHOD OF USE THEREOF FOR TREATING CANCER

(71) Applicant: OSE IMMUNOTHERAPEUTICS, Nantes (FR)

(72) Inventors: Nicolas Poirier, Treillieres (FR); Caroline Mary, Sainte-Pazanne (FR); Bernard Vanhove, Reze (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 260 days.

(21) Appl. No.: 16/754,285

(22) PCT Filed: Oct. 15, 2018

(86) PCT No.: PCT/EP2018/078082
§ 371 (c)(1),
(2) Date: Apr. 7, 2020

(87) PCT Pub. No.: WO2019/073080
PCT Pub. Date: Apr. 18, 2019

(65) Prior Publication Data
US 2021/0179728 A1 Jun. 17, 2021

(30) Foreign Application Priority Data
Oct. 13, 2017 (EP) .................. 17306396

(51) Int. Cl.
*A61P 35/00* (2006.01)
*A61K 39/395* (2006.01)
(Continued)

(52) U.S. Cl.
CPC .......... *C07K 16/2896* (2013.01); *A61K 35/17* (2013.01); *A61K 39/3955* (2013.01);
(Continued)

(58) Field of Classification Search
CPC combination set(s) only.
See application file for complete search history.

(56) References Cited

U.S. PATENT DOCUMENTS

| 11,279,766 B2 * | 3/2022 | Poirier ............... C07K 16/2878 |
| 2010/0215640 A1 | 8/2010 | Clemmons et al. |

(Continued)

FOREIGN PATENT DOCUMENTS

| EP | 1637598 A1 | 3/2006 |
| WO | 2007005874 A2 | 1/2007 |

(Continued)

OTHER PUBLICATIONS

Paul, WE (1993) Fundamental Immunology, 3rd ed. Raven Press, NY, Chap. 9, pp. 292-295.*

(Continued)

*Primary Examiner* — Robert S Landsman
(74) *Attorney, Agent, or Firm* — Thompson Coburn LLP; William A. Holtz

(57) ABSTRACT

The present invention provides new modified anti-SIRPa antibodies linked to an immunotherapeutic agent which are bifunctional and able to specifically enhance the immune response and uses thereof.

34 Claims, 45 Drawing Sheets

Figures 1D, 2:
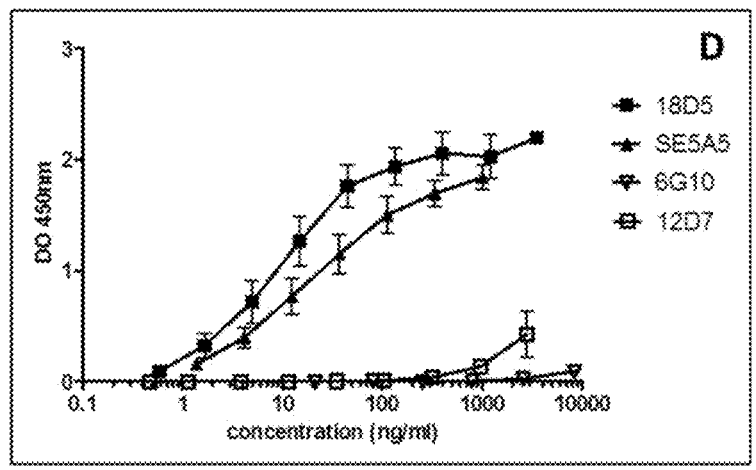

Specification includes a Sequence Listing.

(51) Int. Cl.
*A61K 39/00* (2006.01)
*C07K 16/28* (2006.01)
*A61K 35/17* (2015.01)
*A61K 45/06* (2006.01)

(52) U.S. Cl.
CPC .............. *A61K 45/06* (2013.01); *A61P 35/00* (2018.01); *C07K 16/2827* (2013.01); *C07K 16/2878* (2013.01); *A61K 2039/507* (2013.01); *C07K 2317/24* (2013.01); *C07K 2317/565* (2013.01); *C07K 2317/74* (2013.01); *C07K 2317/76* (2013.01); *C07K 2317/92* (2013.01)

(56) References Cited

U.S. PATENT DOCUMENTS

| | | |
|---|---|---|
| 2010/0233251 A1 | 9/2010 | Von Andrian et al. |
| 2010/0239578 A1 | 9/2010 | Danska et al. |
| 2012/0039896 A1 | 2/2012 | Clemmons et al. |
| 2012/0070461 A1 | 3/2012 | Singh et al. |
| 2014/0141002 A1 | 5/2014 | Clemmons et al. |
| 2014/0242095 A1 | 8/2014 | Wang et al. |
| 2017/0247464 A1 | 8/2017 | Poirier et al. |
| 2018/0312600 A1 | 11/2018 | Poirier et al. |
| 2019/0127477 A1 | 5/2019 | Poirier et al. |
| 2021/0040206 A1 | 2/2021 | Poirier et al. |

FOREIGN PATENT DOCUMENTS

| | | | |
|---|---|---|---|
| WO | 2009131453 | A1 | 10/2009 |
| WO | 2010077634 | A1 | 7/2010 |
| WO | 2010130053 | A1 | 11/2010 |
| WO | 2012149416 | A2 | 11/2012 |
| WO | 2013056352 | A1 | 4/2013 |
| WO | 2013079174 | A1 | 6/2013 |
| WO | 2013109752 | A1 | 7/2013 |
| WO | 2015048312 | A1 | 4/2015 |
| WO | 2015138600 | A2 | 9/2015 |
| WO | 2017178653 | A2 | 10/2017 |
| WO | 2019073080 | A1 | 4/2019 |

OTHER PUBLICATIONS

Rudikoff, S et al. (1982) Proc. Natl. Acad. Sci. USA, 79:1979-1983.*
Colman, PM (1994) Research in Immunology, Elsevier, NY, 145(1):33-36.*
Alblas et al., "Signal Regulatory Protein Ligation Induces Macrophage Nitric Oxide Production Through JAK/STAT and Phosphatidylinositol 3-Kinase/Racl/NAPDH Oxidase/H2O2-Dependent Pathways", Molecular and Cellular Biology, Aug. 15, 2005, pp. 7181-7192, vol. 25, No. 16.
Ansell, "Targeting Immune Checkpoints in Lymphoma", Current Opinion in Hematology, 2015, pp. 337-342, vol. 22, No. 4.
Brahmer et al., "Safety and Activity of Anti-PD-L1 Antibody in Patients with Advanced Cancer", N. Eng. J. Med., 2012, vol. 366, No. 26, pp. 2443-2454.
Chao et al., "Response: Mechanisms of Targeting CD47-SIRP [Alpha] in Hematologic Malignancies", Blood American Society of Hematology, May 3, 2012, pp. 4334-4335, vol. 119, No. 18.
Crepeau et al., "Challenges and Opportunities in Targeting the CD28/CTLA-4 Pathway in Transplantation and Autoimmunity", Expert Opin. Biol. Ther., 2017, pp. 1001-1012, vol. 17, No. 8.
Gilbreth et al., "Crystal Structure of the Human 4-1BB/4-1BBL Complex", J. Biol. Chem., 2018, pp. 9880-9891, vol. 293, No. 25.
Girard et al., "CD80 and CD86 IgC Domains are Important for Quaternary Structure, Receptor Binding and Co-Signaling Function", Immunology Letters, 2014, pp. 65-75.
Hatherly et al., "The Structure of the Macrophage Signal Regulatory Protein (SIRP) Inhibitory Receptor Reveals a Binding Face Reminiscent of That Used by T Cell Receptors", Journal of Biological Chemistry, Mar. 6, 2007, pp. 14567-14575, vol. 282, No. 19.
International Search Report and Written Opinion for PCT/EP2017/059071 dated Jun. 5, 2018.
Ishida et al., "Induced Expression of PD-1, a Novel Member of the immunoglobulin Gene Superfamily, Upon Programmed Cell Death", EMBO J., 1992, pp. 3887-3895, vol. 11, No. 11.
Lee et al., "Novel Structural Determinants on SIRP Alpha That Mediate Binding to CD47", Journal of Immunology, Jan. 1, 2007, pp. 7741-7750.
Lin et al., "The PD-1/PD-1L Complex Resembles the Antigen-Binding Fv Domains of Antibodies and T Cell Receptors", PNAS, 2008, pp. 3011-3016, vol. 15, No. 8.
Liu et al., "Functional Elements on SIRP@a IgV Domain Mediate Cell Surface Binding to CD47", Journal of Molecular Bio, Academic Press, Dec. 23, 2006, pp. 680-693, vol. 365, No. 3.
Liu et al., "Signal Regulatory Protein (SIRPalpha), a Cellular Ligand for CD47, Regulates Neutrophil Transmigration," Journal of Biological Chemistry, Mar. 15, 2002, pp. 10028-10036, vol. 277, No. 12.
Nielsen et al., "Alternative Splice Variants of the Human PD-1-Gene", Cell Immunol., 2005, pp. 109-116, vol. 235.
Ochando et al., "Myeloid-derived Suppressor Cells in Transplantation and Cancer", Immunologic Research, Apr. 26, 2012, pp. 275-285, vol. 54, No. 1-3, Humana Press Inc., New York.
Pan et al., "Signal Regulatory Protein [Alpha] is Associated with Tumor-Polarized Macrophages Phenotype Switch and Plays a Pibotal Role in Tumor Progression", Hepatology, Aug. 1, 203, pp. 680-691, vol. 58, No. 2.
Pardoll, "The Blockade of Immune Checkpoints in Cancer Immunotherapy", Nature Reviews Cancer, 2012, vol. 12, No. 4, pp. 252-264.
Peach et al., "Both Extracellular Immunoglobin-Like Domains of CD80 Contains Residues Critical for Binding T-Cell Surface Receptors CTLA-4 and CD28", J. Biol. Chem., 1995, pp. 21181-21187.
Powles et al., "MPDL3280A (Anti-PD-L1_ Treatment Leads to Clinical Activity in Metastatic Bladder Cancer", Nature, 2014, vol. 515, No. 7528, pp. 558-562.
Sharma et al., "Immune Checkpoint Targeting in Cancer Therapy: Towards Combination Strategies with Curative Potential", Cell, 2015, pp. 205-214, vol. 161, No. 2.
Takenaka et al., "Polymorphism in Sira Modulates Engraftmentof Human Hematopoietic Stem Cells", Nature Immunology, Dec. 1, 2007,pp. 1313-1323, vol. 8, No. 12, Nature Publishing Group US, New York.
Topalian et al., "Safety, Activity, and Immune Correlates of Anti-PD-1 Antibody in Cancer", The new England Journal of Medicine, 2012, pp. 2443 2454, vol. 366, No. 26.
Ueda et al., "Association of the T-Cell Regulatory Gene CTLA4 with Susceptibility to Autoimmune Disease", Nature, 2003, pp. 506-511, vol. 423.
UniProt Sequence Accession O75144 for PDCD1_HUMAN; retrieved from the internet site https://uniprot.org/uniprot/ on Mar. 26, 2020.
UniProt Sequence Accession P23510 for PDCD1_HUMAN; retrieved from the internet site https://uniprot.org/uniprot/ on Mar. 26, 2020.
UniProt Sequence Accession P33681 for PDCD1_HUMAN; retrieved from the internet site https://uniprot.org/uniprot/ on Mar. 26, 2020.
UniProt Sequence Accession P41273 for PDCD1_HUMAN; retrieved from the internet site https://uniprot.org/uniprot/ on Mar. 26, 2020.
UniProt Sequence Accession P42081 for PDCD1_HUMAN; retrieved from the internet site https://uniprot.org/uniprot/ on Mar. 26, 2020.
UniProt Sequence Accession Q15116 for PDCD1_HUMAN; retrieved from the internet site https://uniprot.org/uniprot/ on Mar. 26, 2020.
UniProt Sequence Accession Q9NZQ7 for PDCD1_HUMAN; retrieved from the internet site https://uniprot.org/uniprot/ on Mar. 26, 2020.
Vinay et al., "Therapeutic Potential of Anti-CD137 (4-1BB) Monoclonal Antibodies", Expert Opin. Ther. Targets., 2016, pp. 361-373, vol. 20, No. 3.
Wan et al., "Aberrant Regulation of Synovial T Cell Activation by Soluble Costimulatory molecules in Rheumatoid Arthritis", J. Immunol., 2006, pp. 8844-8850, vol. 177.

(56) References Cited

OTHER PUBLICATIONS

Wang et al., "Immune Regulation by 4-1BB and 4-1BBL: Complexities and Challenges", Immunol. Rev., 2009, pp. 192-215, vol. 229, No. 1.
Weiskopf et al, "Direct SIRPa Blockade Augments Macrophage Responses to Therapeutic Anticancer Antibodies", Blood Journal, Dec. 2014, vol. 124, No. 21, pp. 100 109.
Willoughby et al., "OX40: Structure and Function—What Questions Remain?", Mol. Immunol., 2017, pp. 13-22, vol. 83.
Zak et al., "Structure of the Complex of Human Programmed Death 1, PD-1, and Its Ligand PD-L1", Structure, 2015, pp. 2341-2348, vol. 23, No. 12.
Zhao et al., "CD47-Singal Regulatory Protein—(SIRP) Interactions Form a Barrier for Antibody-Mediated Tumor Cell Destruction", Proceedings of the National Academy of Sciences, Nov. 8, 2011, pp. 18342-18347, vol. 108, No. 45.
Brahmer et al., "Safety and Activity of Anti-PD-L1 Antibody in Patients with Advanced Cancer", N. Eng. J. Med., 2012, pp. 2455-2465, vol. 366, No. 26.
Girard et al., "CD80 and CD86 IgC Domains are Important for Quaternary Structure, Receptor Binding and Co-Signaling Function", Immunology Letters, 2014, Article in Press, pp. 1-11.
Pardoll, "The Blockade of Immune Checkpoints in Cancer Immunotherapy", Nature Reviews Cancer, 2012, pp. 252-264, vol. 12, No. 4.
Powles et al., "MPDL3280A (Anti-PD-L1_ Treatment Leads to Clinical Activity in Metastatic Bladder Cancer", Nature, 2014, pp. 558-562, Methods, Extended Data Figures 1-3, and Extended Data Table 1-3, vol. 515, No. 7528.
Weiskopf et al, "Direct SIRPa Blockade Augments Macrophage Responses to Therapeutic Anticancer Antibodies", Blood Journal, Dec. 2014, vol. 124, No. 21, Abstract.
Justice et al., "Using the Mouse to Model Human Disease: Increasing Validity and Reproducibility", Disease, Models & Mechanisms, 2016, pp. 101-103, vol. 9.
Reuter, "Diet-Induced Models for Obesity and Type 2 Diabetes", Drug Discovery Today: Disease Models, 2007, pp. 3-8, vol. 4/1.
Türkbeyler et al., "Prolidase Could Act as a Diagnosis and Treatment Mediator in Lung Fibrosis", Inflammation, Oct. 2012, pp. 1747-1752, vol. 35, No. 5.
Wakabayashi et al., "Prevention of Metastasis by a Polyamine Synthesis Inhibitor in an Animal Bone Metastasis Model", Oncology, 2000, pp. 75-80, vol. 59.
Abe et al., "Blockade of CD47-Signaling Regulatory Protein Alpha Signaling Enhances the Macrophage Phagocytic Activity Against Cancer Cells", Transplantation, Abstract B1139, Jul. 2014. pp. 313, vol. 98, Suppl. 1, World Transplantation Congress.
Barclay et al., "The Interaction Between Signal Regulatory Protein Alpha (SIRPa) and CD47: Structure, Function, and Therapeutic Target", Annual Review of Immunology, 2014, pp. 25-50, vol. 32.
Borch et al., "Reorienting the Immune System in the Treatment of Cancer by Using Anti-PD-1 and Anti-PD-L1 Antibodies", Drug Discovery Today, Sep. 2015, pp. 1127-1134, vol. 20, No. 9.
Gabrilovich et al., "Myeloid-Derived Suppressor Cells as Regulators of the Immune System", Nature Reviews Immunology, Mar. 2009, pp. 162-174, vol. 9, No. 3.
Gauttier et al., "Dual Targeting of Adaptive and Innate Immune Checkpoints Induce Potent Memory Anti-Tumor Response", European Journal of Cancer, Jul. 2016, pp. S216-S217, vol. 61, Supplement 1.
International Search Report and Written Opinion for PCT/EP2019/056250 dated Jun. 18, 2019.
International Search Report issued in corresponding international Patent Application No. PCT/IB2015/058124 dated Jan. 19, 2016.
Makarova-Rusher et al., "The Yin and Yang of Evasion and Immune Activation in HCC", Journal of Hepatology, Jun. 2015, pp. 1420-1429, vol. 62, No. 6.
McCracken et al., "Molecular Pathways: Activating T Cells after Cancer Cell Phagocytosis from Blockade of CD47 "Don't Eat Me" Signals", Clinical Cancer Research, Aug. 2015, pp. 3597-3601, vol. 21, No. 16.
Mosser et al., "Exploring the Full Spectrum of Macrophage Activation", Nature Reviews Immunology, 2008, pp. 958-969, Vo. 8, No. 12.
Oldenborg et al., "Role of CD47 as a Marker of Self on Red Blood Cells", Science, Jun. 2000, pp. 2051-2054, vol. 288, No. 5473.
Seiffert et al., "Signal-Regulatory Protein Alpha (SIRPalpha) but not SIRPbeta is Involved in T-cell Activation, Binds to CD47 with High Affinity, and is Expressed on Immature CD34(+)CD38(−) Hematopoietic Cells", Blood, May 2001, pp. 2741-2749, vol. 97, No. 9.
Sim et al., "Discovery of High Affinity, Pan-Allelic, and Pan-Mammalian Reactive Antibodies Against the Myeloid Checkpoint Receptor SIRPa", MABS, 2019, pp. 1036-1052, vol. 11, No. 6.
Srivastava et al., "Targeting MDSCs Enhance Therapeutic Vaccination Responses Against Lung Cancer", Oncoimmunology, Dec. 2012, pp. 1650-1651, vol. 1, No. 9.
Stefanidakis et al., "Endothelial CD47 Interaction with SIRPgamma is Required for Human T-cell Transendothelial Migration under Shear Flow Conditions In Vitro", Blood, Aug. 2008, pp. 1280-1289, vol. 112, No. 4, The American Society of Hematology.
Vonderheide, "CD47 Blockade as Another Immune Checkpoint Therapy for Cancer", Nature Medicine, Oct. 2015, pp. 1122-1123, vol. 21, No. 10.
Willingham et al., "The CD47-Signal Regulatory Protein Alpha (SIRPa) Interaction is a Therapeutic Target for Human Solid Tumors", Proceedings of the National Academy of Sciences, Apr. 2012, pp. 6662-6667, vol. 109, No. 17.
Written Opinion issued in corresponding International Patent Application No. PCT/IB2015/058124 dated Jan. 19, 2016.
Yanagita et al., "Anti-SIRPa Antibodies as a Potential New Tool for Cancer Immunotherapy", JCI Insight, Jan. 2017, pp. 1-15, vol. 2, No. 1.

\* cited by examiner

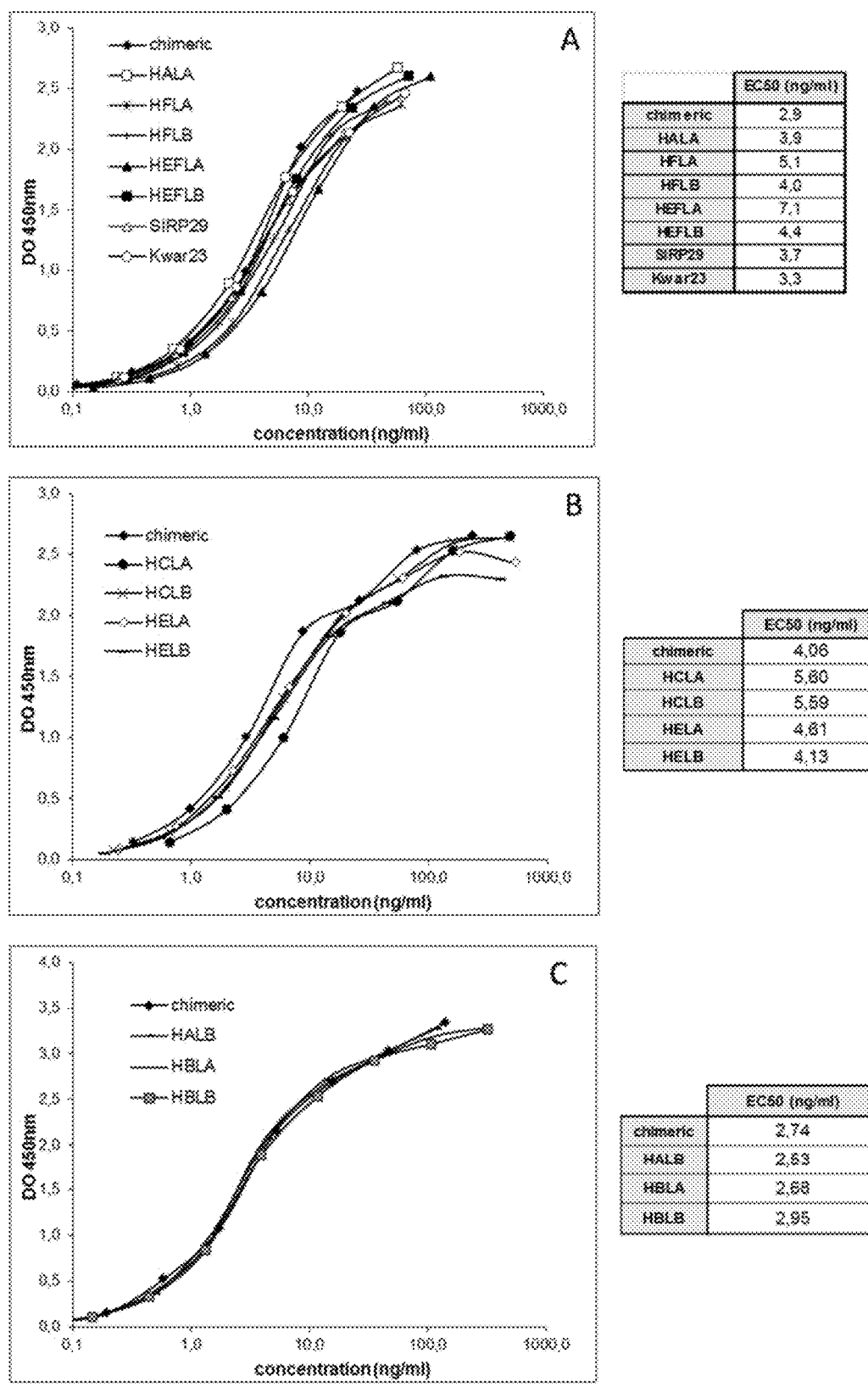
FIGURE 1A,B,C

| | Association (ka) (1/Ms) | Dissociation (kd) (1/s) | Affinity (KD) (M) |
|---|---|---|---|
| mouse 18D5 | 6,23e4 | 1,20e-5 | 1,93e-10 |
| chimeric | 1,49e5 | 5,14e-5 | 3,44e-10 |
| HFLA | 8,57e5 | 1,86e-4 | 2,17e-10 |
| HFLB | 7,91e5 | 2,49e-4 | 3,15e-10 |
| HEFLA | 5,59e5 | 1,48e-4 | 2,64e-10 |
| HEFLB | 6,54e5 | 1,89e-4 | 2,89e-10 |
| SIRP29 | 4,15e4 | 1,01e-5 | 2,43e-10 |
| Kwar23 | 2,44e5 | 8,95e-5 | 3,67e-10 |
| SE7C2 | 5,98e3 | 0,01 | 1,67e-6 |
| SE5A5 | 2,45e4 | 9,49e-4 | 3,87e-8 |

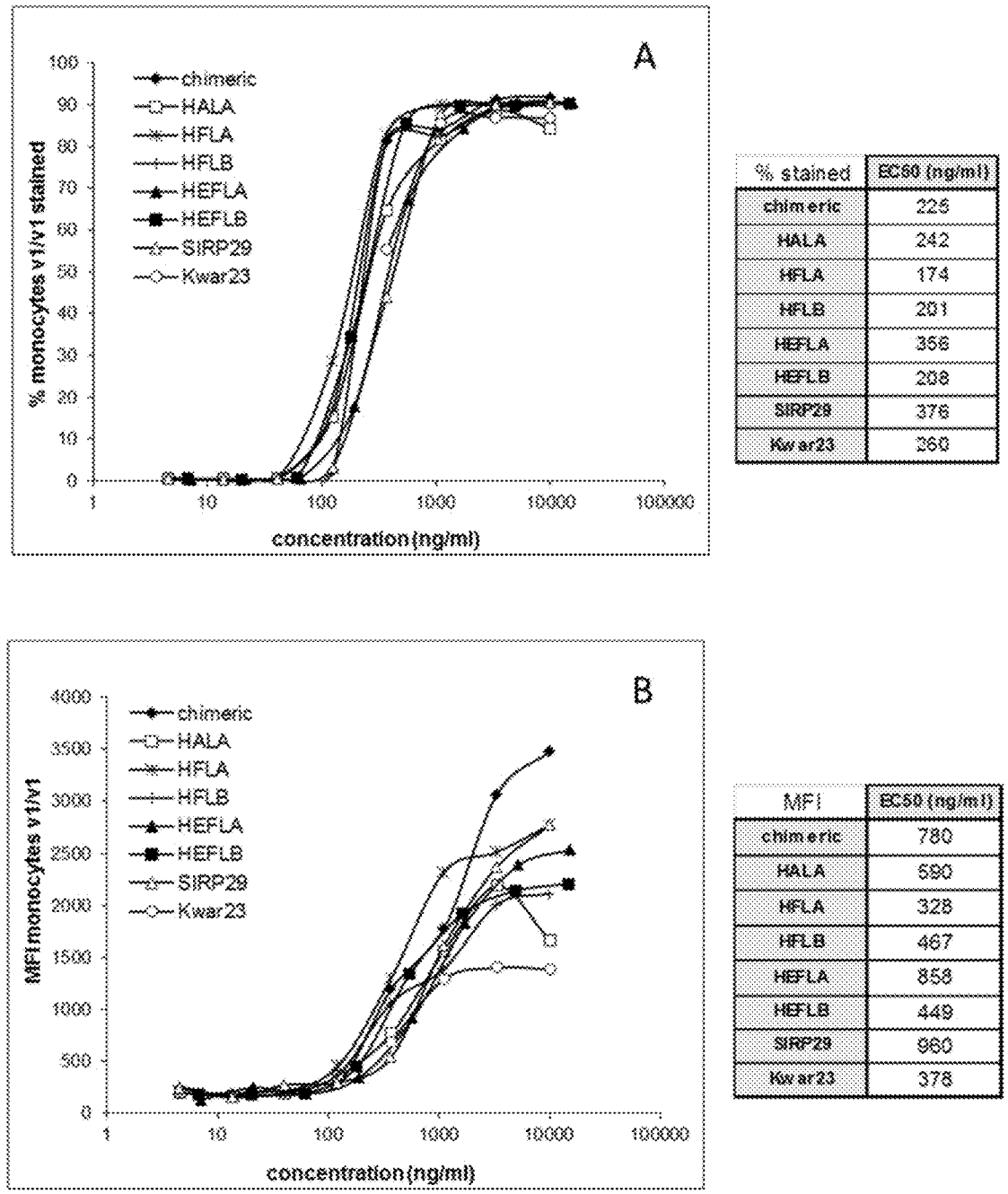
FIGURE 3A,B

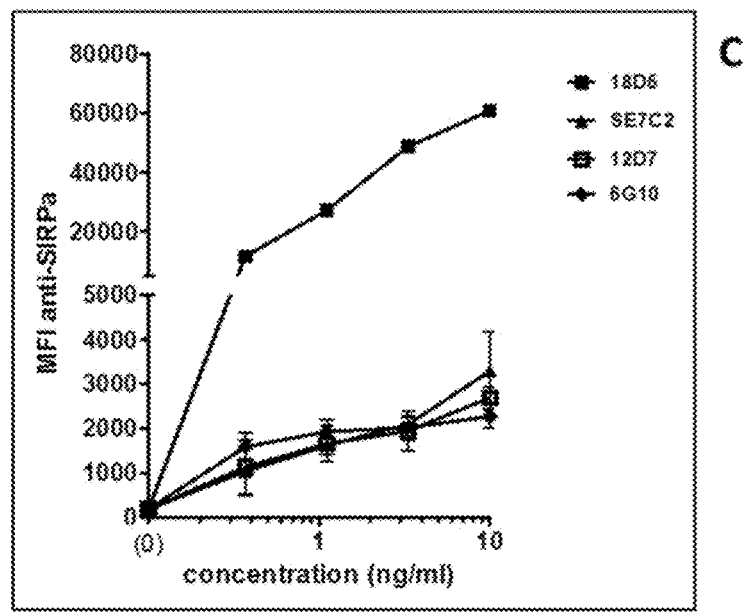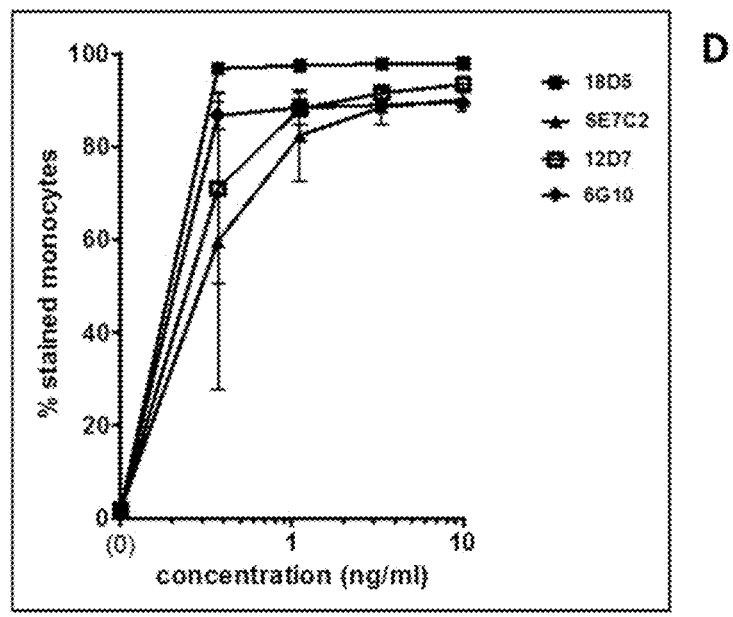
FIGURE 3C,D

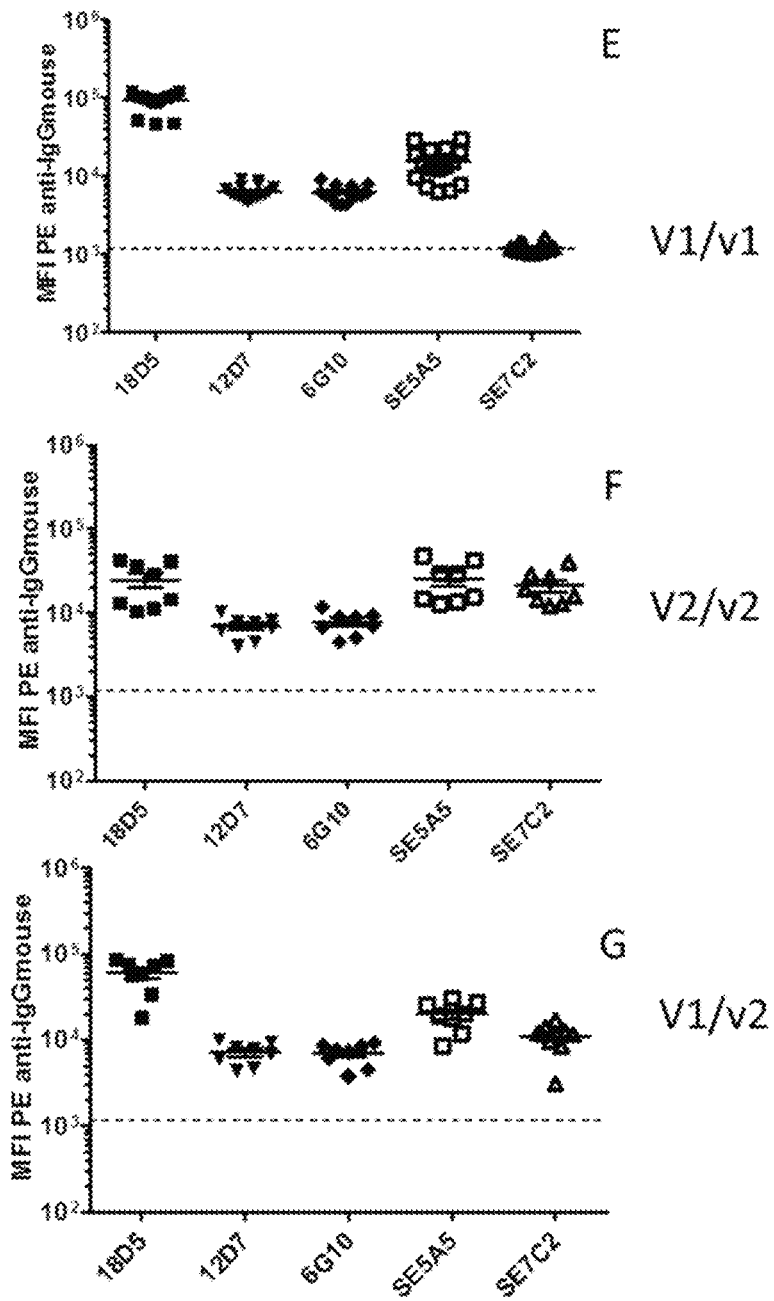
FIGURE 3E,F,G

Figure 4B:
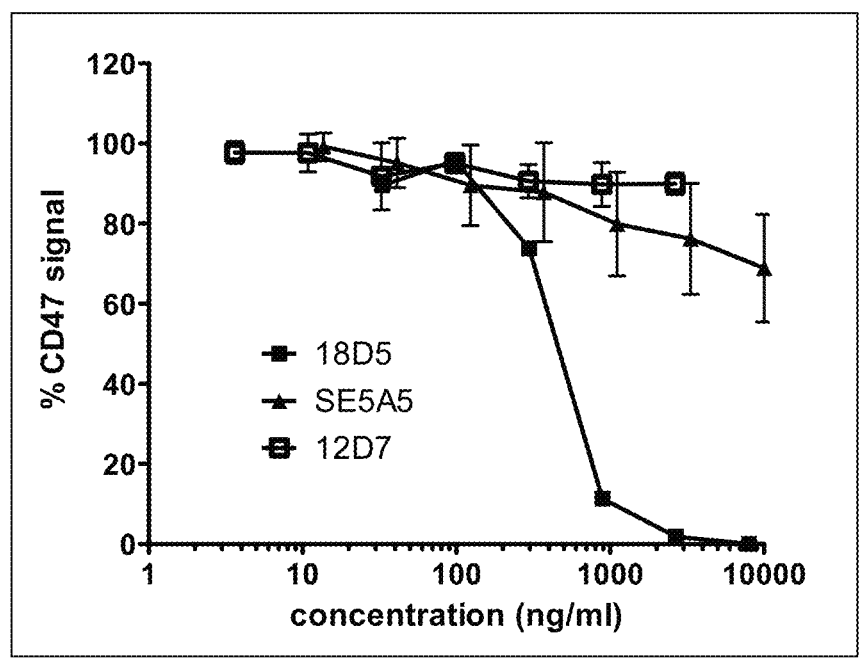

A
First experiment
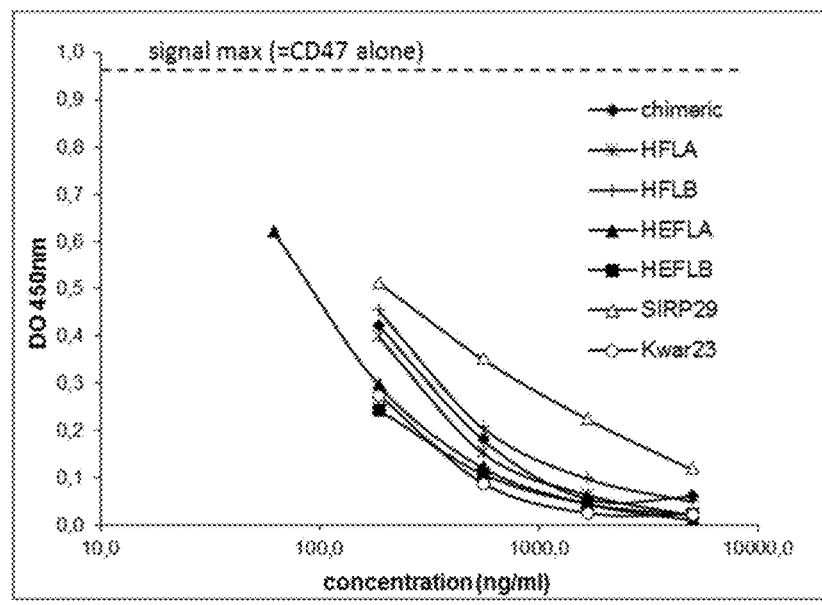
Second experiment
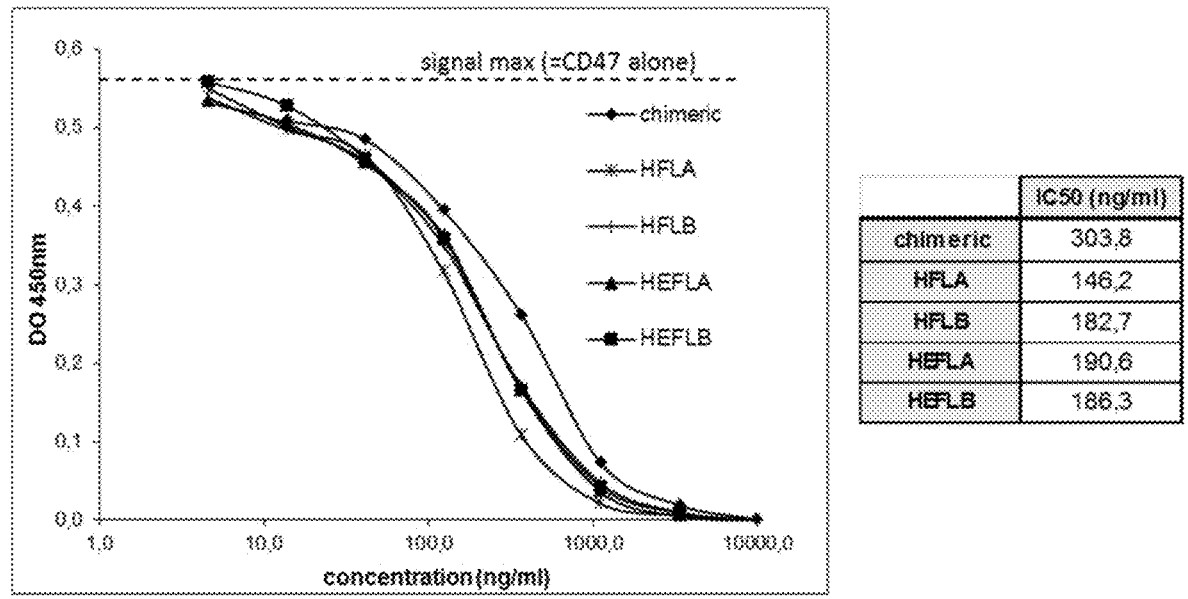
FIGURE 4A

B

Figure 5C:
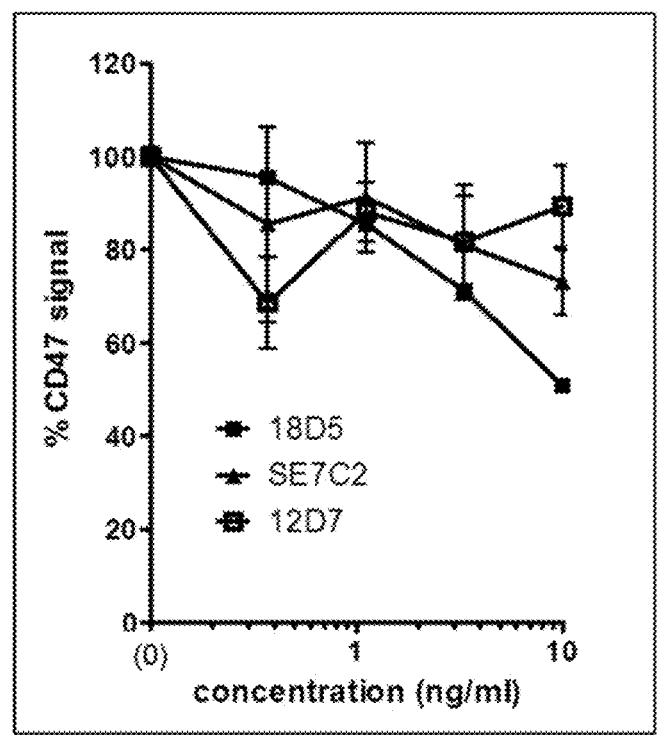

A
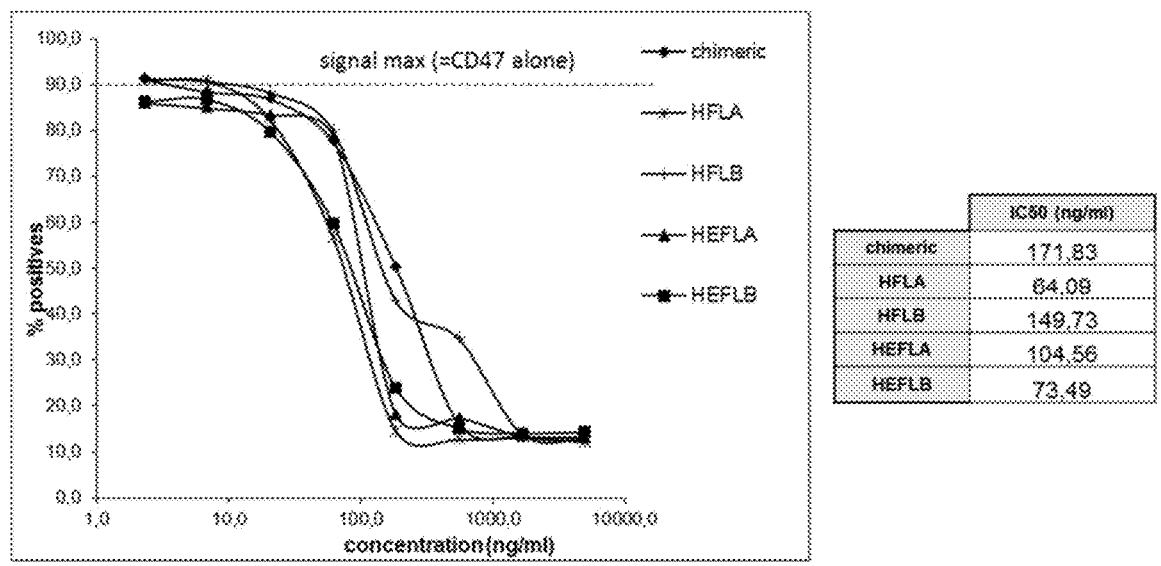
B
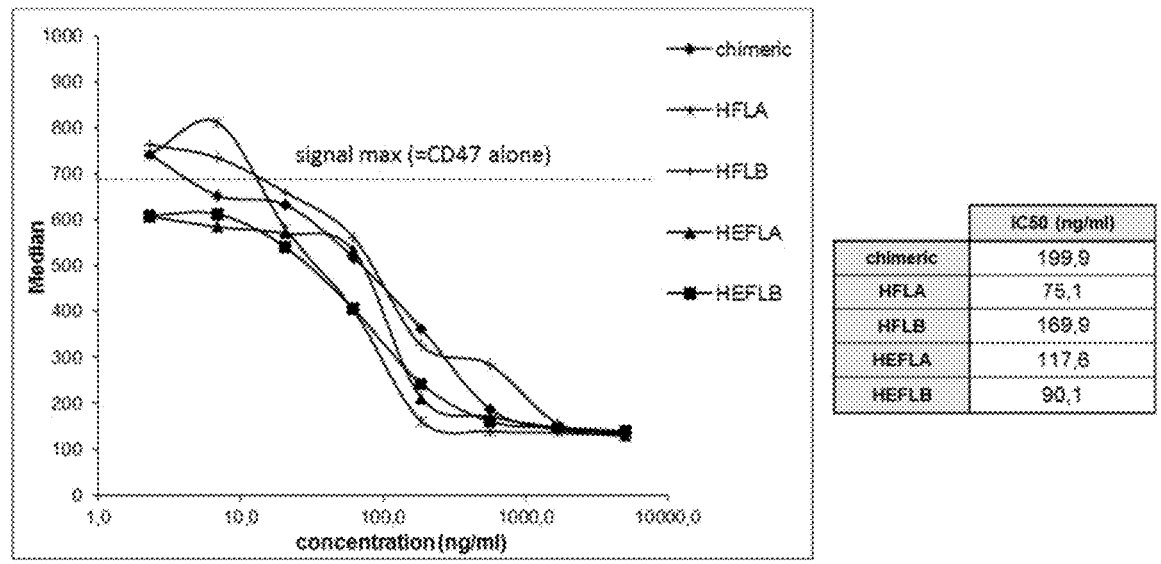
FIGURE 5A,B

C

| A | Association (ka) (1/Ms) | Dissociation (kd) (1/s) | Affinity (KD) (M) |
|---|---|---|---|
| mouse 18D5 | 1,58e4 | 1,76e-3 | 1,11e-7 |
| mouse 18D5 with SP-D | 3,797e5 | 1,088e-2 | 2,865e-8 |

| B | Association (ka) (1/Ms) | Dissociation (kd) (1/s) | Affinity (KD) (M) |
|---|---|---|---|
| SP-D | 2,465e3 | 1,078e-2 | 4,372e-6 |
| SPD with mouse 18D5 | 3,272e3 | 2,405e-3 | 7,35e-7 |

FIGURE 6A,B

A
| | Association (ka) (1/Ms) | Dissociation (kd) (1/s) | Affinity (KD) (M) |
|---|---|---|---|
| Chimeric | 8,837e4 | 1,385e-3 | 1,568e-8 |
| HALA | 1,328e5 | 8,504e-4 | 6,403e-9 |
| HFLA | 7,447e4 | 1,919e-3 | 2,576e-8 |
| HFLB | 6,694e4 | 1,738e-3 | 2,596e-8 |
| HEFLA | 9,827e4 | 1,221e-3 | 1,243e-8 |
| HEFLB | 1,939e4 | 1,711e-3 | 8,69e-8 |
| SIRP29 | 1,078e5 | 8,114e-4 | 7,531e-9 |
| kwar23 | 2,863e5 | 7,935e-4 | 2,772e-9 |
B
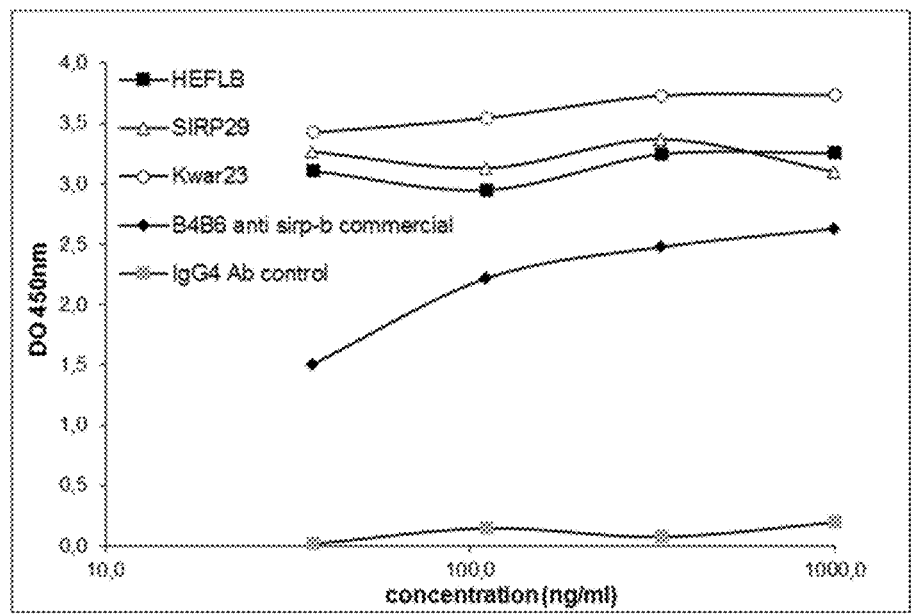
FIGURE 7A,B A
| | Association (ka) (1/Ms) | Dissociation (kd) (1/s) | Affinity (KD) (M) |
|---|---|---|---|
| Chimeric | 4,93e4 | 3,194e-3 | 6,479e-8 |
| HALA | 1,539e5 | 7,093e-3 | 4,609e-8 |
| HFLA | 2,477e5 | 1,18e-2 | 4,764e-8 |
| HFLB | 1,191e5 | 1,234e-2 | 1,036e-7 |
| HEFLA | 2,173e5 | 1,14e-2 | 5,244e-8 |
| HEFLB | 1,92e5 | 1,193e-2 | 6,215e-8 |
| SIRP29 | 1,36e5 | 7,2e-4 | 5,296e-9 |
| kwar23 | 3,57e5 | 7,648e-4 | 2,142e-9 |
B
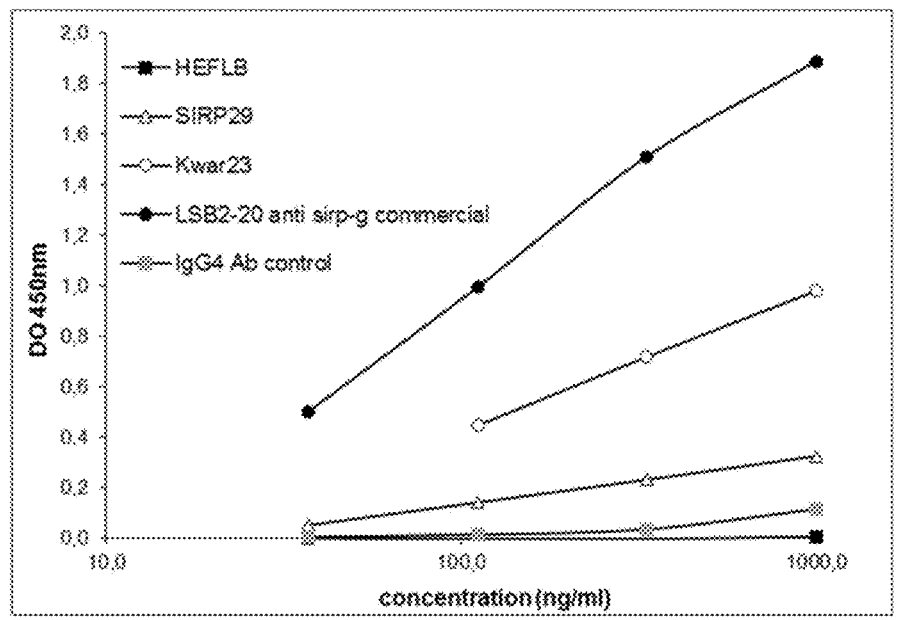
FIGURE 8A,B

|  | Association (ka) (1/Ms) | Dissociation (kd) (1/s) | Affinity (KD) (M) |
|---|---|---|---|
| CD47 alone | 2,193e4 | 1,309e-2 | 5,969e-7 |
| HEFLB +CD47 | 5,372e4 | 5,334e-2 | 9,928e-7 |
| SIRP29 +CD47 | 2,118e4 | 5,525e-2 | 2,572e-6 |
| Kwar23 +CD47 | 4,369e2 | 1,259e-1 | 2,88e-4 |

FIGURE 9

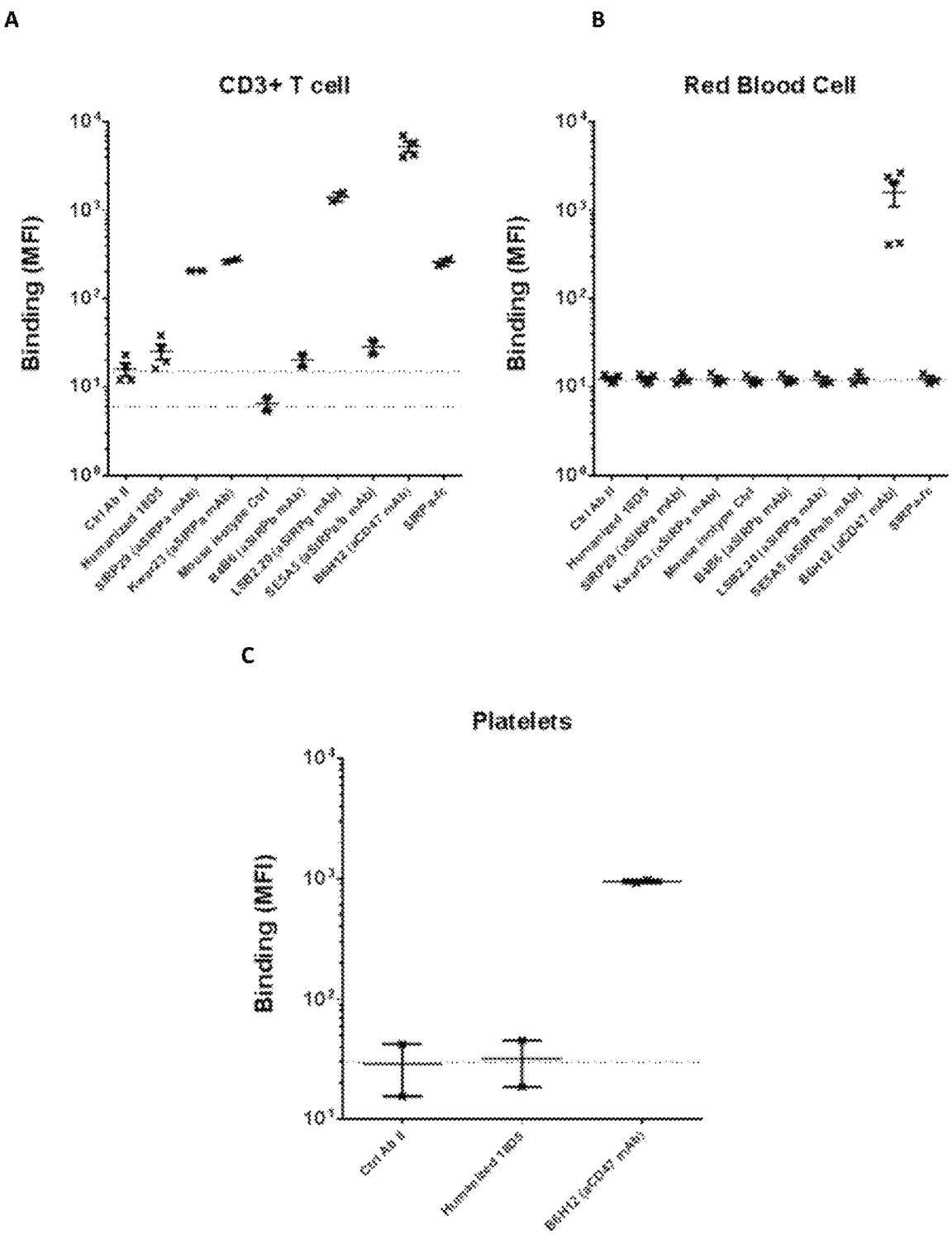
FIGURE 10A,B,C

A
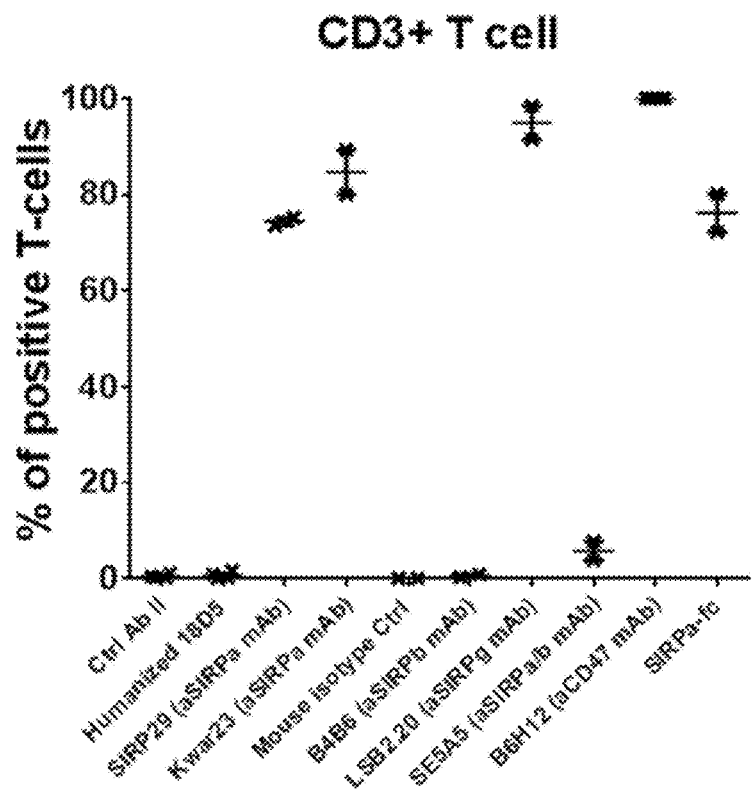
B
|  | Ctrl Ab II | Humanized 18D5 | SIRP29 (aSIRPa mAb) | Kwar23 (aSIRPa mAb) | Mouse isotype Ctrl | B4B6 (aSIRPb mAb) | LSB2.20 (aSIRPg mAb) | SE5A5 (aSIRPa/b mAb) | B6H12 (aCD47 mAb) | SIRPa-fc |
|---|---|---|---|---|---|---|---|---|---|---|
| Exp 1 HV1 | 0,45 | 1,54 | 73,5 | 80 | 0 | 0,87 | 91,4 | 3,72 | 100 | 72,2 |
| Exp 1 HV2 | 1,12 | 0,84 | 75,2 | 89,3 | 0,016 | 0,25 | 98,4 | 7,69 | 100 | 80,1 |
| Exp 2 HV1 | 0,057 | 0,016 |  |  |  |  |  |  | 99,9 |  |
| Exp 2 HV2 | 0,076 | 0,058 |  |  |  |  |  |  | 99,9 |  |
FIGURE 11A,B

Figure 12E:
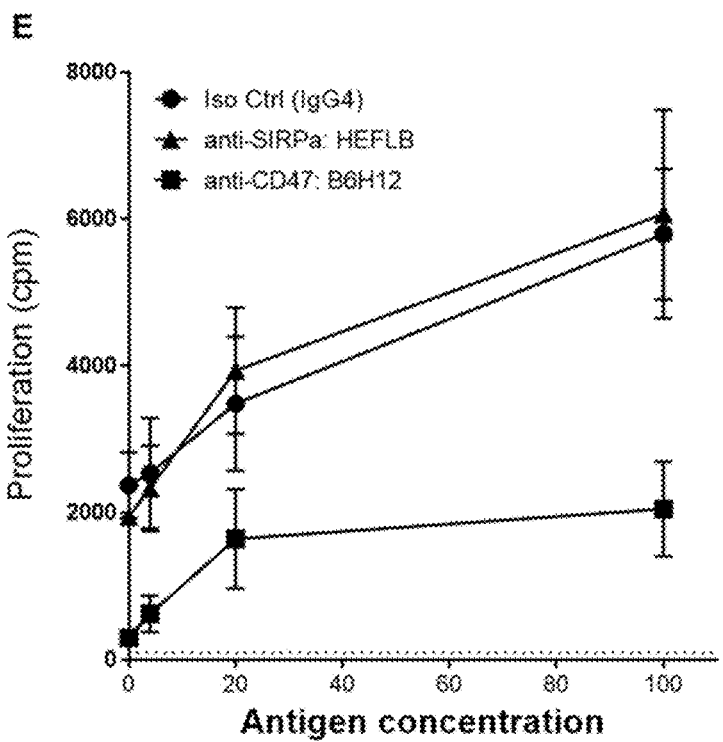

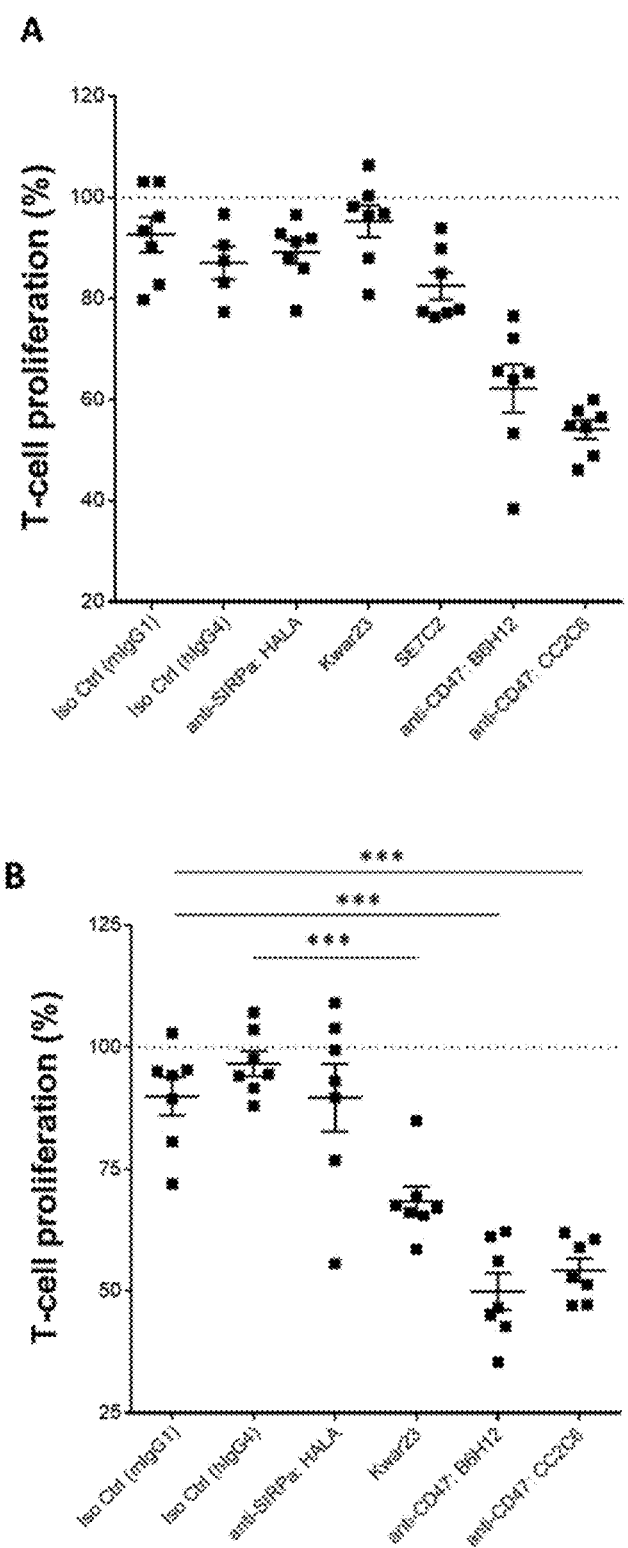
FIGURE 12A,B

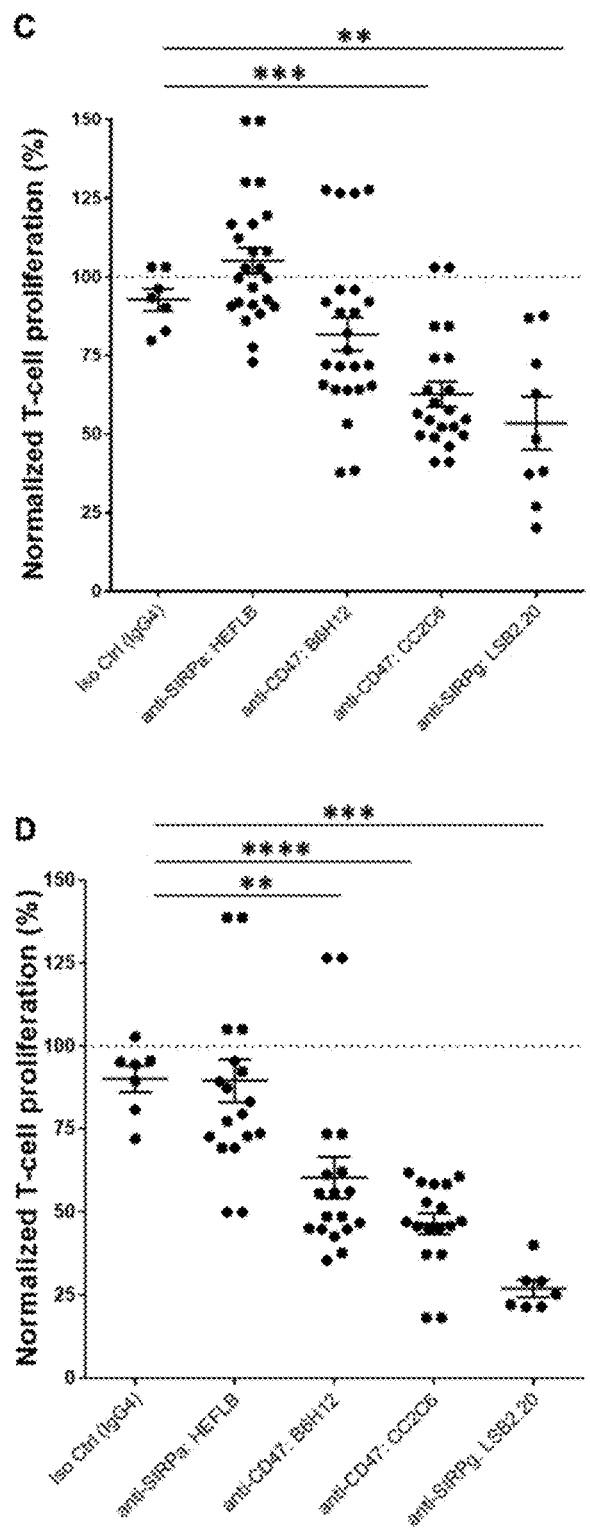
FIGURE 12C,D

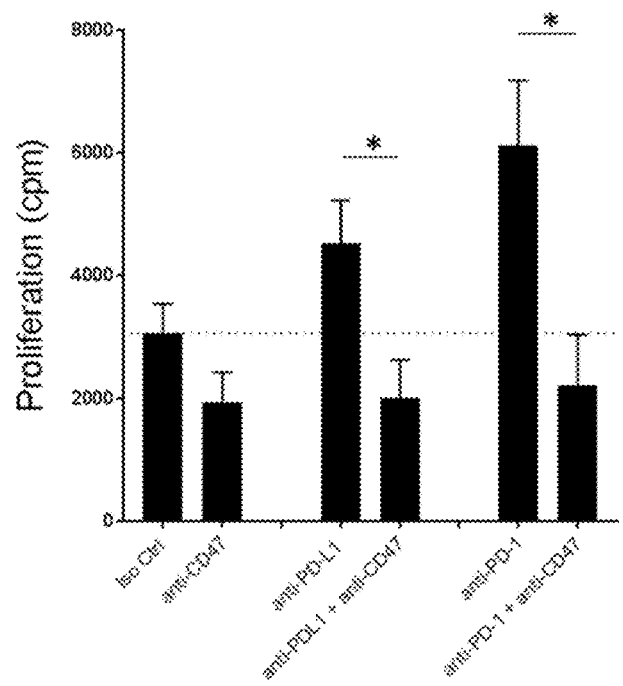
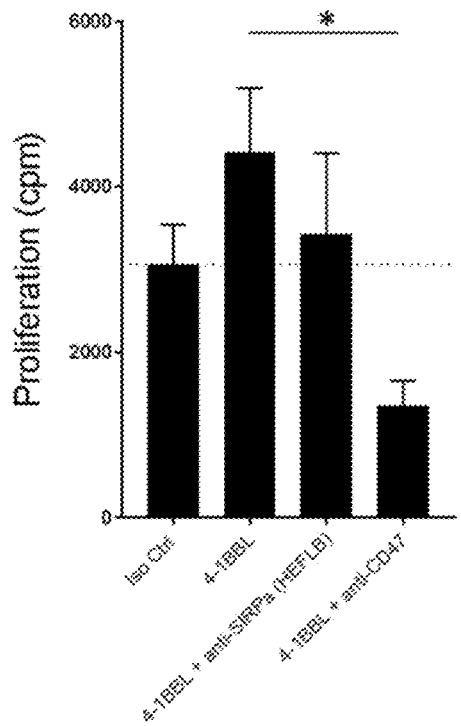
FIGURE 14

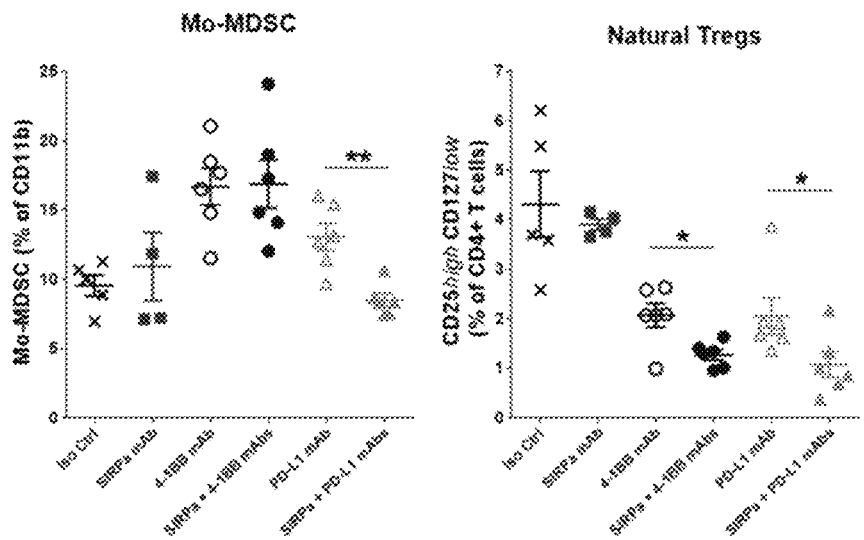
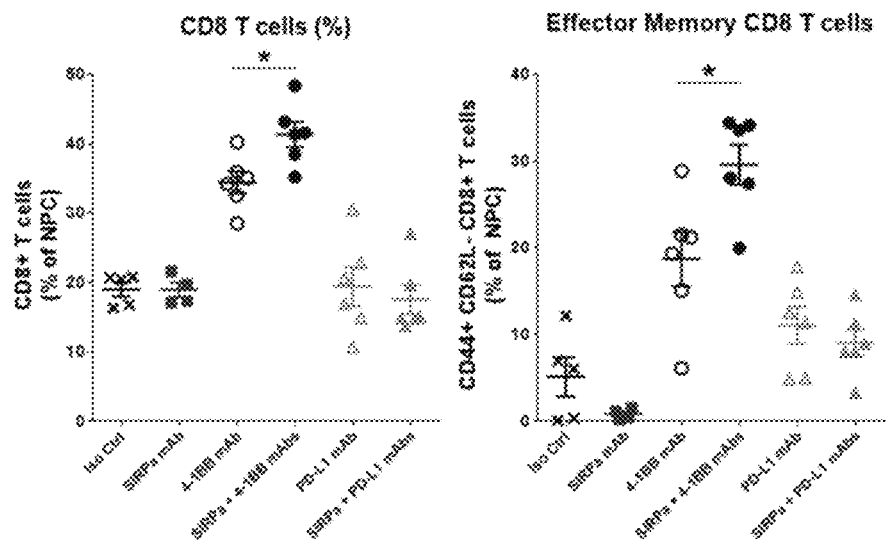
FIGURE 15B

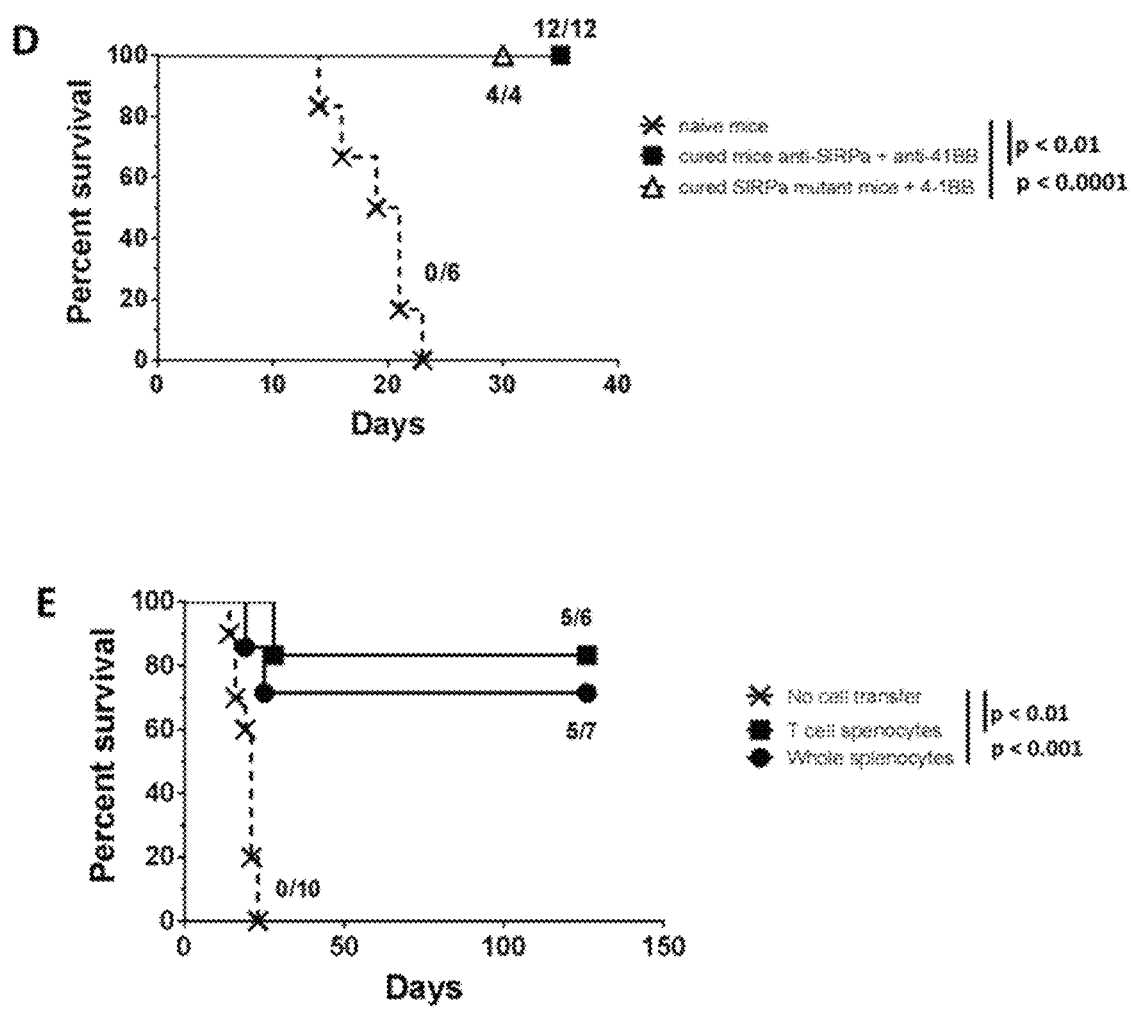
FIGURE 15D,E

FIGURE 21A,B,C

Figure 32C:
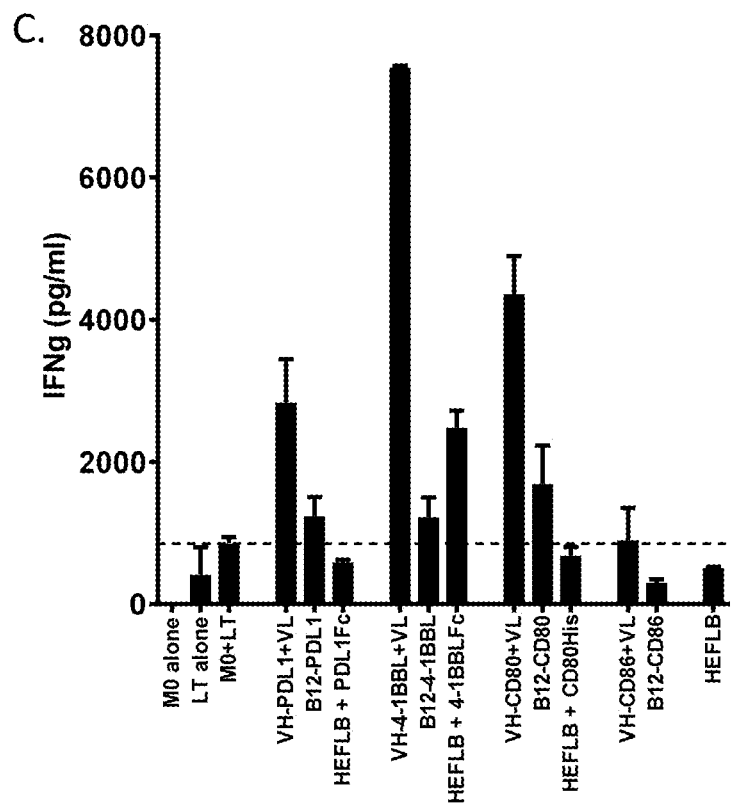

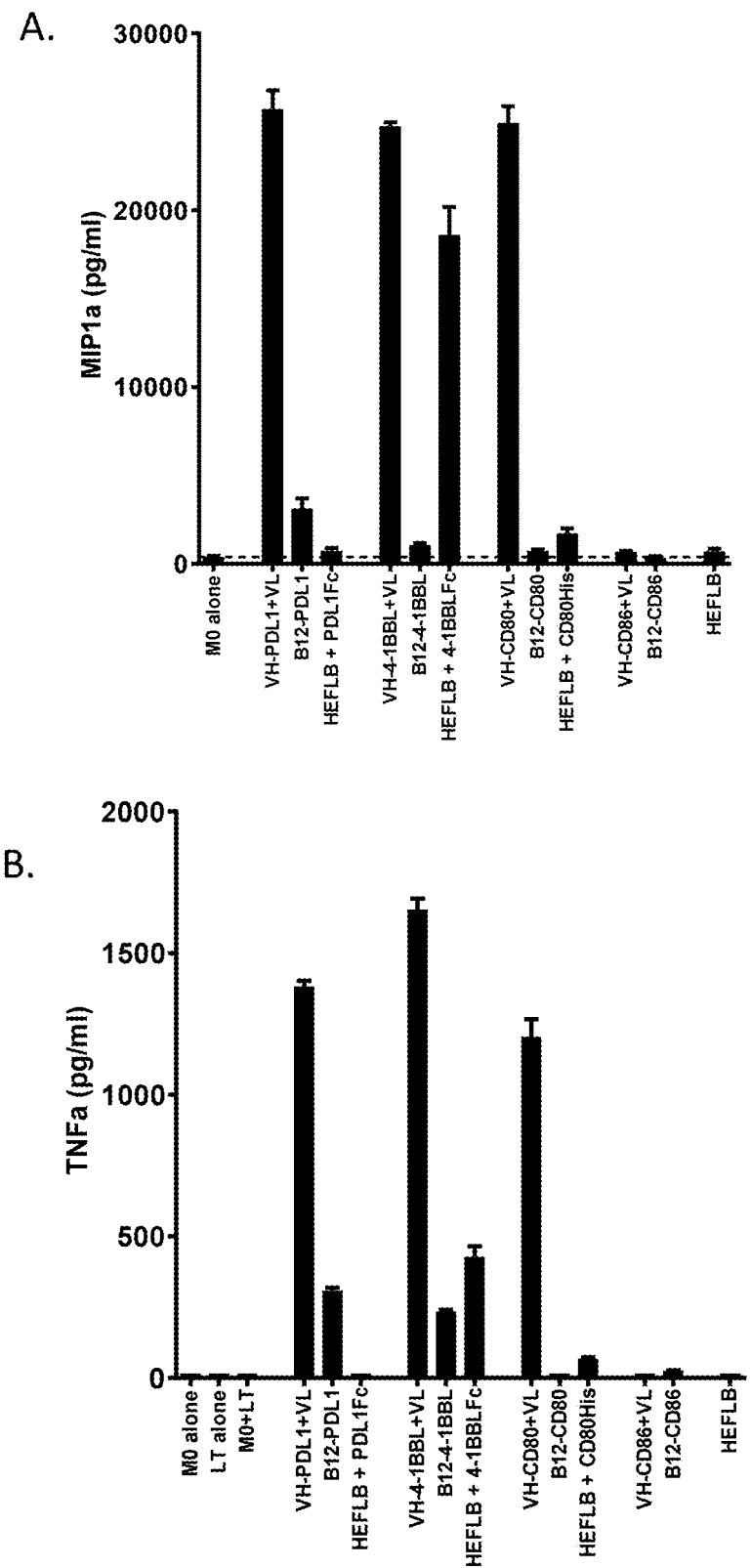
FIGURE 32A,B

SEQUENCE LISTING

```
<160> NUMBER OF SEQ ID NOS: 185

<210> SEQ ID NO 1
<211> LENGTH: 7
<212> TYPE: PRT
<213> ORGANISM: Homo sapiens

<400> SEQUENCE: 1

Ser Leu Ile Pro Val Gly Pro
1               5

<210> SEQ ID NO 2
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = G or A

<400> SEQUENCE: 2

Xaa Arg Glu Leu Ile Tyr Asn Gln Lys Glu Gly His
1               5                   10

<210> SEQ ID NO 3
<211> LENGTH: 10
<212> TYPE: PRT
<213> ORGANISM: Homo sapiens
<220> FEATURE:
<221> NAME/KEY: MISC_FEATURE
<223> OTHER INFORMATION: Xaa = DV or T
<220> FEATURE:
<221> NAME/KEY: misc_feature
<222> LOCATION: (9)..(9)
<223> OTHER INFORMATION: Xaa can be any naturally occurring amino acid
```

```
<400> SEQUENCE: 3

Lys Phe Arg Lys Gly Ser Pro Asp Xaa Glu
1               5                   10

<210> SEQ ID NO 4
<211> LENGTH: 23
<212> TYPE: PRT
<213> ORGANISM: Homo sapiens

<400> SEQUENCE: 4

Gln His Thr Val Ser Phe Thr Cys Glu Ser His Gly Phe Ser Pro Arg
1               5                   10                  15

Asp Ile Thr Leu Lys Trp Phe
            20

<210> SEQ ID NO 5
<211> LENGTH: 11
<212> TYPE: PRT
<213> ORGANISM: Homo sapiens

<400> SEQUENCE: 5

Ile Cys Glu Val Ala His Val Thr Leu Gln Gly
1               5                   10

<210> SEQ ID NO 6
<211> LENGTH: 11
<212> TYPE: PRT
<213> ORGANISM: Homo sapiens

<400> SEQUENCE: 6

Tyr Pro Gln Arg Leu Gln Leu Thr Trp Leu Glu
1               5                   10

<210> SEQ ID NO 7
<211> LENGTH: 12
<212> TYPE: PRT
<213> ORGANISM: Homo sapiens

<400> SEQUENCE: 7

Gly Arg Glu Leu Ile Tyr Asn Gln Lys Glu Gly His
1               5                   10

<210> SEQ ID NO 8
<211> LENGTH: 11
<212> TYPE: PRT
<213> ORGANISM: Homo sapiens

<400> SEQUENCE: 8

Lys Phe Arg Lys Gly Ser Pro Asp Asp Val Glu
1               5                   10

<210> SEQ ID NO 9
<211> LENGTH: 12
<212> TYPE: PRT
<213> ORGANISM: Homo sapiens

<400> SEQUENCE: 9

Ala Arg Glu Leu Ile Tyr Asn Gln Lys Glu Gly His
1               5                   10

<210> SEQ ID NO 10
<211> LENGTH: 10
<212> TYPE: PRT
<213> ORGANISM: Homo sapiens
```

<400> SEQUENCE: 10

Lys Phe Arg Lys Gly Ser Pro Asp Thr Glu
1               5                   10

<210> SEQ ID NO 11
<211> LENGTH: 7
<212> TYPE: PRT
<213> ORGANISM: Homo sapiens

<400> SEQUENCE: 11

Gly Arg Glu Leu Ile Tyr Asn
1               5

<210> SEQ ID NO 12
<211> LENGTH: 22
<212> TYPE: PRT
<213> ORGANISM: Homo sapiens

<400> SEQUENCE: 12

His Thr Val Ser Phe Thr Cys Glu Ser His Gly Phe Ser Pro Arg Asp
1               5                   10                  15

Ile Thr Leu Lys Trp Phe
            20

<210> SEQ ID NO 13
<211> LENGTH: 7
<212> TYPE: PRT
<213> ORGANISM: Homo sapiens

<400> SEQUENCE: 13

Ala Arg Glu Leu Ile Tyr Asn
1               5

<210> SEQ ID NO 14
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 14

Ser Tyr Trp Val His
1               5

<210> SEQ ID NO 15
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 15

Asn Ile Asp Pro Ser Asp Ser Asp Thr His Tyr Asn Gln Lys Phe Lys
1               5                   10                  15

Asp

<210> SEQ ID NO 16
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 16

Asn Ile Asp Pro Ser Asp Ser Asp Thr His Tyr Ser Pro Ser Phe Gln
1               5                   10                  15
Gly

<210> SEQ ID NO 17
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 17

Gly Gly Thr Gly Thr Met Ala Trp Phe Ala Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 18

Gly Gly Thr Gly Thr Leu Ala Trp Phe Ala Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 19

Gly Gly Thr Gly Thr Met Ala Tyr Phe Ala Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 20

Gly Gly Thr Gly Thr Leu Ala Tyr Phe Ala Tyr
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Light chain CDR1

<400> SEQUENCE: 21

Arg Ser Ser Gln Ser Leu Val His Ser Tyr Gly Asn Thr Tyr Leu Tyr
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Light chain CDR2

<400> SEQUENCE: 22

Arg Val Ser Asn Arg Phe Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Light chain CDR3

<400> SEQUENCE: 23

Phe Gln Gly Thr His Val Pro Tyr Thr
1               5

<210> SEQ ID NO 24
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 24

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala
        115                 120

<210> SEQ ID NO 25
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 25

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

```
Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 27

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 28
<211> LENGTH: 120
<212> TYPE: PRT
```

```
<213> ORGANISM: Artificial Sequence
<220> FEATURE:
<223> OTHER INFORMATION: Heavy chain variable domain

<400> SEQUENCE: 28

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 29

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: Heavy chain variable domain

<400> SEQUENCE: 30

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30
```

```
Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
 50                  55                  60

Gln Gly His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser
            115                 120
```

<210> SEQ ID NO 31
<211> LENGTH: 112
<212> TYPE: PRT
<213> ORGANISM: Artificial Sequence
<220> FEATURE:
<223> OTHER INFORMATION: Light chain variable domain

<400> SEQUENCE: 31

```
Asp Val Val Met Thr Gln Thr Pro Leu Ser Leu Pro Val Ser Leu Gly
 1               5                  10                  15

Asp Gln Ala Ser Ile Ser Cys Arg Ser Gln Ser Leu Val His Ser
            20                  25                  30

Tyr Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110
```

<210> SEQ ID NO 32
<211> LENGTH: 112
<212> TYPE: PRT
<213> ORGANISM: Artificial Sequence
<220> FEATURE:
<223> OTHER INFORMATION: Light chain variable domain

<400> SEQUENCE: 32

```
Asp Val Val Met Thr Gln Ser Pro Leu Ser Leu Pro Val Thr Leu Gly
 1               5                  10                  15

Gln Pro Ala Ser Ile Ser Cys Arg Ser Gln Ser Leu Val His Ser
            20                  25                  30

Tyr Gly Asn Thr Tyr Leu Tyr Trp Tyr Gln Gln Arg Pro Gly Gln Ser
            35                  40                  45

Pro Arg Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
```

<210> SEQ ID NO 33
<211> LENGTH: 112
<212> TYPE: PRT
<213> ORGANISM: Artificial Sequence
<220> FEATURE:
<223> OTHER INFORMATION: Light chain variable domain

<400> SEQUENCE: 33

```
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val His Ser
            20                  25                  30
Tyr Gly Asn Thr Tyr Leu Tyr Trp Phe Gln Gln Arg Pro Gly Gln Ser
        35                  40                  45
Pro Arg Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Thr His Val Pro Tyr Thr Phe Gly Gly Gly Thr Lys Val Glu Ile Lys
            100                 105                 110
```

<210> SEQ ID NO 34
<211> LENGTH: 327
<212> TYPE: PRT
<213> ORGANISM: Artificial Sequence
<220> FEATURE:
<223> OTHER INFORMATION: Heavy chain constant domain-IgG4m-S228P

<400> SEQUENCE: 34

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
```

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 35
<211> LENGTH: 107
<212> TYPE: PRT
<213> ORGANISM: Artificial Sequence
<220> FEATURE:
<223> OTHER INFORMATION: Light chain constant domain-CLkappa

<400> SEQUENCE: 35

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 36
<211> LENGTH: 447
<212> TYPE: PRT
<213> ORGANISM: Artificial Sequence
<220> FEATURE:
<223> OTHER INFORMATION: Heavy chain sequence 18D5

<400> SEQUENCE: 36

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
            85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 37
<211> LENGTH: 447
<212> TYPE: PRT
<213> ORGANISM: Artificial Sequence
<220> FEATURE:

<223> OTHER INFORMATION: Heavy chain sequence HA

<400> SEQUENCE: 37

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 38
<211> LENGTH: 447
<212> TYPE: PRT
<213> ORGANISM: Artificial Sequence
<220> FEATURE:
<223> OTHER INFORMATION: Heavy chain sequence HB

<400> SEQUENCE: 38

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 39
<211> LENGTH: 447
<212> TYPE: PRT
<213> ORGANISM: Artificial Sequence
<220> FEATURE:
<223> OTHER INFORMATION: Heavy chain sequence HC

<400> SEQUENCE: 39

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
            85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

-continued

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 40
<211> LENGTH: 447
<212> TYPE: PRT
<213> ORGANISM: Artificial Sequence
<220> FEATURE:
<223> OTHER INFORMATION: Heavy chain sequence HE

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Heavy chain sequence HF

<400> SEQUENCE: 41

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

```
Leu Gln Leu Ser Ser Leu Lys Ala Ser Asp Thr Ala Met Tyr Tyr Cys
                    85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                    180                 185                 190

Ser Ser Ser Leu Gly Thr Lys Thr Tyr Thr Cys Asn Val Asp His Lys
                    195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                    245                 250                 255

Pro Glu Val Thr Cys Val Val Val Asp Val Ser Gln Glu Asp Pro Glu
                    260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                    325                 330                 335

Ser Lys Ala Lys Gly Gln Pro Arg Glu Pro Gln Val Tyr Thr Leu Pro
                    340                 345                 350

Pro Ser Gln Glu Glu Met Thr Lys Asn Gln Val Ser Leu Thr Cys Leu
                    355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                    420                 425                 430

His Asn His Tyr Thr Gln Lys Ser Leu Ser Leu Ser Pro Gly Lys
                    435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Heavy chain sequence HEF

<400> SEQUENCE: 42
```

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
```

420                 425                 430
His Asn His Tyr Thr Gln Lys Ser Leu Ser Leu Ser Pro Gly Lys
            435                 440                 445

<210> SEQ ID NO 43
<211> LENGTH: 219
<212> TYPE: PRT
<213> ORGANISM: Artificial Sequence
<220> FEATURE:
<223> OTHER INFORMATION: Light chain sequence 18D5

<400> SEQUENCE: 43

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 44
<211> LENGTH: 219
<212> TYPE: PRT
<213> ORGANISM: Artificial Sequence
<220> FEATURE:
<223> OTHER INFORMATION: Light chain sequence LA

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 45
<211> LENGTH: 219
<212> TYPE: PRT
<213> ORGANISM: Artificial Sequence
<220> FEATURE:
<223> OTHER INFORMATION: Light chain sequence LB

<400> SEQUENCE: 45

```
Asp Val Val Met Thr Gln Ser Pro Leu Ser Leu Pro Val Thr Leu Gly
 1               5                  10                  15

Gln Pro Ala Ser Ile Ser Cys Arg Ser Gln Ser Leu Val His Ser
             20                  25                  30

Tyr Gly Asn Thr Tyr Leu Tyr Trp Phe Gln Gln Arg Pro Gly Gln Ser
         35                  40                  45

Pro Arg Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210             215

<210> SEQ ID NO 46
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain 18D5

<400> SEQUENCE: 46
caggtgcagc tgcagcagcc aggagctgag ctggtgaggc ctggctccag cgtgaagctg      60
tcctgcaagg ctagcggcta caccttcaca agctattggg tgcactgggt gaagcagcgg     120
ccaatccagg gcctggagtg gatcggcaac atcgacccca gcgactctga tacccattac     180
aatcagaagt ttaaggacaa ggcctctctg accgtggata agtcttccag cacagcttat     240
atgcagctgt cttccctgac attcgaggat tccgccgtgt actattgcgt gaggggagga     300
accggaacaa tggcttggtt tgcttactgg ggccagggca cctggtgac agtgtctgct     360

<210> SEQ ID NO 47
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HA

<400> SEQUENCE: 47
gaggtgcagc tggtgcagag cggagctgag gtgaagaagc caggcgagtc tctgaggatc      60
tcctgcaagg ctagcggcta caccttcaca tcttattggg tgcactgggt gcggcagatg     120
ccaggcaagg gcctggagtg gatcggcaac atcgacccta gcgactctga tacccactac     180
aatcagaagt ttaaggacca tgtgaccctg tctgtggata agtccatcag cacagcctat     240
ctgcagctgt ccagcctgaa ggcctccgat acagctatgt actattgcgt gaggggagga     300
accggaacaa tggcttggtt cgcttactgg ggccagggca cctggtgac agtgtcttcc     360

<210> SEQ ID NO 48
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HB

<400> SEQUENCE: 48
gaggtgcagc tggtgcagtc cggagctgag gtgaagaagc caggcgagtc tctgaggatc      60
tcctgcaagg cttctggcta ctccttcacc agctattggg tgcactgggt gcggcagatg     120
ccaggcaagg gcctggagtg gatgggcaac atcgaccta gcgactctga tacacactac     180
aatcagaagt ttaaggacca tgtgaccctg agcgtggata agtccatcag cacagcctat     240
ctgcagctgt ccagcctgaa ggcctctgat accgctatgt actattgcgt gaggggagga     300
accggaacaa tggcttggtt cgcttactgg ggccagggca cctggtgac agtgtcttcc     360

<210> SEQ ID NO 49
<211> LENGTH: 360
<212> TYPE: DNA
<213> ORGANISM: Artificial Sequence
<220> FEATURE:
<223> OTHER INFORMATION: Nucleic acid sequence coding the heavy chain variable domain HC

<400> SEQUENCE: 49

| | | | | | |
|---|---|---|---|---|---|
| gaggtgcagc | tggtgcagtc | tggcgccgag | gtgaagaagc | caggcgagag | cctgaggatc | 60 |
| tcttgcaagg | ctagcggcta | ctctttcacc | tcctattggg | tgcactgggt | gcggcagatg | 120 |
| ccaggcaagg | gcctggagtg | gatgggcaac | atcgacccca | gcgactctga | tacacactac | 180 |
| tcccctagct | ttcagggcca | tgtgaccctg | tccgtggaca | agtctatctc | cacagcctat | 240 |
| ctgcagctgt | ccagcctgaa | ggccagcgat | accgctatgt | actattgcgt | gaggggagga | 300 |
| accggaacaa | tggcttggtt | cgcttactgg | ggccagggca | cctggtgac | agtgtcttcc | 360 |

<210> SEQ ID NO 50
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HE

<400> SEQUENCE: 50

| | | | | | |
|---|---|---|---|---|---|
| gaggtgcagc | tggtgcagtc | tggcgccgag | gtgaagaagc | caggcgagag | cctgaggatc | 60 |
| tcttgcaagg | ctagcggcta | ctctttcacc | tcctattggg | tgcactgggt | gcggcagatg | 120 |
| ccaggcaagg | gcctggagtg | gatgggcaac | atcgacccca | gcgactctga | tacacactac | 180 |
| tcccctagct | ttcagggcca | tgtgaccctg | tccgtggaca | agtctatctc | cacagcctat | 240 |
| ctgcagctgt | ccagcctgaa | ggccagcgat | accgctatgt | actattgcgt | gaggggagga | 300 |
| accggcacac | tggcttggtt | cgcttactgg | ggccagggca | cctggtgac | agtgtcttcc | 360 |

<210> SEQ ID NO 51
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HF

<400> SEQUENCE: 51

| | | | | | |
|---|---|---|---|---|---|
| gaggtgcagc | tggtgcagtc | tggcgccgag | gtgaagaagc | caggcgagag | cctgaggatc | 60 |
| tcttgcaagg | ctagcggcta | ctctttcacc | tcctattggg | tgcactgggt | gcggcagatg | 120 |
| ccaggcaagg | gcctggagtg | gatgggcaac | atcgacccca | gcgactctga | tacacactac | 180 |
| tcccctagct | ttcagggcca | tgtgaccctg | tccgtggaca | agtctatctc | cacagcctat | 240 |
| ctgcagctgt | ccagcctgaa | ggccagcgat | accgctatgt | actattgcgt | gaggggagga | 300 |
| accggaacaa | tggcttactt | cgcttattgg | ggccagggca | cctggtgac | agtgtcttcc | 360 |

<210> SEQ ID NO 52
<211> LENGTH: 360
<212> TYPE: DNA
<213> ORGANISM: Artificial Sequence
<220> FEATURE:
<223> OTHER INFORMATION: Nucleic acid sequence coding the heavy chain
      variable domain HEF

<400> SEQUENCE: 52

| | | | | | |
|---|---|---|---|---|---|
| gaggtgcagc | tggtgcagtc | tggcgccgag | gtgaagaagc | caggcgagag | cctgaggatc | 60 |
| tcttgcaagg | ctagcggcta | ctctttcacc | tcctattggg | tgcactgggt | gcggcagatg | 120 |
| ccaggcaagg | gcctggagtg | gatgggcaac | atcgacccca | gcgactctga | tacacactac | 180 |

| tcccctagct ttcagggcca tgtgaccctg tccgtggaca agtctatctc cacagcctat | 240 |
| ctgcagctgt ccagcctgaa ggccagcgat accgctatgt actattgcgt gaggggagga | 300 |
| accggcacac tggcttactt cgcttattgg ggccagggca ccctggtgac agtgtcttcc | 360 |

```
<210> SEQ ID NO 53
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain 18D5

<400> SEQUENCE: 53
```

| gacgtggtca tgacccagac accactgagc ctgcccgtgt ccctgggcga tcaggcctct | 60 |
| atctcctgca ggtccagcca gtccctggtg cacagctatg caacacata cctgtattgg | 120 |
| tacctgcaga agccaggcca gtcccccaag ctgctgatct acagggtgtc taatcggttc | 180 |
| tccggcgtgc ctgacaggtt ctccggctct ggctccggca ccgatttcac actgaagatc | 240 |
| agcagggtgg aggctgagga cctgggcgtg tatttctgtt ttcagggcac ccatgtgcca | 300 |
| tacacatttg gctctggcac caagctggag atcaag | 336 |

```
<210> SEQ ID NO 54
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain LA

<400> SEQUENCE: 54
```

| gacgtggtca tgacacagag cccactgtct ctgcctgtga ccctgggaca gccagcctct | 60 |
| atctcctgca ggtccagcca gtccctggtg cacagctatg caacacata cctgtattgg | 120 |
| taccagcaga ggcccggaca gagcccaagg ctgctgatct acagggtgtc taatcggttc | 180 |
| tccggcgtgc ctgacaggtt tagcggctct ggctccggca ccgatttcac actgaagatc | 240 |
| tctagagtgg aggctgagga tgtgggcgtg tatttctgtt ttcagggcac ccatgtgcca | 300 |
| tacacatttg gcggcggcac caaggtggag atcaag | 336 |

```
<210> SEQ ID NO 55
<211> LENGTH: 336
<212> TYPE: DNA
<213> ORGANISM: Artificial Sequence
<220> FEATURE:
<223> OTHER INFORMATION: Nucleic acid sequence coding the light chain
      variable domain LB

<400> SEQUENCE: 55
```

| gacgtggtca tgacacagag cccactgtct ctgcctgtga ccctgggaca gccagcctct | 60 |
| atctcctgca ggtccagcca gtccctggtg cacagctacg caacacata cctgtattgg | 120 |
| ttccagcaga ggcccggaca gagcccaagg ctgctgatct atagggtgtc taatcggttc | 180 |
| tccggcgtgc ctgacaggtt tagcggatct ggatccggaa ccgacttcac cctgaagatc | 240 |
| tctagagtgg aggctgagga tgtgggcgtg tactattgtt tccagggcac ccatgtgcca | 300 |
| tacacatttg gcggcggcac caaggtggag atcaag | 336 |

```
<210> SEQ ID NO 56
<211> LENGTH: 456
<212> TYPE: PRT
```

<213> ORGANISM: Mus musculus

<400> SEQUENCE: 56

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val
145                 150                 155                 160

Trp Asn Ser Gly Ser Leu Ser Ser Val His Thr Phe Pro Ala Leu
            165                 170                 175

Leu Gln Ser Gly Leu Tyr Thr Met Ser Ser Ser Val Thr Val Pro Ser
        180                 185                 190

Ser Thr Trp Pro Ser Gln Thr Val Thr Cys Ser Val Ala His Pro Ala
    195                 200                 205

Ser Ser Thr Thr Val Asp Lys Lys Leu Glu Pro Ser Gly Pro Ile Ser
210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
        260                 265                 270

Val Asp Val Ser Glu Asp Asp Pro Asp Val Gln Ile Ser Trp Phe Val
    275                 280                 285

Asn Asn Val Glu Val His Thr Ala Gln Thr Gln Thr His Arg Glu Asp
290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
        340                 345                 350

Arg Ala Pro Gln Val Tyr Ile Leu Pro Pro Ala Glu Gln Leu Ser
    355                 360                 365

Arg Lys Asp Val Ser Leu Thr Cys Leu Val Val Gly Phe Asn Pro Gly
370                 375                 380

Asp Ile Ser Val Glu Trp Thr Ser Asn Gly His Thr Glu Glu Asn Tyr
385                 390                 395                 400

```
Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
        435                 440                 445

Thr Ile Ser Arg Ser Pro Gly Lys
    450                 455

<210> SEQ ID NO 57
<211> LENGTH: 219
<212> TYPE: PRT
<213> ORGANISM: Mus musculus

<400> SEQUENCE: 57

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 58
<211> LENGTH: 15
<212> TYPE: DNA
<213> ORGANISM: Artificial Sequence
<220> FEATURE:
<223> OTHER INFORMATION: Sequence coding HCDR1

<400> SEQUENCE: 58
agctattggg tgcac                                                15

<210> SEQ ID NO 59
<211> LENGTH: 15
<212> TYPE: DNA
<213> ORGANISM: Artificial Sequence
```

<220> FEATURE:
<223> OTHER INFORMATION: Sequence coding HCDR1

<400> SEQUENCE: 59
tcttattggg tgcac                                                      15

<210> SEQ ID NO 60
<211> LENGTH: 15
<212> TYPE: DNA
<213> ORGANISM: Artificial Sequence
<220> FEATURE:
<223> OTHER INFORMATION: Sequence coding HCDR1

<400> SEQUENCE: 60
tcctattggg tgcac                                                      15

<210> SEQ ID NO 61
<211> LENGTH: 51
<212> TYPE: DNA
<213> ORGANISM: Artificial Sequence
<220> FEATURE:
<223> OTHER INFORMATION: Sequence coding HCDR2

<400> SEQUENCE: 61
aacatcgacc ccagcgactc tgatacccat acaatcaga agtttaagga c                51

<210> SEQ ID NO 62
<211> LENGTH: 51
<212> TYPE: DNA
<213> ORGANISM: Artificial Sequence
<220> FEATURE:
<223> OTHER INFORMATION: Sequence coding HCDR2

<400> SEQUENCE: 62
aacatcgacc ccagcgactc tgatacacac tactcccta gctttcaggg c                51

<210> SEQ ID NO 63
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 63
ggaggaaccg gaacaatggc ttggtttgct tac                                   33

<210> SEQ ID NO 64
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 64
ggaggaaccg gcacactggc ttggttcgct tac                                   33

<210> SEQ ID NO 65
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 65
ggaggaaccg gaacaatggc ttacttcgct tat                                   33

<210> SEQ ID NO 66
<211> LENGTH: 33
<212> TYPE: DNA
<213> ORGANISM: Artificial Sequence
<220> FEATURE:
<223> OTHER INFORMATION: Sequence coding HCDR3

<400> SEQUENCE: 66
ggaggaaccg gcacactggc ttacttcgct tat                                33

<210> SEQ ID NO 67
<211> LENGTH: 48
<212> TYPE: DNA
<213> ORGANISM: Artificial Sequence
<220> FEATURE:
<223> OTHER INFORMATION: Sequence coding LCDR1

<400> SEQUENCE: 67
aggtccagcc agtccctggt gcacagctat ggcaacacat acctgtat               48

<210> SEQ ID NO 68
<211> LENGTH: 21
<212> TYPE: DNA
<213> ORGANISM: Artificial Sequence
<220> FEATURE:
<223> OTHER INFORMATION: Sequence coding LCDR2

<400> SEQUENCE: 68
agggtgtcta atcggttctc c                                            21

<210> SEQ ID NO 69
<211> LENGTH: 27
<212> TYPE: DNA
<213> ORGANISM: Artificial Sequence
<220> FEATURE:
<223> OTHER INFORMATION: Sequence coding LCDR3

<400> SEQUENCE: 69
tttcagggca cccatgtgcc atacaca                                      27

<210> SEQ ID NO 70
<211> LENGTH: 13
<212> TYPE: PRT
<213> ORGANISM: Homo sapiens

<400> SEQUENCE: 70

Glu Leu Ile Tyr Asn Gln Lys Glu Gly His Phe Pro Arg
1               5                   10

<210> SEQ ID NO 71
<211> LENGTH: 12
<212> TYPE: PRT
<213> ORGANISM: Homo sapiens

<400> SEQUENCE: 71

Arg Asn Asn Met Asp Phe Ser Ile Arg Ile Gly Asn
1               5                   10

<210> SEQ ID NO 72
<211> LENGTH: 9
<212> TYPE: PRT
<213> ORGANISM: Homo sapiens

<400> SEQUENCE: 72

Ser Pro Arg Asp Ile Thr Leu Lys Trp

-continued

```
<210> SEQ ID NO 73
<211> LENGTH: 4
<212> TYPE: PRT
<213> ORGANISM: Homo sapiens

<400> SEQUENCE: 73

Tyr Asn Gln Lys
1

<210> SEQ ID NO 74
<211> LENGTH: 288
<212> TYPE: PRT
<213> ORGANISM: Homo sapiens

<400> SEQUENCE: 74

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 75
<211> LENGTH: 290
<212> TYPE: PRT
```

<213> ORGANISM: Homo sapiens

<400> SEQUENCE: 75

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 76
<211> LENGTH: 288
<212> TYPE: PRT
<213> ORGANISM: Homo sapiens

<400> SEQUENCE: 76

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
```

```
                    50                  55                  60
Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
            130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
            210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 77
<211> LENGTH: 183
<212> TYPE: PRT
<213> ORGANISM: Homo sapiens

<400> SEQUENCE: 77

Met Glu Arg Val Gln Pro Leu Glu Glu Asn Val Gly Asn Ala Ala Arg
 1               5                  10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
        50                  55                  60

Gln Phe Thr Glu Tyr Lys Lys Glu Lys Gly Phe Ile Leu Thr Ser Gln
 65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
        130                 135                 140
```

```
Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 78
<211> LENGTH: 254
<212> TYPE: PRT
<213> ORGANISM: Homo sapiens

<400> SEQUENCE: 78

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
            85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 79
<211> LENGTH: 302
<212> TYPE: PRT
<213> ORGANISM: Homo sapiens

<400> SEQUENCE: 79

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30
```

```
Val Glu Leu Ser Cys Ala Cys Pro Glu Gly Ser Arg Phe Asp Leu Asn
         35                  40                  45

Asp Val Tyr Val Tyr Trp Gln Thr Ser Glu Ser Lys Thr Val Val Thr
 50                  55                  60

Tyr His Ile Pro Gln Asn Ser Ser Leu Glu Asn Val Asp Ser Arg Tyr
 65                  70                  75                  80

Arg Asn Arg Ala Leu Met Ser Pro Ala Gly Met Leu Arg Gly Asp Phe
                 85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
290                 295                 300

<210> SEQ ID NO 80
<211> LENGTH: 329
<212> TYPE: PRT
<213> ORGANISM: Homo sapiens

<400> SEQUENCE: 80

Met Asp Pro Gln Cys Thr Met Gly Leu Ser Asn Ile Leu Phe Val Met
1                5                  10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110
```

His His Lys Lys Pro Thr Gly Met Ile Arg Ile His Gln Met Asn Ser
            115                 120                 125

Glu Leu Ser Val Leu Ala Asn Phe Ser Gln Pro Glu Ile Val Pro Ile
        130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

<210> SEQ ID NO 81
<211> LENGTH: 147
<212> TYPE: PRT
<213> ORGANISM: Homo sapiens

<400> SEQUENCE: 81

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln

<210> SEQ ID NO 82
<211> LENGTH: 220
<212> TYPE: PRT
<213> ORGANISM: Homo sapiens

<400> SEQUENCE: 82

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 83
<211> LENGTH: 208
<212> TYPE: PRT
<213> ORGANISM: Homo sapiens

<400> SEQUENCE: 83

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser

```
            100             105              110
Ile Ser Asp Phe Glu Ile Pro Thr Ser Asn Ile Arg Arg Ile Ile Cys
            115                  120                 125

Ser Thr Ser Gly Gly Phe Pro Glu Pro His Leu Ser Trp Leu Glu Asn
            130                  135                 140

Gly Glu Glu Leu Asn Ala Ile Asn Thr Thr Val Ser Gln Asp Pro Glu
145                  150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
                180                 185                 190

Gln Thr Phe Asn Trp Asn Thr Thr Lys Gln Glu His Phe Pro Asp Asn
                195                 200                 205

<210> SEQ ID NO 84
<211> LENGTH: 133
<212> TYPE: PRT
<213> ORGANISM: Homo sapiens

<400> SEQUENCE: 84

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
                35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
                100                 105                 110

Phe His Val Asn Gly Gly Glu Leu Ile Leu Ile His Gln Asn Pro Gly
                115                 120                 125

Glu Phe Cys Val Leu
        130

<210> SEQ ID NO 85
<211> LENGTH: 184
<212> TYPE: PRT
<213> ORGANISM: Homo sapiens

<400> SEQUENCE: 85

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
                35                  40                  45

Ser Leu Thr Gly Gly Leu Ser Tyr Lys Glu Asp Thr Lys Glu Leu Val
                50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
```

```
                    85                  90                  95

Leu Gln Pro Leu Arg Ser Ala Gly Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 86
<211> LENGTH: 238
<212> TYPE: PRT
<213> ORGANISM: Homo sapiens

<400> SEQUENCE: 86

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
                20                  25                  30

Tyr Val Tyr Trp Gln Thr Ser Glu Ser Lys Thr Val Val Thr Tyr His
            35                  40                  45

Ile Pro Gln Asn Ser Ser Leu Glu Asn Val Asp Ser Arg Tyr Arg Asn
50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
                100                 105                 110

Thr Leu His Val Ala Ala Asn Phe Ser Val Pro Val Val Ser Ala Pro
            115                 120                 125

His Ser Pro Ser Gln Asp Glu Leu Thr Phe Thr Cys Thr Ser Ile Asn
130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
                180                 185                 190

Val Asn Ile Gly Cys Cys Ile Glu Asn Val Leu Leu Gln Gln Asn Leu
            195                 200                 205

Thr Val Gly Ser Gln Thr Gly Asn Asp Ile Gly Glu Arg Asp Lys Ile
210                 215                 220

Thr Glu Asn Pro Val Ser Thr Gly Glu Lys Asn Ala Ala Thr
225                 230                 235

<210> SEQ ID NO 87
<211> LENGTH: 222
<212> TYPE: PRT
<213> ORGANISM: Homo sapiens
```

<400> SEQUENCE: 87

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Asp His
210                 215                 220
```

<210> SEQ ID NO 88
<211> LENGTH: 153
<212> TYPE: PRT
<213> ORGANISM: Homo sapiens

<400> SEQUENCE: 88

```
Leu Gln Leu Gly Trp Arg Pro Gly Trp Phe Leu Asp Ser Pro Asp Arg
1               5                   10                  15

Pro Trp Asn Pro Pro Thr Phe Ser Pro Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
130                 135                 140
```

-continued

Ser Pro Arg Pro Ala Gly Gln Phe Gln
145                 150

<210> SEQ ID NO 89
<211> LENGTH: 15
<212> TYPE: PRT
<213> ORGANISM: Artificial Sequence
<220> FEATURE:
<223> OTHER INFORMATION: Linker

<400> SEQUENCE: 89

Gly Gly Gly Gly Ser Gly Gly Gly Ser Gly Gly Gly Gly Ser
1               5                   10                  15

<210> SEQ ID NO 90
<211> LENGTH: 20
<212> TYPE: PRT
<213> ORGANISM: Artificial Sequence
<220> FEATURE:
<223> OTHER INFORMATION: Linker

<400> SEQUENCE: 90

Gly Gly Gly Gly Ser Gly Gly Gly Gly Ser Gly Gly Gly Gly Ser Gly
1               5                   10                  15

Gly Gly Gly Ser
            20

<210> SEQ ID NO 91
<211> LENGTH: 5
<212> TYPE: PRT
<213> ORGANISM: Artificial Sequence
<220> FEATURE:
<223> OTHER INFORMATION: Linker

<400> SEQUENCE: 91

Gly Gly Gly Gly Ser
1               5

<210> SEQ ID NO 92
<211> LENGTH: 4
<212> TYPE: PRT
<213> ORGANISM: Artificial Sequence
<220> FEATURE:
<223> OTHER INFORMATION: Linker

<400> SEQUENCE: 92

Gly Gly Gly Ser
1

<210> SEQ ID NO 93
<211> LENGTH: 15
<212> TYPE: PRT
<213> ORGANISM: Artificial Sequence
<220> FEATURE:
<223> OTHER INFORMATION: Linker

<400> SEQUENCE: 93

Gly Gly Gly Ser Ser Gly Gly Gly Ser Ser Gly Gly Gly Ser Ser
1               5                   10                  15

<210> SEQ ID NO 94
<211> LENGTH: 618
<212> TYPE: PRT
<213> ORGANISM: Artificial Sequence
<220> FEATURE:
<223> OTHER INFORMATION: Heavy chain of the modified antibody

<400> SEQUENCE: 94

```
Gln Val Gln Leu Gln Gln Pro Gly Ala Glu Leu Val Arg Pro Gly Ser
1               5                   10                  15
Ser Val Lys Leu Ser Cys Lys Ala Ser Gly Tyr Thr Phe Thr Ser Tyr
            20                  25                  30
Trp Val His Trp Val Lys Gln Arg Pro Ile Gln Gly Leu Glu Trp Ile
        35                  40                  45
Gly Asn Ile Asp Pro Ser Asp Ser Asp Thr His Tyr Asn Gln Lys Phe
    50                  55                  60
Lys Asp Lys Ala Ser Leu Thr Val Asp Lys Ser Ser Thr Ala Tyr
65                  70                  75                  80
Met Gln Leu Ser Ser Leu Thr Phe Glu Asp Ser Ala Val Tyr Tyr Cys
                85                  90                  95
Val Arg Gly Gly Thr Gly Thr Met Ala Trp Phe Ala Tyr Trp Gly Gln
            100                 105                 110
Gly Thr Leu Val Thr Val Ser Ala Ala Lys Thr Thr Pro Pro Ser Val
        115                 120                 125
Tyr Pro Leu Ala Pro Gly Cys Gly Asp Thr Thr Gly Ser Ser Val Thr
    130                 135                 140
Leu Gly Cys Leu Val Lys Gly Tyr Phe Pro Glu Ser Val Thr Val Thr
145                 150                 155                 160
Trp Asn Ser Gly Ser Leu Ser Ser Val His Thr Phe Pro Ala Leu
                165                 170                 175
Leu Gln Ser Gly Leu Tyr Thr Met Ser Ser Val Thr Val Pro Ser
            180                 185                 190
Ser Thr Trp Pro Ser Gln Thr Val Thr Cys Ser Val Ala His Pro Ala
        195                 200                 205
Ser Ser Thr Thr Val Asp Lys Lys Leu Glu Pro Ser Gly Pro Ile Ser
    210                 215                 220
Thr Ile Asn Pro Cys Pro Pro Cys Lys Glu Cys His Lys Cys Pro Ala
225                 230                 235                 240
Pro Asn Leu Glu Gly Gly Pro Ser Val Phe Ile Phe Pro Pro Asn Ile
                245                 250                 255
Lys Asp Val Leu Met Ile Ser Leu Thr Pro Lys Val Thr Cys Val Val
            260                 265                 270
Val Asp Val Ser Glu Asp Asp Pro Asp Val Gln Ile Ser Trp Phe Val
        275                 280                 285
Asn Asn Val Glu Val His Thr Ala Gln Thr Gln Thr His Arg Glu Asp
    290                 295                 300
Tyr Asn Ser Thr Ile Arg Val Val Ser Thr Leu Pro Ile Gln His Gln
305                 310                 315                 320
Asp Trp Met Ser Gly Lys Glu Phe Lys Cys Lys Val Asn Asn Lys Asp
                325                 330                 335
Leu Pro Ser Pro Ile Glu Arg Thr Ile Ser Lys Ile Lys Gly Leu Val
            340                 345                 350
Arg Ala Pro Gln Val Tyr Ile Leu Pro Pro Ala Glu Gln Leu Ser
        355                 360                 365
Arg Lys Asp Val Ser Leu Thr Cys Leu Val Val Gly Phe Asn Pro Gly
    370                 375                 380
Asp Ile Ser Val Glu Trp Thr Ser Asn Gly His Thr Glu Glu Asn Tyr
385                 390                 395                 400
Lys Asp Thr Ala Pro Val Leu Asp Ser Asp Gly Ser Tyr Phe Ile Tyr
                405                 410                 415
```

-continued

```
Ser Lys Leu Asn Met Lys Thr Ser Lys Trp Glu Lys Thr Asp Ser Phe
        420                 425                 430

Ser Cys Asn Val Arg His Glu Gly Leu Lys Asn Tyr Tyr Leu Lys Lys
        435                 440                 445

Thr Ile Ser Arg Ser Pro Gly Lys Gly Gly Gly Ser Gly Gly Gly
450                 455                 460

Gly Ser Gly Gly Gly Ser Pro Gly Trp Phe Leu Asp Ser Pro Asp
465                 470                 475                 480

Arg Pro Trp Asn Pro Pro Thr Phe Ser Pro Ala Leu Leu Val Val Thr
                485                 490                 495

Glu Gly Asp Asn Ala Thr Phe Thr Cys Ser Phe Ser Asn Thr Ser Glu
                500                 505                 510

Ser Phe Val Leu Asn Trp Tyr Arg Met Ser Pro Ser Asn Gln Thr Asp
                515                 520                 525

Lys Leu Ala Ala Phe Pro Glu Asp Arg Ser Gln Pro Gly Gln Asp Cys
        530                 535                 540

Arg Phe Arg Val Thr Gln Leu Pro Asn Gly Arg Asp Phe His Met Ser
545                 550                 555                 560

Val Val Arg Ala Arg Arg Asn Asp Ser Gly Thr Tyr Leu Cys Gly Ala
                565                 570                 575

Ile Ser Leu Ala Pro Lys Ala Gln Ile Lys Glu Ser Leu Arg Ala Glu
                580                 585                 590

Leu Arg Val Thr Glu Arg Arg Ala Glu Val Pro Thr Ala His Pro Ser
        595                 600                 605

Pro Ser Pro Arg Pro Ala Gly Gln Phe Gln
        610                 615

<210> SEQ ID NO 95
<211> LENGTH: 691
<212> TYPE: PRT
<213> ORGANISM: Artificial Sequence
<220> FEATURE:
<223> OTHER INFORMATION: Heavy chain of the modified antibody

<400> SEQUENCE: 95

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160
```

```
Trp Asn Ser Gly Ser Leu Ser Ser Val His Thr Phe Pro Ala Leu
            165                 170                 175

Leu Gln Ser Gly Leu Tyr Thr Met Ser Ser Val Thr Val Pro Ser
            180                 185                 190

Ser Thr Trp Pro Ser Gln Thr Val Thr Cys Ser Val Ala His Pro Ala
            195                 200                 205

Ser Ser Thr Thr Val Asp Lys Lys Leu Glu Pro Ser Gly Pro Ile Ser
210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
            290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Pro Ala Glu Gln Leu Ser
            355                 360                 365

Arg Lys Asp Val Ser Leu Thr Cys Leu Val Val Gly Phe Asn Pro Gly
            370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
            405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
            435                 440                 445

Thr Ile Ser Arg Ser Pro Gly Lys Gly Gly Gly Ser Gly Gly Gly
            450                 455                 460

Gly Ser Gly Gly Gly Ser Phe Thr Val Thr Val Pro Lys Asp Leu
465                 470                 475                 480

Tyr Val Val Glu Tyr Gly Ser Asn Met Thr Ile Glu Cys Lys Phe Pro
            485                 490                 495

Val Glu Lys Gln Leu Asp Leu Ala Ala Leu Ile Val Tyr Trp Glu Met
            500                 505                 510

Glu Asp Lys Asn Ile Ile Gln Phe Val His Gly Glu Glu Asp Leu Lys
            515                 520                 525

Val Gln His Ser Ser Tyr Arg Gln Arg Ala Arg Leu Leu Lys Asp Gln
            530                 535                 540

Leu Ser Leu Gly Asn Ala Ala Leu Gln Ile Thr Asp Val Lys Leu Gln
545                 550                 555                 560

Asp Ala Gly Val Tyr Arg Cys Met Ile Ser Tyr Gly Gly Ala Asp Tyr
            565                 570                 575
```

```
Lys Arg Ile Thr Val Lys Val Asn Ala Pro Tyr Asn Lys Ile Asn Gln
                580                 585                 590

Arg Ile Leu Val Val Asp Pro Val Thr Ser Glu His Glu Leu Thr Cys
            595                 600                 605

Gln Ala Glu Gly Tyr Pro Lys Ala Glu Val Ile Trp Thr Ser Ser Asp
        610                 615                 620

His Gln Val Leu Ser Gly Lys Thr Thr Thr Asn Ser Lys Arg Glu
625                 630                 635                 640

Glu Lys Leu Phe Asn Val Thr Ser Thr Leu Arg Ile Asn Thr Thr Thr
                645                 650                 655

Asn Glu Ile Phe Tyr Cys Thr Phe Arg Arg Leu Asp Pro Glu Glu Asn
            660                 665                 670

His Thr Ala Glu Leu Val Ile Pro Glu Leu Pro Leu Ala His Pro Pro
        675                 680                 685

Asn Glu Arg
    690

<210> SEQ ID NO 96
<211> LENGTH: 679
<212> TYPE: PRT
<213> ORGANISM: Artificial Sequence
<220> FEATURE:
<223> OTHER INFORMATION: Heavy chain of the modified antibody

<400> SEQUENCE: 96

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Val His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240
```

```
Pro Asn Leu Glu Gly Gly Pro Ser Val Phe Ile Phe Pro Pro Asn Ile
                245                 250                 255
Lys Asp Val Leu Met Ile Ser Leu Thr Pro Lys Val Thr Cys Val Val
            260                 265                 270
Val Asp Val Ser Glu Asp Asp Pro Asp Val Gln Ile Ser Trp Phe Val
        275                 280                 285
Asn Asn Val Glu Val His Thr Ala Gln Thr Gln Thr His Arg Glu Asp
    290                 295                 300
Tyr Asn Ser Thr Ile Arg Val Val Ser Thr Leu Pro Ile Gln His Gln
305                 310                 315                 320
Asp Trp Met Ser Gly Lys Glu Phe Lys Cys Lys Val Asn Asn Lys Asp
                325                 330                 335
Leu Pro Ser Pro Ile Glu Arg Thr Ile Ser Lys Ile Lys Gly Leu Val
            340                 345                 350
Arg Ala Pro Gln Val Tyr Ile Leu Pro Pro Ala Glu Gln Leu Ser
        355                 360                 365
Arg Lys Asp Val Ser Leu Thr Cys Leu Val Val Gly Phe Asn Pro Gly
    370                 375                 380
Asp Ile Ser Val Glu Trp Thr Ser Asn Gly His Thr Glu Glu Asn Tyr
385                 390                 395                 400
Lys Asp Thr Ala Pro Val Leu Asp Ser Asp Gly Ser Tyr Phe Ile Tyr
                405                 410                 415
Ser Lys Leu Asn Met Lys Thr Ser Lys Trp Glu Lys Thr Asp Ser Phe
            420                 425                 430
Ser Cys Asn Val Arg His Glu Gly Leu Lys Asn Tyr Tyr Leu Lys Lys
        435                 440                 445
Thr Ile Ser Arg Ser Pro Gly Lys Gly Gly Gly Ser Gly Gly Gly
    450                 455                 460
Gly Ser Gly Gly Gly Ser Val Ile His Val Thr Lys Glu Val Lys
465                 470                 475                 480
Glu Val Ala Thr Leu Ser Cys Gly His Asn Val Ser Val Glu Glu Leu
                485                 490                 495
Ala Gln Thr Arg Ile Tyr Trp Gln Lys Glu Lys Lys Met Val Leu Thr
            500                 505                 510
Met Met Ser Gly Asp Met Asn Ile Trp Pro Glu Tyr Lys Asn Arg Thr
        515                 520                 525
Ile Phe Asp Ile Thr Asn Asn Leu Ser Ile Val Ile Leu Ala Leu Arg
    530                 535                 540
Pro Ser Asp Glu Gly Thr Tyr Glu Cys Val Val Leu Lys Tyr Glu Lys
545                 550                 555                 560
Asp Ala Phe Lys Arg Glu His Leu Ala Glu Val Thr Leu Ser Val Lys
                565                 570                 575
Ala Asp Phe Pro Thr Pro Ser Ile Ser Asp Phe Glu Ile Pro Thr Ser
            580                 585                 590
Asn Ile Arg Arg Ile Ile Cys Ser Thr Ser Gly Gly Phe Pro Glu Pro
        595                 600                 605
His Leu Ser Trp Leu Glu Asn Gly Glu Glu Leu Asn Ala Ile Asn Thr
    610                 615                 620
Thr Val Ser Gln Asp Pro Glu Thr Glu Leu Tyr Ala Val Ser Ser Lys
625                 630                 635                 640
Leu Asp Phe Asn Met Thr Thr Asn His Ser Phe Met Cys Leu Ile Lys
                645                 650                 655
Tyr Gly His Leu Arg Val Asn Gln Thr Phe Asn Trp Asn Thr Thr Lys
```

Gln Glu His Phe Pro Asp Asn
            675

<210> SEQ ID NO 97
<211> LENGTH: 604
<212> TYPE: PRT
<213> ORGANISM: Artificial Sequence
<220> FEATURE:
<223> OTHER INFORMATION: Heavy chain of the modified antibody

<400> SEQUENCE: 97

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
                245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
        275                 280                 285

Asn Asn Val Glu Val His Thr Ala Gln Thr Gln Thr His Arg Glu Asp
    290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ser Pro Ile Glu Arg Thr Ile Ser Lys Ile Lys Gly Leu Val

Arg Ala Pro Gln Val Tyr Ile Leu Pro Pro Ala Glu Gln Leu Ser
        355                 360                 365
Arg Lys Asp Val Ser Leu Thr Cys Leu Val Val Gly Phe Asn Pro Gly
    370                 375                 380
Asp Ile Ser Val Glu Trp Thr Ser Asn Gly His Thr Glu Glu Asn Tyr
385                 390                 395                 400
Lys Asp Thr Ala Pro Val Leu Asp Ser Asp Gly Ser Tyr Phe Ile Tyr
                405                 410                 415
Ser Lys Leu Asn Met Lys Thr Ser Lys Trp Glu Lys Thr Asp Ser Phe
            420                 425                 430
Ser Cys Asn Val Arg His Glu Gly Leu Lys Asn Tyr Tyr Leu Lys Lys
        435                 440                 445
Thr Ile Ser Arg Ser Pro Gly Lys Gly Gly Gly Ser Gly Gly Gly
    450                 455                 460
Gly Ser Gly Gly Gly Gly Ser Gln Val Ser His Arg Tyr Pro Arg Ile
465                 470                 475                 480
Gln Ser Ile Lys Val Gln Phe Thr Glu Tyr Lys Lys Glu Lys Gly Phe
                485                 490                 495
Ile Leu Thr Ser Gln Lys Glu Asp Glu Ile Met Lys Val Gln Asn Asn
            500                 505                 510
Ser Val Ile Ile Asn Cys Asp Gly Phe Tyr Leu Ile Ser Leu Lys Gly
        515                 520                 525
Tyr Phe Ser Gln Glu Val Asn Ile Ser Leu His Tyr Gln Lys Asp Glu
    530                 535                 540
Glu Pro Leu Phe Gln Leu Lys Lys Val Arg Ser Val Asn Ser Leu Met
545                 550                 555                 560
Val Ala Ser Leu Thr Tyr Lys Asp Lys Val Tyr Leu Asn Val Thr Thr
                565                 570                 575
Asp Asn Thr Ser Leu Asp Asp Phe His Val Asn Gly Gly Glu Leu Ile
            580                 585                 590
Leu Ile His Gln Asn Pro Gly Glu Phe Cys Val Leu
        595                 600

<210> SEQ ID NO 98
<211> LENGTH: 655
<212> TYPE: PRT
<213> ORGANISM: Artificial Sequence
<220> FEATURE:
<223> OTHER INFORMATION: Heavy chain of the modified antibody

<400> SEQUENCE: 98

Gln Val Gln Leu Gln Gln Pro Gly Ala Glu Leu Val Arg Pro Gly Ser
1               5                   10                  15
Ser Val Lys Leu Ser Cys Lys Ala Ser Gly Tyr Thr Phe Thr Ser Tyr
                20                  25                  30
Trp Val His Trp Val Lys Gln Arg Pro Ile Gln Gly Leu Glu Trp Ile
            35                  40                  45
Gly Asn Ile Asp Pro Ser Asp Ser Asp Thr His Tyr Asn Gln Lys Phe
        50                  55                  60
Lys Asp Lys Ala Ser Leu Thr Val Asp Lys Ser Ser Ser Thr Ala Tyr
65                  70                  75                  80
Met Gln Leu Ser Ser Leu Thr Phe Glu Asp Ser Ala Val Tyr Tyr Cys
                85                  90                  95
Val Arg Gly Gly Thr Gly Thr Met Ala Trp Phe Ala Tyr Trp Gly Gln

```
              100                 105                 110
Gly Thr Leu Val Thr Val Ser Ala Ala Lys Thr Thr Pro Pro Ser Val
             115                 120                 125

Tyr Pro Leu Ala Pro Gly Cys Gly Asp Thr Thr Gly Ser Ser Val Thr
             130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
             165                 170                 175

Leu Gln Ser Gly Leu Tyr Thr Met Ser Ser Ser Val Thr Val Pro Ser
             180                 185                 190

Ser Thr Trp Pro Ser Gln Thr Val Thr Cys Ser Val Ala His Pro Ala
             195                 200                 205

Ser Ser Thr Thr Val Asp Lys Lys Leu Glu Pro Ser Gly Pro Ile Ser
             210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
             245                 250                 255

Lys Asp Val Leu Met Ile Ser Leu Thr Pro Lys Val Thr Cys Val Val
             260                 265                 270

Val Asp Val Ser Glu Asp Asp Pro Asp Val Gln Ile Ser Trp Phe Val
             275                 280                 285

Asn Asn Val Glu Val His Thr Ala Gln Thr Gln Thr His Arg Glu Asp
             290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
             325                 330                 335

Leu Pro Ser Pro Ile Glu Arg Thr Ile Ser Lys Ile Lys Gly Leu Val
             340                 345                 350

Arg Ala Pro Gln Val Tyr Ile Leu Pro Pro Pro Ala Glu Gln Leu Ser
             355                 360                 365

Arg Lys Asp Val Ser Leu Thr Cys Leu Val Val Gly Phe Asn Pro Gly
             370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
             405                 410                 415

Ser Lys Leu Asn Met Lys Thr Ser Lys Trp Glu Lys Thr Asp Ser Phe
             420                 425                 430

Ser Cys Asn Val Arg His Glu Gly Leu Lys Asn Tyr Tyr Leu Lys Lys
             435                 440                 445

Thr Ile Ser Arg Ser Pro Gly Lys Gly Gly Gly Ser Gly Gly Gly
             450                 455                 460

Gly Ser Gly Gly Gly Ser Arg Glu Gly Pro Glu Leu Ser Pro Asp
465                 470                 475                 480

Asp Pro Ala Gly Leu Leu Asp Leu Arg Gln Gly Met Phe Ala Gln Leu
             485                 490                 495

Val Ala Gln Asn Val Leu Leu Ile Asp Gly Pro Leu Ser Trp Tyr Ser
             500                 505                 510

Asp Pro Gly Leu Ala Gly Val Ser Leu Thr Gly Gly Leu Ser Tyr Lys
             515                 520                 525
```

Glu Asp Thr Lys Glu Leu Val Ala Lys Ala Gly Val Tyr Tyr Val
            530                 535                 540

Phe Phe Gln Leu Glu Leu Arg Arg Val Val Ala Gly Glu Gly Ser Gly
545                 550                 555                 560

Ser Val Ser Leu Ala Leu His Leu Gln Pro Leu Arg Ser Ala Ala Gly
                565                 570                 575

Ala Ala Ala Leu Ala Leu Thr Val Asp Leu Pro Pro Ala Ser Ser Glu
                580                 585                 590

Ala Arg Asn Ser Ala Phe Gly Phe Gln Gly Arg Leu Leu His Leu Ser
                595                 600                 605

Ala Gly Gln Arg Leu Gly Val His Leu His Thr Glu Ala Arg Ala Arg
            610                 615                 620

His Ala Trp Gln Leu Thr Gln Gly Ala Thr Val Leu Gly Leu Phe Arg
625                 630                 635                 640

Val Thr Pro Glu Ile Pro Ala Gly Leu Pro Ser Pro Arg Ser Glu
                645                 650                 655

<210> SEQ ID NO 99
<211> LENGTH: 709
<212> TYPE: PRT
<213> ORGANISM: Artificial Sequence
<220> FEATURE:
<223> OTHER INFORMATION: Heavy chain of the modified antibody

<400> SEQUENCE: 99

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Val His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240

```
Pro Asn Leu Glu Gly Gly Pro Ser Val Phe Ile Phe Pro Asn Ile
            245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
            290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Ala Glu Gln Leu Ser
            355                 360                 365

Arg Lys Asp Val Ser Leu Thr Cys Leu Val Val Gly Phe Asn Pro Gly
            370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
            405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
            435                 440                 445

Thr Ile Ser Arg Ser Pro Gly Lys Gly Gly Gly Ser Gly Gly Gly
450                 455                 460

Gly Ser Gly Gly Gly Ser Asp Thr Gln Glu Lys Glu Val Arg Ala
465                 470                 475                 480

Met Val Gly Ser Asp Val Glu Leu Ser Cys Ala Cys Pro Glu Gly Ser
            485                 490                 495

Arg Phe Asp Leu Asn Asp Val Tyr Val Tyr Trp Gln Thr Ser Glu Ser
            500                 505                 510

Lys Thr Val Val Thr Tyr His Ile Pro Gln Asn Ser Ser Leu Glu Asn
            515                 520                 525

Val Asp Ser Arg Tyr Arg Asn Arg Ala Leu Met Ser Pro Ala Gly Met
530                 535                 540

Leu Arg Gly Asp Phe Ser Leu Arg Leu Phe Asn Val Thr Pro Gln Asp
545                 550                 555                 560

Glu Gln Lys Phe His Cys Leu Val Leu Ser Gln Ser Leu Gly Phe Gln
            565                 570                 575

Glu Val Leu Ser Val Glu Val Thr Leu His Val Ala Ala Asn Phe Ser
            580                 585                 590

Val Pro Val Val Ser Ala Pro His Ser Pro Ser Gln Asp Glu Leu Thr
            595                 600                 605

Phe Thr Cys Thr Ser Ile Asn Gly Tyr Pro Arg Pro Asn Val Tyr Trp
610                 615                 620

Ile Asn Lys Thr Asp Asn Ser Leu Leu Asp Gln Ala Leu Gln Asn Asp
625                 630                 635                 640

Thr Val Phe Leu Asn Met Arg Gly Leu Tyr Asp Val Val Ser Val Leu
            645                 650                 655
```

```
Arg Ile Ala Arg Thr Pro Ser Val Asn Ile Gly Cys Cys Ile Glu Asn
                660                 665                 670

Val Leu Leu Gln Gln Asn Leu Thr Val Gly Ser Gln Thr Gly Asn Asp
            675                 680                 685

Ile Gly Glu Arg Asp Lys Ile Thr Glu Asn Pro Val Ser Thr Gly Glu
        690                 695                 700

Lys Asn Ala Ala Thr
705

<210> SEQ ID NO 100
<211> LENGTH: 693
<212> TYPE: PRT
<213> ORGANISM: Artificial Sequence
<220> FEATURE:
<223> OTHER INFORMATION: Heavy chain of the modified antibody

<400> SEQUENCE: 100

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
                245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
        275                 280                 285

Asn Asn Val Glu Val His Thr Ala Gln Thr Gln Thr His Arg Glu Asp
    290                 295                 300
```

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Pro Ala Glu Gln Leu Ser
            355                 360                 365

Arg Lys Asp Val Ser Leu Thr Cys Leu Val Val Gly Phe Asn Pro Gly
            370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
            405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
            435                 440                 445

Thr Ile Ser Arg Ser Pro Gly Lys Gly Gly Gly Ser Gly Gly Gly
450                 455                 460

Gly Ser Gly Gly Gly Ser Ala Pro Leu Lys Ile Gln Ala Tyr Phe
465                 470                 475                 480

Asn Glu Thr Ala Asp Leu Pro Cys Gln Phe Ala Asn Ser Gln Asn Gln
            485                 490                 495

Ser Leu Ser Glu Leu Val Val Phe Trp Gln Asp Gln Glu Asn Leu Val
            500                 505                 510

Leu Asn Glu Val Tyr Leu Gly Lys Glu Lys Phe Asp Ser Val His Ser
            515                 520                 525

Lys Tyr Met Gly Arg Thr Ser Phe Asp Ser Asp Ser Trp Thr Leu Arg
            530                 535                 540

Leu His Asn Leu Gln Ile Lys Asp Lys Gly Leu Tyr Gln Cys Ile Ile
545                 550                 555                 560

His His Lys Lys Pro Thr Gly Met Ile Arg Ile His Gln Met Asn Ser
            565                 570                 575

Glu Leu Ser Val Leu Ala Asn Phe Ser Gln Pro Glu Ile Val Pro Ile
            580                 585                 590

Ser Asn Ile Thr Glu Asn Val Tyr Ile Asn Leu Thr Cys Ser Ser Ile
            595                 600                 605

His Gly Tyr Pro Glu Pro Lys Lys Met Ser Val Leu Leu Arg Thr Lys
610                 615                 620

Asn Ser Thr Ile Glu Tyr Asp Gly Val Met Gln Lys Ser Gln Asp Asn
625                 630                 635                 640

Val Thr Glu Leu Tyr Asp Val Ser Ile Ser Leu Ser Val Ser Phe Pro
            645                 650                 655

Asp Val Thr Ser Asn Met Thr Ile Phe Cys Ile Leu Glu Thr Asp Lys
            660                 665                 670

Thr Arg Leu Leu Ser Ser Pro Phe Ser Ile Glu Leu Glu Asp Pro Gln
            675                 680                 685

Pro Pro Pro Asp His
            690

<210> SEQ ID NO 101
<211> LENGTH: 609
<212> TYPE: PRT

<213> ORGANISM: Artificial Sequence
<220> FEATURE:
<223> OTHER INFORMATION: Heavy chain of the modified antibody

<400> SEQUENCE: 101

```
Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
                435                 440                 445

Gly Gly Gly Ser Gly Gly Gly Ser Gly Gly Gly Ser Pro Gly
450                 455                 460

Trp Phe Leu Asp Ser Pro Asp Arg Pro Trp Asn Pro Pro Thr Phe Ser
465                 470                 475                 480

Pro Ala Leu Leu Val Val Thr Glu Gly Asp Asn Ala Thr Phe Thr Cys
                485                 490                 495

Ser Phe Ser Asn Thr Ser Glu Ser Phe Val Leu Asn Trp Tyr Arg Met
                500                 505                 510

Ser Pro Ser Asn Gln Thr Asp Lys Leu Ala Ala Phe Pro Glu Asp Arg
                515                 520                 525

Ser Gln Pro Gly Gln Asp Cys Arg Phe Arg Val Thr Gln Leu Pro Asn
                530                 535                 540

Gly Arg Asp Phe His Met Ser Val Val Arg Ala Arg Arg Asn Asp Ser
545                 550                 555                 560

Gly Thr Tyr Leu Cys Gly Ala Ile Ser Leu Ala Pro Lys Ala Gln Ile
                565                 570                 575

Lys Glu Ser Leu Arg Ala Glu Leu Arg Val Thr Glu Arg Arg Ala Glu
                580                 585                 590

Val Pro Thr Ala His Pro Ser Pro Ser Pro Arg Pro Ala Gly Gln Phe
                595                 600                 605

Gln

<210> SEQ ID NO 102
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 102

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Val His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ala Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Phe Thr
    450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
            485                 490                 495

Leu Ile Val Tyr Trp Glu Met Glu Asp Lys Asn Ile Ile Gln Phe Val
            500                 505                 510

His Gly Glu Glu Asp Leu Lys Val Gln His Ser Ser Tyr Arg Gln Arg
            515                 520                 525

Ala Arg Leu Leu Lys Asp Gln Leu Ser Leu Gly Asn Ala Ala Leu Gln
    530                 535                 540

Ile Thr Asp Val Lys Leu Gln Asp Ala Gly Val Tyr Arg Cys Met Ile
545                 550                 555                 560
```

```
Ser Tyr Gly Gly Ala Asp Tyr Lys Arg Ile Thr Val Lys Val Asn Ala
            565                 570                 575

Pro Tyr Asn Lys Ile Asn Gln Arg Ile Leu Val Val Asp Pro Val Thr
            580                 585                 590

Ser Glu His Glu Leu Thr Cys Gln Ala Glu Gly Tyr Pro Lys Ala Glu
            595                 600                 605

Val Ile Trp Thr Ser Ser Asp His Gln Val Leu Ser Gly Lys Thr Thr
    610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
            660                 665                 670

Leu Pro Leu Ala His Pro Pro Asn Glu Arg
            675                 680

<210> SEQ ID NO 103
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 103

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

```
Phe Leu Phe Pro Pro Lys Pro Lys Asp Thr Leu Met Ile Ser Arg Thr
                245                 250                 255
Pro Glu Val Thr Cys Val Val Asp Val Ser Gln Glu Asp Pro Glu
        260                 265                 270
Val Gln Phe Asn Trp Tyr Val Asp Gly Val Glu Val His Asn Ala Lys
    275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Gly Gly Ser Gly Gly Gly Ser Gly Gly Gly Ser Val Ile
    450                 455                 460
His Val Thr Lys Glu Val Lys Glu Val Ala Thr Leu Ser Cys Gly His
465                 470                 475                 480
Asn Val Ser Val Glu Glu Leu Ala Gln Thr Arg Ile Tyr Trp Gln Lys
                485                 490                 495
Glu Lys Lys Met Val Leu Thr Met Met Ser Gly Asp Met Asn Ile Trp
            500                 505                 510
Pro Glu Tyr Lys Asn Arg Thr Ile Phe Asp Ile Thr Asn Asn Leu Ser
        515                 520                 525
Ile Val Ile Leu Ala Leu Arg Pro Ser Asp Glu Gly Thr Tyr Glu Cys
    530                 535                 540
Val Val Leu Lys Tyr Glu Lys Asp Ala Phe Lys Arg Glu His Leu Ala
545                 550                 555                 560
Glu Val Thr Leu Ser Val Lys Ala Asp Phe Pro Thr Pro Ser Ile Ser
                565                 570                 575
Asp Phe Glu Ile Pro Thr Ser Asn Ile Arg Arg Ile Ile Cys Ser Thr
            580                 585                 590
Ser Gly Gly Phe Pro Glu Pro His Leu Ser Trp Leu Glu Asn Gly Glu
        595                 600                 605
Glu Leu Asn Ala Ile Asn Thr Thr Val Ser Gln Asp Pro Glu Thr Glu
    610                 615                 620
Leu Tyr Ala Val Ser Ser Lys Leu Asp Phe Asn Met Thr Thr Asn His
625                 630                 635                 640
Ser Phe Met Cys Leu Ile Lys Tyr Gly His Leu Arg Val Asn Gln Thr
                645                 650                 655
Phe Asn Trp Asn Thr Thr Lys Gln Glu His Phe Pro Asp Asn
```

<210> SEQ ID NO 104
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 104

```
Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
```

```
                        355                 360                 365
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Gln Val
    450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                485                 490                 495

Ile Met Lys Val Gln Asn Asn Ser Val Ile Ile Asn Cys Asp Gly Phe
            500                 505                 510

Tyr Leu Ile Ser Leu Lys Gly Tyr Phe Ser Gln Glu Val Asn Ile Ser
        515                 520                 525

Leu His Tyr Gln Lys Asp Glu Glu Pro Leu Phe Gln Leu Lys Lys Val
    530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
            580                 585                 590

Cys Val Leu
        595

<210> SEQ ID NO 105
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 105

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
```

```
            115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Gly Gly Ser Gly Gly Gly Ser Gly Gly Gly Ser Arg Glu
    450                 455                 460
Gly Pro Glu Leu Ser Pro Asp Asp Pro Ala Gly Leu Leu Asp Leu Arg
465                 470                 475                 480
Gln Gly Met Phe Ala Gln Leu Val Ala Gln Asn Val Leu Leu Ile Asp
                485                 490                 495
Gly Pro Leu Ser Trp Tyr Ser Asp Pro Gly Leu Ala Gly Val Ser Leu
            500                 505                 510
Thr Gly Gly Leu Ser Tyr Lys Glu Asp Thr Lys Glu Leu Val Val Ala
        515                 520                 525
Lys Ala Gly Val Tyr Tyr Val Phe Phe Gln Leu Glu Leu Arg Arg Val
    530                 535                 540
```

```
Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
            580                 585                 590

Gly Arg Leu Leu His Leu Ser Ala Gly Gln Arg Leu Gly Val His Leu
        595                 600                 605

His Thr Glu Ala Arg Ala Arg His Ala Trp Gln Leu Thr Gln Gly Ala
610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 106
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 106

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser Gln Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Asp Thr
450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
            485                 490                 495

Tyr Trp Gln Thr Ser Glu Ser Lys Thr Val Thr Tyr His Ile Pro
        500                 505                 510

Gln Asn Ser Ser Leu Glu Asn Val Asp Ser Arg Tyr Arg Asn Arg Ala
        515                 520                 525

Leu Met Ser Pro Ala Gly Met Leu Arg Gly Asp Phe Ser Leu Arg Leu
530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
            565                 570                 575

His Val Ala Ala Asn Phe Ser Val Pro Val Val Ser Ala Pro His Ser
            580                 585                 590

Pro Ser Gln Asp Glu Leu Thr Phe Thr Cys Thr Ser Ile Asn Gly Tyr
        595                 600                 605

Pro Arg Pro Asn Val Tyr Trp Ile Asn Lys Thr Asp Asn Ser Leu Leu
        610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
            645                 650                 655

Ile Gly Cys Cys Ile Glu Asn Val Leu Leu Gln Gln Asn Leu Thr Val
            660                 665                 670
```

```
Gly Ser Gln Thr Gly Asn Asp Ile Gly Glu Arg Asp Lys Ile Thr Glu
            675                 680                 685

Asn Pro Val Ser Thr Gly Glu Lys Asn Ala Ala Thr
            690                 695                 700

<210> SEQ ID NO 107
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 107

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Ala Pro
450                 455                 460

Leu Lys Ile Gln Ala Tyr Phe Asn Glu Thr Ala Asp Leu Pro Cys Gln
465                 470                 475                 480

Phe Ala Asn Ser Gln Asn Gln Ser Leu Ser Glu Leu Val Val Phe Trp
                485                 490                 495

Gln Asp Gln Glu Asn Leu Val Leu Asn Glu Val Tyr Leu Gly Lys Glu
            500                 505                 510

Lys Phe Asp Ser Val His Ser Lys Tyr Met Gly Arg Thr Ser Phe Asp
        515                 520                 525

Ser Asp Ser Trp Thr Leu Arg Leu His Asn Leu Gln Ile Lys Asp Lys
530                 535                 540

Gly Leu Tyr Gln Cys Ile Ile His His Lys Lys Pro Thr Gly Met Ile
545                 550                 555                 560

Arg Ile His Gln Met Asn Ser Glu Leu Ser Val Leu Ala Asn Phe Ser
                565                 570                 575

Gln Pro Glu Ile Val Pro Ile Ser Asn Ile Thr Glu Asn Val Tyr Ile
            580                 585                 590

Asn Leu Thr Cys Ser Ser Ile His Gly Tyr Pro Glu Pro Lys Lys Met
        595                 600                 605

Ser Val Leu Leu Arg Thr Lys Asn Ser Thr Ile Glu Tyr Asp Gly Val
610                 615                 620

Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
                645                 650                 655

Cys Ile Leu Glu Thr Asp Lys Thr Arg Leu Leu Ser Ser Pro Phe Ser
            660                 665                 670

Ile Glu Leu Glu Asp Pro Gln Pro Pro Pro Asp His
        675                 680

<210> SEQ ID NO 108
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 108

Glu Val Gln Leu Val Gln Ser Gly Ala Glu Val Lys Lys Pro Gly Glu
1               5                   10                  15
```

```
Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
            35                  40                  45

Gly Asn Ile Asp Pro Ser Asp Ser Asp Thr His Tyr Asn Gln Lys Phe
        50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
```

```
                435                 440                 445
Gly Gly Gly Ser Gly Gly Gly Ser Gly Gly Gly Ser Pro Gly
            450                 455                 460

Trp Phe Leu Asp Ser Pro Asp Arg Pro Trp Asn Pro Pro Thr Phe Ser
465                 470                 475                 480

Pro Ala Leu Leu Val Val Thr Glu Gly Asp Asn Ala Thr Phe Thr Cys
                        485                 490                 495

Ser Phe Ser Asn Thr Ser Glu Ser Phe Val Leu Asn Trp Tyr Arg Met
                500                 505                 510

Ser Pro Ser Asn Gln Thr Asp Lys Leu Ala Ala Phe Pro Glu Asp Arg
            515                 520                 525

Ser Gln Pro Gly Gln Asp Cys Arg Phe Arg Val Thr Gln Leu Pro Asn
            530                 535                 540

Gly Arg Asp Phe His Met Ser Val Val Arg Ala Arg Arg Asn Asp Ser
545                 550                 555                 560

Gly Thr Tyr Leu Cys Gly Ala Ile Ser Leu Ala Pro Lys Ala Gln Ile
                565                 570                 575

Lys Glu Ser Leu Arg Ala Glu Leu Arg Val Thr Glu Arg Arg Ala Glu
            580                 585                 590

Val Pro Thr Ala His Pro Ser Pro Ser Pro Arg Pro Ala Gly Gln Phe
            595                 600                 605

Gln

<210> SEQ ID NO 109
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 109

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
                20                  25                  30

Trp Val His Trp Val Arg Gln Met Pro Gly Lys Gly Leu Glu Trp Ile
            35                  40                  45

Gly Asn Ile Asp Pro Ser Asp Ser Asp Thr His Tyr Asn Gln Lys Phe
        50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

-continued

```
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Phe Thr
450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
            500                 505                 510

His Gly Glu Glu Asp Leu Lys Val Gln His Ser Ser Tyr Arg Gln Arg
        515                 520                 525

Ala Arg Leu Leu Lys Asp Gln Leu Ser Leu Gly Asn Ala Ala Leu Gln
    530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
            580                 585                 590

Ser Glu His Glu Leu Thr Cys Gln Ala Glu Gly Tyr Pro Lys Ala Glu
        595                 600                 605
```

```
Val Ile Trp Thr Ser Ser Asp His Gln Val Leu Ser Gly Lys Thr Thr
610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
            660                 665                 670

Leu Pro Leu Ala His Pro Pro Asn Glu Arg
            675                 680

<210> SEQ ID NO 110
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 110

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Val Ile
450                 455                 460

His Val Thr Lys Glu Val Lys Glu Val Ala Thr Leu Ser Cys Gly His
465                 470                 475                 480

Asn Val Ser Val Glu Glu Leu Ala Gln Thr Arg Ile Tyr Trp Gln Lys
                485                 490                 495

Glu Lys Lys Met Val Leu Thr Met Met Ser Gly Asp Met Asn Ile Trp
            500                 505                 510

Pro Glu Tyr Lys Asn Arg Thr Ile Phe Asp Ile Thr Asn Asn Leu Ser
        515                 520                 525

Ile Val Ile Leu Ala Leu Arg Pro Ser Asp Glu Gly Thr Tyr Glu Cys
530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
                565                 570                 575

Asp Phe Glu Ile Pro Thr Ser Asn Ile Arg Arg Ile Ile Cys Ser Thr
            580                 585                 590

Ser Gly Gly Phe Pro Glu Pro His Leu Ser Trp Leu Glu Asn Gly Glu
        595                 600                 605

Glu Leu Asn Ala Ile Asn Thr Thr Val Ser Gln Asp Pro Glu Thr Glu
610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
                645                 650                 655

Phe Asn Trp Asn Thr Thr Lys Gln Glu His Phe Pro Asp Asn
            660                 665                 670

<210> SEQ ID NO 111
<211> LENGTH: 595
<212> TYPE: PRT
<213> ORGANISM: Artificial Sequence
<220> FEATURE:
<223> OTHER INFORMATION: Heavy chain of the modified antibody
```

<400> SEQUENCE: 111

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
```

```
                    405                 410                 415
Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Gln Val
        450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                485                 490                 495

Ile Met Lys Val Gln Asn Asn Ser Val Ile Ile Asn Cys Asp Gly Phe
                500                 505                 510

Tyr Leu Ile Ser Leu Lys Gly Tyr Phe Ser Gln Glu Val Asn Ile Ser
            515                 520                 525

Leu His Tyr Gln Lys Asp Glu Glu Pro Leu Phe Gln Leu Lys Lys Val
        530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
            580                 585                 590

Cys Val Leu
        595

<210> SEQ ID NO 112
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 112

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
                180                 185                 190

Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Arg Glu
            450                 455                 460

Gly Pro Glu Leu Ser Pro Asp Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
                500                 505                 510

Thr Gly Gly Leu Ser Tyr Lys Glu Asp Thr Lys Glu Leu Val Val Ala
                515                 520                 525

Lys Ala Gly Val Tyr Tyr Val Phe Phe Gln Leu Glu Leu Arg Arg Val
            530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
                580                 585                 590
```

```
Gly Arg Leu Leu His Leu Ser Ala Gly Gln Arg Leu Gly Val His Leu
        595                 600                 605

His Thr Glu Ala Arg Ala Arg His Ala Trp Gln Leu Thr Gln Gly Ala
    610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 113
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 113

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
                20                  25                  30

Trp Val His Trp Val Arg Gln Met Pro Gly Lys Gly Leu Glu Trp Ile
            35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
    435                 440                 445

Gly Gly Gly Ser Gly Gly Gly Ser Gly Gly Gly Ser Asp Thr
450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
            485                 490                 495

Tyr Trp Gln Thr Ser Glu Ser Lys Thr Val Val Thr Tyr His Ile Pro
        500                 505                 510

Gln Asn Ser Ser Leu Glu Asn Val Asp Ser Arg Tyr Arg Asn Arg Ala
    515                 520                 525

Leu Met Ser Pro Ala Gly Met Leu Arg Gly Asp Phe Ser Leu Arg Leu
530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
            565                 570                 575

His Val Ala Ala Asn Phe Ser Val Pro Val Val Ser Ala Pro His Ser
        580                 585                 590

Pro Ser Gln Asp Glu Leu Thr Phe Thr Cys Thr Ser Ile Asn Gly Tyr
    595                 600                 605

Pro Arg Pro Asn Val Tyr Trp Ile Asn Lys Thr Asp Asn Ser Leu Leu
610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
            645                 650                 655

Ile Gly Cys Cys Ile Glu Asn Val Leu Leu Gln Gln Asn Leu Thr Val
        660                 665                 670

Gly Ser Gln Thr Gly Asn Asp Ile Gly Glu Arg Asp Lys Ile Thr Glu
    675                 680                 685

Asn Pro Val Ser Thr Gly Glu Lys Asn Ala Ala Thr
690                 695                 700

<210> SEQ ID NO 114
<211> LENGTH: 684
```

```
<212> TYPE: PRT
<213> ORGANISM: Artificial Sequence
<220> FEATURE:
<223> OTHER INFORMATION: Heavy chain of the modified antibody

<400> SEQUENCE: 114

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Ala Pro
    450                 455                 460

Leu Lys Ile Gln Ala Tyr Phe Asn Glu Thr Ala Asp Leu Pro Cys Gln
465                 470                 475                 480

Phe Ala Asn Ser Gln Asn Gln Ser Leu Ser Glu Leu Val Val Phe Trp
                485                 490                 495

Gln Asp Gln Glu Asn Leu Val Leu Asn Glu Val Tyr Leu Gly Lys Glu
            500                 505                 510

Lys Phe Asp Ser Val His Ser Lys Tyr Met Gly Arg Thr Ser Phe Asp
        515                 520                 525

Ser Asp Ser Trp Thr Leu Arg Leu His Asn Leu Gln Ile Lys Asp Lys
    530                 535                 540

Gly Leu Tyr Gln Cys Ile Ile His His Lys Lys Pro Thr Gly Met Ile
545                 550                 555                 560

Arg Ile His Gln Met Asn Ser Glu Leu Ser Val Leu Ala Asn Phe Ser
                565                 570                 575

Gln Pro Glu Ile Val Pro Ile Ser Asn Ile Thr Glu Asn Val Tyr Ile
            580                 585                 590

Asn Leu Thr Cys Ser Ser Ile His Gly Tyr Pro Glu Pro Lys Lys Met
        595                 600                 605

Ser Val Leu Leu Arg Thr Lys Asn Ser Thr Ile Glu Tyr Asp Gly Val
    610                 615                 620

Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
                645                 650                 655

Cys Ile Leu Glu Thr Asp Lys Thr Arg Leu Leu Ser Ser Pro Phe Ser
            660                 665                 670

Ile Glu Leu Glu Asp Pro Gln Pro Pro Asp His
        675                 680

<210> SEQ ID NO 115
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 115

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Asn Gln Lys Phe
        50                  55                  60
```

```
Lys Asp His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Pro Gly
        450                 455                 460

Trp Phe Leu Asp Ser Pro Asp Arg Pro Trp Asn Pro Pro Thr Phe Ser
465                 470                 475                 480

Pro Ala Leu Leu Val Val Thr Glu Gly Asp Asn Ala Thr Phe Thr Cys
```

485                 490                 495

Ser Phe Ser Asn Thr Ser Glu Ser Phe Val Leu Asn Trp Tyr Arg Met
                        500                 505                 510

Ser Pro Ser Asn Gln Thr Asp Lys Leu Ala Ala Phe Pro Glu Asp Arg
                        515                 520                 525

Ser Gln Pro Gly Gln Asp Cys Arg Phe Arg Val Thr Gln Leu Pro Asn
                        530                 535                 540

Gly Arg Asp Phe His Met Ser Val Val Arg Ala Arg Asn Asp Ser
        545                 550                 555                 560

Gly Thr Tyr Leu Cys Gly Ala Ile Ser Leu Ala Pro Lys Ala Gln Ile
                        565                 570                 575

Lys Glu Ser Leu Arg Ala Glu Leu Arg Val Thr Glu Arg Arg Ala Glu
                        580                 585                 590

Val Pro Thr Ala His Pro Ser Pro Ser Pro Arg Pro Ala Gly Gln Phe
                        595                 600                 605

Gln

<210> SEQ ID NO 116
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 116

Glu Val Gln Leu Val Gln Ser Gly Ala Glu Val Lys Lys Pro Gly Glu
        1               5                   10                  15

Ser Leu Arg Ile Ser Cys Lys Ala Ser Gly Tyr Ser Phe Thr Ser Tyr
                        20                  25                  30

Trp Val His Trp Val Arg Gln Met Pro Gly Lys Gly Leu Glu Trp Met
                        35                  40                  45

Gly Asn Ile Asp Pro Ser Asp Ser Asp Thr His Tyr Asn Gln Lys Phe
                        50                  55                  60

Lys Asp His Val Thr Leu Ser Val Asp Lys Ser Ile Ser Thr Ala Tyr
        65                  70                  75                  80

Leu Gln Leu Ser Ser Leu Lys Ala Ser Asp Thr Ala Met Tyr Tyr Cys
                        85                  90                  95

Val Arg Gly Gly Thr Gly Thr Met Ala Trp Phe Ala Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Cys Ser Arg Ser Thr Ser Glu Ser Thr Ala Ala
                        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Lys Thr Tyr Thr Cys Asn Val Asp His Lys
                        195                 200                 205

Pro Ser Asn Thr Lys Val Asp Lys Arg Val Glu Ser Lys Tyr Gly Pro
                        210                 215                 220

Pro Cys Pro Pro Cys Pro Ala Pro Glu Phe Leu Gly Gly Pro Ser Val
        225                 230                 235                 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Phe Thr
    450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
            500                 505                 510

His Gly Glu Glu Asp Leu Lys Val Gln His Ser Ser Tyr Arg Gln Arg
        515                 520                 525

Ala Arg Leu Leu Lys Asp Gln Leu Ser Leu Gly Asn Ala Ala Leu Gln
    530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
            580                 585                 590

Ser Glu His Glu Leu Thr Cys Gln Ala Glu Gly Tyr Pro Lys Ala Glu
        595                 600                 605

Val Ile Trp Thr Ser Ser Asp His Gln Val Leu Ser Gly Lys Thr Thr
    610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655
```

Arg Leu Asp Pro Glu Asn His Thr Ala Glu Leu Val Ile Pro Glu
            660                 665                 670

Leu Pro Leu Ala His Pro Pro Asn Glu Arg
        675                 680

<210> SEQ ID NO 117
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 117

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

```
Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Gly Ser Val Ile
450                 455                 460

His Val Thr Lys Glu Val Lys Glu Val Ala Thr Leu Ser Cys Gly His
465                 470                 475                 480

Asn Val Ser Val Glu Glu Leu Ala Gln Thr Arg Ile Tyr Trp Gln Lys
                485                 490                 495

Glu Lys Lys Met Val Leu Thr Met Met Ser Gly Asp Met Asn Ile Trp
            500                 505                 510

Pro Glu Tyr Lys Asn Arg Thr Ile Phe Asp Ile Thr Asn Asn Leu Ser
        515                 520                 525

Ile Val Ile Leu Ala Leu Arg Pro Ser Asp Glu Gly Thr Tyr Glu Cys
530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
                565                 570                 575

Asp Phe Glu Ile Pro Thr Ser Asn Ile Arg Arg Ile Ile Cys Ser Thr
            580                 585                 590

Ser Gly Gly Phe Pro Glu Pro His Leu Ser Trp Leu Glu Asn Gly Glu
        595                 600                 605

Glu Leu Asn Ala Ile Asn Thr Thr Val Ser Gln Asp Pro Glu Thr Glu
610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
                645                 650                 655

Phe Asn Trp Asn Thr Thr Lys Gln Glu His Phe Pro Asp Asn
            660                 665                 670

<210> SEQ ID NO 118
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 118

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30
```

Trp Val His Trp Val Arg Gln Met Pro Gly Lys Gly Leu Glu Trp Met
            35                  40                  45

Gly Asn Ile Asp Pro Ser Asp Ser Asp Thr His Tyr Asn Gln Lys Phe
 50                  55                  60

Lys Asp His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Gln Val

```
                    450                 455                 460
Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                    485                 490                 495

Ile Met Lys Val Gln Asn Asn Ser Val Ile Ile Asn Cys Asp Gly Phe
                500                 505                 510

Tyr Leu Ile Ser Leu Lys Gly Tyr Phe Ser Gln Glu Val Asn Ile Ser
                515                 520                 525

Leu His Tyr Gln Lys Asp Glu Glu Pro Leu Phe Gln Leu Lys Lys Val
            530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
            580                 585                 590

Cys Val Leu
        595

<210> SEQ ID NO 119
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 119

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Asn Gln Lys Phe
        50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
```

-continued

```
              210                 215                 220
Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                    260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
                435                 440                 445

Gly Gly Gly Ser Gly Gly Gly Gly Ser Gly Gly Gly Gly Ser Arg Glu
            450                 455                 460

Gly Pro Glu Leu Ser Pro Asp Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
                500                 505                 510

Thr Gly Gly Leu Ser Tyr Lys Glu Asp Thr Lys Glu Leu Val Val Ala
            515                 520                 525

Lys Ala Gly Val Tyr Tyr Val Phe Phe Gln Leu Glu Leu Arg Arg Val
530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
                580                 585                 590

Gly Arg Leu Leu His Leu Ser Ala Gly Gln Arg Leu Gly Val His Leu
            595                 600                 605

His Thr Glu Ala Arg Ala Arg His Ala Trp Gln Leu Thr Gln Gly Ala
        610                 615                 620

Thr Val Leu Gly Leu Phe Arg Val Thr Pro Glu Ile Pro Ala Gly Leu
625                 630                 635                 640
```

```
Pro Ser Pro Arg Ser Glu
            645

<210> SEQ ID NO 120
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 120

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Gly Gly Gly Ser Gly Gly Gly Ser Gly Gly Gly Ser Asp Thr
                450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
                485                 490                 495

Tyr Trp Gln Thr Ser Glu Ser Lys Thr Val Thr Tyr His Ile Pro
                500                 505                 510

Gln Asn Ser Ser Leu Glu Asn Val Asp Ser Arg Tyr Arg Asn Arg Ala
                515                 520                 525

Leu Met Ser Pro Ala Gly Met Leu Arg Gly Asp Phe Ser Leu Arg Leu
                530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
                565                 570                 575

His Val Ala Ala Asn Phe Ser Val Pro Val Val Ser Ala Pro His Ser
                580                 585                 590

Pro Ser Gln Asp Glu Leu Thr Phe Thr Cys Thr Ser Ile Asn Gly Tyr
                595                 600                 605

Pro Arg Pro Asn Val Tyr Trp Ile Asn Lys Thr Asp Asn Ser Leu Leu
                610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
                645                 650                 655

Ile Gly Cys Cys Ile Glu Asn Val Leu Leu Gln Gln Asn Leu Thr Val
                660                 665                 670

Gly Ser Gln Thr Gly Asn Asp Ile Gly Glu Arg Asp Lys Ile Thr Glu
                675                 680                 685

Asn Pro Val Ser Thr Gly Glu Lys Asn Ala Ala Thr
690                 695                 700

<210> SEQ ID NO 121
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 121

Glu Val Gln Leu Val Gln Ser Gly Ala Glu Val Lys Lys Pro Gly Glu
1               5                   10                  15
```

```
Ser Leu Arg Ile Ser Cys Lys Ala Ser Gly Tyr Ser Phe Thr Ser Tyr
             20                  25                  30

Trp Val His Trp Val Arg Gln Met Pro Gly Lys Gly Leu Glu Trp Met
         35                  40                  45

Gly Asn Ile Asp Pro Ser Asp Ser Asp Thr His Tyr Asn Gln Lys Phe
 50                  55                  60

Lys Asp His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu Val
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430
```

```
His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Ala Pro
450                 455                 460

Leu Lys Ile Gln Ala Tyr Phe Asn Glu Thr Ala Asp Leu Pro Cys Gln
465                 470                 475                 480

Phe Ala Asn Ser Gln Asn Gln Ser Leu Ser Glu Leu Val Val Phe Trp
                485                 490                 495

Gln Asp Gln Glu Asn Leu Val Leu Asn Glu Val Tyr Leu Gly Lys Glu
            500                 505                 510

Lys Phe Asp Ser Val His Ser Lys Tyr Met Gly Arg Thr Ser Phe Asp
            515                 520                 525

Ser Asp Ser Trp Thr Leu Arg Leu His Asn Leu Gln Ile Lys Asp Lys
530                 535                 540

Gly Leu Tyr Gln Cys Ile Ile His His Lys Lys Pro Thr Gly Met Ile
545                 550                 555                 560

Arg Ile His Gln Met Asn Ser Glu Leu Ser Val Leu Ala Asn Phe Ser
                565                 570                 575

Gln Pro Glu Ile Val Pro Ile Ser Asn Ile Thr Glu Asn Val Tyr Ile
            580                 585                 590

Asn Leu Thr Cys Ser Ser Ile His Gly Tyr Pro Glu Pro Lys Lys Met
            595                 600                 605

Ser Val Leu Leu Arg Thr Lys Asn Ser Thr Ile Glu Tyr Asp Gly Val
            610                 615                 620

Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
                645                 650                 655

Cys Ile Leu Glu Thr Asp Lys Thr Arg Leu Leu Ser Ser Pro Phe Ser
            660                 665                 670

Ile Glu Leu Glu Asp Pro Gln Pro Pro Asp His
            675                 680

<210> SEQ ID NO 122
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 122

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Ser Asp Ser Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110
```

-continued

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Pro Gly
450                 455                 460

Trp Phe Leu Asp Ser Pro Asp Arg Pro Trp Asn Pro Thr Phe Ser
465                 470                 475                 480

Pro Ala Leu Leu Val Val Thr Glu Gly Asp Asn Ala Thr Phe Thr Cys
                485                 490                 495

Ser Phe Ser Asn Thr Ser Glu Ser Phe Val Leu Asn Trp Tyr Arg Met
            500                 505                 510

Ser Pro Ser Asn Gln Thr Asp Lys Leu Ala Ala Phe Pro Glu Asp Arg
        515                 520                 525

Ser Gln Pro Gly Gln Asp Cys Arg Phe Arg Val Thr Gln Leu Pro Asn
```

Gly Arg Asp Phe His Met Ser Val Val Arg Ala Arg Asn Asp Ser
545                 550                 555                 560

Gly Thr Tyr Leu Cys Gly Ala Ile Ser Leu Ala Pro Lys Ala Gln Ile
            565                 570                 575

Lys Glu Ser Leu Arg Ala Glu Leu Arg Val Thr Glu Arg Arg Ala Glu
            580                 585                 590

Val Pro Thr Ala His Pro Ser Pro Ser Pro Arg Pro Ala Gly Gln Phe
            595                 600                 605

Gln

<210> SEQ ID NO 123
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 123

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Gly Gly Gly Ser Gly Gly Gly Ser Gly Gly Gly Ser Phe Thr
450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
                500                 505                 510

His Gly Glu Glu Asp Leu Lys Val Gln His Ser Ser Tyr Arg Gln Arg
                515                 520                 525

Ala Arg Leu Leu Lys Asp Gln Leu Ser Leu Gly Asn Ala Ala Leu Gln
                530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
                580                 585                 590

Ser Glu His Glu Leu Thr Cys Gln Ala Glu Gly Tyr Pro Lys Ala Glu
                595                 600                 605

Val Ile Trp Thr Ser Ser Asp His Gln Val Leu Ser Gly Lys Thr Thr
610                 615                 620

Thr Thr Asn Ser Lys Arg Glu Glu Lys Leu Phe Asn Val Thr Ser Thr
625                 630                 635                 640

Leu Arg Ile Asn Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
                660                 665                 670

Leu Pro Leu Ala His Pro Pro Asn Glu Arg
                675                 680

<210> SEQ ID NO 124
<211> LENGTH: 670

```
<212> TYPE: PRT
<213> ORGANISM: Artificial Sequence
<220> FEATURE:
<223> OTHER INFORMATION: Heavy chain of the modified antibody

<400> SEQUENCE: 124
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 |

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Val Ile
    450                 455                 460

His Val Thr Lys Glu Val Lys Glu Val Ala Thr Leu Ser Cys Gly His
465                 470                 475                 480

Asn Val Ser Val Glu Glu Leu Ala Gln Thr Arg Ile Tyr Trp Gln Lys
            485                 490                 495

Glu Lys Lys Met Val Leu Thr Met Met Ser Gly Asp Met Asn Ile Trp
        500                 505                 510

Pro Glu Tyr Lys Asn Arg Thr Ile Phe Asp Ile Thr Asn Asn Leu Ser
        515                 520                 525

Ile Val Ile Leu Ala Leu Arg Pro Ser Asp Glu Gly Thr Tyr Glu Cys
530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
            565                 570                 575

Asp Phe Glu Ile Pro Thr Ser Asn Ile Arg Arg Ile Ile Cys Ser Thr
        580                 585                 590

Ser Gly Gly Phe Pro Glu Pro His Leu Ser Trp Leu Glu Asn Gly Glu
        595                 600                 605

Glu Leu Asn Ala Ile Asn Thr Thr Val Ser Gln Asp Pro Glu Thr Glu
    610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
            645                 650                 655

Phe Asn Trp Asn Thr Thr Lys Gln Glu His Phe Pro Asp Asn
        660                 665                 670

<210> SEQ ID NO 125
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 125

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

```
Leu Gln Leu Ser Ser Leu Lys Ala Ser Asp Thr Ala Met Tyr Tyr Cys
                     85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gln Val
450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                485                 490                 495

Ile Met Lys Val Gln Asn Asn Ser Val Ile Ile Asn Cys Asp Gly Phe
```

```
              500                 505                 510
Tyr Leu Ile Ser Leu Lys Gly Tyr Phe Ser Gln Glu Val Asn Ile Ser
            515                 520                 525

Leu His Tyr Gln Lys Asp Glu Glu Pro Leu Phe Gln Leu Lys Lys Val
        530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
            580                 585                 590

Cys Val Leu
        595

<210> SEQ ID NO 126
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 126

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
            260                 265                 270
Val Gln Phe Asn Trp Tyr Val Asp Gly Val Glu Val His Asn Ala Lys
        275                 280                 285

Thr Lys Pro Arg Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Arg Glu
        450                 455                 460

Gly Pro Glu Leu Ser Pro Asp Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
                500                 505                 510

Thr Gly Gly Leu Ser Tyr Lys Glu Asp Thr Lys Glu Leu Val Val Ala
            515                 520                 525

Lys Ala Gly Val Tyr Tyr Val Phe Phe Gln Leu Glu Leu Arg Arg Val
        530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
                580                 585                 590

Gly Arg Leu Leu His Leu Ser Ala Gly Gln Arg Leu Gly Val His Leu
            595                 600                 605

His Thr Glu Ala Arg Ala Arg His Ala Trp Gln Leu Thr Gln Gly Ala
        610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 127
<211> LENGTH: 700
<212> TYPE: PRT
<213> ORGANISM: Artificial Sequence
```

<220> FEATURE:
<223> OTHER INFORMATION: Heavy chain of the modified antibody

<400> SEQUENCE: 127

```
Glu Val Gln Leu Val Gln Ser Gly Ala Glu Val Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400
```

-continued

```
Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
    435                 440                 445

Gly Gly Gly Ser Gly Gly Gly Ser Gly Gly Gly Ser Asp Thr
450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
                485                 490                 495

Tyr Trp Gln Thr Ser Glu Ser Lys Thr Val Thr Tyr His Ile Pro
            500                 505                 510

Gln Asn Ser Ser Leu Glu Asn Val Asp Ser Arg Tyr Arg Asn Arg Ala
        515                 520                 525

Leu Met Ser Pro Ala Gly Met Leu Arg Gly Asp Phe Ser Leu Arg Leu
    530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
                565                 570                 575

His Val Ala Ala Asn Phe Ser Val Pro Val Val Ser Ala Pro His Ser
            580                 585                 590

Pro Ser Gln Asp Glu Leu Thr Phe Thr Cys Thr Ser Ile Asn Gly Tyr
        595                 600                 605

Pro Arg Pro Asn Val Tyr Trp Ile Asn Lys Thr Asp Asn Ser Leu Leu
    610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
                645                 650                 655

Ile Gly Cys Cys Ile Glu Asn Val Leu Leu Gln Gln Asn Leu Thr Val
            660                 665                 670

Gly Ser Gln Thr Gly Asn Asp Ile Gly Glu Arg Asp Lys Ile Thr Glu
        675                 680                 685

Asn Pro Val Ser Thr Gly Glu Lys Asn Ala Ala Thr
690                 695                 700

<210> SEQ ID NO 128
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 128

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60
```

```
Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Ser Ala Pro
            450                 455                 460

Leu Lys Ile Gln Ala Tyr Phe Asn Glu Thr Ala Asp Leu Pro Cys Gln
465                 470                 475                 480
```

```
Phe Ala Asn Ser Gln Asn Gln Ser Leu Ser Glu Leu Val Val Phe Trp
                485                 490                 495
Gln Asp Gln Glu Asn Leu Val Leu Asn Glu Val Tyr Leu Gly Lys Glu
            500                 505                 510
Lys Phe Asp Ser Val His Ser Lys Tyr Met Gly Arg Thr Ser Phe Asp
        515                 520                 525
Ser Asp Ser Trp Thr Leu Arg Leu His Asn Leu Gln Ile Lys Asp Lys
    530                 535                 540
Gly Leu Tyr Gln Cys Ile Ile His His Lys Pro Thr Gly Met Ile
545                 550                 555                 560
Arg Ile His Gln Met Asn Ser Glu Leu Ser Val Leu Ala Asn Phe Ser
                565                 570                 575
Gln Pro Glu Ile Val Pro Ile Ser Asn Ile Thr Glu Asn Val Tyr Ile
            580                 585                 590
Asn Leu Thr Cys Ser Ser Ile His Gly Tyr Pro Glu Pro Lys Lys Met
        595                 600                 605
Ser Val Leu Leu Arg Thr Lys Asn Ser Thr Ile Glu Tyr Asp Gly Val
    610                 615                 620
Met Gln Lys Ser Gln Asp Asn Val Thr Glu Leu Tyr Asp Val Ser Ile
625                 630                 635                 640
Ser Leu Ser Val Ser Phe Pro Asp Val Thr Ser Asn Met Thr Ile Phe
                645                 650                 655
Cys Ile Leu Glu Thr Asp Lys Thr Arg Leu Leu Ser Ser Pro Phe Ser
            660                 665                 670
Ile Glu Leu Glu Asp Pro Gln Pro Pro Asp His
        675                 680

<210> SEQ ID NO 129
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 129

Glu Val Gln Leu Val Gln Ser Gly Ala Glu Val Lys Lys Pro Gly Glu
1               5                   10                  15
Ser Leu Arg Ile Ser Cys Lys Ala Ser Gly Tyr Ser Phe Thr Ser Tyr
            20                  25                  30
Trp Val His Trp Val Arg Gln Met Pro Gly Lys Gly Leu Glu Trp Met
        35                  40                  45
Gly Asn Ile Asp Pro Ser Ser Asp Thr His Tyr Ser Pro Ser Phe
    50                  55                  60
Gln Gly His Val Thr Leu Ser Val Asp Lys Ser Ile Ser Thr Ala Tyr
65                  70                  75                  80
Leu Gln Leu Ser Ser Leu Lys Ala Ser Asp Thr Ala Met Tyr Tyr Cys
                85                  90                  95
Val Arg Gly Gly Thr Gly Thr Leu Ala Trp Phe Ala Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Gly Gly Ser Gly Gly Gly Gly Ser Gly Gly Gly Gly Ser Pro Gly
    450                 455                 460
Trp Phe Leu Asp Ser Pro Asp Arg Pro Trp Asn Pro Pro Thr Phe Ser
465                 470                 475                 480
Pro Ala Leu Leu Val Val Thr Glu Gly Asp Asn Ala Thr Phe Thr Cys
                485                 490                 495
Ser Phe Ser Asn Thr Ser Glu Ser Phe Val Leu Asn Trp Tyr Arg Met
            500                 505                 510
Ser Pro Ser Asn Gln Thr Asp Lys Leu Ala Ala Phe Pro Glu Asp Arg
        515                 520                 525
Ser Gln Pro Gly Gln Asp Cys Arg Phe Arg Val Thr Gln Leu Pro Asn
    530                 535                 540
Gly Arg Asp Phe His Met Ser Val Val Arg Ala Arg Arg Asn Asp Ser
545                 550                 555                 560
Gly Thr Tyr Leu Cys Gly Ala Ile Ser Leu Ala Pro Lys Ala Gln Ile
                565                 570                 575
Lys Glu Ser Leu Arg Ala Glu Leu Arg Val Thr Glu Arg Arg Ala Glu
```

```
                580             585                 590
Val Pro Thr Ala His Pro Ser Pro Ser Pro Arg Pro Ala Gly Gln Phe
        595                 600                 605
Gln

<210> SEQ ID NO 130
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 130

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Phe Thr
    450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
            500                 505                 510

His Gly Glu Glu Asp Leu Lys Val Gln His Ser Ser Tyr Arg Gln Arg
        515                 520                 525

Ala Arg Leu Leu Lys Asp Gln Leu Ser Leu Gly Asn Ala Ala Leu Gln
    530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
            580                 585                 590

Ser Glu His Glu Leu Thr Cys Gln Ala Glu Gly Tyr Pro Lys Ala Glu
        595                 600                 605

Val Ile Trp Thr Ser Ser Asp His Gln Val Leu Ser Gly Lys Thr Thr
    610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
            660                 665                 670

Leu Pro Leu Ala His Pro Pro Asn Glu Arg
        675                 680

<210> SEQ ID NO 131
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 131

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Val Ile
    450                 455                 460

His Val Thr Lys Glu Val Lys Glu Val Ala Thr Leu Ser Cys Gly His
465                 470                 475                 480

Asn Val Ser Val Glu Glu Leu Ala Gln Thr Arg Ile Tyr Trp Gln Lys
                485                 490                 495

Glu Lys Lys Met Val Leu Thr Met Met Ser Gly Asp Met Asn Ile Trp
            500                 505                 510

Pro Glu Tyr Lys Asn Arg Thr Ile Phe Asp Ile Thr Asn Asn Leu Ser
            515                 520                 525

Ile Val Ile Leu Ala Leu Arg Pro Ser Asp Glu Gly Thr Tyr Glu Cys
            530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
                565                 570                 575

Asp Phe Glu Ile Pro Thr Ser Asn Ile Arg Arg Ile Ile Cys Ser Thr
            580                 585                 590

Ser Gly Gly Phe Pro Glu Pro His Leu Ser Trp Leu Glu Asn Gly Glu
            595                 600                 605

Glu Leu Asn Ala Ile Asn Thr Thr Val Ser Gln Asp Pro Glu Thr Glu
            610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
                645                 650                 655

Phe Asn Trp Asn Thr Thr Lys Gln Glu His Phe Pro Asp Asn
            660                 665                 670

<210> SEQ ID NO 132
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 132

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Gln Val
    450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                485                 490                 495

Ile Met Lys Val Gln Asn Asn Ser Val Ile Ile Asn Cys Asp Gly Phe
            500                 505                 510

Tyr Leu Ile Ser Leu Lys Gly Tyr Phe Ser Gln Glu Val Asn Ile Ser
        515                 520                 525

Leu His Tyr Gln Lys Asp Glu Glu Pro Leu Phe Gln Leu Lys Lys Val
    530                 535                 540

Arg Ser Val Asn Ser Leu Met Val Ala Ser Leu Thr Tyr Lys Asp Lys
```

```
545                 550                 555                 560
Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
                580                 585                 590

Cys Val Leu
        595

<210> SEQ ID NO 133
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 133

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
                35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
```

```
                305                 310                 315                 320
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Gly Gly Gly Ser Gly Gly Gly Gly Ser Gly Gly Gly Gly Ser Arg Glu
                450                 455                 460

Gly Pro Glu Leu Ser Pro Asp Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
                500                 505                 510

Thr Gly Gly Leu Ser Tyr Lys Glu Asp Thr Lys Glu Leu Val Val Ala
                515                 520                 525

Lys Ala Gly Val Tyr Tyr Val Phe Phe Gln Leu Glu Leu Arg Arg Val
                530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
                580                 585                 590

Gly Arg Leu Leu His Leu Ser Ala Gly Gln Arg Leu Gly Val His Leu
                595                 600                 605

His Thr Glu Ala Arg Ala Arg His Ala Trp Gln Leu Thr Gln Gly Ala
                610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 134
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 134

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
```

```
                20                  25                  30
Trp Val His Trp Val Arg Gln Met Pro Gly Lys Gly Leu Glu Trp Met
             35                  40                  45
Gly Asn Ile Asp Pro Ser Asp Ser Asp Thr His Tyr Ser Pro Ser Phe
 50                  55                  60
Gln Gly His Val Thr Leu Ser Val Asp Lys Ser Ile Ser Thr Ala Tyr
 65                  70                  75                  80
Leu Gln Leu Ser Ser Leu Lys Ala Ser Asp Thr Ala Met Tyr Tyr Cys
             85                  90                  95
Val Arg Gly Gly Thr Gly Thr Leu Ala Trp Phe Ala Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
            210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
            405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
            435                 440                 445
```

Gly Gly Gly Ser Gly Gly Gly Ser Gly Gly Gly Ser Asp Thr
            450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
                    485                 490                 495

Tyr Trp Gln Thr Ser Glu Ser Lys Thr Val Thr Tyr His Ile Pro
                500                 505                 510

Gln Asn Ser Ser Leu Glu Asn Val Asp Ser Arg Tyr Arg Asn Arg Ala
            515                 520                 525

Leu Met Ser Pro Ala Gly Met Leu Arg Gly Asp Phe Ser Leu Arg Leu
530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
                565                 570                 575

His Val Ala Ala Asn Phe Ser Val Pro Val Val Ser Ala Pro His Ser
            580                 585                 590

Pro Ser Gln Asp Glu Leu Thr Phe Thr Cys Thr Ser Ile Asn Gly Tyr
            595                 600                 605

Pro Arg Pro Asn Val Tyr Trp Ile Asn Lys Thr Asp Asn Ser Leu Leu
            610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
                645                 650                 655

Ile Gly Cys Cys Ile Glu Asn Val Leu Leu Gln Gln Asn Leu Thr Val
            660                 665                 670

Gly Ser Gln Thr Gly Asn Asp Ile Gly Glu Arg Asp Lys Ile Thr Glu
            675                 680                 685

Asn Pro Val Ser Thr Gly Glu Lys Asn Ala Ala Thr
            690                 695                 700

<210> SEQ ID NO 135
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 135

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Ala Pro
    450                 455                 460

Leu Lys Ile Gln Ala Tyr Phe Asn Glu Thr Ala Asp Leu Pro Cys Gln
465                 470                 475                 480

Phe Ala Asn Ser Gln Asn Gln Ser Leu Ser Glu Leu Val Val Phe Trp
                485                 490                 495

Gln Asp Gln Glu Asn Leu Val Leu Asn Glu Val Tyr Leu Gly Lys Glu
            500                 505                 510

Lys Phe Asp Ser Val His Ser Lys Tyr Met Gly Arg Thr Ser Phe Asp
    515                 520                 525
```

Ser Asp Ser Trp Thr Leu Arg Leu His Asn Leu Gln Ile Lys Asp Lys
            530                 535                 540

Gly Leu Tyr Gln Cys Ile Ile His His Lys Lys Pro Thr Gly Met Ile
545                 550                 555                 560

Arg Ile His Gln Met Asn Ser Glu Leu Ser Val Leu Ala Asn Phe Ser
                    565                 570                 575

Gln Pro Glu Ile Val Pro Ile Ser Asn Ile Thr Glu Asn Val Tyr Ile
                580                 585                 590

Asn Leu Thr Cys Ser Ser Ile His Gly Tyr Pro Glu Pro Lys Lys Met
                595                 600                 605

Ser Val Leu Leu Arg Thr Lys Asn Ser Thr Ile Glu Tyr Asp Gly Val
610                 615                 620

Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
                    645                 650                 655

Cys Ile Leu Glu Thr Asp Lys Thr Arg Leu Leu Ser Ser Pro Phe Ser
                660                 665                 670

Ile Glu Leu Glu Asp Pro Gln Pro Pro Asp His
            675                 680

<210> SEQ ID NO 136
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 136

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Pro Gly
450                 455                 460

Trp Phe Leu Asp Ser Pro Asp Arg Pro Trp Asn Pro Pro Thr Phe Ser
465                 470                 475                 480

Pro Ala Leu Leu Val Val Thr Glu Gly Asp Asn Ala Thr Phe Thr Cys
                485                 490                 495

Ser Phe Ser Asn Thr Ser Glu Ser Phe Val Leu Asn Trp Tyr Arg Met
                500                 505                 510

Ser Pro Ser Asn Gln Thr Asp Lys Leu Ala Ala Phe Pro Glu Asp Arg
            515                 520                 525

Ser Gln Pro Gly Gln Asp Cys Arg Phe Arg Val Thr Gln Leu Pro Asn
530                 535                 540

Gly Arg Asp Phe His Met Ser Val Val Arg Ala Arg Arg Asn Asp Ser
545                 550                 555                 560

Gly Thr Tyr Leu Cys Gly Ala Ile Ser Leu Ala Pro Lys Ala Gln Ile
                565                 570                 575

Lys Glu Ser Leu Arg Ala Glu Leu Arg Val Thr Glu Arg Arg Ala Glu
                580                 585                 590

Val Pro Thr Ala His Pro Ser Pro Ser Pro Arg Pro Ala Gly Gln Phe
            595                 600                 605

Gln

<210> SEQ ID NO 137
```

```
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 137

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

-continued

```
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
    435                 440                 445

Gly Gly Gly Ser Gly Gly Gly Ser Gly Gly Gly Ser Phe Thr
450                 455                 460

Val Thr Val Pro Lys Asp Leu Tyr Val Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
            500                 505                 510

His Gly Glu Glu Asp Leu Lys Val Gln His Ser Ser Tyr Arg Gln Arg
        515                 520                 525

Ala Arg Leu Leu Lys Asp Gln Leu Ser Leu Gly Asn Ala Ala Leu Gln
    530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
            580                 585                 590

Ser Glu His Glu Leu Thr Cys Gln Ala Glu Gly Tyr Pro Lys Ala Glu
        595                 600                 605

Val Ile Trp Thr Ser Ser Asp His Gln Val Leu Ser Gly Lys Thr Thr
    610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
            660                 665                 670

Leu Pro Leu Ala His Pro Pro Asn Glu Arg
        675                 680

<210> SEQ ID NO 138
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 138

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60
```

```
Gln Gly His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Gly Gly Gly Ser Gly Gly Gly Gly Ser Gly Gly Gly Gly Ser Val Ile
            450                 455                 460

His Val Thr Lys Glu Val Lys Glu Val Ala Thr Leu Ser Cys Gly His
465                 470                 475                 480
```

Asn Val Ser Val Glu Glu Leu Ala Gln Thr Arg Ile Tyr Trp Gln Lys
                485                 490                 495

Glu Lys Lys Met Val Leu Thr Met Met Ser Gly Asp Met Asn Ile Trp
            500                 505                 510

Pro Glu Tyr Lys Asn Arg Thr Ile Phe Asp Ile Thr Asn Asn Leu Ser
        515                 520                 525

Ile Val Ile Leu Ala Leu Arg Pro Ser Asp Glu Gly Thr Tyr Glu Cys
530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
                565                 570                 575

Asp Phe Glu Ile Pro Thr Ser Asn Ile Arg Arg Ile Ile Cys Ser Thr
            580                 585                 590

Ser Gly Gly Phe Pro Glu Pro His Leu Ser Trp Leu Glu Asn Gly Glu
        595                 600                 605

Glu Leu Asn Ala Ile Asn Thr Thr Val Ser Gln Asp Pro Glu Thr Glu
    610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
                645                 650                 655

Phe Asn Trp Asn Thr Thr Lys Gln Glu His Phe Pro Asp Asn
            660                 665                 670

<210> SEQ ID NO 139
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 139

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

```
Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Gln Val
    450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
                485                 490                 495

Ile Met Lys Val Gln Asn Asn Ser Val Ile Ile Asn Cys Asp Gly Phe
            500                 505                 510

Tyr Leu Ile Ser Leu Lys Gly Tyr Phe Ser Gln Glu Val Asn Ile Ser
        515                 520                 525

Leu His Tyr Gln Lys Asp Glu Glu Pro Leu Phe Gln Leu Lys Lys Val
    530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
                565                 570                 575

Val Asn Gly Gly Glu Leu Ile Leu Ile His Gln Asn Pro Gly Glu Phe
            580                 585                 590

Cys Val Leu
```

<210> SEQ ID NO 140
<211> LENGTH: 646
<212> TYPE: PRT
<213> ORGANISM: Artificial Sequence
<220> FEATURE:
<223> OTHER INFORMATION: Heavy chain of the modified antibody

<400> SEQUENCE: 140

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
```

```
                   355                 360                 365
Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Arg Glu
    450                 455                 460

Gly Pro Glu Leu Ser Pro Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
            500                 505                 510

Thr Gly Gly Leu Ser Tyr Lys Glu Asp Thr Lys Glu Leu Val Val Ala
        515                 520                 525

Lys Ala Gly Val Tyr Tyr Val Phe Phe Gln Leu Glu Leu Arg Arg Val
        530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
            580                 585                 590

Gly Arg Leu Leu His Leu Ser Ala Gly Gln Arg Leu Gly Val His Leu
        595                 600                 605

His Thr Glu Ala Arg Ala Arg His Ala Trp Gln Leu Thr Gln Gly Ala
        610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 141
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 141

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
```

```
                65                  70                  75                  80
Leu Gln Leu Ser Ser Leu Lys Ala Ser Asp Thr Ala Met Tyr Tyr Cys
                    85                  90                  95

Val Arg Gly Gly Thr Gly Thr Met Ala Tyr Phe Ala Tyr Trp Gly Gln
                    100                 105                 110

Gly Thr Leu Val Thr Val Ser Ala Ser Thr Lys Gly Pro Ser Val
                115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                    195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                    245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                    275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                    325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Asp Thr
450                 455                 460

Gln Glu Lys Glu Val Arg Ala Met Val Gly Ser Asp Val Glu Leu Ser
465                 470                 475                 480

Cys Ala Cys Pro Glu Gly Ser Arg Phe Asp Leu Asn Asp Val Tyr Val
                    485                 490                 495
```

```
Tyr Trp Gln Thr Ser Glu Ser Lys Thr Val Thr Tyr His Ile Pro
            500                 505                 510

Gln Asn Ser Ser Leu Glu Asn Val Asp Ser Arg Tyr Arg Asn Arg Ala
            515                 520                 525

Leu Met Ser Pro Ala Gly Met Leu Arg Gly Asp Phe Ser Leu Arg Leu
            530                 535                 540

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
                565                 570                 575

His Val Ala Ala Asn Phe Ser Val Pro Val Val Ser Ala Pro His Ser
            580                 585                 590

Pro Ser Gln Asp Glu Leu Thr Phe Thr Cys Thr Ser Ile Asn Gly Tyr
            595                 600                 605

Pro Arg Pro Asn Val Tyr Trp Ile Asn Lys Thr Asp Asn Ser Leu Leu
            610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
                645                 650                 655

Ile Gly Cys Cys Ile Glu Asn Val Leu Leu Gln Gln Asn Leu Thr Val
            660                 665                 670

Gly Ser Gln Thr Gly Asn Asp Ile Gly Glu Arg Asp Lys Ile Thr Glu
            675                 680                 685

Asn Pro Val Ser Thr Gly Glu Lys Asn Ala Ala Thr
            690                 695                 700

<210> SEQ ID NO 142
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 142

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Ala Pro
    450                 455                 460

Leu Lys Ile Gln Ala Tyr Phe Asn Glu Thr Ala Asp Leu Pro Cys Gln
465                 470                 475                 480

Phe Ala Asn Ser Gln Asn Gln Ser Leu Ser Glu Leu Val Val Phe Trp
                485                 490                 495

Gln Asp Gln Glu Asn Leu Val Leu Asn Glu Val Tyr Leu Gly Lys Glu
            500                 505                 510

Lys Phe Asp Ser Val His Ser Lys Tyr Met Gly Arg Thr Ser Phe Asp
        515                 520                 525

Ser Asp Ser Trp Thr Leu Arg Leu His Asn Leu Gln Ile Lys Asp Lys
    530                 535                 540

Gly Leu Tyr Gln Cys Ile Ile His His Lys Lys Pro Thr Gly Met Ile
545                 550                 555                 560

Arg Ile His Gln Met Asn Ser Glu Leu Ser Val Leu Ala Asn Phe Ser
                565                 570                 575
```

```
Gln Pro Glu Ile Val Pro Ile Ser Asn Ile Thr Glu Asn Val Tyr Ile
            580                 585                 590

Asn Leu Thr Cys Ser Ser Ile His Gly Tyr Pro Glu Pro Lys Lys Met
        595                 600                 605

Ser Val Leu Leu Arg Thr Lys Asn Ser Thr Ile Glu Tyr Asp Gly Val
    610                 615                 620

Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
                645                 650                 655

Cys Ile Leu Glu Thr Asp Lys Thr Arg Leu Leu Ser Ser Pro Phe Ser
            660                 665                 670

Ile Glu Leu Glu Asp Pro Gln Pro Pro Asp His
        675                 680

<210> SEQ ID NO 143
<211> LENGTH: 609
<212> TYPE: PRT
<213> ORGANISM: Artificial Sequence
<220> FEATURE:
<223> OTHER INFORMATION: Heavy chain of the modified antibody

<400> SEQUENCE: 143

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Pro Gly
450                 455                 460

Trp Phe Leu Asp Ser Pro Asp Arg Pro Trp Asn Pro Pro Thr Phe Ser
465                 470                 475                 480

Pro Ala Leu Leu Val Val Thr Glu Gly Asp Asn Ala Thr Phe Thr Cys
                485                 490                 495

Ser Phe Ser Asn Thr Ser Glu Ser Phe Val Leu Asn Trp Tyr Arg Met
            500                 505                 510

Ser Pro Ser Asn Gln Thr Asp Lys Leu Ala Ala Phe Pro Glu Asp Arg
        515                 520                 525

Ser Gln Pro Gly Gln Asp Cys Arg Phe Arg Val Thr Gln Leu Pro Asn
530                 535                 540

Gly Arg Asp Phe His Met Ser Val Val Arg Ala Arg Arg Asn Asp Ser
545                 550                 555                 560

Gly Thr Tyr Leu Cys Gly Ala Ile Ser Leu Ala Pro Lys Ala Gln Ile
                565                 570                 575

Lys Glu Ser Leu Arg Ala Glu Leu Arg Val Thr Glu Arg Arg Ala Glu
            580                 585                 590

Val Pro Thr Ala His Pro Ser Pro Ser Pro Arg Pro Ala Gly Gln Phe
        595                 600                 605

Gln

<210> SEQ ID NO 144
<211> LENGTH: 682
<212> TYPE: PRT
<213> ORGANISM: Artificial Sequence
<220> FEATURE:
<223> OTHER INFORMATION: Heavy chain of the modified antibody

<400> SEQUENCE: 144

Glu Val Gln Leu Val Gln Ser Gly Ala Glu Val Lys Lys Pro Gly Glu

```
1               5                   10                  15
Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
                35                  40                  45

Gly Asn Ile Asp Pro Ser Asp Ser Asp Thr His Tyr Ser Pro Ser Phe
            50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430
```

-continued

```
His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Phe Thr
450                 455                 460

Val Thr Val Pro Lys Asp Leu Tyr Val Glu Tyr Gly Ser Asn Met
465                 470                 475                 480

Thr Ile Glu Cys Lys Phe Pro Val Glu Lys Gln Leu Asp Leu Ala Ala
                485                 490                 495

Leu Ile Val Tyr Trp Glu Met Glu Asp Lys Asn Ile Ile Gln Phe Val
                500                 505                 510

His Gly Glu Glu Asp Leu Lys Val Gln His Ser Ser Tyr Arg Gln Arg
            515                 520                 525

Ala Arg Leu Leu Lys Asp Gln Leu Ser Leu Gly Asn Ala Ala Leu Gln
530                 535                 540

Ile Thr Asp Val Lys Leu Gln Asp Ala Gly Val Tyr Arg Cys Met Ile
545                 550                 555                 560

Ser Tyr Gly Gly Ala Asp Tyr Lys Arg Ile Thr Val Lys Val Asn Ala
                565                 570                 575

Pro Tyr Asn Lys Ile Asn Gln Arg Ile Leu Val Val Asp Pro Val Thr
                580                 585                 590

Ser Glu His Glu Leu Thr Cys Gln Ala Glu Gly Tyr Pro Lys Ala Glu
            595                 600                 605

Val Ile Trp Thr Ser Ser Asp His Gln Val Leu Ser Gly Lys Thr Thr
610                 615                 620

Thr Thr Asn Ser Lys Arg Glu Glu Lys Leu Phe Asn Val Thr Ser Thr
625                 630                 635                 640

Leu Arg Ile Asn Thr Thr Thr Asn Glu Ile Phe Tyr Cys Thr Phe Arg
                645                 650                 655

Arg Leu Asp Pro Glu Glu Asn His Thr Ala Glu Leu Val Ile Pro Glu
            660                 665                 670

Leu Pro Leu Ala His Pro Pro Asn Glu Arg
                675                 680

<210> SEQ ID NO 145
<211> LENGTH: 670
<212> TYPE: PRT
<213> ORGANISM: Artificial Sequence
<220> FEATURE:
<223> OTHER INFORMATION: Heavy chain of the modified antibody

<400> SEQUENCE: 145

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
                100                 105                 110
```

-continued

Gly Thr Leu Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Val Ile
450                 455                 460

His Val Thr Lys Glu Val Lys Glu Val Ala Thr Leu Ser Cys Gly His
465                 470                 475                 480

Asn Val Ser Val Glu Glu Leu Ala Gln Thr Arg Ile Tyr Trp Gln Lys
                485                 490                 495

Glu Lys Lys Met Val Leu Thr Met Met Ser Gly Asp Met Asn Ile Trp
            500                 505                 510

Pro Glu Tyr Lys Asn Arg Thr Ile Phe Asp Ile Thr Asn Asn Leu Ser
        515                 520                 525

```
Ile Val Ile Leu Ala Leu Arg Pro Ser Asp Glu Gly Thr Tyr Glu Cys
    530                 535                 540

Val Val Leu Lys Tyr Glu Lys Asp Ala Phe Lys Arg Glu His Leu Ala
545                 550                 555                 560

Glu Val Thr Leu Ser Val Lys Ala Asp Phe Pro Thr Pro Ser Ile Ser
                565                 570                 575

Asp Phe Glu Ile Pro Thr Ser Asn Ile Arg Arg Ile Ile Cys Ser Thr
            580                 585                 590

Ser Gly Gly Phe Pro Glu Pro His Leu Ser Trp Leu Glu Asn Gly Glu
        595                 600                 605

Glu Leu Asn Ala Ile Asn Thr Thr Val Ser Gln Asp Pro Glu Thr Glu
610                 615                 620

Leu Tyr Ala Val Ser Ser Lys Leu Asp Phe Asn Met Thr Thr Asn His
625                 630                 635                 640

Ser Phe Met Cys Leu Ile Lys Tyr Gly His Leu Arg Val Asn Gln Thr
                645                 650                 655

Phe Asn Trp Asn Thr Thr Lys Gln Glu His Phe Pro Asp Asn
                660                 665                 670
```

<210> SEQ ID NO 146
<211> LENGTH: 595
<212> TYPE: PRT
<213> ORGANISM: Artificial Sequence
<220> FEATURE:
<223> OTHER INFORMATION: Heavy chain of the modified antibody

<400> SEQUENCE: 146

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
    435                 440                 445

Gly Gly Gly Ser Gly Gly Gly Ser Gly Gly Gly Ser Gly Ser Gln Val
450                 455                 460

Ser His Arg Tyr Pro Arg Ile Gln Ser Ile Lys Val Gln Phe Thr Glu
465                 470                 475                 480

Tyr Lys Lys Glu Lys Gly Phe Ile Leu Thr Ser Gln Lys Glu Asp Glu
            485                 490                 495

Ile Met Lys Val Gln Asn Asn Ser Val Ile Ile Asn Cys Asp Gly Phe
        500                 505                 510

Tyr Leu Ile Ser Leu Lys Gly Tyr Phe Ser Gln Glu Val Asn Ile Ser
    515                 520                 525

Leu His Tyr Gln Lys Asp Glu Glu Pro Leu Phe Gln Leu Lys Lys Val
530                 535                 540

Arg Ser Val Asn Ser Leu Met Val Ala Ser Leu Thr Tyr Lys Asp Lys
545                 550                 555                 560

Val Tyr Leu Asn Val Thr Thr Asp Asn Thr Ser Leu Asp Asp Phe His
            565                 570                 575

Val Asn Gly Gly Glu Leu Ile Leu Ile His Gln Asn Pro Gly Glu Phe
        580                 585                 590

Cys Val Leu
        595

<210> SEQ ID NO 147
<211> LENGTH: 646
<212> TYPE: PRT
<213> ORGANISM: Artificial Sequence
<220> FEATURE:
<223> OTHER INFORMATION: Heavy chain of the modified antibody
```

<400> SEQUENCE: 147

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Leu | Arg | Ile | Ser | Cys | Lys | Ala | Ser | Gly | Tyr | Ser | Phe | Thr | Ser | Tyr |
| | | | 20 | | | | | 25 | | | | | 30 | | |
| Trp | Val | His | Trp | Val | Arg | Gln | Met | Pro | Gly | Lys | Gly | Leu | Glu | Trp | Met |
| | | 35 | | | | | 40 | | | | | 45 | | | |
| Gly | Asn | Ile | Asp | Pro | Ser | Asp | Ser | Asp | Thr | His | Tyr | Ser | Pro | Ser | Phe |
| | 50 | | | | | 55 | | | | | 60 | | | | |
| Gln | Gly | His | Val | Thr | Leu | Ser | Val | Asp | Lys | Ser | Ile | Ser | Thr | Ala | Tyr |
| 65 | | | | | 70 | | | | | 75 | | | | | 80 |
| Leu | Gln | Leu | Ser | Ser | Leu | Lys | Ala | Ser | Asp | Thr | Ala | Met | Tyr | Tyr | Cys |
| | | | | 85 | | | | | 90 | | | | | 95 | |
| Val | Arg | Gly | Gly | Thr | Gly | Thr | Leu | Ala | Tyr | Phe | Ala | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Cys | Ser | Arg | Ser | Thr | Ser | Glu | Ser | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Lys | Thr | Tyr | Thr | Cys | Asn | Val | Asp | His | Lys |
| | | 195 | | | | | 200 | | | | | 205 | | | |
| Pro | Ser | Asn | Thr | Lys | Val | Asp | Lys | Arg | Val | Glu | Ser | Lys | Tyr | Gly | Pro |
| | 210 | | | | | 215 | | | | | 220 | | | | |
| Pro | Cys | Pro | Pro | Cys | Pro | Ala | Pro | Glu | Phe | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | Gln | Glu | Asp | Pro | Glu |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Phe | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Gln | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |
| Asp | Gly | Ser | Phe | Phe | Leu | Tyr | Ser | Arg | Leu | Thr | Val | Asp | Lys | Ser | Arg |

```
                    405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Arg Glu
            450                 455                 460

Gly Pro Glu Leu Ser Pro Asp Asp Pro Ala Gly Leu Leu Asp Leu Arg
465                 470                 475                 480

Gln Gly Met Phe Ala Gln Leu Val Ala Gln Asn Val Leu Leu Ile Asp
                485                 490                 495

Gly Pro Leu Ser Trp Tyr Ser Asp Pro Gly Leu Ala Gly Val Ser Leu
            500                 505                 510

Thr Gly Gly Leu Ser Tyr Lys Glu Asp Thr Lys Glu Leu Val Val Ala
            515                 520                 525

Lys Ala Gly Val Tyr Tyr Val Phe Phe Gln Leu Glu Leu Arg Arg Val
            530                 535                 540

Val Ala Gly Glu Gly Ser Gly Ser Val Ser Leu Ala Leu His Leu Gln
545                 550                 555                 560

Pro Leu Arg Ser Ala Ala Gly Ala Ala Ala Leu Ala Leu Thr Val Asp
                565                 570                 575

Leu Pro Pro Ala Ser Ser Glu Ala Arg Asn Ser Ala Phe Gly Phe Gln
            580                 585                 590

Gly Arg Leu Leu His Leu Ser Ala Gly Gln Arg Leu Gly Val His Leu
            595                 600                 605

His Thr Glu Ala Arg Ala Arg His Ala Trp Gln Leu Thr Gln Gly Ala
            610                 615                 620

Thr Val Leu Gly Leu Phe Arg Val Thr Pro Glu Ile Pro Ala Gly Leu
625                 630                 635                 640

Pro Ser Pro Arg Ser Glu
                645

<210> SEQ ID NO 148
<211> LENGTH: 700
<212> TYPE: PRT
<213> ORGANISM: Artificial Sequence
<220> FEATURE:
<223> OTHER INFORMATION: Heavy chain of the modified antibody

<400> SEQUENCE: 148

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
```

-continued

```
                115                 120                 125
    Phe Pro Leu Ala Pro Cys Ser Arg Ser Thr Glu Ser Thr Ala Ala
    130                 135                 140
    Leu Gly Cys Leu Val Lys Asp Tyr Phe Pro Glu Pro Val Thr Val Ser
145                 150                 155                 160
    Trp Asn Ser Gly Ala Leu Thr Ser Gly Val His Thr Phe Pro Ala Val
                    165                 170                 175
    Leu Gln Ser Ser Gly Leu Tyr Ser Leu Ser Ser Val Val Thr Val Pro
                    180                 185                 190
    Ser Ser Ser Leu Gly Thr Lys Thr Tyr Thr Cys Asn Val Asp His Lys
                    195                 200                 205
    Pro Ser Asn Thr Lys Val Asp Lys Arg Val Glu Ser Lys Tyr Gly Pro
                    210                 215                 220
    Pro Cys Pro Pro Cys Pro Ala Pro Glu Phe Leu Gly Gly Pro Ser Val
225                 230                 235                 240
    Phe Leu Phe Pro Pro Lys Pro Lys Asp Thr Leu Met Ile Ser Arg Thr
                    245                 250                 255
    Pro Glu Val Thr Cys Val Val Val Asp Val Ser Gln Glu Asp Pro Glu
                    260                 265                 270
    Val Gln Phe Asn Trp Tyr Val Asp Gly Val Glu Val His Asn Ala Lys
                    275                 280                 285
    Thr Lys Pro Arg Glu Glu Gln Phe Asn Ser Thr Tyr Arg Val Val Ser
    290                 295                 300
    Val Leu Thr Val Leu His Gln Asp Trp Leu Asn Gly Lys Glu Tyr Lys
305                 310                 315                 320
    Cys Lys Val Ser Asn Lys Gly Leu Pro Ser Ser Ile Glu Lys Thr Ile
                    325                 330                 335
    Ser Lys Ala Lys Gly Gln Pro Arg Glu Pro Gln Val Tyr Thr Leu Pro
                    340                 345                 350
    Pro Ser Gln Glu Glu Met Thr Lys Asn Gln Val Ser Leu Thr Cys Leu
                    355                 360                 365
    Val Lys Gly Phe Tyr Pro Ser Asp Ile Ala Val Glu Trp Glu Ser Asn
    370                 375                 380
    Gly Gln Pro Glu Asn Asn Tyr Lys Thr Thr Pro Pro Val Leu Asp Ser
385                 390                 395                 400
    Asp Gly Ser Phe Phe Leu Tyr Ser Arg Leu Thr Val Asp Lys Ser Arg
                    405                 410                 415
    Trp Gln Glu Gly Asn Val Phe Ser Cys Ser Val Met His Glu Ala Leu
                    420                 425                 430
    His Asn His Tyr Thr Gln Lys Ser Leu Ser Leu Ser Pro Gly Lys Gly
                    435                 440                 445
    Gly Gly Gly Ser Gly Gly Gly Ser Gly Gly Gly Ser Asp Thr
                    450                 455                 460
    Gln Glu Lys Glu Val Arg Ala Met Val Gly Ser Asp Val Glu Leu Ser
    465                 470                 475                 480
    Cys Ala Cys Pro Glu Gly Ser Arg Phe Asp Leu Asn Asp Val Tyr Val
                    485                 490                 495
    Tyr Trp Gln Thr Ser Glu Ser Lys Thr Val Val Thr Tyr His Ile Pro
                    500                 505                 510
    Gln Asn Ser Ser Leu Glu Asn Val Asp Ser Arg Tyr Arg Asn Arg Ala
                    515                 520                 525
    Leu Met Ser Pro Ala Gly Met Leu Arg Gly Asp Phe Ser Leu Arg Leu
                    530                 535                 540
```

-continued

Phe Asn Val Thr Pro Gln Asp Glu Gln Lys Phe His Cys Leu Val Leu
545                 550                 555                 560

Ser Gln Ser Leu Gly Phe Gln Glu Val Leu Ser Val Glu Val Thr Leu
                565                 570                 575

His Val Ala Ala Asn Phe Ser Val Pro Val Val Ser Ala Pro His Ser
            580                 585                 590

Pro Ser Gln Asp Glu Leu Thr Phe Thr Cys Thr Ser Ile Asn Gly Tyr
        595                 600                 605

Pro Arg Pro Asn Val Tyr Trp Ile Asn Lys Thr Asp Asn Ser Leu Leu
    610                 615                 620

Asp Gln Ala Leu Gln Asn Asp Thr Val Phe Leu Asn Met Arg Gly Leu
625                 630                 635                 640

Tyr Asp Val Val Ser Val Leu Arg Ile Ala Arg Thr Pro Ser Val Asn
                645                 650                 655

Ile Gly Cys Cys Ile Glu Asn Val Leu Leu Gln Gln Asn Leu Thr Val
            660                 665                 670

Gly Ser Gln Thr Gly Asn Asp Ile Gly Glu Arg Asp Lys Ile Thr Glu
        675                 680                 685

Asn Pro Val Ser Thr Gly Glu Lys Asn Ala Ala Thr
    690                 695                 700

<210> SEQ ID NO 149
<211> LENGTH: 684
<212> TYPE: PRT
<213> ORGANISM: Artificial Sequence
<220> FEATURE:
<223> OTHER INFORMATION: Heavy chain of the modified antibody

<400> SEQUENCE: 149

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Gly Gly Ser Gly Gly Gly Gly Ser Gly Gly Gly Gly Ser Ala Pro
450                 455                 460
Leu Lys Ile Gln Ala Tyr Phe Asn Glu Thr Ala Asp Leu Pro Cys Gln
465                 470                 475                 480
Phe Ala Asn Ser Gln Asn Gln Ser Leu Ser Glu Leu Val Val Phe Trp
                485                 490                 495
Gln Asp Gln Glu Asn Leu Val Leu Asn Glu Val Tyr Leu Gly Lys Glu
            500                 505                 510
Lys Phe Asp Ser Val His Ser Lys Tyr Met Gly Arg Thr Ser Phe Asp
        515                 520                 525
Ser Asp Ser Trp Thr Leu Arg Leu His Asn Leu Gln Ile Lys Asp Lys
530                 535                 540
Gly Leu Tyr Gln Cys Ile Ile His His Lys Lys Pro Thr Gly Met Ile
545                 550                 555                 560
Arg Ile His Gln Met Asn Ser Glu Leu Ser Val Leu Ala Asn Phe Ser
                565                 570                 575
Gln Pro Glu Ile Val Pro Ile Ser Asn Ile Thr Glu Asn Val Tyr Ile
            580                 585                 590
Asn Leu Thr Cys Ser Ser Ile His Gly Tyr Pro Glu Pro Lys Lys Met
        595                 600                 605
Ser Val Leu Leu Arg Thr Lys Asn Ser Thr Ile Glu Tyr Asp Gly Val
610                 615                 620
```

```
Met Gln Lys Ser Gln Asp Asn Val Thr Glu Leu Tyr Asp Val Ser Ile
625                 630                 635                 640

Ser Leu Ser Val Ser Phe Pro Asp Val Thr Ser Asn Met Thr Ile Phe
            645                 650                 655

Cys Ile Leu Glu Thr Asp Lys Thr Arg Leu Leu Ser Ser Pro Phe Ser
        660                 665                 670

Ile Glu Leu Glu Asp Pro Gln Pro Pro Asp His
    675                 680

<210> SEQ ID NO 150
<211> LENGTH: 381
<212> TYPE: PRT
<213> ORGANISM: Artificial Sequence
<220> FEATURE:
<223> OTHER INFORMATION: Light chain of the modified antibody

<400> SEQUENCE: 150

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys Gly Gly Gly Gly Ser
    210                 215                 220

Gly Gly Gly Gly Ser Gly Gly Gly Ser Pro Gly Trp Phe Leu Asp
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Ser Gln Pro Gly
    290                 295                 300
```

Gln Asp Cys Arg Phe Arg Val Thr Gln Leu Pro Asn Gly Arg Asp Phe
305                 310                 315                 320

His Met Ser Val Val Arg Ala Arg Arg Asn Asp Ser Gly Thr Tyr Leu
            325                 330                 335

Cys Gly Ala Ile Ser Leu Ala Pro Lys Ala Gln Ile Lys Glu Ser Leu
            340                 345                 350

Arg Ala Glu Leu Arg Val Thr Glu Arg Arg Ala Glu Val Pro Thr Ala
            355                 360                 365

His Pro Ser Pro Ser Pro Arg Pro Ala Gly Gln Phe Gln
            370                 375                 380

<210> SEQ ID NO 151
<211> LENGTH: 454
<212> TYPE: PRT
<213> ORGANISM: Artificial Sequence
<220> FEATURE:
<223> OTHER INFORMATION: Light chain of the modified antibody

<400> SEQUENCE: 151

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys Gly Gly Gly Gly Ser
210                 215                 220

Gly Gly Gly Gly Ser Gly Gly Gly Ser Phe Thr Val Thr Val Pro
225                 230                 235                 240

Lys Asp Leu Tyr Val Val Glu Tyr Gly Ser Asn Met Thr Ile Glu Cys
                245                 250                 255

Lys Phe Pro Val Glu Lys Gln Leu Asp Leu Ala Ala Leu Ile Val Tyr
            260                 265                 270

Trp Glu Met Glu Asp Lys Asn Ile Ile Gln Phe Val His Gly Glu Glu
        275                 280                 285

-continued

```
Asp Leu Lys Val Gln His Ser Ser Tyr Arg Gln Arg Ala Arg Leu Leu
    290                 295                 300

Lys Asp Gln Leu Ser Leu Gly Asn Ala Ala Leu Gln Ile Thr Asp Val
305                 310                 315                 320

Lys Leu Gln Asp Ala Gly Val Tyr Arg Cys Met Ile Ser Tyr Gly Gly
                325                 330                 335

Ala Asp Tyr Lys Arg Ile Thr Val Lys Val Asn Ala Pro Tyr Asn Lys
            340                 345                 350

Ile Asn Gln Arg Ile Leu Val Val Asp Pro Val Thr Ser Glu His Glu
        355                 360                 365

Leu Thr Cys Gln Ala Glu Gly Tyr Pro Lys Ala Glu Val Ile Trp Thr
    370                 375                 380

Ser Ser Asp His Gln Val Leu Ser Gly Lys Thr Thr Thr Asn Ser
385                 390                 395                 400

Lys Arg Glu Glu Lys Leu Phe Asn Val Thr Ser Thr Leu Arg Ile Asn
                405                 410                 415

Thr Thr Thr Asn Glu Ile Phe Tyr Cys Thr Phe Arg Arg Leu Asp Pro
            420                 425                 430

Glu Glu Asn His Thr Ala Glu Leu Val Ile Pro Glu Leu Pro Leu Ala
        435                 440                 445

His Pro Pro Asn Glu Arg
    450

<210> SEQ ID NO 152
<211> LENGTH: 442
<212> TYPE: PRT
<213> ORGANISM: Artificial Sequence
<220> FEATURE:
<223> OTHER INFORMATION: Light chain of the modified antibody

<400> SEQUENCE: 152

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190
```

Arg His Asn Ser Tyr Thr Cys Glu Ala Thr His Lys Thr Ser Thr Ser
195                 200                 205

Pro Ile Val Lys Ser Phe Asn Arg Asn Glu Cys Gly Gly Gly Gly Ser
210                 215                 220

Gly Gly Gly Gly Ser Gly Gly Gly Ser Val Ile His Val Thr Lys
225                 230                 235                 240

Glu Val Lys Glu Val Ala Thr Leu Ser Cys Gly His Asn Val Ser Val
                245                 250                 255

Glu Glu Leu Ala Gln Thr Arg Ile Tyr Trp Gln Lys Glu Lys Lys Met
            260                 265                 270

Val Leu Thr Met Met Ser Gly Asp Met Asn Ile Trp Pro Glu Tyr Lys
        275                 280                 285

Asn Arg Thr Ile Phe Asp Ile Thr Asn Asn Leu Ser Ile Val Ile Leu
290                 295                 300

Ala Leu Arg Pro Ser Asp Glu Gly Thr Tyr Glu Cys Val Val Leu Lys
305                 310                 315                 320

Tyr Glu Lys Asp Ala Phe Lys Arg Glu His Leu Ala Glu Val Thr Leu
                325                 330                 335

Ser Val Lys Ala Asp Phe Pro Thr Pro Ser Ile Ser Asp Phe Glu Ile
            340                 345                 350

Pro Thr Ser Asn Ile Arg Arg Ile Ile Cys Ser Thr Ser Gly Gly Phe
        355                 360                 365

Pro Glu Pro His Leu Ser Trp Leu Glu Asn Gly Glu Glu Leu Asn Ala
    370                 375                 380

Ile Asn Thr Thr Val Ser Gln Asp Pro Glu Thr Glu Leu Tyr Ala Val
385                 390                 395                 400

Ser Ser Lys Leu Asp Phe Asn Met Thr Thr Asn His Ser Phe Met Cys
                405                 410                 415

Leu Ile Lys Tyr Gly His Leu Arg Val Asn Gln Thr Phe Asn Trp Asn
            420                 425                 430

Thr Thr Lys Gln Glu His Phe Pro Asp Asn
        435                 440

<210> SEQ ID NO 153
<211> LENGTH: 367
<212> TYPE: PRT
<213> ORGANISM: Artificial Sequence
<220> FEATURE:
<223> OTHER INFORMATION: Light chain of the modified antibody

<400> SEQUENCE: 153

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys Gly Gly Gly Gly Ser
            210                 215                 220

Gly Gly Gly Gly Ser Gly Gly Gly Gly Ser Gln Val Ser His Arg Tyr
225                 230                 235                 240

Pro Arg Ile Gln Ser Ile Lys Val Gln Phe Thr Glu Tyr Lys Lys Glu
            245                 250                 255

Lys Gly Phe Ile Leu Thr Ser Gln Lys Glu Asp Glu Ile Met Lys Val
            260                 265                 270

Gln Asn Asn Ser Val Ile Ile Asn Cys Asp Gly Phe Tyr Leu Ile Ser
            275                 280                 285

Leu Lys Gly Tyr Phe Ser Gln Glu Val Asn Ile Ser Leu His Tyr Gln
            290                 295                 300

Lys Asp Glu Glu Pro Leu Phe Gln Leu Lys Lys Val Arg Ser Val Asn
305                 310                 315                 320

Ser Leu Met Val Ala Ser Leu Thr Tyr Lys Asp Lys Val Tyr Leu Asn
            325                 330                 335

Val Thr Thr Asp Asn Thr Ser Leu Asp Asp Phe His Val Asn Gly Gly
            340                 345                 350

Glu Leu Ile Leu Ile His Gln Asn Pro Gly Glu Phe Cys Val Leu
            355                 360                 365

<210> SEQ ID NO 154
<211> LENGTH: 418
<212> TYPE: PRT
<213> ORGANISM: Artificial Sequence
<220> FEATURE:
<223> OTHER INFORMATION: Light chain of the modified antibody

<400> SEQUENCE: 154

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys Gly Gly Gly Gly Ser
210                 215                 220

Gly Gly Gly Gly Ser Gly Gly Gly Ser Arg Glu Gly Pro Glu Leu
225                 230                 235                 240

Ser Pro Asp Asp Pro Ala Gly Leu Leu Asp Leu Arg Gln Gly Met Phe
                245                 250                 255

Ala Gln Leu Val Ala Gln Asn Val Leu Leu Ile Asp Gly Pro Leu Ser
                260                 265                 270

Trp Tyr Ser Asp Pro Gly Leu Ala Gly Val Ser Leu Thr Gly Gly Leu
                275                 280                 285

Ser Tyr Lys Glu Asp Thr Lys Glu Leu Val Val Ala Lys Ala Gly Val
                290                 295                 300

Tyr Tyr Val Phe Phe Gln Leu Glu Leu Arg Arg Val Val Ala Gly Glu
305                 310                 315                 320

Gly Ser Gly Ser Val Ser Leu Ala Leu His Leu Gln Pro Leu Arg Ser
                325                 330                 335

Ala Ala Gly Ala Ala Ala Leu Ala Leu Thr Val Asp Leu Pro Pro Ala
                340                 345                 350

Ser Ser Glu Ala Arg Asn Ser Ala Phe Gly Phe Gln Gly Arg Leu Leu
                355                 360                 365

His Leu Ser Ala Gly Gln Arg Leu Gly Val His Leu His Thr Glu Ala
370                 375                 380

Arg Ala Arg His Ala Trp Gln Leu Thr Gln Gly Ala Thr Val Leu Gly
385                 390                 395                 400

Leu Phe Arg Val Thr Pro Glu Ile Pro Ala Gly Leu Pro Ser Pro Arg
                405                 410                 415

Ser Glu

<210> SEQ ID NO 155
<211> LENGTH: 472
<212> TYPE: PRT
<213> ORGANISM: Artificial Sequence
<220> FEATURE:
<223> OTHER INFORMATION: Light chain of the modified antibody

<400> SEQUENCE: 155

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Tyr Gly Asn Thr Tyr Leu Tyr Trp Tyr Leu Gln Lys Pro Gly Gln Ser
                35                  40                  45

Pro Lys Leu Leu Ile Tyr Arg Val Ser Asn Arg Phe Ser Gly Val Pro

```
            50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                     85                  90                  95

Thr His Val Pro Tyr Thr Phe Gly Ser Gly Thr Lys Leu Glu Ile Lys
                100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
            130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys Gly Gly Gly Gly Ser
210                 215                 220

Gly Gly Gly Gly Ser Gly Gly Gly Ser Asp Thr Gln Glu Lys Glu
225                 230                 235                 240

Val Arg Ala Met Val Gly Ser Asp Val Glu Leu Ser Cys Ala Cys Pro
                245                 250                 255

Glu Gly Ser Arg Phe Asp Leu Asn Asp Val Tyr Val Tyr Trp Gln Thr
                260                 265                 270

Ser Glu Ser Lys Thr Val Val Thr Tyr His Ile Pro Gln Asn Ser Ser
                275                 280                 285

Leu Glu Asn Val Asp Ser Arg Tyr Arg Asn Arg Ala Leu Met Ser Pro
            290                 295                 300

Ala Gly Met Leu Arg Gly Asp Phe Ser Leu Arg Leu Phe Asn Val Thr
305                 310                 315                 320

Pro Gln Asp Glu Gln Lys Phe His Cys Leu Val Leu Ser Gln Ser Leu
                325                 330                 335

Gly Phe Gln Glu Val Leu Ser Val Glu Val Thr Leu His Val Ala Ala
                340                 345                 350

Asn Phe Ser Val Pro Val Val Ser Ala Pro His Ser Pro Ser Gln Asp
            355                 360                 365

Glu Leu Thr Phe Thr Cys Thr Ser Ile Asn Gly Tyr Pro Arg Pro Asn
370                 375                 380

Val Tyr Trp Ile Asn Lys Thr Asp Asn Ser Leu Leu Asp Gln Ala Leu
385                 390                 395                 400

Gln Asn Asp Thr Val Phe Leu Asn Met Arg Gly Leu Tyr Asp Val Val
                405                 410                 415

Ser Val Leu Arg Ile Ala Arg Thr Pro Ser Val Asn Ile Gly Cys Cys
                420                 425                 430

Ile Glu Asn Val Leu Leu Gln Gln Asn Leu Thr Val Gly Ser Gln Thr
            435                 440                 445

Gly Asn Asp Ile Gly Glu Arg Asp Lys Ile Thr Glu Asn Pro Val Ser
            450                 455                 460

Thr Gly Glu Lys Asn Ala Ala Thr
465                 470
```

<210> SEQ ID NO 156
<211> LENGTH: 456
<212> TYPE: PRT
<213> ORGANISM: Artificial Sequence
<220> FEATURE:
<223> OTHER INFORMATION: Light chain of the modified antibody

<400> SEQUENCE: 156

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys Gly Gly Gly Ser
    210                 215                 220

Gly Gly Gly Gly Ser Gly Gly Gly Ser Ala Pro Leu Lys Ile Gln
225                 230                 235                 240

Ala Tyr Phe Asn Glu Thr Ala Asp Leu Pro Cys Gln Phe Ala Asn Ser
                245                 250                 255

Gln Asn Gln Ser Leu Ser Glu Leu Val Val Phe Trp Gln Asp Gln Glu
            260                 265                 270

Asn Leu Val Leu Asn Glu Val Tyr Leu Gly Lys Glu Lys Phe Asp Ser
        275                 280                 285

Val His Ser Lys Tyr Met Gly Arg Thr Ser Phe Asp Ser Asp Ser Trp
    290                 295                 300

Thr Leu Arg Leu His Asn Leu Gln Ile Lys Asp Lys Gly Leu Tyr Gln
305                 310                 315                 320

Cys Ile Ile His His Lys Lys Pro Thr Gly Met Ile Arg Ile His Gln
                325                 330                 335

Met Asn Ser Glu Leu Ser Val Leu Ala Asn Phe Ser Gln Pro Glu Ile
            340                 345                 350

Val Pro Ile Ser Asn Ile Thr Glu Asn Val Tyr Ile Asn Leu Thr Cys
        355                 360                 365
```

Ser Ser Ile His Gly Tyr Pro Glu Pro Lys Lys Met Ser Val Leu Leu
          370                 375                 380

Arg Thr Lys Asn Ser Thr Ile Glu Tyr Asp Gly Val Met Gln Lys Ser
385                 390                 395                 400

Gln Asp Asn Val Thr Glu Leu Tyr Asp Val Ser Ile Ser Leu Ser Val
                405                 410                 415

Ser Phe Pro Asp Val Thr Ser Asn Met Thr Ile Phe Cys Ile Leu Glu
            420                 425                 430

Thr Asp Lys Thr Arg Leu Leu Ser Ser Pro Phe Ser Ile Glu Leu Glu
        435                 440                 445

Asp Pro Gln Pro Pro Pro Asp His
    450                 455

<210> SEQ ID NO 157
<211> LENGTH: 381
<212> TYPE: PRT
<213> ORGANISM: Artificial Sequence
<220> FEATURE:
<223> OTHER INFORMATION: Light chain of the modified antibody

<400> SEQUENCE: 157

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Gly Ser Pro Gly Trp Phe Leu Asp
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

```
Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Ser Gln Pro Gly
    290                 295                 300

Gln Asp Cys Arg Phe Arg Val Thr Gln Leu Pro Asn Gly Arg Asp Phe
305                 310                 315                 320

His Met Ser Val Val Arg Ala Arg Arg Asn Asp Ser Gly Thr Tyr Leu
                325                 330                 335

Cys Gly Ala Ile Ser Leu Ala Pro Lys Ala Gln Ile Lys Glu Ser Leu
            340                 345                 350

Arg Ala Glu Leu Arg Val Thr Glu Arg Ala Glu Val Pro Thr Ala
        355                 360                 365

His Pro Ser Pro Ser Pro Arg Pro Ala Gly Gln Phe Gln
    370                 375                 380

<210> SEQ ID NO 158
<211> LENGTH: 454
<212> TYPE: PRT
<213> ORGANISM: Artificial Sequence
<220> FEATURE:
<223> OTHER INFORMATION: Light chain of the modified antibody

<400> SEQUENCE: 158

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Phe Thr Val Thr Val Pro
225                 230                 235                 240

Lys Asp Leu Tyr Val Val Glu Tyr Gly Ser Asn Met Thr Ile Glu Cys
                245                 250                 255
```

```
Lys Phe Pro Val Glu Lys Gln Leu Asp Leu Ala Ala Leu Ile Val Tyr
            260                 265                 270

Trp Glu Met Glu Asp Lys Asn Ile Ile Gln Phe Val His Gly Glu Glu
        275                 280                 285

Asp Leu Lys Val Gln His Ser Ser Tyr Arg Gln Arg Ala Arg Leu Leu
    290                 295                 300

Lys Asp Gln Leu Ser Leu Gly Asn Ala Ala Leu Gln Ile Thr Asp Val
305                 310                 315                 320

Lys Leu Gln Asp Ala Gly Val Tyr Arg Cys Met Ile Ser Tyr Gly Gly
                325                 330                 335

Ala Asp Tyr Lys Arg Ile Thr Val Lys Val Asn Ala Pro Tyr Asn Lys
            340                 345                 350

Ile Asn Gln Arg Ile Leu Val Val Asp Pro Val Thr Ser Glu His Glu
        355                 360                 365

Leu Thr Cys Gln Ala Glu Gly Tyr Pro Lys Ala Glu Val Ile Trp Thr
    370                 375                 380

Ser Ser Asp His Gln Val Leu Ser Gly Lys Thr Thr Thr Thr Asn Ser
385                 390                 395                 400

Lys Arg Glu Glu Lys Leu Phe Asn Val Thr Ser Thr Leu Arg Ile Asn
                405                 410                 415

Thr Thr Thr Asn Glu Ile Phe Tyr Cys Thr Phe Arg Arg Leu Asp Pro
            420                 425                 430

Glu Glu Asn His Thr Ala Glu Leu Val Ile Pro Glu Leu Pro Leu Ala
        435                 440                 445

His Pro Pro Asn Glu Arg
    450

<210> SEQ ID NO 159
<211> LENGTH: 442
<212> TYPE: PRT
<213> ORGANISM: Artificial Sequence
<220> FEATURE:
<223> OTHER INFORMATION: Light chain of the modified antibody

<400> SEQUENCE: 159

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Val Ile His Val Thr Lys
225                 230                 235                 240

Glu Val Lys Glu Val Ala Thr Leu Ser Cys Gly His Asn Val Ser Val
            245                 250                 255

Glu Glu Leu Ala Gln Thr Arg Ile Tyr Trp Gln Lys Glu Lys Lys Met
            260                 265                 270

Val Leu Thr Met Met Ser Gly Asp Met Asn Ile Trp Pro Glu Tyr Lys
            275                 280                 285

Asn Arg Thr Ile Phe Asp Ile Thr Asn Asn Leu Ser Ile Val Ile Leu
            290                 295                 300

Ala Leu Arg Pro Ser Asp Glu Gly Thr Tyr Glu Cys Val Val Leu Lys
305                 310                 315                 320

Tyr Glu Lys Asp Ala Phe Lys Arg Glu His Leu Ala Glu Val Thr Leu
            325                 330                 335

Ser Val Lys Ala Asp Phe Pro Thr Pro Ser Ile Ser Asp Phe Glu Ile
            340                 345                 350

Pro Thr Ser Asn Ile Arg Arg Ile Ile Cys Ser Thr Ser Gly Gly Phe
            355                 360                 365

Pro Glu Pro His Leu Ser Trp Leu Glu Asn Gly Glu Glu Leu Asn Ala
            370                 375                 380

Ile Asn Thr Thr Val Ser Gln Asp Pro Glu Thr Glu Leu Tyr Ala Val
385                 390                 395                 400

Ser Ser Lys Leu Asp Phe Asn Met Thr Thr Asn His Ser Phe Met Cys
            405                 410                 415

Leu Ile Lys Tyr Gly His Leu Arg Val Asn Gln Thr Phe Asn Trp Asn
            420                 425                 430

Thr Thr Lys Gln Glu His Phe Pro Asp Asn
            435                 440

<210> SEQ ID NO 160
<211> LENGTH: 367
<212> TYPE: PRT
<213> ORGANISM: Artificial Sequence
<220> FEATURE:
<223> OTHER INFORMATION: Light chain of the modified antibody

<400> SEQUENCE: 160

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gln Val Ser His Arg Tyr
225                 230                 235                 240

Pro Arg Ile Gln Ser Ile Lys Val Gln Phe Thr Glu Tyr Lys Lys Glu
                245                 250                 255

Lys Gly Phe Ile Leu Thr Ser Gln Lys Glu Asp Glu Ile Met Lys Val
            260                 265                 270

Gln Asn Asn Ser Val Ile Ile Asn Cys Asp Gly Phe Tyr Leu Ile Ser
        275                 280                 285

Leu Lys Gly Tyr Phe Ser Gln Glu Val Asn Ile Ser Leu His Tyr Gln
    290                 295                 300

Lys Asp Glu Glu Pro Leu Phe Gln Leu Lys Lys Val Arg Ser Val Asn
305                 310                 315                 320

Ser Leu Met Val Ala Ser Leu Thr Tyr Lys Asp Lys Val Tyr Leu Asn
                325                 330                 335

Val Thr Thr Asp Asn Thr Ser Leu Asp Asp Phe His Val Asn Gly Gly
            340                 345                 350

Glu Leu Ile Leu Ile His Gln Asn Pro Gly Glu Phe Cys Val Leu
        355                 360                 365

<210> SEQ ID NO 161
<211> LENGTH: 418
<212> TYPE: PRT
<213> ORGANISM: Artificial Sequence
<220> FEATURE:
<223> OTHER INFORMATION: Light chain of the modified antibody

<400> SEQUENCE: 161

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
               100                 105                 110

Arg Thr Val Ala Ala Pro Ser Val Phe Ile Phe Pro Pro Ser Asp Glu
               115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys Gly Gly Gly Gly Ser
                210                 215                 220

Gly Gly Gly Gly Ser Gly Gly Gly Ser Arg Glu Gly Pro Glu Leu
225                 230                 235                 240

Ser Pro Asp Asp Pro Ala Gly Leu Leu Asp Leu Arg Gln Gly Met Phe
                245                 250                 255

Ala Gln Leu Val Ala Gln Asn Val Leu Leu Ile Asp Gly Pro Leu Ser
                260                 265                 270

Trp Tyr Ser Asp Pro Gly Leu Ala Gly Val Ser Leu Thr Gly Gly Leu
                275                 280                 285

Ser Tyr Lys Glu Asp Thr Lys Glu Leu Val Val Ala Lys Ala Gly Val
                290                 295                 300

Tyr Tyr Val Phe Phe Gln Leu Glu Leu Arg Arg Val Val Ala Gly Glu
305                 310                 315                 320

Gly Ser Gly Ser Val Ser Leu Ala Leu His Leu Gln Pro Leu Arg Ser
                325                 330                 335

Ala Ala Gly Ala Ala Ala Leu Ala Leu Thr Val Asp Leu Pro Pro Ala
                340                 345                 350

Ser Ser Glu Ala Arg Asn Ser Ala Phe Gly Phe Gln Gly Arg Leu Leu
                355                 360                 365

His Leu Ser Ala Gly Gln Arg Leu Gly Val His Leu His Thr Glu Ala
                370                 375                 380

Arg Ala Arg His Ala Trp Gln Leu Thr Gln Gly Ala Thr Val Leu Gly
385                 390                 395                 400

Leu Phe Arg Val Thr Pro Glu Ile Pro Ala Gly Leu Pro Ser Pro Arg
                405                 410                 415

Ser Glu

<210> SEQ ID NO 162
<211> LENGTH: 472
<212> TYPE: PRT
<213> ORGANISM: Artificial Sequence
<220> FEATURE:
<223> OTHER INFORMATION: Light chain of the modified antibody

<400> SEQUENCE: 162

Asp Val Val Met Thr Gln Thr Pro Leu Ser Leu Pro Val Ser Leu Gly
1               5                   10                  15
```

```
Asp Gln Ala Ser Ile Ser Cys Arg Ser Ser Gln Ser Leu Val His Ser
                20                  25                  30

Tyr Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Asp Thr Gln Glu Lys Glu
225                 230                 235                 240

Val Arg Ala Met Val Gly Ser Asp Val Glu Leu Ser Cys Ala Cys Pro
                245                 250                 255

Glu Gly Ser Arg Phe Asp Leu Asn Asp Val Tyr Val Tyr Trp Gln Thr
            260                 265                 270

Ser Glu Ser Lys Thr Val Val Thr Tyr His Ile Pro Gln Asn Ser Ser
        275                 280                 285

Leu Glu Asn Val Asp Ser Arg Tyr Arg Asn Arg Ala Leu Met Ser Pro
    290                 295                 300

Ala Gly Met Leu Arg Gly Asp Phe Ser Leu Arg Leu Phe Asn Val Thr
305                 310                 315                 320

Pro Gln Asp Glu Gln Lys Phe His Cys Leu Val Leu Ser Gln Ser Leu
                325                 330                 335

Gly Phe Gln Glu Val Leu Ser Val Glu Val Thr Leu His Val Ala Ala
            340                 345                 350

Asn Phe Ser Val Pro Val Val Ser Ala Pro His Ser Pro Ser Gln Asp
        355                 360                 365

Glu Leu Thr Phe Thr Cys Thr Ser Ile Asn Gly Tyr Pro Arg Pro Asn
    370                 375                 380

Val Tyr Trp Ile Asn Lys Thr Asp Asn Ser Leu Leu Asp Gln Ala Leu
385                 390                 395                 400

Gln Asn Asp Thr Val Phe Leu Asn Met Arg Gly Leu Tyr Asp Val Val
                405                 410                 415

Ser Val Leu Arg Ile Ala Arg Thr Pro Ser Val Asn Ile Gly Cys Cys
            420                 425                 430

Ile Glu Asn Val Leu Leu Gln Gln Asn Leu Thr Val Gly Ser Gln Thr
```

```
                435                 440                 445
Gly Asn Asp Ile Gly Glu Arg Asp Lys Ile Thr Glu Asn Pro Val Ser
        450                 455                 460

Thr Gly Glu Lys Asn Ala Ala Thr
465                 470

<210> SEQ ID NO 163
<211> LENGTH: 456
<212> TYPE: PRT
<213> ORGANISM: Artificial Sequence
<220> FEATURE:
<223> OTHER INFORMATION: Light chain of the modified antibody

<400> SEQUENCE: 163

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Ala Pro Leu Lys Ile Gln
225                 230                 235                 240

Ala Tyr Phe Asn Glu Thr Ala Asp Leu Pro Cys Gln Phe Ala Asn Ser
                245                 250                 255

Gln Asn Gln Ser Leu Ser Glu Leu Val Val Phe Trp Gln Asp Gln Glu
            260                 265                 270

Asn Leu Val Leu Asn Glu Val Tyr Leu Gly Lys Glu Lys Phe Asp Ser
        275                 280                 285

Val His Ser Lys Tyr Met Gly Arg Thr Ser Phe Asp Ser Asp Ser Trp
    290                 295                 300

Thr Leu Arg Leu His Asn Leu Gln Ile Lys Asp Lys Gly Leu Tyr Gln
305                 310                 315                 320

Cys Ile Ile His His Lys Lys Pro Thr Gly Met Ile Arg Ile His Gln
```

```
                    325                 330                 335
Met Asn Ser Glu Leu Ser Val Leu Ala Asn Phe Ser Gln Pro Glu Ile
                340                 345                 350

Val Pro Ile Ser Asn Ile Thr Glu Asn Val Tyr Ile Asn Leu Thr Cys
                355                 360                 365

Ser Ser Ile His Gly Tyr Pro Glu Pro Lys Lys Met Ser Val Leu Leu
            370                 375                 380

Arg Thr Lys Asn Ser Thr Ile Glu Tyr Asp Gly Val Met Gln Lys Ser
385                 390                 395                 400

Gln Asp Asn Val Thr Glu Leu Tyr Asp Val Ser Ile Ser Leu Ser Val
                405                 410                 415

Ser Phe Pro Asp Val Thr Ser Asn Met Thr Ile Phe Cys Ile Leu Glu
                420                 425                 430

Thr Asp Lys Thr Arg Leu Leu Ser Ser Pro Phe Ser Ile Glu Leu Glu
            435                 440                 445

Asp Pro Gln Pro Pro Asp His
        450                 455

<210> SEQ ID NO 164
<211> LENGTH: 381
<212> TYPE: PRT
<213> ORGANISM: Artificial Sequence
<220> FEATURE:
<223> OTHER INFORMATION: Light chain of the modified antibody

<400> SEQUENCE: 164

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Tyr Gly Asn Thr Tyr Leu Tyr Trp Tyr Gln Gln Arg Pro Gly Gln Ser
            35                  40                  45

Pro Arg Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
        210                 215                 220

Gly Gly Gly Gly Ser Gly Gly Gly Gly Ser Pro Gly Trp Phe Leu Asp
```

```
            225                 230                 235                 240
Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
                260                 265                 270

Thr Ser Glu Ser Phe Val Leu Asn Trp Tyr Arg Met Ser Pro Ser Asn
                275                 280                 285

Gln Thr Asp Lys Leu Ala Ala Phe Pro Glu Asp Arg Ser Gln Pro Gly
                290                 295                 300

Gln Asp Cys Arg Phe Arg Val Thr Gln Leu Pro Asn Gly Arg Asp Phe
305                 310                 315                 320

His Met Ser Val Val Arg Ala Arg Arg Asn Asp Ser Gly Thr Tyr Leu
                325                 330                 335

Cys Gly Ala Ile Ser Leu Ala Pro Lys Ala Gln Ile Lys Glu Ser Leu
                340                 345                 350

Arg Ala Glu Leu Arg Val Thr Glu Arg Arg Ala Glu Val Pro Thr Ala
                355                 360                 365

His Pro Ser Pro Ser Pro Arg Pro Ala Gly Gln Phe Gln
                370                 375                 380

<210> SEQ ID NO 165
<211> LENGTH: 454
<212> TYPE: PRT
<213> ORGANISM: Artificial Sequence
<220> FEATURE:
<223> OTHER INFORMATION: Light chain of the modified antibody

<400> SEQUENCE: 165

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Tyr Gly Asn Thr Tyr Leu Tyr Trp Tyr Gln Gln Arg Pro Gly Gln Ser
            35                  40                  45

Pro Arg Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
```

```
                    210                 215                 220
Gly Gly Gly Gly Ser Gly Gly Gly Ser Phe Thr Val Thr Val Pro
225                 230                 235                 240

Lys Asp Leu Tyr Val Val Glu Tyr Gly Ser Asn Met Thr Ile Glu Cys
                245                 250                 255

Lys Phe Pro Val Glu Lys Gln Leu Asp Leu Ala Ala Leu Ile Val Tyr
                260                 265                 270

Trp Glu Met Glu Asp Lys Asn Ile Ile Gln Phe Val His Gly Glu Glu
            275                 280                 285

Asp Leu Lys Val Gln His Ser Ser Tyr Arg Gln Arg Ala Arg Leu Leu
            290                 295                 300

Lys Asp Gln Leu Ser Leu Gly Asn Ala Ala Leu Gln Ile Thr Asp Val
305                 310                 315                 320

Lys Leu Gln Asp Ala Gly Val Tyr Arg Cys Met Ile Ser Tyr Gly Gly
                325                 330                 335

Ala Asp Tyr Lys Arg Ile Thr Val Lys Val Asn Ala Pro Tyr Asn Lys
                340                 345                 350

Ile Asn Gln Arg Ile Leu Val Val Asp Pro Val Thr Ser Glu His Glu
                355                 360                 365

Leu Thr Cys Gln Ala Glu Gly Tyr Pro Lys Ala Glu Val Ile Trp Thr
            370                 375                 380

Ser Ser Asp His Gln Val Leu Ser Gly Lys Thr Thr Thr Thr Asn Ser
385                 390                 395                 400

Lys Arg Glu Glu Lys Leu Phe Asn Val Thr Ser Thr Leu Arg Ile Asn
                405                 410                 415

Thr Thr Thr Asn Glu Ile Phe Tyr Cys Thr Phe Arg Arg Leu Asp Pro
                420                 425                 430

Glu Glu Asn His Thr Ala Glu Leu Val Ile Pro Glu Leu Pro Leu Ala
            435                 440                 445

His Pro Pro Asn Glu Arg
    450

<210> SEQ ID NO 166
<211> LENGTH: 442
<212> TYPE: PRT
<213> ORGANISM: Artificial Sequence
<220> FEATURE:
<223> OTHER INFORMATION: Light chain of the modified antibody

<400> SEQUENCE: 166

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Tyr Gly Asn Thr Tyr Leu Tyr Trp Tyr Gln Gln Arg Pro Gly Gln Ser
            35                  40                  45

Pro Arg Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
```

```
                115                 120                 125
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Val Ile His Val Thr Lys
225                 230                 235                 240

Glu Val Lys Glu Val Ala Thr Leu Ser Cys Gly His Asn Val Ser Val
                245                 250                 255

Glu Glu Leu Ala Gln Thr Arg Ile Tyr Trp Gln Lys Glu Lys Lys Met
            260                 265                 270

Val Leu Thr Met Met Ser Gly Asp Met Asn Ile Trp Pro Glu Tyr Lys
        275                 280                 285

Asn Arg Thr Ile Phe Asp Ile Thr Asn Leu Ser Ile Val Ile Leu
    290                 295                 300

Ala Leu Arg Pro Ser Asp Glu Gly Thr Tyr Glu Cys Val Val Leu Lys
305                 310                 315                 320

Tyr Glu Lys Asp Ala Phe Lys Arg Glu His Leu Ala Glu Val Thr Leu
                325                 330                 335

Ser Val Lys Ala Asp Phe Pro Thr Pro Ser Ile Ser Asp Phe Glu Ile
            340                 345                 350

Pro Thr Ser Asn Ile Arg Arg Ile Ile Cys Ser Thr Ser Gly Gly Phe
        355                 360                 365

Pro Glu Pro His Leu Ser Trp Leu Glu Asn Gly Glu Glu Leu Asn Ala
    370                 375                 380

Ile Asn Thr Thr Val Ser Gln Asp Pro Glu Thr Glu Leu Tyr Ala Val
385                 390                 395                 400

Ser Ser Lys Leu Asp Phe Asn Met Thr Thr Asn His Ser Phe Met Cys
                405                 410                 415

Leu Ile Lys Tyr Gly His Leu Arg Val Asn Gln Thr Phe Asn Trp Asn
            420                 425                 430

Thr Thr Lys Gln Glu His Phe Pro Asp Asn
        435                 440

<210> SEQ ID NO 167
<211> LENGTH: 367
<212> TYPE: PRT
<213> ORGANISM: Artificial Sequence
<220> FEATURE:
<223> OTHER INFORMATION: Light chain of the modified antibody

<400> SEQUENCE: 167

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Tyr Gln Gln Arg Pro Gly Gln Ser
```

```
            35                  40                  45
Pro Arg Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gln Val Ser His Arg Tyr
225                 230                 235                 240

Pro Arg Ile Gln Ser Ile Lys Val Gln Phe Thr Glu Tyr Lys Lys Glu
                245                 250                 255

Lys Gly Phe Ile Leu Thr Ser Gln Lys Glu Asp Glu Ile Met Lys Val
            260                 265                 270

Gln Asn Asn Ser Val Ile Ile Asn Cys Asp Gly Phe Tyr Leu Ile Ser
        275                 280                 285

Leu Lys Gly Tyr Phe Ser Gln Glu Val Asn Ile Ser Leu His Tyr Gln
    290                 295                 300

Lys Asp Glu Glu Pro Leu Phe Gln Leu Lys Lys Val Arg Ser Val Asn
305                 310                 315                 320

Ser Leu Met Val Ala Ser Leu Thr Tyr Lys Asp Lys Val Tyr Leu Asn
                325                 330                 335

Val Thr Thr Asp Asn Thr Ser Leu Asp Asp Phe His Val Asn Gly Gly
            340                 345                 350

Glu Leu Ile Leu Ile His Gln Asn Pro Gly Glu Phe Cys Val Leu
        355                 360                 365

<210> SEQ ID NO 168
<211> LENGTH: 418
<212> TYPE: PRT
<213> ORGANISM: Artificial Sequence
<220> FEATURE:
<223> OTHER INFORMATION: Light chain of the modified antibody

<400> SEQUENCE: 168

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Tyr Gln Gln Arg Pro Gly Gln Ser
```

```
                35                  40                  45
Pro Arg Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                 85                  90                  95

Thr His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Arg Glu Gly Pro Glu Leu
225                 230                 235                 240

Ser Pro Asp Asp Pro Ala Gly Leu Leu Asp Leu Arg Gln Gly Met Phe
                245                 250                 255

Ala Gln Leu Val Ala Gln Asn Val Leu Leu Ile Asp Gly Pro Leu Ser
            260                 265                 270

Trp Tyr Ser Asp Pro Gly Leu Ala Gly Val Ser Leu Thr Gly Gly Leu
        275                 280                 285

Ser Tyr Lys Glu Asp Thr Lys Glu Leu Val Val Ala Lys Ala Gly Val
290                 295                 300

Tyr Tyr Val Phe Phe Gln Leu Glu Leu Arg Arg Val Val Ala Gly Glu
305                 310                 315                 320

Gly Ser Gly Ser Val Ser Leu Ala Leu His Leu Gln Pro Leu Arg Ser
                325                 330                 335

Ala Ala Gly Ala Ala Ala Leu Ala Leu Thr Val Asp Leu Pro Pro Ala
            340                 345                 350

Ser Ser Glu Ala Arg Asn Ser Ala Phe Gly Phe Gln Gly Arg Leu Leu
        355                 360                 365

His Leu Ser Ala Gly Gln Arg Leu Gly Val His Leu His Thr Glu Ala
        370                 375                 380

Arg Ala Arg His Ala Trp Gln Leu Thr Gln Gly Ala Thr Val Leu Gly
385                 390                 395                 400

Leu Phe Arg Val Thr Pro Glu Ile Pro Ala Gly Leu Pro Ser Pro Arg
                405                 410                 415

Ser Glu

<210> SEQ ID NO 169
<211> LENGTH: 472
<212> TYPE: PRT
<213> ORGANISM: Artificial Sequence
<220> FEATURE:
```

<223> OTHER INFORMATION: Light chain of the modified antibody

<400> SEQUENCE: 169

```
Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val His Ser
            20                  25                  30
Tyr Gly Asn Thr Tyr Leu Tyr Trp Tyr Gln Gln Arg Pro Gly Gln Ser
        35                  40                  45
Pro Arg Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Phe Cys Phe Gln Gly
                85                  90                  95
Thr His Val Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys Gly Gly Gly Gly Ser
    210                 215                 220
Gly Gly Gly Gly Ser Gly Gly Gly Ser Asp Thr Gln Glu Lys Glu
225                 230                 235                 240
Val Arg Ala Met Val Gly Ser Asp Val Glu Leu Ser Cys Ala Cys Pro
                245                 250                 255
Glu Gly Ser Arg Phe Asp Leu Asn Asp Val Tyr Val Tyr Trp Gln Thr
            260                 265                 270
Ser Glu Ser Lys Thr Val Val Thr Tyr His Ile Pro Gln Asn Ser Ser
        275                 280                 285
Leu Glu Asn Val Asp Ser Arg Tyr Arg Asn Arg Ala Leu Met Ser Pro
    290                 295                 300
Ala Gly Met Leu Arg Gly Asp Phe Ser Leu Arg Leu Phe Asn Val Thr
305                 310                 315                 320
Pro Gln Asp Glu Gln Lys Phe His Cys Leu Val Leu Ser Gln Ser Leu
                325                 330                 335
Gly Phe Gln Glu Val Leu Ser Val Glu Val Thr Leu His Val Ala Ala
            340                 345                 350
Asn Phe Ser Val Pro Val Val Ser Ala Pro His Ser Pro Ser Gln Asp
        355                 360                 365
Glu Leu Thr Phe Thr Cys Thr Ser Ile Asn Gly Tyr Pro Arg Pro Asn
    370                 375                 380
Val Tyr Trp Ile Asn Lys Thr Asp Asn Ser Leu Leu Asp Gln Ala Leu
385                 390                 395                 400
```

Gln Asn Asp Thr Val Phe Leu Asn Met Arg Gly Leu Tyr Asp Val Val
            405                 410                 415

Ser Val Leu Arg Ile Ala Arg Thr Pro Ser Val Asn Ile Gly Cys Cys
        420                 425                 430

Ile Glu Asn Val Leu Leu Gln Gln Asn Leu Thr Val Gly Ser Gln Thr
        435                 440                 445

Gly Asn Asp Ile Gly Glu Arg Asp Lys Ile Thr Glu Asn Pro Val Ser
    450                 455                 460

Thr Gly Glu Lys Asn Ala Ala Thr
465                 470

<210> SEQ ID NO 170
<211> LENGTH: 456
<212> TYPE: PRT
<213> ORGANISM: Artificial Sequence
<220> FEATURE:
<223> OTHER INFORMATION: Light chain of the modified antibody

<400> SEQUENCE: 170

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Ala Pro Leu Lys Ile Gln
225                 230                 235                 240

Ala Tyr Phe Asn Glu Thr Ala Asp Leu Pro Cys Gln Phe Ala Asn Ser
                245                 250                 255

Gln Asn Gln Ser Leu Ser Glu Leu Val Val Phe Trp Gln Asp Gln Glu
            260                 265                 270

Asn Leu Val Leu Asn Glu Val Tyr Leu Gly Lys Glu Lys Phe Asp Ser
        275                 280                 285

-continued

```
Val His Ser Lys Tyr Met Gly Arg Thr Ser Phe Asp Ser Asp Ser Trp
290                 295                 300
Thr Leu Arg Leu His Asn Leu Gln Ile Lys Asp Lys Gly Leu Tyr Gln
305                 310                 315                 320
Cys Ile Ile His His Lys Lys Pro Thr Gly Met Ile Arg Ile His Gln
                325                 330                 335
Met Asn Ser Glu Leu Ser Val Leu Ala Asn Phe Ser Gln Pro Glu Ile
            340                 345                 350
Val Pro Ile Ser Asn Ile Thr Glu Asn Val Tyr Ile Asn Leu Thr Cys
        355                 360                 365
Ser Ser Ile His Gly Tyr Pro Glu Pro Lys Lys Met Ser Val Leu Leu
370                 375                 380
Arg Thr Lys Asn Ser Thr Ile Glu Tyr Asp Gly Val Met Gln Lys Ser
385                 390                 395                 400
Gln Asp Asn Val Thr Glu Leu Tyr Asp Val Ser Ile Ser Leu Ser Val
                405                 410                 415
Ser Phe Pro Asp Val Thr Ser Asn Met Thr Ile Phe Cys Ile Leu Glu
            420                 425                 430
Thr Asp Lys Thr Arg Leu Leu Ser Ser Pro Phe Ser Ile Glu Leu Glu
        435                 440                 445
Asp Pro Gln Pro Pro Asp His
450                 455

<210> SEQ ID NO 171
<211> LENGTH: 381
<212> TYPE: PRT
<213> ORGANISM: Artificial Sequence
<220> FEATURE:
<223> OTHER INFORMATION: Light chain of the modified antibody

<400> SEQUENCE: 171

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Val His Ser
            20                  25                  30
Tyr Gly Asn Thr Tyr Leu Tyr Trp Phe Gln Gln Arg Pro Gly Gln Ser
        35                  40                  45
Pro Arg Leu Leu Ile Tyr Arg Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Thr His Val Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
        210                 215                 220

Gly Gly Gly Gly Ser Gly Gly Gly Ser Pro Gly Trp Phe Leu Asp
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Ser Gln Pro Gly
    290                 295                 300

Gln Asp Cys Arg Phe Arg Val Thr Gln Leu Pro Asn Gly Arg Asp Phe
305                 310                 315                 320

His Met Ser Val Val Arg Ala Arg Arg Asn Asp Ser Gly Thr Tyr Leu
                325                 330                 335

Cys Gly Ala Ile Ser Leu Ala Pro Lys Ala Gln Ile Lys Glu Ser Leu
            340                 345                 350

Arg Ala Glu Leu Arg Val Thr Glu Arg Arg Ala Glu Val Pro Thr Ala
        355                 360                 365

His Pro Ser Pro Ser Pro Arg Pro Ala Gly Gln Phe Gln
    370                 375                 380

<210> SEQ ID NO 172
<211> LENGTH: 454
<212> TYPE: PRT
<213> ORGANISM: Artificial Sequence
<220> FEATURE:
<223> OTHER INFORMATION: Light chain of the modified antibody

<400> SEQUENCE: 172

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Phe Thr Val Thr Val Pro
225                 230                 235                 240

Lys Asp Leu Tyr Val Val Glu Tyr Gly Ser Asn Met Thr Ile Glu Cys
                245                 250                 255

Lys Phe Pro Val Glu Lys Gln Leu Asp Leu Ala Ala Leu Ile Val Tyr
            260                 265                 270

Trp Glu Met Glu Asp Lys Asn Ile Ile Gln Phe Val His Gly Glu Glu
        275                 280                 285

Asp Leu Lys Val Gln His Ser Ser Tyr Arg Gln Arg Ala Arg Leu Leu
    290                 295                 300

Lys Asp Gln Leu Ser Leu Gly Asn Ala Ala Leu Gln Ile Thr Asp Val
305                 310                 315                 320

Lys Leu Gln Asp Ala Gly Val Tyr Arg Cys Met Ile Ser Tyr Gly Gly
                325                 330                 335

Ala Asp Tyr Lys Arg Ile Thr Val Lys Val Asn Ala Pro Tyr Asn Lys
            340                 345                 350

Ile Asn Gln Arg Ile Leu Val Val Asp Pro Val Thr Ser Glu His Glu
        355                 360                 365

Leu Thr Cys Gln Ala Glu Gly Tyr Pro Lys Ala Glu Val Ile Trp Thr
    370                 375                 380

Ser Ser Asp His Gln Val Leu Ser Gly Lys Thr Thr Thr Thr Asn Ser
385                 390                 395                 400

Lys Arg Glu Glu Lys Leu Phe Asn Val Thr Ser Thr Leu Arg Ile Asn
                405                 410                 415

Thr Thr Thr Asn Glu Ile Phe Tyr Cys Thr Phe Arg Arg Leu Asp Pro
            420                 425                 430

Glu Glu Asn His Thr Ala Glu Leu Val Ile Pro Glu Leu Pro Leu Ala
        435                 440                 445

His Pro Pro Asn Glu Arg
    450

<210> SEQ ID NO 173
<211> LENGTH: 442
<212> TYPE: PRT
<213> ORGANISM: Artificial Sequence
<220> FEATURE:
<223> OTHER INFORMATION: Light chain of the modified antibody

<400> SEQUENCE: 173

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

-continued

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Val Ile His Val Thr Lys
225                 230                 235                 240

Glu Val Lys Glu Val Ala Thr Leu Ser Cys Gly His Asn Val Ser Val
                245                 250                 255

Glu Glu Leu Ala Gln Thr Arg Ile Tyr Trp Gln Lys Glu Lys Lys Met
            260                 265                 270

Val Leu Thr Met Met Ser Gly Asp Met Asn Ile Trp Pro Glu Tyr Lys
        275                 280                 285

Asn Arg Thr Ile Phe Asp Ile Thr Asn Asn Leu Ser Ile Val Ile Leu
    290                 295                 300

Ala Leu Arg Pro Ser Asp Glu Gly Thr Tyr Glu Cys Val Val Leu Lys
305                 310                 315                 320

Tyr Glu Lys Asp Ala Phe Lys Arg Glu His Leu Ala Glu Val Thr Leu
                325                 330                 335

Ser Val Lys Ala Asp Phe Pro Thr Pro Ser Ile Ser Asp Phe Glu Ile
            340                 345                 350

Pro Thr Ser Asn Ile Arg Arg Ile Ile Cys Ser Thr Ser Gly Gly Phe
        355                 360                 365

Pro Glu Pro His Leu Ser Trp Leu Glu Asn Gly Glu Glu Leu Asn Ala
    370                 375                 380

Ile Asn Thr Thr Val Ser Gln Asp Pro Glu Thr Glu Leu Tyr Ala Val
385                 390                 395                 400

Ser Ser Lys Leu Asp Phe Asn Met Thr Thr Asn His Ser Phe Met Cys
                405                 410                 415

Leu Ile Lys Tyr Gly His Leu Arg Val Asn Gln Thr Phe Asn Trp Asn
            420                 425                 430

Thr Thr Lys Gln Glu His Phe Pro Asp Asn
        435                 440

<210> SEQ ID NO 174
<211> LENGTH: 367
<212> TYPE: PRT
<213> ORGANISM: Artificial Sequence
<220> FEATURE:
<223> OTHER INFORMATION: Light chain of the modified antibody

<400> SEQUENCE: 174

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gln Val Ser His Arg Tyr
225                 230                 235                 240

Pro Arg Ile Gln Ser Ile Lys Val Gln Phe Thr Glu Tyr Lys Lys Glu
            245                 250                 255

Lys Gly Phe Ile Leu Thr Ser Gln Lys Glu Asp Glu Ile Met Lys Val
        260                 265                 270

Gln Asn Asn Ser Val Ile Ile Asn Cys Asp Gly Phe Tyr Leu Ile Ser
    275                 280                 285

Leu Lys Gly Tyr Phe Ser Gln Glu Val Asn Ile Ser Leu His Tyr Gln
290                 295                 300

Lys Asp Glu Glu Pro Leu Phe Gln Leu Lys Lys Val Arg Ser Val Asn
305                 310                 315                 320

Ser Leu Met Val Ala Ser Leu Thr Tyr Lys Asp Lys Val Tyr Leu Asn
                325                 330                 335

Val Thr Thr Asp Asn Thr Ser Leu Asp Asp Phe His Val Asn Gly Gly
            340                 345                 350

Glu Leu Ile Leu Ile His Gln Asn Pro Gly Glu Phe Cys Val Leu
        355                 360                 365

<210> SEQ ID NO 175
<211> LENGTH: 418
<212> TYPE: PRT
<213> ORGANISM: Artificial Sequence
<220> FEATURE:
<223> OTHER INFORMATION: Light chain of the modified antibody

<400> SEQUENCE: 175

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
            35                  40                  45

Pro Arg Leu Leu Ile Tyr Arg Val Ser Asn Arg Phe Ser Gly Val Pro
50                      55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Arg Glu Gly Pro Glu Leu
225                 230                 235                 240

Ser Pro Asp Asp Pro Ala Gly Leu Leu Asp Leu Arg Gln Gly Met Phe
            245                 250                 255

Ala Gln Leu Val Ala Gln Asn Val Leu Leu Ile Asp Gly Pro Leu Ser
            260                 265                 270

Trp Tyr Ser Asp Pro Gly Leu Ala Gly Val Ser Leu Thr Gly Gly Leu
    275                 280                 285

Ser Tyr Lys Glu Asp Thr Lys Glu Leu Val Val Ala Lys Ala Gly Val
    290                 295                 300

Tyr Tyr Val Phe Phe Gln Leu Glu Leu Arg Arg Val Val Ala Gly Glu
305                 310                 315                 320

Gly Ser Gly Ser Val Ser Leu Ala Leu His Leu Gln Pro Leu Arg Ser
            325                 330                 335

Ala Ala Gly Ala Ala Ala Leu Ala Leu Thr Val Asp Leu Pro Pro Ala
            340                 345                 350

Ser Ser Glu Ala Arg Asn Ser Ala Phe Gly Phe Gln Gly Arg Leu Leu
            355                 360                 365

His Leu Ser Ala Gly Gln Arg Leu Gly Val His Leu His Thr Glu Ala
    370                 375                 380

Arg Ala Arg His Ala Trp Gln Leu Thr Gln Gly Ala Thr Val Leu Gly
385                 390                 395                 400

Leu Phe Arg Val Thr Pro Glu Ile Pro Ala Gly Leu Pro Ser Pro Arg
                405                 410                 415

Ser Glu
```

```
<210> SEQ ID NO 176
<211> LENGTH: 472
<212> TYPE: PRT
<213> ORGANISM: Artificial Sequence
<220> FEATURE:
<223> OTHER INFORMATION: Light chain of the modified antibody

<400> SEQUENCE: 176
```

| | | | | | | | | | | | | | | |
|---|---|---|---|---|---|---|---|---|---|---|---|---|---|---|
| Asp | Val | Val | Met | Thr | Gln | Ser | Pro | Leu | Ser | Leu | Pro | Val | Thr | Leu | Gly |
| 1 | | | | 5 | | | | | 10 | | | | | 15 | |
| Gln | Pro | Ala | Ser | Ile | Ser | Cys | Arg | Ser | Ser | Gln | Ser | Leu | Val | His | Ser |
| | | | 20 | | | | | 25 | | | | | 30 | | |
| Tyr | Gly | Asn | Thr | Tyr | Leu | Tyr | Trp | Phe | Gln | Gln | Arg | Pro | Gly | Gln | Ser |
| | | | 35 | | | | 40 | | | | | 45 | | | |
| Pro | Arg | Leu | Leu | Ile | Tyr | Arg | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Phe | Gln | Gly |
| | | | | 85 | | | | | 90 | | | | | 95 | |
| Thr | His | Val | Pro | Tyr | Thr | Phe | Gly | Gly | Gly | Thr | Lys | Val | Glu | Ile | Lys |
| | | | 100 | | | | | 105 | | | | | 110 | | |
| Arg | Thr | Val | Ala | Ala | Pro | Ser | Val | Phe | Ile | Phe | Pro | Pro | Ser | Asp | Glu |
| | | | 115 | | | | | 120 | | | | | 125 | | |
| Gln | Leu | Lys | Ser | Gly | Thr | Ala | Ser | Val | Val | Cys | Leu | Leu | Asn | Asn | Phe |
| | 130 | | | | | 135 | | | | | 140 | | | | |
| Tyr | Pro | Arg | Glu | Ala | Lys | Val | Gln | Trp | Lys | Val | Asp | Asn | Ala | Leu | Gln |
| 145 | | | | | 150 | | | | | 155 | | | | | 160 |
| Ser | Gly | Asn | Ser | Gln | Glu | Ser | Val | Thr | Glu | Gln | Asp | Ser | Lys | Asp | Ser |
| | | | | 165 | | | | | 170 | | | | | 175 | |
| Thr | Tyr | Ser | Leu | Ser | Ser | Thr | Leu | Thr | Leu | Ser | Lys | Ala | Asp | Tyr | Glu |
| | | | 180 | | | | | 185 | | | | | 190 | | |
| Lys | His | Lys | Val | Tyr | Ala | Cys | Glu | Val | Thr | His | Gln | Gly | Leu | Ser | Ser |
| | | | 195 | | | | | 200 | | | | | 205 | | |
| Pro | Val | Thr | Lys | Ser | Phe | Asn | Arg | Gly | Glu | Cys | Gly | Gly | Gly | Gly | Ser |
| | 210 | | | | | 215 | | | | | 220 | | | | |
| Gly | Gly | Gly | Gly | Ser | Gly | Gly | Gly | Ser | Asp | Thr | Gln | Glu | Lys | Glu |
| 225 | | | | | 230 | | | | | 235 | | | | | 240 |
| Val | Arg | Ala | Met | Val | Gly | Ser | Asp | Val | Glu | Leu | Ser | Cys | Ala | Cys | Pro |
| | | | | 245 | | | | | 250 | | | | | 255 | |
| Glu | Gly | Ser | Arg | Phe | Asp | Leu | Asn | Asp | Val | Tyr | Val | Tyr | Trp | Gln | Thr |
| | | | 260 | | | | | 265 | | | | | 270 | | |
| Ser | Glu | Ser | Lys | Thr | Val | Val | Thr | Tyr | His | Ile | Pro | Gln | Asn | Ser | Ser |
| | | | 275 | | | | | 280 | | | | | 285 | | |
| Leu | Glu | Asn | Val | Asp | Ser | Arg | Tyr | Arg | Asn | Arg | Ala | Leu | Met | Ser | Pro |
| | 290 | | | | | 295 | | | | | 300 | | | | |
| Ala | Gly | Met | Leu | Arg | Gly | Asp | Phe | Ser | Leu | Arg | Leu | Phe | Asn | Val | Thr |
| 305 | | | | | 310 | | | | | 315 | | | | | 320 |
| Pro | Gln | Asp | Glu | Gln | Lys | Phe | His | Cys | Leu | Val | Leu | Ser | Gln | Ser | Leu |
| | | | | 325 | | | | | 330 | | | | | 335 | |
| Gly | Phe | Gln | Glu | Val | Leu | Ser | Val | Glu | Val | Thr | Leu | His | Val | Ala | Ala |
| | | | 340 | | | | | 345 | | | | | 350 | | |
| Asn | Phe | Ser | Val | Pro | Val | Val | Ser | Ala | Pro | His | Ser | Pro | Ser | Gln | Asp |
| | | | 355 | | | | | 360 | | | | | 365 | | |

```
Glu Leu Thr Phe Thr Cys Thr Ser Ile Asn Gly Tyr Pro Arg Pro Asn
    370                 375                 380

Val Tyr Trp Ile Asn Lys Thr Asp Asn Ser Leu Leu Asp Gln Ala Leu
385                 390                 395                 400

Gln Asn Asp Thr Val Phe Leu Asn Met Arg Gly Leu Tyr Asp Val Val
                405                 410                 415

Ser Val Leu Arg Ile Ala Arg Thr Pro Ser Val Asn Ile Gly Cys Cys
            420                 425                 430

Ile Glu Asn Val Leu Leu Gln Gln Asn Leu Thr Val Gly Ser Gln Thr
        435                 440                 445

Gly Asn Asp Ile Gly Glu Arg Asp Lys Ile Thr Glu Asn Pro Val Ser
    450                 455                 460

Thr Gly Glu Lys Asn Ala Ala Thr
465                 470

<210> SEQ ID NO 177
<211> LENGTH: 456
<212> TYPE: PRT
<213> ORGANISM: Artificial Sequence
<220> FEATURE:
<223> OTHER INFORMATION: Light chain of the modified antibody

<400> SEQUENCE: 177

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Ala Pro Leu Lys Ile Gln
225                 230                 235                 240

Ala Tyr Phe Asn Glu Thr Ala Asp Leu Pro Cys Gln Phe Ala Asn Ser
                245                 250                 255
```

Gln Asn Gln Ser Leu Ser Glu Leu Val Val Phe Trp Gln Asp Gln Glu
        260                 265                 270

Asn Leu Val Leu Asn Glu Val Tyr Leu Gly Lys Glu Lys Phe Asp Ser
        275                 280                 285

Val His Ser Lys Tyr Met Gly Arg Thr Ser Phe Asp Ser Asp Ser Trp
290                 295                 300

Thr Leu Arg Leu His Asn Leu Gln Ile Lys Asp Lys Gly Leu Tyr Gln
305                 310                 315                 320

Cys Ile Ile His His Lys Lys Pro Thr Gly Met Ile Arg Ile His Gln
                325                 330                 335

Met Asn Ser Glu Leu Ser Val Leu Ala Asn Phe Ser Gln Pro Glu Ile
        340                 345                 350

Val Pro Ile Ser Asn Ile Thr Glu Asn Val Tyr Ile Asn Leu Thr Cys
        355                 360                 365

Ser Ser Ile His Gly Tyr Pro Glu Pro Lys Lys Met Ser Val Leu Leu
        370                 375                 380

Arg Thr Lys Asn Ser Thr Ile Glu Tyr Asp Gly Val Met Gln Lys Ser
385                 390                 395                 400

Gln Asp Asn Val Thr Glu Leu Tyr Asp Val Ser Ile Ser Leu Ser Val
                405                 410                 415

Ser Phe Pro Asp Val Thr Ser Asn Met Thr Ile Phe Cys Ile Leu Glu
                420                 425                 430

Thr Asp Lys Thr Arg Leu Leu Ser Ser Pro Phe Ser Ile Glu Leu Glu
                435                 440                 445

Asp Pro Gln Pro Pro Asp His
        450                 455

<210> SEQ ID NO 178
<211> LENGTH: 624
<212> TYPE: PRT
<213> ORGANISM: Artificial Sequence
<220> FEATURE:
<223> OTHER INFORMATION: Heavy chain of the modified antibody

<400> SEQUENCE: 178

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Val His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ala Ala Lys Thr Thr Pro Pro Ser Val
            115                 120                 125

Tyr Pro Leu Ala Pro Gly Cys Gly Asp Thr Thr Gly Ser Ser Val Thr
        130                 135                 140

Leu Gly Cys Leu Val Lys Gly Tyr Phe Pro Glu Ser Val Thr Val Thr
145                 150                 155                 160

-continued

```
Trp Asn Ser Gly Ser Leu Ser Ser Val His Thr Phe Pro Ala Leu
                165                 170                 175

Leu Gln Ser Gly Leu Tyr Thr Met Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
                245                 250                 255

Lys Asp Val Leu Met Ile Ser Leu Thr Pro Lys Val Thr Cys Val Val
                260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
                340                 345                 350

Arg Ala Pro Gln Val Tyr Ile Leu Pro Pro Pro Ala Glu Gln Leu Ser
            355                 360                 365

Arg Lys Asp Val Ser Leu Thr Cys Leu Val Val Gly Phe Asn Pro Gly
            370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
        435                 440                 445

Thr Ile Ser Arg Ser Pro Gly Lys Gly Gly Gly Ser Gly Gly Gly
    450                 455                 460

Gly Ser Gly Gly Gly Ser Leu Gln Leu Gly Trp Arg Pro Gly Trp
465                 470                 475                 480

Phe Leu Asp Ser Pro Asp Arg Pro Trp Asn Pro Pro Thr Phe Ser Pro
            485                 490                 495

Ala Leu Leu Val Val Thr Glu Gly Asp Asn Ala Thr Phe Thr Cys Ser
            500                 505                 510

Phe Ser Asn Thr Ser Glu Ser Phe Val Leu Asn Trp Tyr Arg Met Ser
        515                 520                 525

Pro Ser Asn Gln Thr Asp Lys Leu Ala Ala Phe Pro Glu Asp Arg Ser
    530                 535                 540

Gln Pro Gly Gln Asp Cys Arg Phe Arg Val Thr Gln Leu Pro Asn Gly
545                 550                 555                 560

Arg Asp Phe His Met Ser Val Val Arg Ala Arg Arg Asn Asp Ser Gly
                565                 570                 575
```

-continued

```
Thr Tyr Leu Cys Gly Ala Ile Ser Leu Ala Pro Lys Ala Gln Ile Lys
            580                 585                 590

Glu Ser Leu Arg Ala Glu Leu Arg Val Thr Glu Arg Arg Ala Glu Val
        595                 600                 605

Pro Thr Ala His Pro Ser Pro Ser Pro Arg Pro Ala Gly Gln Phe Gln
    610                 615                 620

<210> SEQ ID NO 179
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 179

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

-continued

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Leu Gln
450                 455                 460

Leu Gly Trp Arg Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
            485                 490                 495

Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
            515                 520                 525

Ala Phe Pro Glu Asp Arg Ser Gln Pro Gly Gln Asp Cys Arg Phe Arg
        530                 535                 540

Val Thr Gln Leu Pro Asn Gly Arg Asp Phe His Met Ser Val Val Arg
545                 550                 555                 560

Ala Arg Arg Asn Asp Ser Gly Thr Tyr Leu Cys Gly Ala Ile Ser Leu
                565                 570                 575

Ala Pro Lys Ala Gln Ile Lys Glu Ser Leu Arg Ala Glu Leu Arg Val
            580                 585                 590

Thr Glu Arg Arg Ala Glu Val Pro Thr Ala His Pro Ser Pro Ser Pro
            595                 600                 605

Arg Pro Ala Gly Gln Phe Gln
        610                 615

<210> SEQ ID NO 180
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 180

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
50                  55                  60

```
Lys Asp His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Gly Ser Gly Gly Gly Gly Ser Leu Gln
450                 455                 460

Leu Gly Trp Arg Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
```

```
              485                 490                 495
Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
        515                 520                 525

Ala Phe Pro Glu Asp Arg Ser Gln Pro Gly Gln Asp Cys Arg Phe Arg
    530                 535                 540

Val Thr Gln Leu Pro Asn Gly Arg Asp Phe His Met Ser Val Val Arg
545                 550                 555                 560

Ala Arg Arg Asn Asp Ser Gly Thr Tyr Leu Cys Gly Ala Ile Ser Leu
                565                 570                 575

Ala Pro Lys Ala Gln Ile Lys Glu Ser Leu Arg Ala Glu Leu Arg Val
            580                 585                 590

Thr Glu Arg Arg Ala Glu Val Pro Thr Ala His Pro Ser Pro Ser Pro
        595                 600                 605

Arg Pro Ala Gly Gln Phe Gln
    610                 615

<210> SEQ ID NO 181
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 181

Glu Val Gln Leu Val Gln Ser Gly Ala Glu Val Lys Lys Pro Gly Glu
1               5                  10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

```
              225                 230                 235                 240

Phe Leu Phe Pro Pro Lys Pro Lys Asp Thr Leu Met Ile Ser Arg Thr
                     245                 250                 255

Pro Glu Val Thr Cys Val Val Asp Val Ser Gln Glu Asp Pro Glu
                     260                 265                 270

Val Gln Phe Asn Trp Tyr Val Asp Gly Val Glu Val His Asn Ala Lys
                     275                 280                 285

Thr Lys Pro Arg Glu Glu Gln Phe Asn Ser Thr Tyr Arg Val Val Ser
             290                 295                 300

Val Leu Thr Val Leu His Gln Asp Trp Leu Asn Gly Lys Glu Tyr Lys
         305                 310                 315                 320

Cys Lys Val Ser Asn Lys Gly Leu Pro Ser Ser Ile Glu Lys Thr Ile
                         325                 330                 335

Ser Lys Ala Lys Gly Gln Pro Arg Glu Pro Gln Val Tyr Thr Leu Pro
                     340                 345                 350

Pro Ser Gln Glu Glu Met Thr Lys Asn Gln Val Ser Leu Thr Cys Leu
                     355                 360                 365

Val Lys Gly Phe Tyr Pro Ser Asp Ile Ala Val Glu Trp Glu Ser Asn
             370                 375                 380

Gly Gln Pro Glu Asn Asn Tyr Lys Thr Thr Pro Pro Val Leu Asp Ser
         385                 390                 395                 400

Asp Gly Ser Phe Phe Leu Tyr Ser Arg Leu Thr Val Asp Lys Ser Arg
                         405                 410                 415

Trp Gln Glu Gly Asn Val Phe Ser Cys Ser Val Met His Glu Ala Leu
                     420                 425                 430

His Asn His Tyr Thr Gln Lys Ser Leu Ser Leu Ser Pro Gly Lys Gly
                     435                 440                 445

Gly Gly Gly Ser Gly Gly Gly Ser Gly Gly Gly Ser Leu Gln
                 450                 455                 460

Leu Gly Trp Arg Pro Gly Trp Phe Leu Asp Ser Pro Asp Arg Pro Trp
         465                 470                 475                 480

Asn Pro Pro Thr Phe Ser Pro Ala Leu Leu Val Val Thr Glu Gly Asp
                     485                 490                 495

Asn Ala Thr Phe Thr Cys Ser Phe Ser Asn Thr Ser Glu Ser Phe Val
                     500                 505                 510

Leu Asn Trp Tyr Arg Met Ser Pro Ser Asn Gln Thr Asp Lys Leu Ala
             515                 520                 525

Ala Phe Pro Glu Asp Arg Ser Gln Pro Gly Gln Asp Cys Arg Phe Arg
         530                 535                 540

Val Thr Gln Leu Pro Asn Gly Arg Asp Phe His Met Ser Val Val Arg
         545                 550                 555                 560

Ala Arg Arg Asn Asp Ser Gly Thr Tyr Leu Cys Gly Ala Ile Ser Leu
                         565                 570                 575

Ala Pro Lys Ala Gln Ile Lys Glu Ser Leu Arg Ala Glu Leu Arg Val
                     580                 585                 590

Thr Glu Arg Arg Ala Glu Val Pro Thr Ala His Pro Ser Pro Ser Pro
                     595                 600                 605

Arg Pro Ala Gly Gln Phe Gln
             610                 615

<210> SEQ ID NO 182
<211> LENGTH: 615
<212> TYPE: PRT
<213> ORGANISM: Artificial Sequence
```

<220> FEATURE:
<223> OTHER INFORMATION: Heavy chain of the modified antibody

<400> SEQUENCE: 182

```
Glu Val Gln Leu Val Gln Ser Gly Ala Glu Val Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Leu Gln
    450                 455                 460

Leu Gly Trp Arg Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
            485                 490                 495

Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
            515                 520                 525

Ala Phe Pro Glu Asp Arg Ser Gln Pro Gly Gln Asp Cys Arg Phe Arg
            530                 535                 540

Val Thr Gln Leu Pro Asn Gly Arg Asp Phe His Met Ser Val Val Arg
545                 550                 555                 560

Ala Arg Arg Asn Asp Ser Gly Thr Tyr Leu Cys Gly Ala Ile Ser Leu
                565                 570                 575

Ala Pro Lys Ala Gln Ile Lys Glu Ser Leu Arg Ala Glu Leu Arg Val
                580                 585                 590

Thr Glu Arg Arg Ala Glu Val Pro Thr Ala His Pro Ser Pro Ser Pro
            595                 600                 605

Arg Pro Ala Gly Gln Phe Gln
    610                 615

<210> SEQ ID NO 183
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 183

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Gly Gly Gly Ser Leu Gln
    450                 455                 460

Leu Gly Trp Arg Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
                485                 490                 495

Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
        515                 520                 525

Ala Phe Pro Glu Asp Arg Ser Gln Pro Gly Gln Asp Cys Arg Phe Arg
    530                 535                 540

Val Thr Gln Leu Pro Asn Gly Arg Asp Phe His Met Ser Val Val Arg
545                 550                 555                 560
```

Ala Arg Arg Asn Asp Ser Gly Thr Tyr Leu Cys Gly Ala Ile Ser Leu
                565                 570                 575

Ala Pro Lys Ala Gln Ile Lys Glu Ser Leu Arg Ala Glu Leu Arg Val
            580                 585                 590

Thr Glu Arg Arg Ala Glu Val Pro Thr Ala His Pro Ser Pro Ser Pro
        595                 600                 605

Arg Pro Ala Gly Gln Phe Gln
    610                 615

<210> SEQ ID NO 184
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 184

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Leu Gln
450                 455                 460

Leu Gly Trp Arg Pro Gly Trp Phe Leu Asp Ser Pro Asp Arg Pro Trp
465                 470                 475                 480

Asn Pro Pro Thr Phe Ser Pro Ala Leu Leu Val Val Thr Glu Gly Asp
            485                 490                 495

Asn Ala Thr Phe Thr Cys Ser Phe Ser Asn Thr Ser Glu Ser Phe Val
            500                 505                 510

Leu Asn Trp Tyr Arg Met Ser Pro Ser Asn Gln Thr Asp Lys Leu Ala
            515                 520                 525

Ala Phe Pro Glu Asp Arg Ser Gln Pro Gly Gln Asp Cys Arg Phe Arg
            530                 535                 540

Val Thr Gln Leu Pro Asn Gly Arg Asp Phe His Met Ser Val Val Arg
545                 550                 555                 560

Ala Arg Arg Asn Asp Ser Gly Thr Tyr Leu Cys Gly Ala Ile Ser Leu
            565                 570                 575

Ala Pro Lys Ala Gln Ile Lys Glu Ser Leu Arg Ala Glu Leu Arg Val
            580                 585                 590

Thr Glu Arg Arg Ala Glu Val Pro Thr Ala His Pro Ser Pro Ser Pro
            595                 600                 605

Arg Pro Ala Gly Gln Phe Gln
            610                 615

<210> SEQ ID NO 185
<211> LENGTH: 615
<212> TYPE: PRT
<213> ORGANISM: Artificial Sequence
<220> FEATURE:
<223> OTHER INFORMATION: Heavy chain of the modified antibody

<400> SEQUENCE: 185

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45
```

-continued

```
Gly Asn Ile Asp Pro Ser Asp Ser Asp Thr His Tyr Ser Pro Ser Phe
 50                  55                  60

Gln Gly His Val Thr Leu Ser Val Asp Lys Ser Ile Ser Thr Ala Tyr
 65                  70                  75                  80

Leu Gln Leu Ser Ser Leu Lys Ala Ser Asp Thr Ala Met Tyr Tyr Cys
                 85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Gly Gly Gly Ser Leu Gln
450                 455                 460

Leu Gly Trp Arg Pro Gly Trp Phe Leu Asp Ser Pro Asp Arg Pro Trp
```

```
465                 470                 475                 480
Asn Pro Pro Thr Phe Ser Pro Ala Leu Leu Val Val Thr Glu Gly Asp
                485                 490                 495
Asn Ala Thr Phe Thr Cys Ser Phe Ser Asn Thr Ser Glu Ser Phe Val
                500                 505                 510
Leu Asn Trp Tyr Arg Met Ser Pro Ser Asn Gln Thr Asp Lys Leu Ala
            515                 520                 525
Ala Phe Pro Glu Asp Arg Ser Gln Pro Gly Gln Asp Cys Arg Phe Arg
        530                 535                 540
Val Thr Gln Leu Pro Asn Gly Arg Asp Phe His Met Ser Val Val Arg
545                 550                 555                 560
Ala Arg Arg Asn Asp Ser Gly Thr Tyr Leu Cys Gly Ala Ile Ser Leu
                565                 570                 575
Ala Pro Lys Ala Gln Ile Lys Glu Ser Leu Arg Ala Glu Leu Arg Val
                580                 585                 590
Thr Glu Arg Arg Ala Glu Val Pro Thr Ala His Pro Ser Pro Ser Pro
            595                 600                 605
Arg Pro Ala Gly Gln Phe Gln
        610                 615
```

MODIFIED BIFUNCTIONAL ANTI-HUMAN SIGNAL REGULATORY PROTEIN ALPHA (SIRPA) ANTIBODY AND METHOD OF USE THEREOF FOR TREATING CANCER

CROSS-REFERENCE TO RELATED APPLICATIONS

This application is the US national stage of International Patent Application No. PCT/EP2018/078082, filed on Oct. 15, 2018, which claims the benefit of European Patent Application No. 17306396.7 filed on Oct. 13, 2017, both of which are incorporated herein by reference in their entireties.

The invention pertains to the field of immunotherapy. The present invention provides new modified anti-SIRPa antibodies linked to an immunotherapeutic agent which are bifunctional and able to specifically enhance the immune response and uses thereof.

Targeting immune checkpoints of the adaptive immunity has shown great therapeutic efficacy to fight numerous diseases notably cancers, but in a limited proportion of patients. Immune checkpoint on innate myeloid cells (macrophages, dendritic cells, MDSC, PMN) remain poorly studied while these cells represent the most abundant immune cell type in many solid tumors and are often associated with a poor outcome. Combining immune checkpoint therapies targeting both innate (mediated by myeloid cells) and adaptive (mediated by T cells) immune responses has demonstrated great efficiency in preclinical models but remains a challenge in the clinic.

The present invention discloses bifunctional anti-SIRPa antibodies or antigen-binding fragments thereof with unique structure showing enhanced efficiency when the immunotherapeutic agent is grafted onto the heavy chain of the anti-SIRPa antibody or antigen-binding fragment thereof but not on the light chain of the anti-SIRPa antibody. Here, the Inventors provide modified anti-SIRPa antibodies, in particular humanized antibodies, 0 that antagonize the SIRPa-CD47 interaction (to release the brake on myeloid cells) but do not specifically bind SIRPg (to not affect the SIRPg-CD47 interaction required for effective T-cell activation and adhesion) and, in the same time, ii) that are capable of inducing T cells activation and/or proliferation through inhibition of the PD1/PDL1 or CTLA-4/CD80 or CD80/PDL1 axis as well as potentializing the 4-1BB/4-1BBL or CD80/CD28 signals (to induce potent adaptative immune response, in particular anti-tumor response and/or inducing long-live memory T cells).

As compared to other antibodies, or combination of antibodies brought separately, the effect of compounds according to the invention is enhanced on the myeloid cells and on the T cell activation and/or proliferation.

The particular structure confers to the molecule an unexpected efficiency to its targets and suggests an interesting potential for a greater clinical effectiveness and a lower therapeutic cost.

Signal regulatory protein alpha, or SIRPa (also designated as SIRPa, CD172a or SHPS-1), is expressed on monocytes, most subpopulations of tissue macrophages, granulocytes, subsets of dendritic cells in lymphoid tissues, some bone marrow progenitor cells, and to varying levels on neurons, with a notably high expression in synapse-rich areas of the brain. Interaction of SIRPa, expressed by myeloid cells, with the ubiquitous receptor CD47, widely expressed at lower levels by most healthy cells but also overexpressed in some cancer cells, is an important immune checkpoint of the innate response, involved in the regulation of myeloid functions. CD47 interacts with SIRPa and leads to the transmission of a "don't eat me" signal to phagocytic macrophages, which then leave target cells unaffected. The SIRPa/CD47 pathway is nowadays subject to different pharmaceutical developments to enhance macrophages phagocytosis. Blockade of the CD47/SIRPa pathway via agents targeting CD47, by enhancing antibody-dependent phagocytosis by macrophages, has been described to synergize with depleting therapeutic anticancer antibodies such as Trastuzumab (anti-Her2), Cetuximab (anti-EGFR), Rituximab (anti-CD20) and Alemtuzumab (anti-CD52).

However, it has recently been shown that agents targeting CD47 (anti-CD47 or SIRPa-Fc) present hematological toxicity (anemia or thrombocytopenia) related to CD47 physiological role. Besides, CD47 also engages with another member of the SIRP family, SIRP-gamma (also designated as SIRPg, SIRPγ, CD172g or SIRP beta 2) that is present at the surface of human T cells and not on human myeloid cells. SIRPg is the result of a duplication of SIRPb gene in old-world primates nearly 35 million years ago and it is expressed in a restricted manner on T lymphocytes as opposed to SIRPa expression on myeloid cells. SIRPg is absent in mice. It has been shown that the SIRPg-CD47 interaction mediates cell-cell adhesion, enhances superantigen-dependent T-cell-mediated proliferation and co-stimulates T-cell activation (Piccio et al., Blood, 105:6, 2005). Due to the high similarity of sequences between SIRPa and SIRPg, in particular in the region that interacts with CD47, the anti-SIRPa antibodies disclosed in the prior art also bind SIRPg and have undesirable effects in humans, such as an inhibition of the proliferation of T-cells and a decrease of the immune response. Such side effects of anti-CD47 or non-selective anti-SIRPa antibodies could not be predicted since the tests of the known antibodies were performed in mice models, which do not possess the SIRPg gene, and thus such side effects were absent.

Immune cells activation is governed by the integration of balance co-stimulatory and co-inhibitory signals. T cell receptor (TCR)-mediated T cell activation is modulated by both co-stimulatory and co-inhibitory signals. The antigen-independent second signal modifies first signal, provided by interaction of antigenic peptide-MHC complex with the TCR, which confers specificity to the response. T cell co-stimulatory and co-inhibitory pathways have a broad immunoregulatory functions, controlling effector, memory and regulatory T cells, as well as naïve T cells. Therapeutic modulation of those pathways is translating to effective new strategies for treating cancer (For review see Schildberg et al., 44(5), Immunity, 2016). This second signal is mediated by two types of molecules: the Ig superfamily (such as LAG3, CD226-TIGIT-CD96) and the TNF-TNF receptor superfamily. T-cell activation is initiated by the recognition of the antigen by the TCR (first signal) and then costimulatory signals (second signal) mediated mainly by the CD28 costimulatory molecules expressed by T-cells which engage with CD80 and CD86 molecules expressed by antigen-presenting cells.

These two signals induce T-cell activation and, in the same time, the expression of inducible co-stimulatory and co-inhibitory molecules, which will determine the threshold of activation of already antigen-experienced and/or memory T lymphocytes. OX40 interaction with OX40-ligand (OX40L), ICOS interaction with ICOS ligand (ICOSL) and 4-1BB engagement with 4-1BB ligand (4-1BBL) are the major sources of inducible co-stimulatory molecules. In parallel, inducible CTLA-4 engagement with CD80 and CD86 (same ligand which is CD28) and inducible PD-1 engagement with PD-L1 or PD-L2 are the major sources of immune cell inhibition to counter-balance excess of activation. Inter-connection between this pathway complicates the interpretation of a given molecule since, to date, interaction between CD80 and PDL-1 and interaction between ICOSL with CD28 or CTLA-4 have been described in humans. PD1 is only expressed on activated T cells and PDL1 can be expressed on many cell types comprising the immune system, epithelial and endothelial cells. PD1 has two ligands: PDL1 and PDL2, with a better affinity for PDL2. PD1 has four splice variants expressed on human PBMC. The function of many of these splice variants is still unclear but a soluble variant missing a transmembrane part is involved in autoimmune diseases and is detected in inflammatory diseases (Nielsen et al., Cell Immunol, 2005, 235:109-116; Ueda et al., Nature, 2003 423:506-511; Wan et al., J. Immunol, 2006, 177:8844-8850). The inclusion of the soluble PD1 in a vaccine vector improves vaccine efficacy, probably by binding its ligands and inhibiting PD1 signal activation. PD1 ligation reduces signals downstream of TCR stimulation on T cells, inhibiting T cell response and resulting in decreased activation and cytokine production. Both strategy using anti-PD1 or anti-PDL1 to disrupt the interaction was a success in cancer therapy (Brahmer et al., N Eng J Med, 366(26), 2012; Powles et al., Nature, 515(7528), 2014; Topalian et al., N Eng J Med, 366(26), 2012; Ansell, Curr Opin Hematol, 22(4), 2015).

PDL1 is more widely expressed than PDL2, the other PD1 ligand. PDL1 is expressed by a variety of hematopoietic and non-hematopoietic cells. Its expression in tissues enables to regulate T cell responses locally. Proinflammatory stimuli induce PDL1 expression to downstream regulate T cell responses in tissues protecting tissues from immune mediated damages of tumors from immune attack. Tumors and microbes that causes chronic infections have exploited the co-inhibitory pathways to evade immune defense.

Ongoing studies on regulation of the immune responses have led to the identification of multiple other immunologic pathways that may be targeted for the development of cancer therapies. Those molecules are referred herein as immune checkpoint co-activators or co-inhibitors such as CTLA4, CD28, CD80, CD86, OX40, OX40L and 4-1BB, 4-1BBL (see review Sharma et al., Cell, 161(2), 2015 and Pardoll, Nature Reviews Cancer, 12(4), 2012).

A role for CD80 (B7-1) and CD86 (B7-2) on T cells also may contribute to downregulation of immune responses. Although CD80 and CD86 on antigen-presenting cells (APCs) have well-recognized roles as T cell costimulatory molecules, the functional significance of CD80 and CD86 expression on T cells is not well understood. CD86 is constitutively expressed on some resting T cells, whereas CD80 is not present on resting T cells. Both molecules can be upregulated on T cells. Tumors do not express B7 molecule and can evade immune system regulation. CD80 and CD86 bind to CTLA4 with a better avidity than to CD28, which eventually attenuates or prevents CD28 co-stimulation by competition and negative signaling. Since CD28 co-stimulation is crucial for T-cell activation, immunomodulation via blockade of CD28/CD80/CD86 is a promising approach to prevent inappropriate T-cell activation in the setting of transplantation and also to potentially treat T-cell mediated autoimmune diseases. (Crepeau et al., Expert Opin Biol Ther. 2017; 17(8):1001-1012).

ICOSL, OX40L and 4-1BBL are ligands of the co-stimulatory molecules ICOS, OX40 and 4-1BB respectively, new immune checkpoints that are being evaluated in preclinical tumor models and/or in the clinic with cancer patients. ICOSL acts as a costimulatory signal for T-cell proliferation and cytokine secretion, induces B-cell proliferation and differentiation into plasma cells and could play an important role in mediating local tissue responses to inflammatory conditions, as well as in modulating the secondary immune response by co-stimulating memory T-cell function. The binding of OX40 to its ligand OX40L plays an important role in antigen-specific T-cell expansion and survival. While OX40 is expressed predominantly on T-lymphocytes early after antigen activation, OX40L is expressed on activated antigen presenting cells and endothelial cells within acute inflammatory environments. Modulating OX40 signaling and/or deleting different T-cell subsets has the potential to mediate both immune suppression for autoimmunity and immune stimulation for anti-cancer therapeutics (Willoughby et al., Mol. Immunol., 2017 March; 83:13-22).

OX40L and 4-1BBL are members of TNF Ligand superfamily and are membrane ligands with no known soluble form. 4-1BBL is expressed on myeloid, lymphoid and stromal cells and binds to 4-1BB (CD137), which is a member of the TNF receptor family. Targeting 4-1BB or 4-1BBL has important implications in many clinical conditions such as autoimmune diseases or viral infections and as well, including cancers (Wang et al., Immunol. Rev., 2009: 229(1): 192-215) (for review see Vinay et al., Expert Opin Ther Targets. 2016; 20(3):361-73). 4-1BB-mediated anti-cancer effects are based on its ability to induce activation of cytotoxic T lymphocytes (CTL), and among others, high amounts of IFN-γ. 4-1BB receptor is constitutively expressed on a number of cells, albeit at low levels, including Foxp3+ Tregs and dendritic cells. CD4+ and CD8+ T cells express 4-1BB at comparable levels, upon activation, signals through 4-1BB are more biased toward CD8+ T cells, both in vitro, and in vivo.

SUMMARY OF THE INVENTION

The accumulation of immunosuppressive and hypo-stimulatory myeloid cells within tumor microenvironment limits the efficiency of T-cell responses and the efficacy of immunotherapies, in particular those targeting at immune checkpoint such as CTLA-4 or PD-1/PD-L1. However, in parallel, immunotherapies targeting at innate immune checkpoint have shown limited efficacy alone, since T-cell responses remained blocked mainly by absence of co-stimulation within tumor-microenvironment and/or the engagement of co-inhibitory molecules with the ligand expressed by tumor cells or antigen-presenting cells. Combining immunotherapies targeting at both immune checkpoint of adaptive (T-cells) and innate (myeloid cells) cells have demonstrated potent efficacy at preclinical levels. However, the validation and development of combined immunotherapies are strongly limited by the cost of bio-therapies and the limited access to such immunotherapies. There remains therefore a significant need in the art for new and improved agents for safe immunotherapy, notably against cancer, targeting innate myeloid immune cells with an effective positive impact on adaptive immune response, in particular T cell immune responses. The present inventors have made a significant step forward with the invention disclosed herein.

Here, the Inventors provide modified anti-SIRPa antibodies, in particular humanized antibodies, 0 that antagonize the SIRPa-CD47 interaction (to release the brake on myeloid cells) but do not specifically bind SIRPg (to not affect the SIRPg-CD47 interaction required for effective T-cell activation and adhesion) and, in the same time, ii) that are capable of inducing T cells activation and/or proliferation through inhibition of the PD1/PDL1 or CTLA-4/CD80 or CD80/PDL1 axis as well as potentializing the 4-1BB/4-1BBL or CD80/CD28 signals (to induce potent adaptative immune response, in particular anti-tumor response and/or inducing long-live memory T cells).

The modified antibodies of the invention are bifunctional since they combine the specific anti-SIRPa effects and the effects of an immunotherapeutic agent engrafted to the antibody.

They have in particular the following advantages:

They activate innate and adaptive immune responses with a synergistic effect on checkpoint inhibitor and costimulatory agents;

They avoid hematological toxicity due to restricted expression of SIRPa (no binding to human Red Blood Cells (RBC) and platelets) in contrast to CD47-targeting agents (anti-CD47 mAbs or SIRPa-fc recombinant proteins);

They reduce tumor growth and modify tumor microenvironment in monotherapy; They stimulate adaptive immune responses, by modifying immune microenvironment and removing immunosuppression, leading to durable and robust memory T-cell responses in cancers, vaccine strategies, infectious disease or post-trauma;

They induce durable and robust anti-tumor memory T lymphocytes responses;

They enable human T cell immune responses, being selective antagonist of SIRPa-CD47 interaction, not disturbing the CD47/SIRPg interaction.

Unexpectedly, the Inventors provide such selective and functional antibodies despite the high sequence identity between SIRPa and SIRPg sequences and despite the fact that some immunotherapeutic agents grafted to an antibody may lose their functional properties.

These modified antibodies are particularly promising for numerous therapeutic applications, in particular for the treatment of cancer including inflammatory cancers and cancers with infiltrated myeloid cells (in particular with infiltrated MDSCs and/or TAM cells).

Modified SIRPa Antibodies (with Epitopes)

In an aspect, the invention relates to a modified anti-SIRPa antibody or antigen-binding fragment thereof that specifically binds to at least one peptide comprising or consisting of amino acid sequence selected from the group consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFT-CESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment comprising, in particular being linked to, an immunotherapeutic agent.

The modified anti-SIRPa antibodies of the present invention correspond to the anti-SIRPa antibodies described in the patent application PCT/EP/2017/059071 that have been coupled with an immunotherapeutic agent.

The functional properties of the modified antibodies of the invention are unexpected for several reasons. In particular, it is shown in the present application that an immunotherapeutic agent grafted to an antibody can lose its functional properties, despite the fact that it is still able to bind its ligand. Also, two immunotherapeutic agents that bind the same ligand may be different in terms of efficiency when grafted on an antibody (see CD80 and CD86 in the Examples). Unexpectedly, the present application shows synergistic effects by combination of the anti-SIRPa and the immunotherapeutic agent into one bifunctional antibody according to the invention (in particular regarding the secretion of TNFa by PBMC in the Examples).

Unless defined otherwise, all technical and scientific terms used herein have the same meaning as commonly understood to one skilled in the relevant art. For convenience, the meaning of certain terms and phrases employed in the specification, examples, and claims are provided.

As used herein, the term "antibody" refers to any kind of antibodies, such as monoclonal antibodies, polyclonal antibodies, recombinant antibodies, chimeric antibodies and humanized antibodies.

The antibodies of the present invention include monoclonal and polyclonal antibodies. As used herein, a "monoclonal antibody" is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several known technologies like phage, bacteria, yeast or ribosomal display, as well as by classical methods exemplified by hybridoma-derived antibodies. Thus, the term "monoclonal" is used to refer to all antibodies derived from one nucleic acid clone.

The antibodies of the present invention include recombinant antibodies. As used herein, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

The antibodies of the present invention include chimeric antibodies. As used herein, a "chimeric antibody" refers to an antibody in which the sequence of the variable domain derived from the germline of a mammalian species, such as a mouse, have been grafted onto the sequence of the constant domain derived from the germline of another mammalian species, such as a human.

The antibodies of the present invention include humanized antibodies. As used herein, a "humanized antibody" refers to an antibody in which CDR sequences derived from the germline of another mammalian species, such as a mouse, have been grafted onto human framework sequences.

As used herein, an "antigen-binding fragment of an antibody" means a part of an antibody, i.e. a molecule corresponding to a portion of the structure of the antibody of the invention, that exhibits antigen-binding capacity for SIRPa, possibly in its native form; such fragment especially exhibits the same or substantially the same antigen-binding specificity for said antigen compared to the antigen-binding specificity of the corresponding four-chain antibody. To this end, an antigen-binding fragment of an antibody comprises a heavy chain comprising a heavy chain variable domain comprising HCDR1, HCDR2 and HCDR3, and a fragment of a heavy chain constant domain. By a fragment of a heavy chain constant domain, it should be understood that the antigen-binding fragment therefore comprises at least a portion of a full heavy chain constant domain. As examples, a heavy chain constant domain may comprise or consist of at least the $C_H1$ domain of a heavy chain, or at least the $C_H1$ and the $C_H2$ domains of a heavy chain, or at least the $C_H1$, $C_H2$ and $C_H3$ domains of a heavy chain. A fragment of a heavy chain constant domain may also be defined as comprising at least a portion of the Fc (Fragment crystallisable) domain of the heavy chain. Accordingly, antigen-binding fragment of an antibody encompasses the Fab portion of a full antibody, the $F(ab')_2$ portion of a full antibody, the Fab' portion of a full antibody. The heavy chain constant domain may also comprise or consist in a full heavy chain constant domain, for example illustrated in the present description, wherein several full heavy chain constant domains are described. In a particular embodiment of the invention, and when the antigen-binding fragment of an antibody comprises a fragment of a heavy chain constant domain comprising or consisting in a portion of a full heavy chain constant domain, the heavy chain constant domain fragment may consist of at least 10 amino acid residues; or may consist of 10 to 300 amino acid residues, in particular 210 amino acid residues.

Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity between the antibody and the target fragment. These antigen-binding fragments may also be designated as "functional fragments" of antibodies.

Antigen-binding fragments of antibodies are fragments which comprise their hypervariable domains designated CDRs (Complementary Determining Regions) or part(s) thereof encompassing the recognition site for the antigen, i.e. the extracellular domain of SIRPa, thereby defining antigen recognition specificity.

Each Light and Heavy chain variable domains (respectively VL and VH) of a four-chain immunoglobulin has three CDRs, designated VL-CDR1 (or LCDR1), VL-CDR2 (or LCDR2), VL-CDR3 (or LCDR3) and VH-CDR1 (or HCDR1), VH-CDR2 (or HCDR2), VH-CDR3 (or HCDR3), respectively.

The skilled person is able to determine the location of the various regions/domains of antibodies by reference to the standard definitions in this respect set forth, including a reference numbering system, a reference to the numbering system of KABAT or by application of the IMGT "collier de perle" algorithm. In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

Based on the structure of four-chain immunoglobulins, antigen-binding fragments can thus be defined by comparison with sequences of antibodies in the available databases and prior art, and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen binding fragments of an antibody that contain the variable domains comprising the CDRs of said antibody encompass Fv, dsFv, scFv, Fab, Fab', F(ab')2. Fv fragments consist of the VL and VH domains of an antibody associated together by hydrophobic interactions; in dsFv fragments, the VH:VL heterodimer is stabilized by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen binding sites, like the native immunoglobulin molecule; on the other hand, Fv (a VHVL dimmer constituting the variable part of Fab), dsFv, scFv, Fab, and Fab' fragments are monovalent, i.e. they comprise a single antigen-binding site. These basic antigen-binding fragments of the invention can be combined together to obtain multivalent antigen-binding fragments, such as diabodies, tribodies or tetrabodies. These multivalent antigen-binding fragments are also part of the present invention.

As used herein, the term "bispecific" antibodies refers to antibodies that recognize two different antigens by virtue of possessing at least one region (e.g. derived from a variable region of a first antibody) that is specific for a first antigen, and at least a second region (e.g. derived from a variable region of a second antibody) that is specific for a second antigen. A bispecific antibody specifically binds to two target antigens and is thus one type of multispecific antibody. Multispecific antibodies, which recognize two or more different antigens, can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen such as BiME (Bispecific Macrophage Enhancing antibodies), BiTE (bispecific T cell engager), DART (Dual affinity retargeting); DNL (dock-and-lock), DVD-Ig (dual variable domain immunoglobulins), HAS (human serum albumin), kih (knobs into holes).

Accordingly, some bispecific antibodies can be directed against SIRPa and a second antigen. In particular said second antigen is different from the ligand of the immunotherapeutic agent.

In an embodiment, the invention relates to a modified anti-SIRPa antibody or antigen-binding fragment thereof as defined above that is bispecific. Exemplary modified antibodies include those targeting SIRPa as a first antigen and an immunomodulatory checkpoint immune cell marker, such as PD1, PDL1, PDL2, CTLA-4, CD80, CD86, CD28, 4-1BB, 4-1BBL, CD40, CD40L, ICOS, ICOS-L, OX40L, GITR, HVEM, BTLA, CD160, LIGHT, TNFRSF25, 2B4, CD48, Tim1, Tim3, Tim4, Gal9, LAG-3, CD40, CD40L, CD70, CD27, VISTA, B7H3, B7H4 (B7x), TIGIT, CD112, HHLA2 (B7-H7), TMIGD2 (CD28H) and Butyrophilin-like2 (BTNL2), in particular PDL1, PD1, CD80, CD86, OX40L, 4-1BBL or ICOSL, as a second antigen.

Several researches to develop therapeutic antibodies had led to engineer the Fc regions to optimize antibody properties allowing the generation of molecules that are better suited to the pharmacology activity required of them. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Several mutations located at the interface between the CH2 and CH3 domains, such as T250Q/M428L and M252Y/S254T/T256E+H433K/N434F, have been shown to increase the binding affinity to FcRn and the half-life of IgG1 in vivo. However, there is not always a direct relationship between increased FcRn binding and improved half-life. One approach to improve the efficacy of a therapeutic antibody is to increase its serum persistence, thereby allowing higher circulating levels, less frequent administration and reduced doses. Engineering Fc regions may be desired to either reduce or increase the effector function of the antibody. For antibodies that target cell-surface molecules, especially those on immune cells, abrogating effector functions is required. Conversely, for antibodies intended for oncology use, increasing effector functions may improve the therapeutic activity. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions. Binding of IgG to the FcγRs or C1q depends on residues located in the hinge region and the CH2 domain. Two regions of the CH2 domain are critical for FcγRs and C1q binding, and have unique sequences in IgG2 and IgG4.

The invention comprises antibodies and fragments thereof but also comprises macromolecules such as artificial proteins, peptides and any chemical compounds with the capacity to bind antigens mimicking that of antibodies, also termed herein "antigen-binding antibody mimetics". Such proteins comprise affitins and anticalins. Affitins are artificial proteins with the ability to selectively bind antigens. They are structurally derived from the DNA binding protein Sac7d, found in *Sulfolobus acidocaldarius*, a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., J. mol. Biol., 383:5, 2008). The skilled person may readily develop anticalins with the required binding properties using methods know in the art, in particular as disclosed in patent application WO2008068637 and the above-cited publication, in particular the generation of phage display and/or ribosome display libraries and their screening using an antigen as disclosed herein. Anticalins are artificial proteins that are able to bind to antigens, either to proteins or to small molecules. They are antibody mimetic derived from human lipocalins which are a family of naturally binding proteins. Anticalins are about eight times smaller with a size of about 180 amino acids and a mass of about 20 kDa (Skerra, Febs J., 275:11, 2008). Anticalin phage display libraries have been generated which allow for the screening and selection, in particular of anticalins with specific binding properties. The skilled person may readily develop affitins with the required binding properties using methods know in the art, in particular as disclosed in EP patent EP1270725 B1, U.S. Pat. No. 8,536,307 B2, (Schlehuber and Skerra, Biophys. Chem., 96:2-3, 2002) and the above-cited publication, in particular the generation of phage display and/or ribosome display libraries and their screening using an antigen as disclosed herein. Anticalins and affitins may both be produced in a number of expression system comprising bacterial expressin systems. Thus, the invention provides affitins, anticalins and other similar antibody mimetics with the features of the modified antibodies described herein, in particular with regard to the binding to SIRPa, the inhibition of the interaction between SIRPa and CD47, the non-binding to SIRPg, the non inhibition of the proliferation of T cells, the increase of the proliferation of T cells, the non-inhibition of the interaction between SIRPg and CD47 all of which are contemplated as macromolecules of the invention. All the embodiments disclosed herein for antibodies or fragments thereof are transposed mutatis mutandis to the macromolecules of the invention, in particular to antigen-binding antibody mimetics.

As used herein, the term "epitope" means the part of an antigen to which the antibody binds. The epitopes of protein antigens can be divided into two categories, conformational epitope and linear epitope. A conformational epitope corresponds to discontinuous sections of the antigen's amino acid sequence. A linear epitope corresponds to a continuous sequence of amino acids from the antigen. In the invention, the peptides that are present within SIRPa and that are bound by the anti-SIRPa antibodies are constitutive of the epitope specifically recognized by these antibodies.

As used herein, a "modified antibody" corresponds to a molecule comprising an antibody or an antigen-binding fragment thereof, wherein said antibody or functional fragment thereof is associated with a functionally different molecule. A modified antibody of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. With similar techniques, especially by chemical coupling or grafting, a modified antibody can be prepared with a biologically active molecule, said active molecule being for example chosen among toxins, in particular *Pseudomonas* exotoxin A, the A-chain of plant toxin ricin or saporin toxin, especially a therapeutic active ingredient, a vector (including especially a protein vector) suitable for targeting the antibody or functional fragment to specific cells or tissues of the human body, or it may be associated with a label or with a linker, especially when fragments of the antibody are used. PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free cysteine residues present in the sequence of the antibody or functional fragment or through added free Cysteine residues in the amino sequence of the antibody or functional fragment.

In the invention, the modified anti-SIRPa antibodies or fragments thereof comprised, in particular are linked to, an immunotherapeutic agent. Such modified antibodies are also referred to as "bifunctional", i.e. they have two therapeutic effects: a first effect resulting from the interaction of the anti-SIRPa antibody with SIRPa and a second effect resulting from the interaction of the immunotherapeutic agent with its ligand. The bifunctional antibodies of the invention not only bind SIRPa and the ligand of the immunotherapeutic agent, but they have also kept the functional properties associated to both interactions CD47-SIRPa and immunotherapeutic agent-ligand. As used herein, the term "immunotherapeutic agents" refers in particular to agents that could take cancer vaccines from interesting biological phenomena to effective therapeutic agents including: T-cell growth factors to increase number and repertoire of naive T cells, growth factors to increase the number of dendritic cells (DCs), agonists to activate DCs and other antigen-presenting cells (APCs), adjuvants to allow and augment cancer vaccines, agonists to activate and stimulate T cells, inhibitors of T-cell checkpoint blockade, T-cell growth factors to increase the growth and survival of immune T cells, agents to inhibit, block, or neutralize cancer cell and immune cell-derived immunosuppressive cytokine.

More particularly, immunotherapeutic agents useful in the context of the invention are selected from the group consisting of immune checkpoint blockers or activators, in particular of adaptive immune cells (T or B lymphocytes), therapeutic vaccines (DNA, RNA or peptide vaccines) or immunoconjugates such as antibody-drug conjugates.

Numerous immune checkpoint blockers or activators are known in the art. In the context of the invention, examples of immune checkpoint blockers or activators of adaptive immune cells (B or T lymphocytes) that could be useful are PD1, PDL1, PDL2, CTLA-4, CD80, CD86, CD28, 4-16B, 4-1BBL, CD40, CD40L, ICOS, ICOS-L, OX40L, GITR, HVEM, BTLA, CD160, LIGHT, TNFRSF25, 2B4, CD48, Tim1, Tim3, Tim4, Gal9, LAG-3, CD40, CD40L, CD70, CD27, VISTA, B7H3, B7H4 (B7x), TIGIT, CD112, HHLA2 (B7-H7), TMIGD2 (CD28H), Butyrophilin-like2 (BTNL2), variants and fragments thereof, in particular PDL1, PD1, CD80, CD86, OX40L, 4-1BBL, ICOSL, variants and fragments thereof, more particularly PD1, PDL1, CD80, 4-1BBL, and variants and fragments thereof.

In particular, the antibodies of the invention can be obtained by adding functional variants or functional fragments of immune checkpoint blockers or activators to anti-SIRPa antibodies. Preferably, the functional fragments correspond to the extracellular domains (ECD) of immune checkpoint blockers or activators.

In particular, the variants and fragments of the immunotherapeutic agent comprised in the bifunctional antibodies of the invention keep the functional properties associated to interaction of the immunotherapeutic agent-ligand.

In an embodiment, the invention relates to a modified anti-SIRPa antibody or antigen-binding fragment thereof as defined above that specifically binds to at least two, three, four or five peptides comprising or consisting of amino acid sequence selected from the group consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptide comprising or consisting of amino acid sequence SEQ ID NO: 3 (KFRKGSPD[DV]/[T]E) within SIRPa and to at least one peptide comprising or consisting of amino acid sequence selected from the group consisting of SEQ ID NO: 1 (SLIPVGP), SEQ ID NO: 2 (G/ARELIYNQKEGH), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptides comprising or consisting of amino acid sequence SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to at least one peptide comprising or consisting of amino acid sequence selected from the group consisting of SEQ ID NO: 1 (SLIPVGP), SEQ ID NO: 7 (GRELIYNQKEGH), SEQ ID NO: 8 (KFRKGSPDDVE), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptides of SEQ ID NO: 1 (SLIPVGP), SEQ ID NO: 7 (GRELIYNQKEGH), SEQ ID NO: 8 (KFRKGSPDDVE), SEQ ID NO: 4 (QHTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to at least one peptide comprising or consisting of amino acid sequence selected from the group consisting of SEQ ID NO: 1 (SLIPVGP), SEQ ID NO: 9 (ARELIYNQKEGH), SEQ ID NO: 10 (KFRKGSPDTE), SEQ ID NO: 4 (QHTVSFTCESHGFSPRDITLKWF), SEQ ID NO: 5 (ICEVAHVTLQG) and SEQ ID NO: 6 (YPQRLQLTWLE), said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptides of SEQ ID NO: 1 (SLIPVGP), SEQ ID NO: 9 (ARELIYNQKEGH), SEQ ID NO: 10 (KFRKGSPDTE), SEQ ID NO: 4 (QHTVSFTCESHGFSPRDITLKWF), SEQ ID NO: 5 (ICEVAHVTLQG) and SEQ ID NO: 6 (YPQRLQLTWLE)

within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to at least one peptide comprising or consisting of amino acid sequence selected from the group consisting of SEQ ID NO: 1 (SLIPVGP), SEQ ID NO: 11 (GRELIYN), DVE, SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptides of SEQ ID NO: 1 (SLIPVGP), SEQ ID NO: 11 (GRELIYN), DVE, SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to at least one peptide comprising or consisting of amino acid sequence selected from the group consisting of SEQ ID NO: 1 (SLIPVGP), SEQ ID NO: 13 (ARELIYN), SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to the peptides of SEQ ID NO: 1 (SLIPVGP), SEQ ID NO: 13 (ARELIYN), SEQ ID NO: 12 (HTVSFTCESHGFSPRDITLKWF), SEQ ID NO: 5 (ICEVAHVTLQG) and SEQ ID NO: 6 (YPQRLQLTWLE) within SIRPa, said modified anti-SIRPa antibody or antigen-binding fragment being linked to an immunotherapeutic agent.

The peptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 correspond to linear epitopes.

These linear epitopes have been identified by the inventors by array-based oligopeptide scanning (sometimes called overlapping peptide scan or pepscan analysis). This technique uses a library of oligopeptide sequences from overlapping and non-overlapping segments of a target protein and tests for their ability to bind the antibody of interest. By combining non-adjacent peptide sequences from different parts of the target protein and enforcing conformational rigidity onto this combined peptide (such as by using CLIPS scaffolds) (Timmerman et al., 2007, J Mol Recognit., September-October; 20(5):283-99), discontinuous epitopes can be mapped with very high reliability and precision (Gaseitsiwe et al., 2010—Clin Vaccine Immunol. January; 17(1): 168-175). All of the tested antibodies of the invention, including HEFLB, specifically bind to said epitopes.

In an embodiment, the invention relates to a modified anti-SIRPa antibody or antigen-binding fragment thereof as defined above that specifically binds to a conformational epitope comprising at least one peptide selected from the group consisting of SEQ ID NO: 70 (ELIYNQKEGHFPR), SEQ ID NO: 71 (RNNMDFSIRIGN) and SEQ ID NO: 72 (SPRDITLKW) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to a conformational epitope comprising or consisting of the peptides of SEQ ID NO: 70 (ELIYNQKEGHFPR), SEQ ID NO: 71 (RNNMDFSIRIGN) and SEQ ID NO: 72 (SPRDITLKW) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to a conformational epitope comprising at least one peptide selected from the group consisting of SEQ ID NO: 70 (ELIYNQKEGHFPR) and SEQ ID NO: 71 (RNNMDFSIRIGN), said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to a conformational epitope comprising or consisting of the peptides of SEQ ID NO: 70 (ELIYNQKEGHFPR) and SEQ ID NO: 71 (RNNMDFSIRIGN) within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to a conformational epitope comprising at least one peptide selected from the group consisting of SEQ ID NO: 73 (YNQK) and "SIR" within SIRPa, said modified anti-SIRPa antibody or antigen-binding fragment being linked to an immunotherapeutic agent.

In an embodiment, the invention relates to a modified anti-SIRPa antibody or antigen-binding fragment thereof as defined above that specifically binds to a conformational epitope comprising or consisting of the peptide of amino acid sequence set forth in SEQ ID NO: 73 (YNQK) and the peptide of SIR amino acid sequence within SIRPa, said modified anti-SIRPa antibody or antigen-binding fragment being linked to an immunotherapeutic agent.

The peptides of SEQ ID NO: 70, SEQ ID NO: 71, SEQ ID NO: 72, SEQ ID NO: 73 and SIRP correspond to conformational epitopes. These conformational epitopes have been determined by the inventors using proteolysis protection procedures (enzymatic digestion: chymotrypsin, trypsin of the antibody-antigen complex immobilized on affinity chromatography) following by mass spectrometry analyses (MALDI-TOF/TOF) to detect and sequence such peptides of interest, as well known by one skilled in the art (Van de Water et al., Clinical Immunology and Immunopathology, 1997, vol. 85). The antigen used was the human SIRPa (accession numbers NP_542970) and one of the antibodies of the invention used was the HEFLB variant.

The anti-SIRPa antibody or antigen-binding fragment thereof according to the invention specifically bind said conformational epitopes comprising or consisting of said peptides in their conformational arrangement within the native SIRPa.

The peptide of amino acid sequence set forth in SEQ ID NO: 73 (YNQK) corresponds to the peptide consisting of amino acids at position 80 to 83 in the human SIRPa amino acid sequence referenced by the NP_542970 accession number.

The peptide of SIR amino acid sequence, the SIR peptide, corresponds to the peptide consisting of amino acids at position 105 to 107 in the human SIRPa amino acid sequence referenced by the NP_542970 accession number.

As used herein, the term "SIRPa" refers to a SIRPa protein from a mammal species, preferably a human SIRPa (e.g. accession numbers NP_542970 (P78324) and CAA71403).

As used herein, the term "anti-SIRPa antibody" refers to an antibody which specifically binds to SIRPa, in particular to a human SIRPa.

The specific binding between the antibody or antigen-binding fragment thereof of the invention and the epitope (or the region comprising the epitope) implies that the antibody exhibits appreciable affinity for the epitope (the region comprising the epitope) on a particular protein or antigen (here SIRPa or the ligand of an immunotherapeutic agent coupled to the antibody). "Appreciable affinity" includes binding with an affinity of about $10^{-9}$ M (KD) or stronger. Preferably, binding is considered specific when the binding affinity is between $10^{-9}$ M and $10^{-12}$ M, optionally between $10^{-9}$ M and $10^{-10}$ M, in particular $10^{-10}$ M. Whether a binding domain specifically reacts with or binds to a target can be tested readily by, inter alia, comparing the reaction of said binding domain with a target protein or antigen with the reaction of said binding domain with proteins or antigens other than the target protein.

The affinity can be determined by various methods well known from the one skilled in the art. These methods include, but are not limited to, Biacore Analysis, Blitz analysis and Scatchard plot.

In an embodiment, the invention relates to a modified anti-SIRPa antibody or antigen-binding fragment thereof as defined above that has a KD value inferior to $10^{-9}$ M, preferably inferior to $10^{-10}$ M for SIRPa, more preferably inferior to $1 \cdot 10^{-11}$ M, particularly by Biacore Analysis.

In an embodiment, the invention relates to a modified anti-SIRPa antibody or antigen-binding fragment thereof as defined above that decreases the interaction between SIRPa and CD47.

In an embodiment, the invention relates to a modified anti-SIRPa antibody or antigen-binding fragment thereof as defined above that partially or fully, in particular fully, inhibits the binding of CD47 to SIRPa, in particular of human CD47 to human SIRPa.

Such an antibody of the invention specifically binds SIRPa and antagonizes the interaction between SIRPa and CD47.

In particular, the anti-SIRPa antagonist antibody of the invention is capable of reducing or inhibiting the binding of CD47 to SIRPa by at least 50%, 60%, 70%, preferably 80%, more preferably 90% or most preferably 100%, as compared to a negative control molecule, in a binding assay.

In particular, the anti-SIRPa antagonist antibody of the invention is capable of reducing or inhibiting the binding of CD47 to SIRPa by from 50% to 100%, preferably from 60% to 90%, more preferably from 70% to 80%, as compared to a negative control molecule, in a binding assay.

Methods for determining antibody specificity and affinity by competitive inhibition are known in the art (see, e.g., Harlow et al., Antibodies: A Laboratory Manual, Cold Spring Harbor Laboratory Press, Cold Spring Harbor, N.Y. (1998); Colligan et al., Current Protocols in Immunology, Green Publishing Assoc., NY (1992; 1993); Muller, Meth. Enzym., 92:589-601 (1983)) and described in the examples below.

These methods include, but are not limited to, Biacore Analysis, Blitz analysis, flow cytometry and ELISA assay.

In an embodiment, the invention relates to a modified anti-SIRPa antibody as defined above that has an IC50 lower than 500 ng/ml, in particular lower than 400 ng/ml, 300 ng/ml, more particularly lower than 200 ng/ml, as determined in a competitive SIRPa binding assay between CD47 and the anti-SIRPa antibody by ELISA.

In an embodiment, the invention relates to a modified anti-SIRPa antibody as defined above that has an IC50 lower than 500 ng/ml, in particular lower than 400 ng/ml, 300 ng/ml, more particularly lower than 200 ng/ml, lower than 150 ng/ml and even more particularly lower than 100 ng/ml as determined by competition cytometry assay on human monocytes between CD47 and the anti-SIRPa antibody.

In an embodiment, the invention relates to a modified anti-SIRPa antibody or antigen-binding fragment thereof as defined above that does not specifically bind to SIRPg, preferably to human SIRPg. Such an antibody of the invention does not affect or does not prevent the interaction between SIRPg and CD47.

As used herein, the term "SIRPg" relates to a signal regulatory protein gamma (also designated SIRP gamma, CD172g or SIRP beta 2), from a mammal species, preferably a human SIRPg.

A reference sequence of the human SIRPg protein, used in the examples of the present application, corresponds to the sequence associated to the Accession number Q9P1W8.

In an embodiment, the invention relates to a modified anti-SIRPa antibody or antigen-binding fragment thereof as defined above that has a KD value superior to $10^{-9}$ M, preferably superior to $10^{-8}$ M, more preferably superior to $10^{-7}$ M for SIRPg, in particular by Blitz analysis.

In an embodiment, the invention relates to a modified anti-SIRPa antibody or antigen-binding fragment thereof as defined above that does not significantly inhibit, antagonize, the binding of CD47 to SIRPg, that does not significantly compete with the binding of CD47 to SIRPg.

This antagonist effect can be determined using the methods as defined the examples of the present application.

In the invention, it can be considered that an antibody (or antigen-binding fragment thereof) does not antagonize the binding of CD47 to SIRPg if said antibody (or antigen-binding fragment) induces no increase, or induces an increase inferior to 1 of the KD value of CD47 in a SIRPg binding competitive assay by Blitz.

In an embodiment, the invention relates to a modified anti-SIRPa antibody or antigen-binding fragment thereof as defined above that does not specifically bind to T-cells, in particular to CD3+ T-cells, via SIRPg.

In particular, the modified anti-SIRPa antibody or antigen-binding fragment thereof of the invention does not bind to T-cells from mammal species, in particular to human T-cells, via SIRPg.

This effect can be measured by the methods as described in the examples of the present application.

In an embodiment, the invention relates to a modified anti-SIRPa antibody or antigen-binding fragment thereof as defined above that does not significantly inhibit the proliferation of T-cells, in particular CD3+ T-cells, preferably from mammal species and more preferably of human T cells.

In particular, it is considered that an anti-SIRPa antibody does not significantly inhibit the proliferation of T-cells if the proliferation of T-cells is reduced by less than 30%, preferably less than 20%, more preferably less than 10%, most preferably less than 5% as compared with a positive control in absence of said antibody, in particular with a positive control in absence of said antibody but comprising an agent producing a first activating signal (such as an anti-CD3).

Preferably, the invention relates to a modified anti-SIRPa antibody or antigen-binding fragment thereof as defined above that increases the proliferation of T-cells, in particular CD3+ T-cells, preferably from mammal species and more preferably of human T cells.

It is considered that an antibody (or antigen-binding fragment thereof) increases the proliferation of T-cells if said antibody (or antigen-binding fragment thereof) induces a proliferation of T-cells at least 1.5 times, preferably at least 2 times, more preferably at least 10 times, greater than the proliferation of T-cells as compared with a control in absence of said antibody, in particular with a control in absence of said antibody but comprising an agent producing a first activating signal (such as an anti-CD3). The proliferation of T-cells can be determined by various methods. For example, the proliferation of T-cells can be measured by incorporation of $H^3$-thymidine as described in the examples of the present application.

In an embodiment, the invention relates to a modified anti-SIRPa antibody or antigen-binding fragment thereof as defined above that does not significantly inhibit, antagonize, the binding of the surfactant proteins to SIRPa, that does not significantly compete with the binding of the surfactant proteins to SIRPa.

As used herein, the "surfactant proteins" are collagen-containing C-type (calcium dependent) lectins, which contribute significantly to surfactant homeostasis and pulmonary immunity (for review, see Kishore et al., Surfactant proteins SP-A and SP-D: structure, function and receptors, Mol Immunol, 43(9), 1293-315, 2006).

As used herein, the term "surfactant protein" refers to a surfactant protein from a mammal species, preferably a human surfactant protein.

In an embodiment, the invention relates to a modified anti-SIRPa antibody or antigen-binding fragment thereof as defined above that does not inhibit the binding of the human surfactant protein D (SP-D) to SIRPa.

In an embodiment, the invention relates to a modified anti-SIRPa antibody or antigen-binding fragment thereof as defined above that does not inhibit the binding of the human surfactant protein A (SP-A) to SIRPa.

In an embodiment, the invention relates to a modified anti-SIRPa antibody or antigen-binding fragment thereof as defined above that does not antagonize the interaction between the surfactant proteins and SIRPa.

The competition between SIRPa and surfactant proteins can be determined by competitive assay using methods well known from the one skilled in the art. These methods include, but are not limited to, Biacore Analysis, Blitz analysis and ELISA assay.

In the invention, it can be considered that an antibody (or antigen-binding fragment thereof) does not antagonize the binding of a surfactant protein to SIRPa if said antibody (or antigen-binding fragment thereof) induces no increase, or induces an increase inferior to 1 log, of the KD value of the surfactant protein in a SIRPa binding competitive assay by Blitz.

In an embodiment, the invention relates to a modified anti-SIRPa antibody or antigen-binding fragment thereof as defined above that weakly binds, or does not specifically bind to SIRPb.

As used herein, the term "SIRPb" refers to a SIRPb protein (also designated as SIRPβ, signal-regulatory protein beta-1, SIRP-beta-1, CD172 antigen-like family member B or CD172b) from a mammal species, preferably a human SIRPb.

A reference sequence of the human SIRPb protein, used in the examples of the present application, corresponds to the sequence associated to the Accession number Q5TFQ8-1.

In an embodiment, the invention relates to a modified anti-SIRPa antibody or antigen-binding fragment thereof as defined above that has KD value superior to $10^{-9}$ M, preferably superior to $10^{-8}$ M for SIRPb, in particular by Blitz analysis.

In an embodiment, the invention relates to a modified anti-SIRPa antibody or antigen-binding fragment thereof as defined above that increases the secretion of TNFa by PBMC and/or by T-lymphocytes. The secretion of TNFa can be determined by ELISA assay using methods well known from the one skilled in the art (as shown in the Examples of the present invention).

In the invention, it can be considered that an antibody (or antigen-binding fragment thereof) increases the secretion of TNFa if said antibody (or antigen-binding fragment thereof) induces a secretion of TNFa at least 1.5 times, preferably at least 2 times, greater than the secretion of TNFa in as compared to a negative control in absence of said antibody, in particular a negative control in absence of said antibody but comprising an agent producing a first activating signal (such as an anti-CD3).

In an embodiment, the invention relates to a modified anti-SIRPa antibody or antigen-binding fragment thereof as defined above that increases the secretion of IFNg by PBMC.

The secretion of IFNg can be determined by ELISA assay using methods well known from the one skilled in the art (as shown in the Examples of the present invention).

In the invention, it can be considered that an antibody (or antigen-binding fragment thereof) increases the secretion of IFNg if said antibody (or antigen-binding fragment thereof) induces an secretion of IFNg at least 1.5 times, preferably at least 2 times, more preferably at least 4 times, greater than the secretion of IFNg as compared to a negative control in absence of said antibody, in particular a negative control in absence of said antibody but comprising an agent producing a first activating signal (such as an anti-CD3).

In an embodiment, the invention relates to a modified anti-SIRPa antibody or antigen-binding fragment thereof as defined above that increases the secretion of MIP1a by macrophages.

The secretion of MIP1a can be determined by ELISA assay using methods well known from the one skilled in the art (as shown in the Examples of the present invention).

In the invention, it can be considered that an antibody (or antigen-binding fragment thereof) increases the secretion of MIP1a if said antibody (or antigen-binding fragment thereof) induces an secretion of MIP1a at least 1.5 times, preferably at least 2 times, more preferably at least 10 times, greater than the secretion of MIP1a as compared to a negative control in absence of said antibody, in particular a negative control in absence of said antibody but comprising an agent producing a first activating signal (such as an anti-CD3).

In an embodiment, the invention relates to a modified anti-SIRPa antibody or antigen-binding fragment thereof as defined above that increases the activation of human T cells, in particular human T lymphocytes. As used herein, T cells and T lymphocytes have the same meaning and can be used interchangeably.

The activation of human T cells and human T lymphocytes can be determined by methods known in the art, like but not limited to, analysis of CD markers, in particular CD25 and/or CD69, flow cytometry, western blot, ELISA, and/or by assessing the secretion of IFNg as exemplified in the examples of the present invention, or by Time-lapse analysis of calcium incorporation by human T cells, i.e. human T lymphocytes, as illustrated in the examples of the present invention.

In the invention, it can be considered than an antibody or an antigen-binding fragment thereof increases the activation of human T cells (i.e. human T lymphocytes) if said antibody or antigen-binding fragment thereof increases at least 1.5 times preferably at least 2 times, more preferably at least 4 times, greater than the activation of human T cells (i.e. human T lymphocytes) as compared to a negative control in absence of said antibody, in particular a negative control in absence of said antibody but comprising an agent producing a first activating signal (such as an anti-CD3).

According to a first embodiment, the invention relates to a bifunctional anti-human SIRPa antibody or antigen-binding fragment thereof, which comprises:
a) a heavy chain variable domain comprising HCDR1, HCDR2 and HCDR3, and
b) a light chain variable domain comprising LCDR1, LCDR2 and LCDR3,
wherein:
HCDR1 comprises or consists of the amino acid sequence set forth in SEQ ID NO: 14,
HCDR2 comprises or consists of the amino acid sequence set forth in SEQ ID NO: 15 or SEQ ID NO: 16,
HCDR3 comprises or consists of the amino acid sequence set forth in SEQ ID NO: 17 SEQ ID NO: 18, SEQ ID NO: 19, or SEQ ID NO: 20,
LCDR1 comprises or consists of the amino acid sequence set forth in SEQ ID NO: 21,
LCDR2 comprises or consists of the amino acid sequence set forth in SEQ ID NO: 22 and
LCDR3 comprises or consists of the amino acid sequence set forth in SEQ ID NO: 23,
and which comprises a heavy chain constant domain or fragment thereof, said heavy chain constant domain or fragment thereof being linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof.

According to another embodiment, the invention relates to a modified anti-SIRPa antibody or antigen-binding fragment thereof that comprises:
a) a heavy chain comprising a heavy chain variable domain comprising HCDR1, HCDR2 and HCDR3, and a heavy chain constant domain or a fragment thereof; and
b) a light chain comprising a light chain variable domain comprising LCDR1, LCDR2 and LCDR3,
wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD) or SEQ ID NO: 16 (NIDPSDSDTHYSPSFQG),
HCDR3 comprising or consisting of the amino acid sequence set forth in SEQ ID NO: 17 (GGTGTMAWFAY) SEQ ID NO: 18 (GGTGTLAWFAY), SEQ ID NO: 19 (GGTGTMAYFAY) or SEQ ID NO: 20 (GGTGTLAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
and which comprises a heavy chain constant domain or fragment thereof, said heavy chain constant domain or fragment thereof being linked, in particular by its C-terminal extremity, to an immunotherapeutic agent, said immunotherapeutic agent comprising or consisting of a protein selected from the group consisting of PD1, PDL1, CD80 and 4-1BBL, immunotherapeutic agent variants thereof and immunotherapeutic agent fragments thereof, preferably the extracellular domain thereof.

According to another embodiment, the invention relates to an anti-SIRPa antibody or antigen-binding fragment thereof, that comprises:
a) a heavy chain comprising HCDR1, HCDR2, HDCR3 and at least a fragment of a heavy chain constant domain, in particular a fragment comprising at least the $C_H1$ domain of the heavy chain constant domain; or at least the $C_H1$ domain and the $C_H3$ domain; or at least the $C_H2$ domain and the $C_H3$ domain, or at least the $C_H1$ domain, the $C_H2$ domain and the $C_H3$ domain; in particular in combination with at least a fragment of the Fc region and/or the hinge region; and
b) a light chain comprising LCDR1, LCDR2 and LCDR3, wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD) or SEQ ID NO: 16 (NIDPSDSDTHYSPSFQG),
HCDR3 comprising or consisting of the amino acid sequence set forth in SEQ ID NO: 17 (GGTGTMAWFAY) SEQ ID NO: 18 (GGTGTLAWFAY), SEQ ID NO: 19 (GGTGTMAYFAY) or SEQ ID NO: 20 (GGTGTLAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
and wherein the heavy chain constant domain or fragment thereof is linked, in particular by its C-terminal extremity, to an immunotherapeutic agent, said immunotherapeutic agent comprising or consisting of a protein selected from the group consisting of PD1, PDL1, CD80 and 4-1BBL, immunotherapeutic agent variants thereof and immunotherapeutic agent fragments thereof, preferably the extracellular domain thereof.

In the following part of the description, the term "heavy chain comprising HCDR1, HCDR2 and HCDR3" also encompasses the terms "heavy chain comprising a heavy chain variable domain comprising HCDR1, HCDR2 and HCDR3, and a heavy chain constant domain or a fragment thereof", "heavy chain variable domain comprising HCDR1, HCDR2 and HCDR3" and "a heavy chain comprising from its N-terminal extremity to its C-terminal extremity HCDR1, HCDR2, HDCR3 and at least a fragment of a heavy chain constant domain, in particular a fragment comprising at least the C₁H domain of the heavy chain constant domain".

In the following part of the description, when the feature "wherein the heavy chain or a fragment thereof is linked to an immunotherapeutic agent" is recited, it also encompasses "a modified anti-SIRPa antibody or antigen-binding fragment comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof".

In an embodiment, the invention relates to a modified anti-SIRPa antibody or antigen-binding fragment thereof as defined above that comprises:
a) a heavy chain comprising HCDR1, HCDR2 and HCDR3, and/or
b) a light chain comprising LCDR1, LCDR2 and LCDR3,
wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD) or SEQ ID NO: 16 (NIDPSDSDTHYSPSFQG),
HCDR3 comprising or consisting of the amino acid sequence set forth in SEQ ID NO: 17 (GGTGTMAWFAY) SEQ ID NO: 18 (GGTGTLAWFAY), SEQ ID NO: 19 (GGTGTMAYFAY) or SEQ ID NO: 20 (GGTGTLAYFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
said modified anti-SIRPa antibody or antigen-binding fragment being linked to an immunotherapeutic agent,
in particular wherein the antibody or antigen-binding fragment thereof comprises a heavy chain constant domain or a fragment thereof, said heavy chain constant domain or fragment thereof being linked to an immunotherapeutic agent.

18D5/Variant A/Variant 8

In an embodiment, the invention relates to a modified anti-SIRPa antibody or antigen-binding fragment thereof as defined above that comprises:
a) a heavy chain comprising HCDR1, HCDR2 and HCDR3, and/or
b) a light chain comprising LCDR1, LCDR2 and LCDR3,
wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 15 (NIDPSDSDTHYNQKFKD),
HCDR3 comprising or consisting of the amino acid sequence set forth in SEQ ID NO: 17 (GGTGTMAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
said modified anti-SIRPa antibody or antigen-binding fragment being linked to an immunotherapeutic agent.

Variant C

In an embodiment, the invention relates to a modified anti-SIRPa antibody or antigen-binding fragment thereof as defined above that comprises:
a) a heavy chain comprising HCDR1, HCDR2 and HCDR3, and/or
b) a light chain comprising LCDR1, LCDR2 and LCDR3,
wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 17 (GGTGTMAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
said modified anti-SIRPa antibody or antigen-binding fragment being linked to an immunotherapeutic agent.

Variant E

In an embodiment, the invention relates to a modified anti-SIRPa antibody or antigen-binding fragment thereof as defined above that comprises:
a) a heavy chain comprising HCDR1, HCDR2 and HCDR3, and/or
b) a light chain comprising LCDR1, LCDR2 and LCDR3,
wherein said CDRs are defined as follows:
HCDR1 comprising or consisting of the amino acid sequence set forth in SEQ ID NO: 14 (SYWVH),
HCDR2 comprising or consisting of the amino acid sequence set forth in SEQ ID NO: 16 (NIDPSDSDTHYSPSFQG),
HCDR3 comprising or consisting of the amino acid sequence set forth in SEQ ID NO: 18 (GGTGTLAWFAY),
LCDR1 comprising or consisting of the amino acid sequence set forth in SEQ ID NO: 21 (RSSQSLVHSYGNTYLY),
LCDR2 comprising or consisting of the amino acid sequence set forth in SEQ ID NO: 22 (RVSNRFS), and
LCDR3 comprising or consisting of the amino acid sequence set forth in SEQ ID NO: 23 (FQGTHVPYT),
said modified anti-SIRPa antibody or antigen-binding fragment being linked to an immunotherapeutic agent.

Variant F

In an embodiment, the invention relates to a modified anti-SIRPa antibody or antigen-binding fragment thereof as defined above that comprises:
a) a heavy chain comprising HCDR1, HCDR2 and HCDR3, and/or
b) a light chain comprising LCDR1, LCDR2 and LCDR3,
wherein said CDRs are defined as follows:

HCDR1 comprising or consisting of the amino acid sequence set forth in SEQ ID NO: 14 (SYWVH), HCDR2 comprising or consisting of the amino acid sequence set forth in SEQ ID NO: 16 (NIDPSDSDTHYSPSFQG), HCDR3 comprising or consisting of the amino acid sequence set forth in SEQ ID NO: 19 (GGTGTMAYFAY), LCDR1 comprising or consisting of the amino acid sequence set forth in SEQ ID NO: 21 (RSSQSLVHSYGNTYLY), LCDR2 comprising or consisting of the amino acid sequence set forth in SEQ ID NO: 22 (RVSNRFS), and LCDR3 comprising or consisting of the amino acid sequence set forth in SEQ ID NO: 23 (FQGTHVPYT), said modified anti-SIRPa antibody or antigen-binding fragment being linked to an immunotherapeutic agent.

Variant EF

In an embodiment, the invention relates to a modified anti-SIRPa antibody or antigen-binding fragment thereof as defined above that comprises:

a) a heavy chain comprising HCDR1, HCDR2 and HCDR3, and/or b) a light chain comprising LCDR1, LCDR2 and LCDR3, wherein said CDRs are defined as follows:

HCDR1 comprising or consisting of the amino acid sequence set forth in SEQ ID NO: 14 (SYWVH), HCDR2 comprising or consisting of the amino acid sequence set forth in SEQ ID NO: 16 (NIDPSDSDTHYSPSFQG), HCDR3 comprising or consisting of the amino acid sequence set forth in SEQ ID NO: 20 (GGTGTLAYFAY), LCDR1 comprising or consisting of the amino acid sequence set forth in SEQ ID NO: 21 (RSSQSLVHSYGNTYLY), LCDR2 comprising or consisting of the amino acid sequence set forth in SEQ ID NO: 22 (RVSNRFS), and LCDR3 comprising or consisting of the amino acid sequence set forth in SEQ ID NO: 23 (FQGTHVPYT), said modified anti-SIRPa antibody or antigen-binding fragment being linked to an immunotherapeutic agent.

The anti-SIRPa antibodies of the invention may have a heavy chain variable region comprising the amino acid sequence of HCDR1 and/or HCDR2 and/or HCDR3 of the human antibodies as provided herein; and/or a light chain variable region comprising the amino acid sequence of LCDR1 and/or LCDR2 and/or LCDR3 of the human antibodies as provided herein.

In an embodiment, the modified antibody comprises an amino acid sequence variant of one or more of the CDRs of the provided human antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants).

In an embodiment, the invention relates to a modified anti-SIRPa antibody or antigen-binding fragment thereof as defined above that comprises:

a heavy chain variable domain comprising or consisting of the amino acid sequence selected from SEQ ID NO: 24, SEQ ID NO: 25, SEQ ID NO: 26, SEQ ID NO: 27, SEQ ID NO: 28, SEQ ID NO: 29 and SEQ ID NO: 30, and/or a light chain variable domain comprising or consisting of the amino acid sequence selected from the group consisting of SEQ ID NO: 31, SEQ ID NO: 32 and SEQ ID NO: 33, said modified anti-SIRPa antibody or antigen-binding fragment being linked to an immunotherapeutic agent.

In an embodiment, the invention relates to a modified anti-SIRPa antibody or antigen-binding fragment thereof as defined above that comprises:

a heavy chain variable domain comprising or consisting of the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30, and a light chain variable domain comprising or consisting of the amino acid sequence selected from the group consisting of SEQ ID NO: 31, SEQ ID NO: 32 and SEQ ID NO: 33, said modified anti-SIRPa antibody or antigen-binding fragment being linked to an immunotherapeutic agent.

The sequences of the specific variable domains are given in Table 1 below.

TABLE 1

Examples of heavy chain variable domains and light chain variable domains of antibodies according to the invention.

| | | |
|---|---|---|
| Heavy chain variable domain of the wild-type antibody (chimeric and mouse 18D5) | QVQLQQPGAELVRPGSSVKLSCKASGYTFTSYWVHWVKQ RPIQGLEWIGNIDPSDSDTHYNQKFKDKASLTVDKSSSTAY MQLSSLTFEDSAVYYCVRGGTGTMAWFAYWGQGTLVTVS A | SEQ ID NO: 24 |
| Heavy chain variable domain of humanized variant (HA) | EVQLVQSGAEVKKPGESLRISCKASGYTFTSYWVHWVRQM PGKGLEWIGNIDPSDSDTHYNQKFKDHVTLSVDKSISTAYL QLSSLKASDTAMYYCVRGGTGTMAWFAYWGQGTLVTVSS | SEQ ID NO: 25 |
| Heavy chain variable domain of humanized variant (HB) | EVQLVQSGAEVKKPGESLRISCKASGYSFTSYWVHWVRQM PGKGLEWMGNIDPSDSDTHYNQKFKDHVTLSVDKSISTAYL QLSSLKASDTAMYYCVRGGTGTMAWFAYWGQGTLVTVSS | SEQ ID NO: 26 |
| Heavy chain variable domain of humanized variant (HC) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMAWFAYWGQGTLVTVSS | SEQ ID NO: 27 |
| Heavy chain variable domain of humanized variant (HE) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTLAWFAYWGQGTLVTVSS | SEQ ID NO: 28 |

TABLE 1-continued

Examples of heavy chain variable domains and light chain variable domains of antibodies according to the invention.

| | | |
|---|---|---|
| Heavy chain variable domain of humanized variant (HF) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMAYFAYWGQGTLVTVSS | SEQ ID NO: 29 |
| Heavy chain variable domain of humanized variant (HEF) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTLAYFAYWGQGTLVTVSS | SEQ ID NO: 30 |
| Light chain of the wild-type antibody (chimeric and mouse 18D5) | DVVMTQTPLSLPVSLGDQASISCRSSQSLVHSYGNTYLYWY LQKPGQSPKLLIYRVSNRFSGVPDRFSGSGSGTDFTLKISRVE AEDLGVYFCFQGTHVPYTFGSGTKLEIK | SEQ ID NO: 31 |
| Light chain variable domain of humanized variant A (LA) | DVVMTQSPLSLPVTLGQPASISCRSSQSLVHSYGNTYLYWY QQRPGQSPRLLIYRVSNRFSGVPDRFSGSGSGTDFTLKISRV EAEDVGVYFCFQGTHVPYTFGGGTKVEIK | SEQ ID NO: 32 |
| Light chain variable domain of humanized variant (LB) | DVVMTQSPLSLPVTLGQPASISCRSSQSLVHSYGNTYLYWF QQRPGQSPRLLIYRVSNRFSGVPDRFSGSGSGTDFTLKISRV EAEDVGVYYCFQGTHVPYTFGGGTKVEIK | SEQ ID NO: 33 |

The sequences of the variable domains of the antibodies exemplified in the present invention can be deduced from the combinations of the sequences shown in Table 2.

TABLE 2

Heavy chain variable domain and light chain variable domain of specific antibodies according to the invention.

| Antibody | Heavy chain variable domain | Light chain variable domain |
|---|---|---|
| 18D5 (chimeric and mouse) | SEQ ID NO: 24 | SEQ ID NO: 31 |
| HALA | SEQ ID NO: 25 | SEQ ID NO: 32 |
| HALB | SEQ ID NO: 25 | SEQ ID NO: 33 |
| HBLA | SEQ ID NO: 26 | SEQ ID NO: 32 |
| HBLB | SEQ ID NO: 26 | SEQ ID NO: 33 |
| HCLA | SEQ ID NO: 27 | SEQ ID NO: 32 |
| HCLB | SEQ ID NO: 27 | SEQ ID NO: 33 |
| HELA | SEQ ID NO: 28 | SEQ ID NO: 32 |
| HELB | SEQ ID NO: 28 | SEQ ID NO: 33 |
| HFLA | SEQ ID NO: 29 | SEQ ID NO: 32 |
| HFLB | SEQ ID NO: 29 | SEQ ID NO: 33 |
| HEFLA | SEQ ID NO: 30 | SEQ ID NO: 32 |
| HEFLB | SEQ ID NO: 30 | SEQ ID NO: 33 |

In an embodiment, the invention relates to a modified anti-SIRPa antibody or antigen-binding fragment thereof as defined above that comprises a light chain variable domain comprising or consisting of the amino acid sequence SEQ ID NO: 33, said modified anti-SIRPa antibody or antigen-binding fragment being linked to an immunotherapeutic agent.

In an embodiment, the invention relates to a modified anti-SIRPa antibody or antigen-binding fragment thereof as defined above that comprises:
  a light chain variable domain comprising or consisting of the amino acid sequence SEQ ID NO: 33, and
  a heavy chain variable domain comprising or consisting of the amino acid sequence selected from the group consisting of SEQ ID NO: 24, SEQ ID NO: 25, SEQ ID NO: 26, SEQ ID NO:27, SEQ ID NO: 28, SEQ ID NO: 29 and SEQ ID NO: 30,
  preferably
    a heavy chain variable domain comprising or consisting of the amino acid sequence selected from the group consisting of SEQ ID NO: 29 and SEQ ID NO: 30,
  more preferably
    a heavy chain variable domain comprising or consisting of the amino acid sequence selected from the group consisting of SEQ ID NO: 30,
  said modified anti-SIRPa antibody or antigen-binding fragment being linked to an immunotherapeutic agent.

In an embodiment, the invention relates to a modified anti-SIRPa antibody or antigen-binding fragment thereof as defined above that comprises:
  a heavy chain variable domain comprising or consisting of amino acid sequence set forth in SEQ ID NO: 24, and
  a light chain variable domain comprising or consisting of amino acid sequence set forth in SEQ ID NO: 31,
  or
  a heavy chain variable domain comprising or consisting of amino acid sequence set forth in SEQ ID NO: 25, and
  a light chain variable domain comprising or consisting of amino acid sequence set forth in SEQ ID NO: 32,
  or
  a heavy chain variable domain comprising or consisting of amino acid sequence set forth in SEQ ID NO: 25, and
  a light chain variable domain comprising or consisting of amino acid sequence set forth in SEQ ID NO: 33,
  or
  a heavy chain variable domain comprising or consisting of amino acid sequence set forth in SEQ ID NO: 26, and
  a light chain variable domain comprising or consisting of amino acid sequence set forth in SEQ ID NO: 32,
  or
  a heavy chain variable domain comprising or consisting of amino acid sequence set forth in SEQ ID NO: 26, and
  a light chain variable domain comprising or consisting of amino acid sequence set forth in SEQ ID NO: 33,
  or
  a heavy chain variable domain comprising or consisting of amino acid sequence set forth in SEQ ID NO: 27, and
  a light chain variable domain comprising or consisting of amino acid sequence set forth in SEQ ID NO: 32, or a heavy chain variable domain comprising or consisting of amino acid sequence set forth in SEQ ID NO: 27, and a light chain variable domain comprising or consisting of amino acid sequence set forth in SEQ ID NO: 33, or a heavy chain variable domain comprising or consisting of amino acid sequence set forth in SEQ ID NO: 28, and a light chain variable domain comprising or consisting of amino acid sequence set forth in SEQ ID NO: 32, or a heavy chain variable domain comprising or consisting of amino acid sequence set forth in SEQ ID NO: 28, and a light chain variable domain comprising or consisting of amino acid sequence set forth in SEQ ID NO: 33, or a heavy chain variable domain comprising or consisting of amino acid sequence set forth in SEQ ID NO: 29, and a light chain variable domain comprising or consisting of amino acid sequence set forth in SEQ ID NO: 32, or a heavy chain variable domain comprising or consisting of amino acid sequence set forth in SEQ ID NO: 29, and a light chain variable domain comprising or consisting of amino acid sequence set forth in SEQ ID NO: 33, or a heavy chain variable domain comprising or consisting of amino acid sequence set forth in SEQ ID NO: 30, and a light chain variable domain comprising or consisting of amino acid sequence set forth in SEQ ID NO: 32, or a heavy chain variable domain comprising or consisting of amino acid sequence set forth in SEQ ID NO: 30, and a light chain variable domain comprising or consisting of amino acid sequence set forth in SEQ ID NO: 33, said modified anti-SIRPa antibody or antigen-binding fragment being linked to an immunotherapeutic agent.

In an embodiment, the modified antibody or antigen-binding fragment has no substitution of the amino acid W at position 33 (W33) in the heavy chain variable domain, said position being identified with respect to SEQ ID NO: 24, SEQ ID NO: 25, SEQ ID NO: 26, SEQ ID NO: 27, SEQ ID NO: 28, SEQ ID NO: 29 or SEQ ID NO: 30, and/or no substitution of the amino acids Y at position 39 (Y39), Rat position 55 (R55) and/or F at position 60 (F60) in the light chain variable domain, said positions being identified with respect to SEQ ID NO: 31, SEQ ID NO: 32 or SEQ ID: 33, in particular has no substitution at position W33 in the heavy chain variable domain and no substitution at positions Y39, R55 and F60 in the light chain variable domain.

In the invention, the modified antibodies can be produced with any heavy chain and light chain constant domains and fragments thereof.

In one embodiment, the modified anti-human SIRPa antibody of the invention is a humanized monoclonal antibody, in particular wherein the antibody light chain constant domain is derived from a human kappa light chain constant domain, more particularly wherein the light chain constant domain consists of the sequence of SEQ ID NO: 35, and/or wherein the antibody heavy chain constant domain is derived from a human IgG1, IgG2, IgG3, or IgG4 (wild type or mutated) heavy chain constant domain, in particular from a human IgG4 heavy chain constant domain, more particularly wherein the antibody heavy chain constant domain consists of the sequence with SEQ ID NO: 34.

As well known by one skilled in the art, the choice of IgG isotypes of the heavy chain constant domain centers on whether specific functions are required and the need for a suitable in vivo half-life. For example, antibodies designed for selective eradication of cancer cells typically require an active isotype that permits complement activation and effector-mediated cell killing by antibody-dependent cell-mediated cytotoxicity. Both human IgG1 and IgG3 (shorter half-life) isotypes meet these criteria, particularly human IgG1 isotype (wild type and variants). In particular, depending of the IgG isotype of the heavy chain constant domain (particularly human wild type and variants IgG1 isotype), the anti-human SIRPa antibody of the invention can be cytotoxic towards cells expressing SIRPa via a CDC, ADCC and/or ADCP mechanism (Salfeld, nature biotechnology, vol. 25, No 12, 2007; Irani et al. Molecular Immunology, vol. 67, issue 2, part A, 2015). In fact, the fragment crystallizable (Fc) region interacts with a variety of accessory molecules to mediate indirect effector functions such as antibody-dependent cellular cytotoxicity (ADCC), antibody-dependent cellular phagocytosis (ADCP) and complement-dependent cytotoxicity (CDC).

TABLE 3

Examples of a heavy chain constant domain and a light chain constant domain suitable for the antibodies according to the invention.

| | |
|---|---|
| Heavy chain constant domain (IgG4m-S228P) SEQ ID NO: 34 | ASTKGPSVFPLAPCSRSTSESTAALGCLVKDYFPEPVTVSWNSGALTSGVHTFPAVL QSSGLYSLSSVVTVPSSSLGTKTYTCNVDHKPSNTKVDKRVESKYGPPCPPCPAPEFL GGPSVFLFPPKPKDTLMISRTPEVTCVVVDVSQEDPEVQFNWYVDGVEVHNAKTK PREEQFNSTYRVVSVLTVLHQDWLNGKEYKCKVSNKGLPSSIEKTISKAKGQPREPQ VYTLPPSQEEMTKNQVSLTCLVKGFYPSDIAVEWESNGQPENNYKTTPPVLDSDGS FFLYSRLTVDKSRWQEGNVFSCSVMHEALHNHYTQKSLSLSPGK |
| Light chain constant domain (CLkappa) SEQ ID NO: 35 | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |

In an embodiment, the invention relates to a modified anti-SIRPa antibody as defined above that comprises:

- a heavy chain comprising or consisting of the amino acid sequence SEQ ID NO: 56, and
- a light chain comprising or consisting of the amino acid sequence SEQ ID NO: 57, or

- a heavy chain comprising or consisting of the amino acid sequence SEQ ID NO: 36, and
- a light chain comprising or consisting of the amino acid sequence SEQ ID NO: 43, or

- a heavy chain comprising or consisting of the amino acid sequence SEQ ID NO: 37, and
- a light chain comprising or consisting of the amino acid sequence SEQ ID NO: 44, or

- a heavy chain comprising or consisting of the amino acid sequence SEQ ID NO: 37, and
- a light chain comprising or consisting of the amino acid sequence SEQ ID NO: 45, or

- a heavy chain comprising or consisting of the amino acid sequence SEQ ID NO: 38, and
- a light chain comprising or consisting of the amino acid sequence SEQ ID NO: 44, or

- a heavy chain comprising or consisting of the amino acid sequence SEQ ID NO: 38, and
- a light chain comprising or consisting of the amino acid sequence SEQ ID NO: 45, or

- a heavy chain comprising or consisting of the amino acid sequence SEQ ID NO: 39, and
- a light chain comprising or consisting of the amino acid sequence SEQ ID NO: 44, or

- a heavy chain comprising or consisting of the amino acid sequence SEQ ID NO: 39, and
- a light chain comprising or consisting of the amino acid sequence SEQ ID NO: 45, or

- a heavy chain comprising or consisting of the amino acid sequence SEQ ID NO: 40, and
- a light chain comprising or consisting of the amino acid sequence SEQ ID NO: 44, or

- a heavy chain comprising or consisting of the amino acid sequence SEQ ID NO: 40, and
- a light chain comprising or consisting of the amino acid sequence SEQ ID NO: 45, or

- a heavy chain comprising or consisting of the amino acid sequence SEQ ID NO: 41, and
- a light chain comprising or consisting of the amino acid sequence SEQ ID NO: 44, or

- a heavy chain comprising or consisting of the amino acid sequence SEQ ID NO: 41, and
- a light chain comprising or consisting of the amino acid sequence SEQ ID NO: 45, or

- a heavy chain comprising or consisting of the amino acid sequence SEQ ID NO: 42, and
- a light chain comprising or consisting of the amino acid sequence SEQ ID NO: 44, or

- a heavy chain comprising or consisting of the amino acid sequence SEQ ID NO: 42, and
- a light chain comprising or consisting of the amino acid sequence SEQ ID NO: 45, said modified anti-SIRPa antibody being linked to an immunotherapeutic agent.

TABLE 4

| Heavy chain and light chain sequences of specific antibodies according to the invention. | | |
| --- | --- | --- |
| Heavy chain of the wild-type antibody (mouse 18D5) | QVQLQQPGAELVRPGSSVKLSCKASGYTFTSYWVHWVKQ RPIQGLEWIGNIDPSDSDTHYNQKFKDKASLTVDKSSSTAY MQLSSLTFEDSAVYYCVRGGTGTMAWFAYWGQGTLVTVS AAKTTPPSVYPLAPGCGDTTGSSVTLGCLVKGYFPESVTVT WNSGSLSSSVHTFPALLQSGLYTMSSSVTVPSSTWPSQTVT CSVAHPASSTTVDKKLEPSGPISTINPCPPCKECHKCPA PNLEGGPSVFIFPPNIKDVLMISLTPKVTCVVVDVSEDDPDV QISWFVNNVEVHTAQTQTHREDYNSTIRVVSTLPIQHQDW MSGKEFKCKVNNKDLPSPIERTISKIKGLVRAPQVYILPPPAE QLSRKDVSLTCLVVGFNPGDISVEWTSNGHTEENYKDTAPV LDSDGSYFIYSKLNMKTSKWEKTDSFSCNVRHEGLKNYYLKK TISRSPGK | SEQ ID NO: 56 |
| Heavy chain of the wild-type antibody (chimeric 18D5) | QVQLQQPGAELVRPGSSVKLSCKASGYTFTSYWVHWVKQ RPIQGLEWIGNIDPSDSDTHYNQKFKDKASLTVDKSSSTAY MQLSSLTFEDSAVYYCVRGGTGTMAWFAYWGQGTLVTVS AASTKGPSVFPLAPCSRSTSESTAALGCLVKDYFPEPVTVSW NSGALTSGVHTFPAVLQSSGLYSLSSVVTVPSSSLGTKTYTC NVDHKPSNTKVDKRVESKYGPPCPPCPAPEFLGGPSVFLFP PKPKDTLMISRTPEVTCVVVDVSQEDPEVQFNWYVDGVEV HNAKTKPREEQFNSTYRVVSVLTVLHQDWLNGKEYKCKVS NKGLPSSIEKTISKAKGQPREPQVYTLPPSQEEMTKNQVSLT CLVKGFYPSDIAVEWESNGQPENNYKTTPPVLDSDGSFFLY SRLTVDKSRWQEGNVFSCSVMHEALHNHYTQKSLSLSPGK | SEQ ID NO: 36 |
| Heavy chain of humanized variant (HA) | EVQLVQSGAEVKKPGESLRISCKASGYTFTSYWVHWVRQM PGKGLEWIGNIDPSDSDTHYNQKFKDHVTLSVDKSISTAYL QLSSLKASDTAMYYCVRGGTGTMAWFAYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCNV DHKPSNTKVDKRVESKYGPPCPPCPAPEFLGGPSVFLFPPKP | SEQ ID NO: 37 |

TABLE 4-continued

Heavy chain and light chain sequences of specific antibodies according to the invention.

| | | |
|---|---|---|
| | KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | |
| Heavy chain of humanized variant (HB) | EVQLVQSGAEVKKPGESLRISCKASGYSFTSYWVHWVRQM PGKGLEWMGNIDPSDSDTHYNQKFKDHVTLSVDKSISTAYL QLSSLKASDTAMYYCVRGGTGTMAWFAYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCNV DHKPSNTKVDKRVESKYGPPCPPCPAPEFLGGPSVFLFPPKP KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | SEQ ID NO: 38 |
| Heavy chain of humanized variant (HC) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMAWFAYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCNV DHKPSNTKVDKRVESKYGPPCPPCPAPEFLGGPSVFLFPPKP KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | SEQ ID NO: 39 |
| Heavy chain of humanized variant (HE) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMLAWFAYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCNV DHKPSNTKVDKRVESKYGPPCPPCPAPEFLGGPSVFLFPPKP KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | SEQ ID NO: 40 |
| Heavy chain of humanized variant (HF) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMAYFAYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCNV DHKPSNTKVDKRVESKYGPPCPPCPAPEFLGGPSVFLFPPKP KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | SEQ ID NO: 41 |
| Heavy chain of humanized variant (HEF) | EVQLVQSGAEVKKPGESLRISCKASGYSFTSYWVHWVRQM PGKGLEWMGNIDPSDSDTHYSPSFQGHVTLSVDKSISTAYL QLSSLKASDTAMYYCVRGGTGTMLAYFAYWGQGTLVTVSSA STKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKP KDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCL VKGFYPSDIAVEWESNGQPENNYKTTPPVLDSDGSFFLYSR LTVDKSRWQEGNVFSCSVMHEALHNHYTQKSLSLSPGK | SEQ ID NO: 42 |
| Light chain of the wild-type antibody (mouse 18D5) | DVVMTQTPLSLPVSLGDQASISCRSSQSLVHSYGNTYLYWY LQKPGQSPKLLIYRVSNRFSGVPDRFSGSGSGTDFTLKISRVE AEDLGVYFCFQGTHVPYTFGSGTKLEIKRADAAPTVSIFPPSS EQLTSGGASVVCFLNNFYPKDINVKWKIDGSERQNGVLNS WTDQDSKDSTYSMSSTLTLTKDEYERHNSYTCEATHKTSTS PIVKSFNRNEC | SEQ ID NO: 57 |

TABLE 4-continued

Heavy chain and light chain sequences of specific antibodies according to the invention.

| | | |
|---|---|---|
| Light chain of the wild-type antibody (chimeric 18D5) | DVVMTQTPLSLPVSLGDQASISCRSSQSLVHSYGNTYLYWY LQKPGQSPKLLIYRVSNRFSGVPDRFSGSGSGTDFTLKISRVE AEDLGVYFCFQGTHVPYTFGSGTKLEIKRTVAAPSVFIFP PSDEQLKSGTASVVCLLNNFYPREAKVQWKVDNA LQSGNSQESVTEQDSKDSTYSLSSTLTLSKADYEKH KVYACEVTHQGLSSPVTKSFNRGEC | SEQ ID NO: 43 |
| Light chain of humanized variant A (LA) | DVVMTQSPLSLPVTLGQPASISCRSSQSLVHSYGNTYLYWY QQRPGQSPRLLIYRVSNRFSGVPDRFSGSGSGTDFTLKISRV EAEDVGVYFCFQGTHVPYTFGGGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGLSS PVTKSFNRGEC | SEQ ID NO: 44 |
| Light chain of humanized variant (LB) | DVVMTQSPLSLPVTLGQPASISCRSSQSLVHSYGNTYLYWF QQRPGQSPRLLIYRVSNRFSGVPDRFSGSGSGTDFTLKISRV EAEDVGVYYCFQGTHVPYTFGGGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGLSS PVTKSFNRGEC | SEQ ID NO: 45 |

In an embodiment, the invention relates to a modified anti-SIRPa antibody or antigen-binding fragment thereof as defined above that is able to induce the differentiation of myeloid-derived suppressor cells (MDSC) into differentiated MDSC, in particular into differentiated MDSC expressing at least one human marker selected from the group consisting of CD80, CD86 and CD103, in particular at least two human markers selected from the group consisting of CD80, CD86 and CD103, and more particularly into cells expressing human markers CD80, CD86 and CD103; and/or into differentiated MDSC expressing CD11b.

In an embodiment, the invention relates to a modified anti-SIRPa antibody or antigen-binding fragment thereof as defined above, wherein said non suppressive cells secrete pro-inflammatory cytokines such as IL6, IL12 and TNF, and no or low level of anti-inflammatory cytokines such as IL10 and TGFβ.

In an embodiment, the invention relates to a modified anti-SIRPa antibody or antigen-binding fragment thereof as defined above, wherein said non suppressive cells express iNOS.

In an embodiment, the invention relates to a modified anti-SIRPa antibody or antigen-binding fragment thereof as defined above, wherein said non suppressive cells do not express the MHC Class II markers and express the markers CD80-CD86.

In an embodiment, the invention relates to a modified anti-SIRPa antibody or antigen-binding fragment thereof as defined above, wherein said non suppressive cells express at least one marker of the natural killer (NK) cells.

In an embodiment, the invention relates to a modified anti-SIRPa antibody or antigen-binding fragment thereof as defined above, wherein said modified antibody or antigen-binding fragment thereof is able to inhibit M2 polarization of macrophages and/or favors pro-inflammatory M1-type macrophages.

The modified antibodies of the invention can modify the macrophage polarization in order to induce a pro-inflammatory environment, i.e. they can inhibit the anti-inflammatory signal provided by M2-type macrophages and/or favor the pro-inflammatory signal provided by M1-type macrophages This approach allows to reestablish an inflammatory environment favorable to the action of the T effector cells, in particular in eliminating the cancer cells.

In an embodiment, the invention relates to a modified anti-SIRPa antibody or antigen-binding fragment thereof as defined above, wherein the heavy chain or fragment thereof in particular the heavy chain constant domain or fragment thereof, is linked to an immunotherapeutic agent.

Unexpectedly, the Inventors have observed that the tested immunotherapeutic agents remain functional when grafted on the heavy chain or fragment thereof but not when grafted on the light chain although all of them are able to bind to their ligand.

In an embodiment, the invention relates to a modified anti-SIRPa antibody or antigen-binding fragment thereof as defined above, wherein said immunotherapeutic agent is linked to the C-terminal extremity of the heavy chain constant domain or fragment thereof of said antibody.

In an embodiment, the invention relates to a modified anti-SIRPa antibody or antigen-binding fragment thereof as defined above, wherein said immunotherapeutic agent is linked to the N-terminal extremity of the heavy chain constant domain or fragment thereof of said antibody.

In an embodiment, the invention relates to a modified anti-SIRPa antibody or antigen-binding fragment thereof as defined above, wherein the light chain, in particular the light chain constant domain or fragment thereof, is linked to an immunotherapeutic agent.

In an embodiment, the invention relates to a modified anti-SIRPa antibody or antigen-binding fragment thereof as defined above, wherein said immunotherapeutic agent is linked to the C-terminal extremity of the light chain constant domain of said antibody.

In an embodiment, the invention relates to a modified anti-SIRPa antibody or antigen-binding fragment thereof as defined above, wherein said immunotherapeutic agent is linked to the N-terminal extremity of the light chain constant domain of said antibody.

In an embodiment, the invention relates to a modified anti-SIRPa antibody or antigen-binding fragment thereof as defined above, wherein the immunotherapeutic agent is selected from the group consisting of PD1, PDL1, PDL2, CTLA-4, CD80, CD86, CD28, 4-1BB, 4-1BBL, CD40, CD40L, ICOS, ICOS-L, OX40L, GITR, HVEM, BTLA, CD160, LIGHT, TNFRSF25, 2B4, CD48, Tim1, Tim3, Tim4, Gal9, LAG-3, CD40, CD40L, CD70, CD27, VISTA, B7H3, B7H4 (B7x), TIGIT, CD112, HHLA2 (B7-H7), TMIGD2 (CD28H), Butyrophilin-like2 (BTNL2), their variants and fragments thereof, in particular from the group consisting of PDL1, PD1, CD80, CD86, OX40L, 4-1BBL, ICOSL, their variants and fragments thereof, more particularly from the group consisting of PD1, PDL1, CD80, 4-1BBL, their variants and fragments thereof.

In an embodiment, the invention relates to a modified anti-SIRPa antibody or antigen-binding fragment thereof as A reference sequence of human OX40L corresponds to the sequence SEQ ID NO: 77.

A reference sequence of human 4-1BBL corresponds to the sequence SEQ ID NO: 78.

A reference sequence of human ICOSL corresponds to the sequence SEQ ID NO: 79.

A reference sequence of human CD86 corresponds to the sequence SEQ ID NO: 80.

TABLE 5

Reference sequences of PD1, PDL1, CD80, OX40L, 4-1BBL, ICOSL and CD86.

| | |
|---|---|
| PD1<br>(UniProt Q15116)<br>SEQ ID NO: 74 | MQIPQAPWPVVWAVLQLGWRPGWFLDSPDRPWNPPTFSPALLVVTEGDNATFT<br>CSFSNTSESFVLNWYRMSPSNQTDKLAAFPEDRSQPGQDCRFRVTQLPNGRDF<br>HMSVVRARRNDSGTYLCGAISLAPKAQIKESLRAELRVTERRAEVPTAHPSPS<br>PRPAGQFQTLVVGVVGGLLGSLVLLVWVLAVICSRAARGTIGARRTGQPLKED<br>PSAVPVFSVDYGELDFQWREKTPEPPVPCVPEQTEYATIVFPSGMGTSSPARR<br>GSADGPRSAQPLRPEDGHCSWPL |
| PDL1<br>(UniProt Q9NZQ7)<br>SEQ ID NO: 75 | MRIFAVFIFMTYWHLLNAFTVTVPKDLYVVEYGSNMTIECKFPVEKQLDLAAL<br>IVYWEMEDKNIIQFVHGEEDLKVQHSSYRQRARLLKDQLSLGNAALQITDVKL<br>QDAGVYRCMISYGGADYKRITVKVNAPYNKINQRILVVDPVTSEHELTCQAEG<br>YPKAEVIWTSSDHQVLSGKTTTTNSKREEKLFNVTSTLRINTTTNEIFYCTFR<br>RLDPEENHTAELVIPELPLAHPPNERTHLVILGAILLCLGVALTFIFRLRKGR<br>MMDVKKCGIQDTNSKKQSDTHLEET |
| CD80<br>(UniProt P33681)<br>SEQ ID NO: 76 | MGHTRRQGTSPSKCPYLNFFQLLVLAGLSHFCSGVIHVTKEVKEVATLSCGHN<br>VSVEELAQTRIYWQKEKKMVLTMMSGDMNIWPEYKNRTIFDITNNLSIVILAL<br>RPSDEGTYECVVLKYEKDAFKREHLAEVTLSVKADFPTPSISDFEIPTSNIRR<br>IICSTSGGFPEPHLSWLENGEELNAINTTVSQDPETELYAVSSKLDFNMTTNH<br>SFMCLIKYGHLRVNQTFNWNTTKQEHFPDNLLPSWAITLISVNGIFVICCLTY<br>CFAPRCRERRRNERLRRESVRPV |
| OX40L<br>(UniProt P23510)<br>SEQ ID NO: 77 | MERVQPLEENVGNAARPRFERNKLLLVASVIQGLGLLLCFTYICLHFSALQVS<br>HRYPRIQSIKVQFTEYKKEKGFILTSQKEDEIMKVQNNSVIINCDGFYLISLK<br>GYFSQEVNISLHYQKDEEPLFQLKKVRSVNSLMVASLTYKDKVYLNVTTDNTS<br>LDDFHVNGGELILIHQNPGEFCVL |
| 4-1BBL<br>(UniProt P41273)<br>SEQ ID NO: 78 | MEYASDASLDPEAPWPPAPRARACRVLPWALVAGLLLLLLAAACAVFLACPW<br>AVSGARASPGSAASPRLREGPELSPDDPAGLLDLRQGMFAQLVAQNVLLIDGP<br>LSWYSDPGLAGVSLTGGLSYKEDTKELVVAKAGVYYVFFQLELRRVVAGEGSG<br>SVSLALHLQPLRSAAGAAALALTVDLPPASSEARNSAFGFQGRLLHLSAGQRL<br>GVHLHTEARARHAWQLTQGATVLGLFRVTPEIPAGLPSPRSE |
| ICOSL<br>(UniProt O75144)<br>SEQ ID NO: 79 | MRLGSPGLLFLLFSSLRADTQEKEVRAMVGSDVELSCACPEGSRFDLNDVYVY<br>WQTSESKTVVTYHIPQNSSLENVDSRYRNRALMSPAGMLRGDFSLRLFNVTPQ<br>DEQKFHCLVLSQSLGFQEVLSVEVTLHVAANFSVPVVSAPHSPSQDELTFTCT<br>SINGYPRPNVYWINKTDNSLLDQALQNDTVFLNMRGLYDVVSVLRIARTPSVN<br>IGCCIENVLLQQNLTVGSQTGNDIGERDKITENPVSTGEKNAATWSILAVLCL<br>LVVVAVAIGWVCRDRCLQHSYAGAWAVSPETELTGHV |
| CD86<br>(UniProt P42081)<br>SEQ ID NO: 80 | MDPQCTMGLSNILFVMAFLLSGAAPLKIQAYFNETADLPCQFANSQNQSLSEL<br>VVFWQDQENLVLNEVYLGKEKFDSVHSKYMGRTSFDSDSWTLRLHNLQIKDKG<br>LYQCIIHHKKPTGMIRIHQMNSELSVLANFSQPEIVPISNITENVYINLTCSS<br>IHGYPEPKKMSVLLRTKNSTIEYDGVMQKSQDNVTELYDVSISLSVSFPDVTS<br>NMTIFCILETDKTRLLSSPFSIELEDPQPPPDHIPWITAVLPTVIICVMVFCL<br>ILWKWKKKKRPRNSYKCGTNTMEREESEQTKKREKIHIPERSDEAQRVFKSSK<br>TSSCDKSDTCF | defined above, wherein the immunotherapeutic agent is from mammal species, in particular human.

A reference sequence of human PD1 corresponds to the sequence SEQ ID NO: 74. As mentioned above, four splice variants are known for the PD1 protein, including a soluble form of PD1 (Nielsen et al., Cellular immunology, 235:2, 109-116, 2005). In the invention, the term "PD1" covers the four PD1 variants described in Nielsen et al., 2005.

A reference sequence of human PDL1 corresponds to the sequence SEQ ID NO: 75.

A reference sequence of human CD80 corresponds to the sequence SEQ ID NO: 76.

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 74, SEQ ID NO: 75, SEQ ID NO: 76, SEQ ID NO: 77, SEQ ID NO: 78, SEQ ID NO: 79 and SEQ ID NO: 80, preferably from the group consisting of: SEQ ID NO: 74, SEQ ID NO: 75, SEQ ID NO: 76 and SEQ ID NO: 78.

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 74, SEQ ID NO: 75, SEQ ID NO: 76, SEQ ID NO: 77, SEQ ID NO: 78, SEQ ID NO: 79 and SEQ ID NO: 80, preferably from the group consisting of: SEQ ID NO: 74, SEQ ID NO: 75, SEQ ID NO: 76 and SEQ ID NO: 78, that is linked to the C-terminal extremity of the heavy chain constant domain or fragment thereof of said antibody.

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 74, SEQ ID NO: 75, SEQ ID NO: 76, SEQ ID NO: 77, SEQ ID NO: 78, SEQ ID NO: 79 and SEQ ID NO: 80, preferably from the group consisting of: SEQ ID NO: 74, SEQ ID NO: 75, SEQ ID NO: 76 and SEQ ID NO: 78, that is linked to the C-terminal extremity of the light chain constant domain or fragment thereof of said antibody.

In an embodiment, the invention relates to a modified anti-SIRPa antibody or antigen-binding fragment thereof as defined above, wherein the immunotherapeutic agent comprises or consists of a protein, selected from the group consisting of PD1, PDL1, PDL2, CTLA-4, CD80, CD86, CD28, 4-1BB, 4-1BBL, CD40, CD40L, ICOS, ICOS-L, OX40L, GITR, HVEM, BTLA, CD160, LIGHT, TNFRSF25, 2B4, CD48, Tim1, Tim3, Tim4, Gal9, LAG-3, CD40, CD40L, CD70, CD27, VISTA, B7H3, B7H4 (B7x), TIGIT, CD112, HHLA2 (B7-H7), TMIGD2 (CD28H), Butyrophilin-like2 (BTNL2), variants and fragments thereof, preferably the extracellular domain (or ECD) thereof, in particular from the group consisting of PDL1, PD1, CD80, CD86, OX40L, 4-1BBL, ICOSL, variants and fragments thereof, preferably the extracellular domain thereof, or a polypeptide consisting of the extracellular domain thereof, more particularly from the group consisting of PD1, PDL1, CD80, 4-1BBL, variants and fragments thereof, preferably the extracellular domain thereof, or a polypeptide consisting of the extracellular domain thereof.

In particular, the fragments of the immunotherapeutic agents according to the invention have a size inferior or equal to 500, 400, 300, 200, 100 or 50 amino acids or consist of less or equal than 500, 400, 300, 200, 100 or 50 amino acids) and/or, preferably and, have at least the capacity to bind its ligand. In particular, the fragments of the immunotherapeutic agents according to the invention have a size from 80 to 500, in particular from 100 to 500, in particular from 100 to 300, in particular from 80 to 160, more particularly from 100 to 200 amino acids (or consist of 80 to 500 amino acids, in particular from 100 to 500, in particular from 100 to 300, in particular from 80 to 160, more particularly from 100 to 200 amino acids), and have at least the capacity to bind its ligand.

In particular, fragments of the immunotherapeutic agents according to the invention, namely PD1, PDL1, CD80, OX40L, 4-1BBL, ICOSL and CD86 correspond respectively to a fragment of at least 30%, more preferably at least 40%, and most preferably at least 50% of the amino acid sequences set forth in SEQ ID No. 74, SEQ ID No. 75, SEQ ID No. 76, SEQ ID No. 77, SEQ ID No. 78, SEQ ID No. 79 and SEQ ID No. 80.

In particular, fragments of the immunotherapeutic agents according to the invention, namely fragments of the extracellular domain PD1, PDL1, CD80, OX40L, 4-1BBL, ICOSL and CD86 correspond respectively to a fragment of at least 30%, more preferably at least 40%, more preferably at least 50%, more preferably at least 60%, and most preferably at least 70% of the amino acid sequences set forth in SEQ ID No. 81, SEQ ID No. 82, SEQ ID No. 83, SEQ ID No. 84, SEQ ID No. 85, SEQ ID No. 86, SEQ ID No. 87 and SEQ ID No. 88.

In a particular embodiment, a fragment of the immunotherapeutic agents CD80, PD1, PDL1 and 4-1BBL may comprise or consist of the fragments illustrated in the following table:

TABLE 6

Description of several active fragments of the immunotherapeutic agents of the invention and their position into the sequence of CD80, PD1, PDL1 and 4-1BBL described therein.

| Immunotherapeutic agents | ECD size | Active fragment size (amino acids and position into the sequence | References |
|---|---|---|---|
| CD80 | 208 | 101 (35-135 of Seq ID NO 76) Ig-like V-type | Girard et al, immunology letters 2014 |
| | | 86 (142-230 of SEQ ID NO: 76) Ig-like C2-type | Peach R.J. et al, J. Biol. Chem 1995 |
| PD1 | 147 or 153 | 111 (35-145 of SEQ ID NO: 74) (Ig-like V-type) | Ishida Y. et al, EMBO J. 1992 Zak et al, Structure. 2015 |
| PDL1 | 219 | 109 (19-127 of SEQ ID NO: 75) (Ig-like V-type) | Lin D.Y. et al, Proc Natl Acad Sci U.S.A. 2008 |
| | | 93 (133-225 of SEQ ID NO: 75) (Ig-like C2-type) | |
| 4-1BBL | 205 | 154 (93-254 of SEQ ID NO 78) (TNF homology domain) | Gilbreth R.N. et al, J. of Biol. Chem., 2018 |

In particular, variants of the immunotherapeutic agents according to the invention, namely PD1, PDL1, CD80, OX40L, 4-1BBL, ICOSL and CD86 are substitution variants of respectively SEQ ID No. 74, SEQ ID No. 75, SEQ ID No. 76, SEQ ID No. 77, SEQ ID No. 78, SEQ ID No. 79 and SEQ ID No. 80, and have at least the capacity to bind its ligand.

In particular, variants of the immunotherapeutic agents according to the invention, namely PD1, PDL1, CD80, OX40L, 4-1BBL, ICOSL and CD86 have respectively an identity with SEQ ID No. 74, SEQ ID No. 75, SEQ ID No. 76, SEQ ID No. 77, SEQ ID No. 78, SEQ ID No. 79 and SEQ ID No. 80 of at least 70%, more preferably at least 80%, still more preferably at least 90%, and most preferably at least 95% over their entire length.

In particular, variants of the immunotherapeutic agents according to the invention, namely variants of the extracellular domain of PD1, PDL1, CD80, OX40L, 4-1BBL, ICOSL and CD86 have respectively an identity with SEQ ID No. 81, SEQ ID No. 82, SEQ ID No. 83, SEQ ID No. 84, SEQ ID No. 85, SEQ ID No. 86, SEQ ID No. 87 and SEQ ID No. 88 of at least 70%, more preferably at least 80%, still more preferably at least 90%, and most preferably at least 95% over their entire length.

In particular, the variants of the immunotherapeutic agents of the invention have a sequence comprising or consisting of a sequence having at least 80% of identity with the sequence of the native immunotherapeutic agent over its entire length and have at least one of the biological activity of the native immunotherapeutic agent, the sequence of the native immunotherapeutic agent being in particular the amino acid sequences of SEQ ID No. 74, SEQ ID No. 75, SEQ ID No. 76, SEQ ID No. 77, SEQ ID No. 78, SEQ ID No. 79 and SEQ ID No. 80. In an alternative embodiment, the sequence of the native immunotherapeutic agent may be a consensus sequence made by alignment of known variable forms of the immunotherapeutic agent.

In particular, the variants of the immunotherapeutic agents of the invention have a sequence comprising or consisting of a sequence having at least 80%, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with the sequence of the native immunotherapeutic agent over its entire length.

The percentages of identity to which reference is made in the presentation of the present invention are determined on the basis of a global alignment of sequences to be compared, that is to say, on an alignment of sequences over their entire length, using for example the algorithm of Needleman and Wunsch 1970. This sequence comparison can be done for example using the needle software by using the parameter "Gap open" equal to 10.0, the parameter "Gap Extend" equal to 0.5, and a matrix "BLOSUM 62". Software such as needle is available on the website ebi.ac.uk worldwide, under the name "needle".

A reference sequence of the extracellular domain of human PD1, used in the examples of the present application, corresponds to the sequence associated to SEQ ID NO: 81.

A reference sequence of the extracellular domain of human PDL1, used in the examples of the present application, corresponds to the sequence associated to SEQ ID NO: 82.

A reference sequence of the extracellular domain of human CD80, used in the examples of the present application, corresponds to the sequence associated to SEQ ID NO: 83.

A reference sequence of the extracellular domain of human OX40L, used in the examples of the present application, corresponds to the sequence associated to SEQ ID NO: 84.

A reference sequence of the extracellular domain of human 4-1BBL, used in the examples of the present application, corresponds to the sequence associated to SEQ ID NO: 85.

A reference sequence of the extracellular domain of human ICOSL, used in the examples of the present application, corresponds to the sequence associated to SEQ ID NO: 86.

A reference sequence of the extracellular domain of human CD86, used in the examples of the present application, corresponds to the sequence associated to SEQ ID NO: 87.

TABLE 7

Reference sequences of the ECDs of PD1, PDL1, CD80, OX40L, 4-1BBL, ICOSL and CD86: the functional active domain described in Table 6 are indicated in bold or are underlined.

| | |
|---|---|
| ECD of PD1<br>SEQ ID NO: 81 | PGWFLDSPDRPWNPPTFSPALLVVTEGDNATFTCSFSNTSESFVLN<br>WYRMSPSNQTDKLAAFPEDRSQPGQDCRFRVTQLPNGRDFHMSVVR<br>ARRNDSGTYLCGAISLAPKAQIKESLRAELRVTERRAEVPTAHPSP<br>SPRPAGQFQ |
| ECD of PDL1<br>SEQ ID NO: 82 | FTVTVPKDLYVVEYGSNMTIECKFPVEKQLDLAALIVYWEMEDKNI<br>IQFVHGEEDLKVQHSSYRQRARLLKDQLSLGNAALQITDVKLQDAG<br>VYRCMISYGGADYKRITVKVNAPYNKINQRILVVDPVTSEHELTCQ<br>AEGYPKAEVIWTSSDHQVLSGKTTTTNSKREEKLFNVTSTLRINTT<br>TNEIFYCTFRRLDPEENHTAELVIPELPLAHPPNER |
| ECD of CD80<br>SEQ ID NO: 83 | VIHVTKEVKEVATLSCGHNVSVEELAQTRIYWQKEKKMVLTMMSGD<br>MNIWPEYKNRTIFDITNNLSIVILALRPSDEGTYECVVLKYEKDAF<br>KREHLAEVTLSVKADFPTPSISDFEIPTSNIRRIICSTSGGFPEPH<br>LSWLENGEELNAINTTVSQDPETELYAVSSKLDFNMTTNHSFMCLI<br>KYGHLRVNQTFNWNTTKQEHFPDN |
| ECD of OX40L<br>SEQ ID NO: 84 | QVSHRYPRIQSIKVQFTEYKKEKGFILTSQKEDEIMKVQNNSVIIN<br>CDGFYLISLKGYFSQEVNISLHYQKDEEPLFQLKKVRSVNSLMVAS<br>LTYKDKVYLNVTTDNTSLDDFHVNGGELILIHQNPGEFCVL |
| ECD of 4-1BBL<br>SEQ ID NO: 85 | REGPELSPDDPAGLLDLRQGMFAQLVAQNVLLIDGPLSWYSDPGLA<br>GVSLTGGLSYKEDTKELVVAKAGVYYVFFQLELRRVVAGEGSGSVS<br>LALHLQPLRSAAGAAALALTVDLPPASSEARNSAFGFQGRLLHLSA<br>GQRLGVHLHTEARARHAWQLTQGATVLGLFRVTPEIPAGLPSPRSE |
| ECD of ICOSL<br>SEQ ID NO: 86 | DTQEKEVRAMVGSDVELSCACPEGSRFDLNDVYVYWQTSESKTVVT<br>YHIPQNSSLENVDSRYRNRALMSPAGMLRGDFSLRLFNVTPQDEQK<br>FHCLVLSQSLGFQEVLSVEVTLHVAANFSVPVVSAPHSPSQDELTF<br>TCTSINGYPRPNVYWINKTDNSLLDQALQNDTVFLNMRGLYDVVSV |

TABLE 7-continued

Reference sequences of the ECDs of PD1, PDL1, CD80, OX40L, 4-1BBL, ICOSL and CD86: the functional active domain described in Table 6 are indicated in bold or are underlined.

|  |  |
|---|---|
|  | LRIARTPSVNIGCCIENVLLQQNLTVGSQTGNDIGERDKITENPVS<br>TGEKNAAT |
| ECD of CD86<br>SEQ ID NO: 87 | APLKIQAYFNETADLPCQFANSQNQSLSELVVFWQDQENLVLNEVY<br>LGKEKFDSVHSKYMGRTSFDSDSWTLRLHNLQIKDKGLYQCIIHHK<br>KPTGMIRIHQMNSELSVLANFSQPEIVPISNITENVYINLTCSSIH<br>GYPEPKKMSVLLRTKNSTIEYDGVMQKSQDNVTELYDVSISLSVSF<br>PDVTSNMTIFCILETDKTRLLSSPFSIELEDPQPPPDH |

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86 and SEQ ID NO: 87, preferably from the group consisting of: SEQ ID NO: 81, SEQ ID NO: 82, SEQ ID NO: 83 and SEQ ID NO: 85.

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 88

TABLE 8

Long version of the ECD of PD1: the IgV domain is indicated in bold.

| SEQ ID NO: 88<br>Long version of the<br>ECD of PD1 (LvPD1) | LQLGWRPGWFLDSPDRPWNPPTFSPALLVVTEGDNATFTCSFSN<br>TSESFVLNWYRMSPSNQTDKLAAFPEDRSQPGQDCRFRVTQLP<br>NGRDFHMSVVRARRNDSGTYLCGAISLAPKAQIKESLRAELRV<br>TERRAEVPTAHPSPSPRPAGQFQ |

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, that is linked to the C-terminal extremity of the heavy chain constant domain or fragment thereof of said antibody.

In an embodiment, the invention relates to a modified anti-SIRPa antibody or antigen-binding fragment thereof as defined above, wherein the immunotherapeutic agent is a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87, and SEQ ID NO: 88, preferably from the group consisting of: SEQ ID NO: 81, SEQ ID NO: 82, SEQ ID NO: 83, SEQ ID NO: 85 and SEQ ID NO: 88, that is linked to the C-terminal extremity of the light chain constant domain of said antibody.

In an embodiment, the invention relates to a modified anti-SIRPa antibody or antigen-binding fragment thereof as defined above that comprises:
- a heavy chain variable domain comprising or consisting of the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30, and
- a light chain variable domain comprising or consisting of the amino acid sequence selected from the group consisting of SEQ ID NO: 31, SEQ ID NO: 32 and SEQ ID NO: 33, in particular
- a heavy chain variable domain comprising or consisting of amino acid sequence set forth in SEQ ID NO: 24, and
- a light chain variable domain comprising or consisting of amino acid sequence set forth in SEQ ID NO: 31, or
- a heavy chain variable domain comprising or consisting of amino acid sequence set forth in SEQ ID NO: 25, and
- a light chain variable domain comprising or consisting of amino acid sequence set forth in SEQ ID NO: 32, or
- a heavy chain variable domain comprising or consisting of amino acid sequence set forth in SEQ ID NO: 25, and
- a light chain variable domain comprising or consisting of amino acid sequence set forth in SEQ ID NO: 33, or
- a heavy chain variable domain comprising or consisting of amino acid sequence set forth in SEQ ID NO: 26, and
- a light chain variable domain comprising or consisting of amino acid sequence set forth in SEQ ID NO: 32, or
- a heavy chain variable domain comprising or consisting of amino acid sequence set forth in SEQ ID NO: 26, and
- a light chain variable domain comprising or consisting of amino acid sequence set forth in SEQ ID NO: 33, or
- a heavy chain variable domain comprising or consisting of amino acid sequence set forth in SEQ ID NO: 27, and
- a light chain variable domain comprising or consisting of amino acid sequence set forth in SEQ ID NO: 32, or
- a heavy chain variable domain comprising or consisting of amino acid sequence set forth in SEQ ID NO: 27, and a light chain variable domain comprising or consisting of amino acid sequence set forth in SEQ ID NO: 33, or
a heavy chain variable domain comprising or consisting of amino acid sequence set forth in SEQ ID NO: 28, and
a light chain variable domain comprising or consisting of amino acid sequence set forth in SEQ ID NO: 32, or
a heavy chain variable domain comprising or consisting of amino acid sequence set forth in SEQ ID NO: 28, and
a light chain variable domain comprising or consisting of amino acid sequence set forth in SEQ ID NO: 33, or
a heavy chain variable domain comprising or consisting of amino acid sequence set forth in SEQ ID NO: 29, and
a light chain variable domain comprising or consisting of amino acid sequence set forth in SEQ ID NO: 32, or
a heavy chain variable domain comprising or consisting of amino acid sequence set forth in SEQ ID NO: 29, and
a light chain variable domain comprising or consisting of amino acid sequence set forth in SEQ ID NO: 33, or
a heavy chain variable domain comprising or consisting of amino acid sequence set forth in SEQ ID NO: 30, and
a light chain variable domain comprising or consisting of amino acid sequence set forth in SEQ ID NO: 32, or
a heavy chain variable domain comprising or consisting of amino acid sequence set forth in SEQ ID NO: 30, and
a light chain variable domain comprising or consisting of amino acid sequence set forth in SEQ ID NO: 33,
wherein the heavy chain constant domain or fragment thereof is linked at its C-terminal extremity to an immunotherapeutic agent comprising or consisting of a protein selected from the group consisting of PDL1, PD1, CD80, CD86, OX40L, 4-1BBL, ICOSL, variants and fragments thereof, preferably the extracellular domain (ECD) thereof,
more particularly from the group consisting of PD1, PDL1, CD80, 4-1BBL, variants and fragments thereof, preferably the extracellular domain thereof.

In an embodiment, the invention relates to a modified anti-SIRPa antibody as defined above that comprises:

a heavy chain comprising or consisting of the amino acid sequence SEQ ID NO: 56 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 57, or
a heavy chain comprising or consisting of the amino acid sequence SEQ ID NO: 36 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 43, or
a heavy chain comprising or consisting of the amino acid sequence SEQ ID NO: 37 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 44, or
a heavy chain comprising or consisting of the amino acid sequence SEQ ID NO: 37 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 45, or
a heavy chain comprising or consisting of the amino acid sequence SEQ ID NO: 38 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 44, or
a heavy chain comprising or consisting of the amino acid sequence SEQ ID NO: 38 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 45, or
a heavy chain comprising or consisting of the amino acid sequence SEQ ID NO: 39 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and
a light chain comprising or consisting of the amino acid sequence SEQ ID NO: 44, or a heavy chain comprising or consisting of the amino acid sequence SEQ ID NO: 39 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 45, or a heavy chain comprising or consisting of the amino acid sequence SEQ ID NO: 40 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 44, or a heavy chain comprising or consisting of the amino acid sequence SEQ ID NO: 40 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 45, or a heavy chain comprising or consisting of the amino acid sequence SEQ ID NO: 41 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 44, or a heavy chain comprising or consisting of the amino acid sequence SEQ ID NO: 41 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 45, or a heavy chain comprising or consisting of the amino acid sequence SEQ ID NO: 42 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 44, or a heavy chain comprising or consisting of the amino acid sequence SEQ ID NO: 42 linked at its C-terminal extremity to a protein comprising or consisting of a fragment, preferably the extracellular domain (or ECD), of an immunotherapeutic agent selected from the group consisting of PDL1, PD1, CD80, CD86, OX40L, 4-1BBL, ICOSL and their variants, more particularly from the group consisting of PD1, PDL1, CD80, 4-1BBL and their variants, and a light chain comprising or consisting of the amino acid sequence SEQ ID NO: 45.

In an embodiment, the invention relates to a modified anti-SIRPa antibody as defined above that comprises:

a heavy chain comprising or consisting of the amino acid sequence SEQ ID NO: 56 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87, and SEQ ID NO: 88, preferably from the group consisting of: SEQ ID NO: 81, SEQ ID NO: 82, SEQ ID NO: 83 and SEQ ID NO: 85, and SEQ ID NO: 88, and a light chain comprising or consisting of the amino acid sequence SEQ ID NO: 57, or a heavy chain comprising or consisting of the amino acid sequence SEQ ID NO: 36 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87, and SEQ ID NO: 88, preferably from the group consisting of: SEQ ID NO: 81, SEQ ID NO: 82, SEQ ID NO: 83, SEQ ID NO: 85, and SEQ ID NO: 88, and a light chain comprising or consisting of the amino acid sequence SEQ ID NO: 43, or a heavy chain comprising or consisting of the amino acid sequence SEQ ID NO: 37 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87, and SEQ ID NO: 88, preferably from the group consisting of: SEQ ID NO: 81, SEQ ID NO: 82, SEQ ID NO: 83, SEQ ID NO: 85, and SEQ ID NO: 88, and a light chain comprising or consisting of the amino acid sequence SEQ ID NO: 44, or a heavy chain comprising or consisting of the amino acid sequence SEQ ID NO: 37 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87, and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 45, or a heavy chain comprising or consisting of the amino acid sequence SEQ ID NO: 38 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 44, or a heavy chain comprising or consisting of the amino acid sequence SEQ ID NO: 38 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85, and SEQ ID NO: 88, and a light chain comprising or consisting of the amino acid sequence SEQ ID NO: 45, or a heavy chain comprising or consisting of the amino acid sequence SEQ ID NO: 39 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 44, or a heavy chain comprising or consisting of the amino acid sequence SEQ ID NO: 39 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 45, or a heavy chain comprising or consisting of the amino acid sequence SEQ ID NO: 40 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 44, or a heavy chain comprising or consisting of the amino acid sequence SEQ ID NO: 40 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 45, or a heavy chain comprising or consisting of the amino acid sequence SEQ ID NO: 41 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 44, or a heavy chain comprising or consisting of the amino acid sequence SEQ ID NO: 41 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 45, or a heavy chain comprising or consisting of the amino acid sequence SEQ ID NO: 42 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 83, SEQ ID NO: 85 and SEQ ID NO: 88, and a light chain comprising or consisting of the amino acid sequence SEQ ID NO: 44, or a heavy chain comprising or consisting of the amino acid sequence SEQ ID NO: 42 linked at its C-terminal extremity to a protein comprising or consisting of a sequence selected from the group consisting of: SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88, preferably from the group consisting of: SEQ ID NO: 81, SEQ ID NO: 82, SEQ ID NO: 85, SEQ ID NO: 85 and SEQ ID NO: 88, and a light chain comprising or consisting of the amino acid sequence SEQ ID NO: 45.

In particular, in the invention, the modified antibody is linked to the immunotherapeutic agent by a linker. In other words, the invention relates to modified antibodies wherein a chain or a fragment thereof, preferably its heavy chain or a fragment thereof, more preferably its heavy chain constant domain or fragment thereof, is linked to an immunotherapeutic agent, in particular by a linker. As used herein, the term "linker" refers to a sequence of at least one amino acid that links the immunotherapeutic agent and the anti-SIRPa immunoglobulin sequence portion. Such a linker may be useful to prevent steric hindrances. In some embodiments, the linker has 3, 4, 5, 6, 7, 8, 9, 10, 11, 12, 13, 14, 15, 16, 17, 18, 19, 20, 21, 22, 23, 24, 25, 26, 27, 28, 29 or 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences. Further preferred examples of linker sequences are Gly/Ser linkers of different length including (gly4ser)$_3$ (SEQ ID NO: 89, GGGGS GGGGS GGGGS), (gly4ser)$_4$ (SEQ ID NO: 90, GGGGS GGGGS GGGGS GGGGS), (gly4ser) (SEQ ID NO: 91, GGGGS), (gly3ser) (SEQ ID NO: 92, GGGS), (gly3) (GGG), (gly2ser) (GGS) and (gly3ser2)$_3$ (SEQ ID NO: 93, GGGSS GGGSS GGGSS), in particular (gly4ser)$_3$.

In an embodiment, the invention relates to a modified anti-SIRPa antibody (or a fragment thereof) as defined above wherein the antibody (or a fragment thereof) is linked to an immunotherapeutic agent by a linker sequence, preferably selected from the group consisting of SEQ ID NO: 89, SEQ ID NO: 90, SEQ ID NO: 91, SEQ ID NO: 92, GGG, GGS and SEQ ID NO: 93, in particular SEQ ID NO: 89. In an embodiment, the invention relates to a modified anti-SIRPa antibody or a fragment thereof as defined above, wherein the heavy chain of the antibody (or of a fragment thereof), in particular the heavy chain constant domain or fragment thereof, is linked to an immunotherapeutic agent by a linker sequence, preferably selected from the group consisting of SEQ ID NO: 89, SEQ ID NO: 90, SEQ ID NO: 91, SEQ ID NO: 92, GGG, GGS and SEQ ID NO: 93, in particular SEQ ID NO: 89.

In an embodiment, the invention relates to a modified anti-SIRPa antibody or a fragment thereof as defined above, wherein the light chain of the antibody (or of a fragment thereof) is linked to an immunotherapeutic agent by a linker sequence, preferably selected from the group consisting of SEQ ID NO: 89, SEQ ID NO: 90, SEQ ID NO: 91, SEQ ID NO: 92, GGG, GGS and SEQ ID NO: 93, in particular SEQ ID NO: 89.

In an embodiment, the invention relates to a modified anti-SIRPa antibody as defined above that comprises:
- a heavy chain comprising or consisting of the amino acid sequence selected from the group consisting of: SEQ ID NO: 94, SEQ ID NO: 95, SEQ ID NO: 96, SEQ ID NO: 97, SEQ ID NO: 98, SEQ ID NO: 99, SEQ ID NO: 100 and SEQ ID NO: 178, preferably from the group consisting of: SEQ ID NO: 94, SEQ ID NO: 95, SEQ ID NO: 96, SEQ ID NO: 98 and SEQ ID NO: 178, and
- a light chain comprising or consisting of the amino acid sequence SEQ ID NO: 57,
or
- a heavy chain comprising or consisting of the amino acid sequence selected from the group consisting of: SEQ ID NO: 101, SEQ ID NO: 102, SEQ ID NO: 103, SEQ ID NO: 104, SEQ ID NO: 105, SEQ ID NO: 106, SEQ ID NO: 107 and SEQ ID NO: 179, preferably from the group consisting of: SEQ ID NO: 101, SEQ ID NO: 102, SEQ ID NO: 103, SEQ ID NO: 105 and SEQ ID NO: 179, and
- a light chain comprising or consisting of the amino acid sequence SEQ ID NO: 43,
or
- a heavy chain comprising or consisting of the amino acid sequence selected from the group consisting of: SEQ ID NO: 108, SEQ ID NO: 109, SEQ ID NO: 110, SEQ ID NO: 111, SEQ ID NO: 112, SEQ ID NO: 113, SEQ ID NO: 114 and SEQ ID NO: 180, preferably from the group consisting of: SEQ ID NO: 108, SEQ ID NO: 109, SEQ ID NO: 110, SEQ ID NO: 112 and SEQ ID NO: 180, and
- a light chain comprising or consisting of the amino acid sequence SEQ ID NO: 44,
or
- a heavy chain comprising or consisting of the amino acid sequence selected from the group consisting of: SEQ ID NO: 108, SEQ ID NO: 109, SEQ ID NO: 110, SEQ ID NO: 111, SEQ ID NO: 112, SEQ ID NO: 113, SEQ ID NO: 114 and SEQ ID NO: 180, preferably from the group consisting of: SEQ ID NO: 108, SEQ ID NO: 109, SEQ ID NO: 110, SEQ ID NO: 112 and SEQ ID NO: 180, and
- a light chain comprising or consisting of the amino acid sequence SEQ ID NO: 45,
or
- a heavy chain comprising or consisting of the amino acid sequence selected from the group consisting of: SEQ ID NO: 115, SEQ ID NO: 116, SEQ ID NO: 117, SEQ ID NO: 118, SEQ ID NO: 119, SEQ ID NO: 120, SEQ ID NO: 121 and SEQ ID NO: 181, preferably from the group consisting of: SEQ ID NO: 115, SEQ ID NO: 116, SEQ ID NO: 117, SEQ ID NO: 119 and SEQ ID NO: 181, and
- a light chain comprising or consisting of the amino acid sequence SEQ ID NO: 44,
or
- a heavy chain comprising or consisting of the amino acid sequence selected from the group consisting of: SEQ ID NO: 115, SEQ ID NO: 116, SEQ ID NO: 117, SEQ ID NO: 118, SEQ ID NO: 119, SEQ ID NO: 120, SEQ ID NO: 121 and SEQ ID NO: 181, preferably from the group consisting of: SEQ ID NO: 115, SEQ ID NO: 116, SEQ ID NO: 117, SEQ ID NO: 119 and SEQ ID NO: 181, and
- a light chain comprising or consisting of the amino acid sequence SEQ ID NO: 45,
or
- a heavy chain comprising or consisting of the amino acid sequence selected from the group consisting of: SEQ ID NO: 122, SEQ ID NO: 123, SEQ ID NO: 124, SEQ ID NO: 125, SEQ ID NO: 126, SEQ ID NO: 127, SEQ ID NO: 128 and SEQ ID NO: 182, preferably from the group consisting of: SEQ ID NO: 122, SEQ ID NO: 123, SEQ ID NO: 124, SEQ ID NO: 126 and SEQ ID NO: 182, and
- a light chain comprising or consisting of the amino acid sequence SEQ ID NO: 44,
or
- a heavy chain comprising or consisting of the amino acid sequence selected from the group consisting of: SEQ ID NO: 122, SEQ ID NO: 123, SEQ ID NO: 124, SEQ ID NO: 125, SEQ ID NO: 126, SEQ ID NO: 127, SEQ ID NO: 128 and SEQ ID NO: 182, preferably from the group consisting of: SEQ ID NO: 122, SEQ ID NO: 123, SEQ ID NO: 124, SEQ ID NO: 126 and SEQ ID NO: 182, and
- a light chain comprising or consisting of the amino acid sequence SEQ ID NO: 45,
or
- a heavy chain comprising or consisting of the amino acid sequence selected from the group consisting of: SEQ ID NO: 129, SEQ ID NO: 130, SEQ ID NO: 131, SEQ ID NO: 132, SEQ ID NO: 133, SEQ ID NO: 134, SEQ ID NO: 135 and SEQ ID NO: 183, preferably from the group consisting of: SEQ ID NO: 129, SEQ ID NO: 130, SEQ ID NO: 131, SEQ ID NO: 133 and SEQ ID NO: 183, and
a light chain comprising or consisting of the amino acid sequence SEQ ID NO: 44,
or
a heavy chain comprising or consisting of the amino acid sequence selected from the group consisting of: SEQ ID NO: 129, SEQ ID NO: 130, SEQ ID NO: 131, SEQ ID NO: 132, SEQ ID NO: 133, SEQ ID NO: 134, SEQ ID NO: 135 and SEQ ID NO: 183, preferably from the group consisting of: SEQ ID NO: 129, SEQ ID NO: 130, SEQ ID NO: 131, SEQ ID NO: 133 and SEQ ID NO: 183, and
a light chain comprising or consisting of the amino acid sequence SEQ ID NO: 45,
or
a heavy chain comprising or consisting of the amino acid sequence selected from the group consisting of: SEQ ID NO: 136, SEQ ID NO: 137, SEQ ID NO: 138, SEQ ID NO: 139, SEQ ID NO: 140, SEQ ID NO: 141, SEQ ID NO: 142 and SEQ ID NO: 184, preferably from the group consisting of: SEQ ID NO: 136, SEQ ID NO: 137, SEQ ID NO: 138, SEQ ID NO: 140 and SEQ ID NO: 184, and
a light chain comprising or consisting of the amino acid sequence SEQ ID NO: 44,
or
a heavy chain comprising or consisting of the amino acid sequence selected from the group consisting of: SEQ ID NO: 136, SEQ ID NO: 137, SEQ ID NO: 138, SEQ ID NO: 139, SEQ ID NO: 140, SEQ ID NO: 141, SEQ ID NO: 142 and SEQ ID NO: 184, preferably from the group consisting of: SEQ ID NO: 136, SEQ ID NO: 137, SEQ ID NO: 138, SEQ ID NO: 140 and SEQ ID NO: 184, and
a light chain comprising or consisting of the amino acid sequence SEQ ID NO: 45,
or
a heavy chain comprising or consisting of the amino acid sequence selected from the group consisting of: SEQ ID NO: 143, SEQ ID NO: 144, SEQ ID NO: 145, SEQ ID NO: 146, SEQ ID NO: 147, SEQ ID NO: 148, SEQ ID NO: 149 and SEQ ID NO: 185, preferably from the group consisting of: SEQ ID NO: 143, SEQ ID NO: 144, SEQ ID NO: 145, SEQ ID NO: 147 and SEQ ID NO: 185, and
a light chain comprising or consisting of the amino acid sequence SEQ ID NO: 44,
or
a heavy chain comprising or consisting of the amino acid sequence selected from the group consisting of: SEQ ID NO: 143, SEQ ID NO: 144, SEQ ID NO: 145, SEQ ID NO: 146, SEQ ID NO: 147, SEQ ID NO: 148, SEQ ID NO: 149 and SEQ ID NO: 185, preferably from the group consisting of: SEQ ID NO: 143, SEQ ID NO: 144, SEQ ID NO: 145, SEQ ID NO: 147 and SEQ ID NO: 185, and
a light chain comprising or consisting of the amino acid sequence SEQ ID NO: 45.

TABLE 9

Specific heavy chains of the modified antibodies of the invention. The modified heavy chain consists, from N-ter to C-ter, of a heavy chain linked by a linker (gly4ser)3 to the extracellular domain of an immunotherapeutic agent.

| Heavy chain | Linker | ECD of an immunotherapeutic agent | Heavy chain linked to the immunotherapeutic agent |
|---|---|---|---|
| SEQ ID NO: 56 | SEQ ID NO: 89 | SEQ ID NO: 81 | SEQ ID NO: 94 (18D5-PD1) |
| SEQ ID NO: 56 | SEQ ID NO: 89 | SEQ ID NO: 82 | SEQ ID NO: 95 (18D5-PDL1) |
| SEQ ID NO: 56 | SEQ ID NO: 89 | SEQ ID NO: 83 | SEQ ID NO: 96 (18D5-CD80) |
| SEQ ID NO: 56 | SEQ ID NO: 89 | SEQ ID NO: 84 | SEQ ID NO: 97 (18D5-OX40L) |
| SEQ ID NO: 56 | SEQ ID NO: 89 | SEQ ID NO: 85 | SEQ ID NO: 98 (18D5-4-1BBL) |
| SEQ ID NO: 56 | SEQ ID NO: 89 | SEQ ID NO: 86 | SEQ ID NO: 99 (18D5-ICOSL) |
| SEQ ID NO: 56 | SEQ ID NO: 89 | SEQ ID NO: 87 | SEQ ID NO: 100 (18D5-CD86) |
| SEQ ID NO: 36 | SEQ ID NO: 89 | SEQ ID NO: 81 | SEQ ID NO: 101 (18D5c-PD1) |
| SEQ ID NO: 36 | SEQ ID NO: 89 | SEQ ID NO: 82 | SEQ ID NO: 102 (18D5c-PDL1) |
| SEQ ID NO: 36 | SEQ ID NO: 89 | SEQ ID NO: 83 | SEQ ID NO: 103 (18D5c-CD80) |
| SEQ ID NO: 36 | SEQ ID NO: 89 | SEQ ID NO: 84 | SEQ ID NO: 104 (18D5c-OX40L) |
| SEQ ID NO: 36 | SEQ ID NO: 89 | SEQ ID NO: 85 | SEQ ID NO: 105 (18D5c-4-1BBL) |
| SEQ ID NO: 36 | SEQ ID NO: 89 | SEQ ID NO: 86 | SEQ ID NO: 106 (18D5c-ICOSL) |
| SEQ ID NO: 36 | SEQ ID NO: 89 | SEQ ID NO: 87 | SEQ ID NO: 107 (18D5c-CD86) |
| SEQ ID NO: 37 | SEQ ID NO: 89 | SEQ ID NO: 81 | SEQ ID NO: 108 (HA-PD1) |
| SEQ ID NO: 37 | SEQ ID NO: 89 | SEQ ID NO: 82 | SEQ ID NO: 109 (HA-PDL1) |
| SEQ ID NO: 37 | SEQ ID NO: 89 | SEQ ID NO: 83 | SEQ ID NO: 110 (HA-CD80) |
| SEQ ID NO: 37 | SEQ ID NO: 89 | SEQ ID NO: 84 | SEQ ID NO: 111 (HA-OX40L) |
| SEQ ID NO: 37 | SEQ ID NO: 89 | SEQ ID NO: 85 | SEQ ID NO: 112 (HA-4-1BBL) |
| SEQ ID NO: 37 | SEQ ID NO: 89 | SEQ ID NO: 86 | SEQ ID NO: 113 (HA-ICOSL) |
| SEQ ID NO: 37 | SEQ ID NO: 89 | SEQ ID NO: 87 | SEQ ID NO: 114 (HA-CD86) |
| SEQ ID NO: 38 | SEQ ID NO: 89 | SEQ ID NO: 81 | SEQ ID NO: 115 (HB-PD1) |
| SEQ ID NO: 38 | SEQ ID NO: 89 | SEQ ID NO: 82 | SEQ ID NO: 116 (HB-PDL1) |
| SEQ ID NO: 38 | SEQ ID NO: 89 | SEQ ID NO: 83 | SEQ ID NO: 117 (HB-CD80) |
| SEQ ID NO: 38 | SEQ ID NO: 89 | SEQ ID NO: 84 | SEQ ID NO: 118 (HB-OX40L) |
| SEQ ID NO: 38 | SEQ ID NO: 89 | SEQ ID NO: 85 | SEQ ID NO: 119 (HB-4-1BBL) |
| SEQ ID NO: 38 | SEQ ID NO: 89 | SEQ ID NO: 86 | SEQ ID NO: 120 (HB-ICOSL) |
| SEQ ID NO: 38 | SEQ ID NO: 89 | SEQ ID NO: 87 | SEQ ID NO: 121 (HB-CD86) |
| SEQ ID NO: 39 | SEQ ID NO: 89 | SEQ ID NO: 81 | SEQ ID NO: 122 (HC-PD1) |
| SEQ ID NO: 39 | SEQ ID NO: 89 | SEQ ID NO: 82 | SEQ ID NO: 123 (HC-PDL1) |
| SEQ ID NO: 39 | SEQ ID NO: 89 | SEQ ID NO: 83 | SEQ ID NO: 124 (HC-CD80) |
| SEQ ID NO: 39 | SEQ ID NO: 89 | SEQ ID NO: 84 | SEQ ID NO: 125 (HC-OX40L) |
| SEQ ID NO: 39 | SEQ ID NO: 89 | SEQ ID NO: 85 | SEQ ID NO: 126 (HC-4-1BBL) |

TABLE 9-continued

Specific heavy chains of the modified antibodies of the invention. The modified heavy chain consists, from N-ter to C-ter, of a heavy chain linked by a linker (gly4ser)₃ to the extracellular domain of an immunotherapeutic agent.

| Heavy chain | Linker | ECD of an immunotherapeutic agent | Heavy chain linked to the immunotherapeutic agent |
| --- | --- | --- | --- |
| SEQ ID NO: 39 | SEQ ID NO: 89 | SEQ ID NO: 86 | SEQ ID NO: 127 (HC-ICOSL) |
| SEQ ID NO: 39 | SEQ ID NO: 89 | SEQ ID NO: 87 | SEQ ID NO: 128 (HC-CD86) |
| SEQ ID NO: 40 | SEQ ID NO: 89 | SEQ ID NO: 81 | SEQ ID NO: 129 (HE-PD1) |
| SEQ ID NO: 40 | SEQ ID NO: 89 | SEQ ID NO: 82 | SEQ ID NO: 130 (HE-PDL1) |
| SEQ ID NO: 40 | SEQ ID NO: 89 | SEQ ID NO: 83 | SEQ ID NO: 131 (HE-CD80) |
| SEQ ID NO: 40 | SEQ ID NO: 89 | SEQ ID NO: 84 | SEQ ID NO: 132 (HE-OX40L) |
| SEQ ID NO: 40 | SEQ ID NO: 89 | SEQ ID NO: 85 | SEQ ID NO: 133 (HE-4-1BBL) |
| SEQ ID NO: 40 | SEQ ID NO: 89 | SEQ ID NO: 86 | SEQ ID NO: 134 (HE-ICOSL) |
| SEQ ID NO: 40 | SEQ ID NO: 89 | SEQ ID NO: 87 | SEQ ID NO: 135 (HE-CD86) |
| SEQ ID NO: 41 | SEQ ID NO: 89 | SEQ ID NO: 81 | SEQ ID NO: 136 (HF-PD1) |
| SEQ ID NO: 41 | SEQ ID NO: 89 | SEQ ID NO: 82 | SEQ ID NO: 137 (HF-PDL1) |
| SEQ ID NO: 41 | SEQ ID NO: 89 | SEQ ID NO: 83 | SEQ ID NO: 138 (HF-CD80) |
| SEQ ID NO: 41 | SEQ ID NO: 89 | SEQ ID NO: 84 | SEQ ID NO: 139 (HF-OX40L) |
| SEQ ID NO: 41 | SEQ ID NO: 89 | SEQ ID NO: 85 | SEQ ID NO: 140 (HF-4-1BBL) |
| SEQ ID NO: 41 | SEQ ID NO: 89 | SEQ ID NO: 86 | SEQ ID NO: 141 (HF-ICOSL) |
| SEQ ID NO: 41 | SEQ ID NO: 89 | SEQ ID NO: 87 | SEQ ID NO: 142 (HF-CD86) |
| SEQ ID NO: 42 | SEQ ID NO: 89 | SEQ ID NO: 81 | SEQ ID NO: 143 (HEF-PD1) |
| SEQ ID NO: 42 | SEQ ID NO: 89 | SEQ ID NO: 82 | SEQ ID NO: 144 (HEF-PDL1) |
| SEQ ID NO: 42 | SEQ ID NO: 89 | SEQ ID NO: 83 | SEQ ID NO: 145 (HEF-CD80) |
| SEQ ID NO: 42 | SEQ ID NO: 89 | SEQ ID NO: 84 | SEQ ID NO: 146 (HEF-OX40L) |
| SEQ ID NO: 42 | SEQ ID NO: 89 | SEQ ID NO: 85 | SEQ ID NO: 147 (HEF-4-1BBL) |
| SEQ ID NO: 42 | SEQ ID NO: 89 | SEQ ID NO: 86 | SEQ ID NO: 148 (HEF-ICOSL) |
| SEQ ID NO: 42 | SEQ ID NO: 89 | SEQ ID NO: 87 | SEQ ID NO: 149 (HEF-CD86) |
| SEQ ID NO: 56 | SEQ ID NO: 89 | SEQ ID NO: 88 | SEQ ID NO: 178 (18D5-LvPD1) |
| SEQ ID NO: 36 | SEQ ID NO: 89 | SEQ ID NO: 88 | SEQ ID NO: 179 (18D5c-LvPD1) |
| SEQ ID NO: 37 | SEQ ID NO: 89 | SEQ ID NO: 88 | SEQ ID NO: 180 (HA-LvPD1) |
| SEQ ID NO: 38 | SEQ ID NO: 89 | SEQ ID NO: 88 | SEQ ID NO: 181 (HB-LvPD1) |
| SEQ ID NO: 39 | SEQ ID NO: 89 | SEQ ID NO: 88 | SEQ ID NO: 182 (HC-LvPD1) |
| SEQ ID NO: 40 | SEQ ID NO: 89 | SEQ ID NO: 88 | SEQ ID NO: 183 (HE-LvPD1) |
| SEQ ID NO: 41 | SEQ ID NO: 89 | SEQ ID NO: 88 | SEQ ID NO: 184 (HF-LvPD1) |
| SEQ ID NO: 42 | SEQ ID NO: 89 | SEQ ID NO: 88 | SEQ ID NO: 185 (HEF-LvPD1) |

In an embodiment, the invention relates to a modified anti-SIRPa antibody as defined above that comprises:

- a heavy chain comprising or consisting of the amino acid sequence SEQ ID NO: 56, and
- a light chain comprising or consisting of the amino acid sequence selected from the group consisting of: SEQ ID NO: 150, SEQ ID NO: 151, SEQ ID NO: 152, SEQ ID NO: 153, SEQ ID NO: 154, SEQ ID NO: 155 and SEQ ID NO: 156, preferably from the group consisting of: SEQ ID NO: 150, SEQ ID NO: 151, SEQ ID NO: 152 and SEQ ID NO: 154, or

- a heavy chain comprising or consisting of the amino acid sequence SEQ ID NO: 36, and
- a light chain comprising or consisting of the amino acid sequence selected from the group consisting of: SEQ ID NO: 157, SEQ ID NO: 158, SEQ ID NO: 159, SEQ ID NO: 160, SEQ ID NO: 161, SEQ ID NO: 162 and SEQ ID NO: 163, preferably from the group consisting of: SEQ ID NO: 157, SEQ ID NO: 158, SEQ ID NO: 159 and SEQ ID NO: 161, or

- a heavy chain comprising or consisting of the amino acid sequence SEQ ID NO: 37, and
- a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168, or

- a heavy chain comprising or consisting of the amino acid sequence SEQ ID NO: 37, and
- a light chain comprising or consisting of the amino acid sequence selected from the group consisting of: SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175, or

- a heavy chain comprising or consisting of the amino acid sequence SEQ ID NO: 38, and
- a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168, or

- a heavy chain comprising or consisting of the amino acid sequence SEQ ID NO: 38, and
- a light chain comprising or consisting of the amino acid sequence selected from the group consisting of:
SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175, or
a heavy chain comprising or consisting of the amino acid sequence SEQ ID NO: 39, and
a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168,
or
a heavy chain comprising or consisting of the amino acid sequence SEQ ID NO: 39, and
a light chain comprising or consisting of the amino acid sequence selected from the group consisting of:
SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175,
or
a heavy chain comprising or consisting of the amino acid sequence SEQ ID NO: 40, and
a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168,
or
a heavy chain comprising or consisting of the amino acid sequence SEQ ID NO: 40, and
a light chain comprising or consisting of the amino acid sequence selected from the group consisting of: SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175, or
a heavy chain comprising or consisting of the amino acid sequence SEQ ID NO: 41, and
a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168,
or
a heavy chain comprising or consisting of the amino acid sequence SEQ ID NO: 41, and
a light chain comprising or consisting of the amino acid sequence selected from the group consisting of:
SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175,
or
a heavy chain comprising or consisting of the amino acid sequence SEQ ID NO: 42, and
a light chain comprising or consisting of the amino acid sequence selected from the group consisting of: SEQ ID NO: 164, SEQ ID NO: 165, SEQ ID NO: 166, SEQ ID NO: 167, SEQ ID NO: 168, SEQ ID NO: 169 and SEQ ID NO: 170, preferably from the group consisting of: SEQ ID NO: 164, SEQ ID NO: 165, SEQ ID NO: 166 and SEQ ID NO: 168,
or
a heavy chain comprising or consisting of the amino acid sequence SEQ ID NO: 42, and
a light chain comprising or consisting of the amino acid sequence selected from the group consisting of:
SEQ ID NO: 171, SEQ ID NO: 172, SEQ ID NO: 173, SEQ ID NO: 174, SEQ ID NO: 175, SEQ ID NO: 176 and SEQ ID NO: 177, preferably from the group consisting of: SEQ ID NO: 171, SEQ ID NO: 172, SEQ ID NO: 173 and SEQ ID NO: 175.

TABLE 10

Specific light chains of the modified antibodies of the invention. The modified light chain consists, from N-ter to C-ter, of a light chain linked by a linker (gly4ser)$_3$ to the extracellular domain of an immunotherapeutic agent.

| Light chain | Linker | ECD of an immunotherapeutic agent | Light chain linked to the immunotherapeutic agent |
| --- | --- | --- | --- |
| SEQ ID NO: 57 | SEQ ID NO: 89 | SEQ ID NO: 81 | SEQ ID NO: 150 (18D5-PD1) |
| SEQ ID NO: 57 | SEQ ID NO: 89 | SEQ ID NO: 82 | SEQ ID NO: 151 (18D5-PDL1) |
| SEQ ID NO: 57 | SEQ ID NO: 89 | SEQ ID NO: 83 | SEQ ID NO: 152 (18D5-CD80) |
| SEQ ID NO: 57 | SEQ ID NO: 89 | SEQ ID NO: 84 | SEQ ID NO: 153 (18D5-OX40L) |
| SEQ ID NO: 57 | SEQ ID NO: 89 | SEQ ID NO: 85 | SEQ ID NO: 154 (18D5-4-1BBL) |
| SEQ ID NO: 57 | SEQ ID NO: 89 | SEQ ID NO: 86 | SEQ ID NO: 155 (18D5-ICOSL) |
| SEQ ID NO: 57 | SEQ ID NO: 89 | SEQ ID NO: 87 | SEQ ID NO: 156 (18D5-CD86) |
| SEQ ID NO: 43 | SEQ ID NO: 89 | SEQ ID NO: 81 | SEQ ID NO: 157 (18D5c-PD1) |
| SEQ ID NO: 43 | SEQ ID NO: 89 | SEQ ID NO: 82 | SEQ ID NO: 158 (18D5c-PDL1) |
| SEQ ID NO: 43 | SEQ ID NO: 89 | SEQ ID NO: 83 | SEQ ID NO: 159 (18D5c-CD80) |
| SEQ ID NO: 43 | SEQ ID NO: 89 | SEQ ID NO: 84 | SEQ ID NO: 160 (18D5cc-OX40L) |
| SEQ ID NO: 43 | SEQ ID NO: 89 | SEQ ID NO: 85 | SEQ ID NO: 161 (18D5-4-1BBL) |
| SEQ ID NO: 43 | SEQ ID NO: 89 | SEQ ID NO: 86 | SEQ ID NO: 162 (18D5c-ICOSL) |
| SEQ ID NO: 43 | SEQ ID NO: 89 | SEQ ID NO: 87 | SEQ ID NO: 163 (18D5c-CD86) |
| SEQ ID NO: 44 | SEQ ID NO: 89 | SEQ ID NO: 81 | SEQ ID NO: 164 (LA-PD1) |
| SEQ ID NO: 44 | SEQ ID NO: 89 | SEQ ID NO: 82 | SEQ ID NO: 165 (LA-PDL1) |
| SEQ ID NO: 44 | SEQ ID NO: 89 | SEQ ID NO: 83 | SEQ ID NO: 166 (LA-CD80) |
| SEQ ID NO: 44 | SEQ ID NO: 89 | SEQ ID NO: 84 | SEQ ID NO: 167 (LA-OX40L) |
| SEQ ID NO: 44 | SEQ ID NO: 89 | SEQ ID NO: 85 | SEQ ID NO: 168 (LA-4-1BBL) |
| SEQ ID NO: 44 | SEQ ID NO: 89 | SEQ ID NO: 86 | SEQ ID NO: 169 (LA-ICOSL) |
| SEQ ID NO: 44 | SEQ ID NO: 89 | SEQ ID NO: 87 | SEQ ID NO: 170 (LA-CD86) |

TABLE 10-continued

Specific light chains of the modified antibodies of the invention. The modified light chain consists, from N-ter to C-ter, of a light chain linked by a linker (gly4ser)3 to the extracellular domain of an immunotherapeutic agent.

| Light chain | Linker | ECD of an immunotherapeutic agent | Light chain linked to the immunotherapeutic agent |
|---|---|---|---|
| SEQ ID NO: 45 | SEQ ID NO: 89 | SEQ ID NO: 81 | SEQ ID NO: 171 (LB-PD1) |
| SEQ ID NO: 45 | SEQ ID NO: 89 | SEQ ID NO: 82 | SEQ ID NO: 172 (LB-PDL1) |
| SEQ ID NO: 45 | SEQ ID NO: 89 | SEQ ID NO: 83 | SEQ ID NO: 173 (LB-CD80) |
| SEQ ID NO: 45 | SEQ ID NO: 89 | SEQ ID NO: 84 | SEQ ID NO: 174 (LB-OX40L) |
| SEQ ID NO: 45 | SEQ ID NO: 89 | SEQ ID NO: 85 | SEQ ID NO: 175 (LB-4-1BBL) |
| SEQ ID NO: 45 | SEQ ID NO: 89 | SEQ ID NO: 86 | SEQ ID NO: 176 (LB-ICOSL) |
| SEQ ID NO: 45 | SEQ ID NO: 89 | SEQ ID NO: 87 | SEQ ID NO: 177 (LB-CD86) |

In an embodiment, the invention relates to a modified anti-SIRPa antibody or antigen-binding fragment thereof as defined above that comprises:

a heavy chain comprising or consisting of amino acid sequence set forth in SEQ ID NO: 143, and
a light chain comprising or consisting of amino acid sequence set forth in SEQ ID NO: 45,
or
a heavy chain comprising or consisting of amino acid sequence set forth in SEQ ID NO: 144, and
a light chain comprising or consisting of amino acid sequence set forth in SEQ ID NO: 45,
or
a heavy chain comprising or consisting of amino acid sequence set forth in SEQ ID NO: 145, and
a light chain comprising or consisting of amino acid sequence set forth in SEQ ID NO: 45,
or
a heavy chain comprising or consisting of amino acid sequence set forth in SEQ ID NO: 146, and
a light chain comprising or consisting of amino acid sequence set forth in SEQ ID NO: 45,
or
a heavy chain comprising or consisting of amino acid sequence set forth in SEQ ID NO: 147, and
a light chain comprising or consisting of amino acid sequence set forth in SEQ ID NO: 45,
or
a heavy chain comprising or consisting of amino acid sequence set forth in SEQ ID NO: 148, and
a light chain comprising or consisting of amino acid sequence set forth in SEQ ID NO: 45,
or
a heavy chain comprising or consisting of amino acid sequence set forth in SEQ ID NO: 149, and
a light chain comprising or consisting of amino acid sequence set forth in SEQ ID NO: 45,
or
a heavy chain comprising or consisting of amino acid sequence set forth in SEQ ID NO: 185, and
a light chain comprising or consisting of amino acid sequence set forth in SEQ ID NO: 45,
or
a heavy chain comprising or consisting of amino acid sequence set forth in SEQ ID NO: 42, and
a light chain comprising or consisting of amino acid sequence set forth in SEQ ID NO: 171,
or
a heavy chain comprising or consisting of amino acid sequence set forth in SEQ ID NO: 42, and
a light chain comprising or consisting of amino acid sequence set forth in SEQ ID NO: 172,
or
a heavy chain comprising or consisting of amino acid sequence set forth in SEQ ID NO: 42, and
a light chain comprising or consisting of amino acid sequence set forth in SEQ ID NO: 173,
or
a heavy chain comprising or consisting of amino acid sequence set forth in SEQ ID NO: 42, and
a light chain comprising or consisting of amino acid sequence set forth in SEQ ID NO: 174,
or
a heavy chain comprising or consisting of amino acid sequence set forth in SEQ ID NO: 42, and
a light chain comprising or consisting of amino acid sequence set forth in SEQ ID NO: 175,
or
a heavy chain comprising or consisting of amino acid sequence set forth in SEQ ID NO: 42, and
a light chain comprising or consisting of amino acid sequence set forth in SEQ ID NO: 176,
or
a heavy chain comprising or consisting of amino acid sequence set forth in SEQ ID NO: 42, and
a light chain comprising or consisting of amino acid sequence set forth in SEQ ID NO: 177.

TABLE 11

Specific sequences of modified antibody HEFLB wherein the variable regions are in bold, the constant regions are underlined, the linkers are in italic, and the immunotherapeutic agents are normal characters.

| | |
|---|---|
| Heavy chain HEF-PD1 (SEQ ID NO: 143) | EVQLVQSGAEVKKPGESLRISCKASGYSFTSYWVHWVRQMPGKGLEWMGNIDPSDS DTHYSPSFQGHVTLSVDKSISTAYLQLSSLKASDTAMYYCVRGGTGTLAYFAYWGQ GTLVTVSSASTKGPSVFPLAPCSRSTSESTAALGCLVKDYFPEPVTVSW NSGALTSGVHTFPAVLQSSGLYSLSSVVTVPSSSLGTKTYTCNVDHKP SNTKVDKRVESKYGPPCPPCPAPEFLGGPSVFLFPPKPKDTLMISRTP EVTCVVVDVSQEDPEVQFNWYVDGVEVHNAKTKPREEQFNSTYRVVSV LTVLHQDWLNGKEYKCKVSNKGLPSSIEKTISKAKGQPREPQVYTLPP |

TABLE 11-continued

Specific sequences of modified antibody HEFLB wherein the variable regions are in bold, the constant regions are underlined, the linkers are in italic, and the immunotherapeutic agents are normal characters.

| | |
|---|---|
| | SQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSPGK*GG*<br>*GGSGGGGSGGGGS*PGWFLDSPDRPWNPPTFSPALLVVTEGDNATFTCS<br>FSNTSESFVLNWYRMSPSNQTDKLAAFPEDRSQPGQDCRFFRVTQLPNG<br>RDFHMSVVRARRNDSGTYLCGAISLAPKAQIKESLRAELRVTERRAEV<br>PTAHPSPSPRPAGQFQ |
| Heavy chain<br>HEF-PDL1<br>(SEQ ID NO:<br>144) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKP<br>SNTKVDKRVESKYGPPQPPQPAPEFLGGPSVFLFPPKPKDTLMISRTP<br>EVTCVVVDVSQEDPEVQFNWYVDGVEVHNAKTKPREEQFNSTYRVVSV<br>LTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSPGK*GG*<br>*GGSGGGGSGGGGS*FTVTVPKDLYVVEYGSNMTIECKFPVEKQLDLAAL<br>IVYWEMEDKNIIQFVHGEEDLKVQHSSYRQRARLLKDQLSLGNAALQI<br>TDVKLQDAGVYRCMISYGGADYKRITVKVNAPYNKINQRILVVDPVTS<br>EHELTCQAEGYPKAEVIWTSSDHQVLSGKTTTTNSKREEKLFNVTSTL<br>RINTTTNEIFYCTFRRLDPEENHTAELVIPELPLAHPPNER |
| Heavy chain<br>HEF-CD80<br>(SEQ ID NO:<br>145) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKP<br>SNTKVDKRVESKYGPPCPPCPAPEFLGGPSVFLFPPKPKDTLMISRTP<br>EVTCVVVDVSQEDPEVQFNWYVDGVEVHNAKTKPREEQFNSTYRVVSV<br>LTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSD<br>GSFFLYSRLTVDKSRWQEGNVFSCSVMHEALHNHYITQKSLSLSPGK*GG*<br>*GGSGGGGSGGGGS*VIHVTKEVKEVATLSCGHNVSVEELAQTRIYWQKE<br>KKMVLTMMSGDMNIWPEYKNRT1FDITNNLSIVILALRPSDEGTYECV<br>VLKYEKDAFKREHLAEVTLSVKADFPTPSISDFEIPTSNIRRIICSTS<br>GGFPEPHLSWLENGEELNAINTTVSQDPETELYAVSSKLDFNMTTNHS<br>FMCLIKYGHLRVNQTFNWNTTKQEHFPDN |
| Heavy chain<br>HEF-OX40L<br>(SEQ ID NO:<br>146) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKP<br>SNTKVDKRVESKYGPPCPPCPAPEFLGGPSVFLFPPKPKDTLMISRTP<br>EVTCVVVDVSQEDPEVQFNWYVDGVEVHNAKTKPREEQFNSTYRVVSV<br>LTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSPGKI*GG*<br>*GGSGGGGSGGGGS*QVSHRYPRIQSIKVQFTEYKKEKGFILTSQKEDEI<br>MKVQNNSVIINCDGFYLISLKGYFSQEVNISLHYQKDEEPLFQLKKVR<br>SVNSLMVASLTYKDKVYLNVTTDNTSLDDFHVNGGELILIHQNPGEFC<br>VL |
| Heavy chain<br>HEF-4-1-BBL<br>(SEQ ID NO:<br>147) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKP<br>SNTKVDKRVESKYGPPCPPCPAPEFLGGPSVFLFPPKPKDTLMISRTP<br>EVTCVVVDVSQEDPEVQFNWYVDGVEVHNAKTKPREEQFNSTYRVVSV<br>LTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSPGK*GG*<br>*GGSGGGGSGGGGS*REGPELSPDDPAGLLDLRQGMFAQLVAQNVLLIDG<br>PLSWYSDPGLAGVSLTGGLSYKEDTKELVVAKAGVYYVFFQLELRRVV<br>AGEGSGSVSLALHLQPLRSAAGAAALALTVDLPPASSEARNSAFGFQG<br>RLLHLSAGQRLGVHLHTEARARHAWQLTQGATVLGLFRVTPEIPAGLP<br>SPRSE |
| Heavy chain<br>HEF-ICOSL<br>(SEQ ID NO:<br>148) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKP<br>SNTKVDKRVESKYGPPCPPCPAPEFLGGPSVFLFPPKPKDTLMISRTP<br>EVTCVVVDVSQEDPEVQFNWYVDGVEVHNAKTKPREEQFNSTYRVVSV<br>LTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSD<br>GSFFLYSRLTVDKSRWQEGNVFSCSVMHEALHNHYTQKSLSLSPGK*GG*<br>*GGSGGGGSGGGGS*DTQEKEVRAMVGSDVELSCACPEGSRFDLNDVYVY |

TABLE 11-continued

Specific sequences of modified antibody HEFLB wherein the variable regions are in bold, the constant regions are underlined, the linkers are in italic, and the immunotherapeutic agents are normal characters.

| | |
|---|---|
| | WQTSESKTVVTYHIPQNSSLENVDSRYRNRALMSPAGMLRGDFSLRLF<br>NVTPQDEQKFHCLVLSQSLGFQEVLSVEVTLHVAANFSVPVVSAPHSP<br>SQDELTFTCTSINGYPRPNVYWINKTDNSLLDQALQNDTVFLNMRGLY<br>DVVSVLRIARTPSVNIGCCIENVLLQQNLTVGSQTGNDIGERDKITEN<br>PVSTGEKNAAT |
| Heavy chain<br>HEF-CD86<br>(SEQ ID NO:<br>149) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSS<u>ASTKGPSVFPLAPCSRSTSESTAALGCLVKDYFPEPVTVW</u><br><u>NSGALTSGVHTFPAVLQSSGLYSLSSVVTVPSSSLGTKTYTCNVDHKP</u><br><u>SNTKVDKRVESKYGPPCPPCPAPEFLGGPSVFLFPPKPKDTLM1SRTP</u><br><u>EVTCVVVDVSQEDPEVQFNWYVDGVEVHNAKTKPREEQFNSTYRVVSV</u><br><u>LTVLHQDWLNGKEYKCKVSNKGLPSSIEKTISKAKGQPREPQVYTLPP</u><br><u>SQEEMTKNQVSLTCLVKGFYPSDIAVEWESNGQPENNYKTTPPVLDSD</u><br><u>GSFFLYSRLTVDKSRWQEGNVFSCSVMHEALHNHYTQKSLSLSPGK</u>*GG*<br>*GGSGGGGSGGGGS*APLKIQAYFNETADLPCQFANSQNQSLSELVVFWQ<br>DQENLVLNEVYLGKEKFDSVHSKYMGRTSFDSDSWTLRLHNLQIKDKG<br>LYQCIIHHKKPTGMIRIHQMNSELSVLANFSQPEIVPISNITENVYIN<br>LTCSSIHGYPEPKKMSVLLRTKNSTIEYDGVMQKSQDNVTELYDVSIS<br>LSVSFPDVTSNMTIFCILETDKTRLLSSPFSIELEDPQPPPDH |
| HEF-LvPD1<br>(SEQ ID NO:<br>185) | EVQLVQSGAEVKKPGESLRISCKASGYSFTSYWVHWVRQMPGKGLEWMGNIDPSDS<br>DTHYSPSFQGHVTLSVDKSISTAYLQLSSLKASDTAMYYCVRGGTGTLAYFAYWGQ<br>GTLVTVSS<u>ASTKGPSVFPLAPCSRSTSESTAALGCLVKDYFPEPVTVSW</u><br><u>NSGALTSGVHTFPAVLQSSGLYSLSSVVTVPSSSLGTKTYTCNVDHKP</u><br><u>SNTKVDKRVESKYGPPCPPCPAPEFLGGPSVFLFPPKPKDTLMISRTP</u><br><u>EVTCVVVDVSQEDPEVQFNWYVDGVEVHNAKTKPREEQFNSTYRVVSV</u><br><u>LTVLHQDWLNGKEYKCKVSNKGLPSSIEKTISKAKGQPREPQVYTLPP</u><br><u>SQEEMTKNQVSLTCLVKGFYPSDIAVEWESNGQPENNYKTTPPVLDSD</u><br><u>GSFFLYSRLTVDKSRWQEGNVFSCSVMHEALHNHYTQKSLSLSPGK</u>*GG*<br>*GGSGGGGSGGGGS*LQLGWRPGWFLDSPDRPWNPPTFSPALLVVTEGDNATF<br>TCSFSNTSESFVLNWYRMSPSNQTDKLAAFPEDRSQPGQDCRFRVTQLPNGR<br>DFHMSVVRARRNDSGTYLCGAISLAPKAQIKESLRAELRVTERRAEVPTAHPSP<br>SPRPAGQFQ |
| Light chain<br>LB-PD1<br>(SEQ ID NO:<br>171) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br><u>RTVAAPSVFIFPPSDEQLKSGTASVVCLLNNFYPREAKVQWKVDNALQ</u><br><u>SGNSQESVTEQDSKDSTYSLSSTLTLSKADYEKHKVYACEVTHQGLSS</u><br><u>PVTKSFNRGEC</u>*GGGGSGGGGSGGGGS*PGWFLDSPDRPWNPPTFSPALL<br>VVTEGDNATFTCSFSNTSESFVLNWYRMSPSNQTDKLAAFPEDRSQPG<br>QDCRFRVTQLPNGRDFHMSVVRARRNDSGTYLCGAISLAPKAQIKESL<br>RAELRVTERRAEVPTAHPSPSPRPAGQFQ |
| Light chain<br>LB-PDL1<br>(SEQ ID NO:<br>172) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br><u>RTVAAPSVFIFPPSDEQLKSGTASVVCLLNNFYPREAKVQWKVDNALQ</u><br><u>SGNSQESVTEQDSKDSTYSLSSTLTLSKADYEKHKVYACEVTHQGLSS</u><br><u>PVTKSFNRGEC</u>*GGGGSGGGGSGGGGS*FTVTVPKDLYVVEYGSNMTIEC<br>KFPVEKQLDLAALIVYWEMEDKNIIQFVHGEEDLKVQHSSYRQRARLL<br>KDQLSLGNAALQITDVKLQDAGVYRCMISYGGADYKRITVKVNAPYNK<br>INQRILVVDPVTSEHELTCQAEGYPKAEVIWTSSDHQVLSGKTTTTNS<br>KREEKLFNVTSTLRINTTTNEIFYCTFRRLDPEENHTAELVIPELPLA<br>HPPNER |
| Light chain<br>LB-CD80<br>(SEQ ID NO:<br>173) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br><u>RTVAAPSVFIFPPSDEQLKSGTASVVCLLNNFYPREAKVQWKVDNALQ</u><br><u>SGNSQESVTEQDSKDSTYSLSSTLTLSKADYEKHKVYACEVTHQGLSS</u><br><u>PVTKSFNRGEC</u>*GGGGSGGGGSGGGGS*VIHVTKEVKEVATLSCGHNVSV<br>EELAQTRIYWQKEKKMVLTMMSGDMNIWPEYKNRTIFDITNNLSIVIL<br>ALRPSDEGTYECVVLKYEKDAFKREHLAEVTLSVKADFPTPSISDFEI<br>PTSNIRRIICSTSGGFPEPHLSWLENGEELNAINTTVSQDPETELYAV<br>SSKLDFNMTTNHSFMCLIKYGHLRVNQTFNWNTTKQEHFPDN |
| Light chain<br>LB-OX40L<br>(SEQ ID NO:<br>174) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br><u>RTVAAPSVFIFPPSDEQLKSGTASVVCLLNNFYPREAKVQWKVDNALQ</u><br><u>SGNSQESVTEQDSKDSTYSLSSTLTLSKADYEKHKVYACEVTHQGLSS</u><br><u>PVTKSFNRGEC</u>*GGGGSGGGGSGGGGS*QVSHRYPRIQSIKVQFTEYKKE<br>KGFILTSQKEDEIMKVQNNSVIINCDGFYLISLKGYFSQEVNISLHYQ<br>KDEEPLFQLKKVRSVNSLMVASLTYKDKVYLNVTTDNTSLDDFHVNGG<br>ELILIHQNPGEFCVL |
| LB-4-1-BBL<br>(SEQ ID | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK |

TABLE 11-continued

Specific sequences of modified antibody HEFLB wherein the variable regions are in bold, the constant regions are underlined, the linkers are in italic, and the immunotherapeutic agents are normal characters.

| | |
|---|---|
| 175) | RTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSS<br>PVTKSFNRGEC*GGGGSGGGGSGGGGS*REGPELSPDDPAGLLDLRQGMF<br>AQLVAQNVLLIDGPLSWYSDPGLAGVSLTGGLSYKEDTKELVVAKAGV<br>YYVFFQLELRRVVAGEGSGSVSLALHLQPLRSAAGAAALALTVDLPPA<br>SSEARNSAFGFQGRLLHLSAGQRLGVHLHTEARARHAWQLTQGATVLG<br>LFRVTPEIPAGLPSPRSE |
| Light chain<br>LB-ICOSL<br>(SEQ ID NO: 176) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br>RTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSS<br>PVTKSFNRGEC*GGGGSGGGGSGGGGS*DTQEKEVRAMVGSDVELSCACP<br>EGSRFDLNDVYVYWQTSESKTVVTYHIPQNSSLENVDSRYRNRALMSP<br>AGMLRGDFSLRLFNVTPQDEQKFHCLVLSQSLGFQEVLSVEVTLHVAA<br>NFSVPVVSAPHSPSQDELTFTCTSINGYPRPNVYWINKTDNSLLDQAL<br>QNDTVFLNMRGLYDVVSVLRIARTPSVNIGCCIENVLLQQNLTVGSQT<br>GNDIGERDKITENPVSTGEKNAAT |
| Light chain<br>LB-CD86<br>(SEQ ID NO: 177) | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK<br>RTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSS<br>PVTKSFNRGEC*GGGGSGGGGSGGGGS*APLKIQAYFNETADLPCQFANS<br>QNQSLSELVVFWQDQENLVLNEVYLGKEKFDSVHSKYMGRTSFDSDSW<br>TLRLHNLQIKDKGLYQCIIHHKKPTGMIRIHQMNSELSVLANFSQPEI<br>VPISNITENVYINLTCSSIHGYPEPKKMSVLLRTKNSTIEYDGVMQKS<br>QDNVTELYDVSISLSVSFPDVTSNMTIFCILETDKTRLLSSPFSIELE<br>DPQPPPDH |

Modified SIRPa Antibodies

The embodiments recited for the modified antibodies as defined above are repeated mutadis mutandis to the modified antibodies recited in the other aspects of the invention.

In another aspect, the invention relates to a modified anti-SIRPa antibody or antigen-binding fragment thereof that specifically binds to a conformational epitope comprising at least one peptide selected from the group consisting of SEQ ID NO: 70 (ELIYNQKEGHFPR), SEQ ID NO: 71 (RNNMDFSIRIGN) and SEQ ID NO: 72 (SPRDITLKW) within SIRPa, said modified anti-SIRPa antibody or antigen-binding fragment being linked to an immunotherapeutic agent.

In another aspect, the invention relates to a modified anti-SIRPa antibody or antigen-binding fragment thereof that specifically binds to a conformational epitope comprising or consisting of the peptides of SEQ ID NO: 70 (ELIYNQKEGHFPR), SEQ ID NO: 71 (RNNMDFSIRIGN) and SEQ ID NO: 72 (SPRDITLKW) within SIRPa, said modified anti-SIRPa antibody or antigen-binding fragment being linked to an immunotherapeutic agent.

In another aspect, the invention relates to a modified anti-SIRPa antibody or antigen-binding fragment thereof that specifically binds to a conformational epitope comprising at least one peptide selected from the group consisting of SEQ ID NO: 70 (ELIYNQKEGHFPR) and SEQ ID NO: 71 (RNNMDFSIRIGN), said modified anti-SIRPa antibody or antigen-binding fragment being linked to an immunotherapeutic agent.

In another aspect, the invention relates to a modified anti-SIRPa antibody or antigen-binding fragment thereof that specifically binds to a conformational epitope comprising or consisting of the peptides of SEQ ID NO: 70 (ELIYNQKEGHFPR) and SEQ ID NO: 71 (RNNMDFSIRIGN) within SIRPa, said modified anti-SIRPa antibody or antigen-binding fragment being linked to an immunotherapeutic agent.

In another aspect, the invention relates to a modified anti-SIRPa antibody or antigen-binding fragment thereof that specifically binds to a conformational epitope comprising at least one peptide selected from the group consisting of SEQ ID NO: 73 (YNQK) and SIR, said modified anti-SIRPa antibody or antigen-binding fragment being linked to an immunotherapeutic agent.

In another aspect, the invention relates to a modified anti-SIRPa antibody or antigen-binding fragment thereof that specifically binds to a conformational epitope comprising or consisting of the peptides of SEQ ID NO: 73 (YNQK) and SIR within SIRPa, said modified anti-SIRPa antibody or antigen-binding fragment being linked to an immunotherapeutic agent.

In another aspect, the invention relates to a modified anti-SIRPa antibody or antigen-binding fragment thereof that comprises:
  a) a heavy chain comprising HCDR1, HCDR2 and HCDR3, and/or
  b) a light chain comprising LCDR1, LCDR2 and LCDR3,
wherein said CDRs are defined as follows:
  HCDR1 comprising or consisting of a peptide of the amino acid sequence SEQ ID NO: 14 (SYWVH),
  HCDR2 comprising or consisting of a peptide of the amino acid sequence SEQ ID NO: 15 (NIDPSDSDTHYNQKFKD) or SEQ ID NO: 16 (NIDPSDSDTHYSPSFQG),
  HCDR3 comprising or consisting of a peptide of the amino acid sequence SEQ ID NO: 17 (GGTGTMAWFAY), SEQ ID NO: 18 (GGTGTLAWFAY), SEQ ID NO: 19 (GGTGTMAYFAY) or SEQ ID NO: 20 (GGTGTLAYFAY),
  LCDR1 comprising or consisting of a peptide of the amino acid sequence SEQ ID NO: 21 (RSSQSLVHSYGNTYLY), LCDR2 comprising or consisting of a peptide of the amino acid sequence SEQ ID NO: 22 (RVSNRFS), and LCDR3 comprising or consisting of a peptide of the amino acid sequence SEQ ID NO: 23 (FQGTHVPYT), said modified anti-SIRPa antibody or antigen-binding fragment comprising a heavy chain constant domain or a fragment thereof, said heavy chain constant domain or fragment thereof being linked to an immunotherapeutic agent.

The invention also relates to a modified anti-SIRPa antibody or antigen-binding fragment thereof which inhibits the binding of human CD47 to human SIRPa and which does not bind specifically to human SIRPg, and/or which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and/or which does not inhibit, preferably which increases, the proliferation of human T-cells, and/or which does not inhibit the binding of human CD47 to human SIRPg, and/or which increases the secretion of TNFa by human PBMC and/or T-cells, and/or which increases the secretion of IFNg by human PBMC, and/or which increases the secretion of MIP1a by human macrophages, and/or which increases the activation of human T cells, in particular which inhibits the binding of human CD47 to human SIRPa and which does not bind specifically to human SIRPg and which does not inhibit, preferably which increases, the proliferation of human T-cells and which does not inhibit the binding of human CD47 to human SIRPg and which increases the secretion of TNFa by human PBMC and T-cells and which increases the secretion of IFNg by human PBMC and which increases the secretion of MIP1a by human macrophages, and which increases the activation of human T cells, said modified anti-SIRPa antibody or antigen-binding fragment being linked to an immunotherapeutic agent, particularly said modified anti-SIRPa antibody or antigen-binding fragment comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof.

Applications

The applications recited for the modified antibodies of the invention as defined above are repeated mutatis mutandis for the isolated nucleic acid molecule and group of isolated nucleic acid molecules of the invention, the vectors of the invention, the host cells of the invention, the pharmaceutical compositions of the invention and the combination of products according to the invention.

In another aspect, the invention relates to:

a modified anti-SIRPa antibody or antigen-binding fragment thereof as defined above, or a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg, and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg, and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells.

for use as a medicament.

The present invention also relates to a method of treatment in a subject in need thereof comprising administering to said subject an effective amount of:

a modified anti-SIRPa antibody or antigen-binding fragment thereof as defined above, or an anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages, and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells.

The present invention also relates to the use of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages, and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, in the manufacture of a medicament.

In another aspect, the invention relates to:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, for use in the treatment of any condition susceptible of being improved or prevented by differentiating myeloid-derived suppressor cells (MDSC) into differentiated MDSC, in particular into differentiated MDSC expressing at least one human marker selected from the group consisting of CD80, CD86 and CD103, in particular at least two human markers selected from the group consisting of CD80, CD86 and CD103, and more particularly into cells expressing human markers CD80, CD86 and CD103; and/or into differentiated MDSC expressing CD11b.

As defined herein, "a condition susceptible of being improved or prevented by differentiating myeloid-derived suppressor cells (MDSC) into differentiated MDSC" corresponds to a cancer including inflammatory cancers and cancers with infiltrated myeloid cells (in particular with infiltrated MDSCs and/or TAM cells), an infectious disease, a trauma, an auto-immune disease (such as rheumatoid arthritis, type 1 diabetes, lupus, psoriasis), a vaccination, a chronic inflammatory diseases (such as Inflammatory bowel diseases including Crohn disease and Ulcerative colitis), a sceptic shock, a chronic infectious disease (such as with *Pseudomonas* or CMV), fibrosis, atherosclerosis or a transplant dysfunctions.

The present invention also relates to a method of treatment of any condition susceptible of being improved or prevented by differentiating myeloid-derived suppressor cells (MDSC) into differentiated MDSC in a subject in need thereof comprising administering to said subject an effective amount of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells.

The present invention also relates to the use of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, in the manufacture of a medicament for the treatment of any condition susceptible of being improved or prevented by differentiating monocytic myeloid-derived suppressor cells (Mo-MDSC) into non suppressive cells.

In an embodiment, the invention relates to:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, for use in the treatment of any condition susceptible of being improved or prevented by modifying macrophage polarization to pro-inflammatory macrophages.

Indeed, SIRPa acts as a checkpoint inhibitor and participates to macrophage polarization. In particular, blocking SIRPa induces a pro-inflammatory function of macrophages associated to type 1 macrophages (M1 pro-inflammatory=M (IFNg)) and inhibits the suppressive activity of macrophages in the tumor, since the pro-inflammatory profile of macrophages is obtained at the expense of type 2 macrophages (M2 type high phagocytic activity=M (IL4)). Thus, an antagonist of SIRPa is able to inhibit M2 phenotypic polarization of macrophages and/or favors pro-inflammatory M1-type macrophage function and can be used in therapeutic.

As defined herein, "a condition susceptible of being improved or prevented by modifying macrophage polarization to favor pro-inflammatory macrophages" corresponds for example to a solid cancer, a liquid cancer, an infectious disease, a trauma, an auto-immune disease, a vaccination, a brain injury, a nerve injury, a polycythemia, a hemochromatosis or a chronic inflammatory disease.

The present invention also relates to a method of treatment of any condition susceptible of being improved or prevented by modifying macrophage polarization to pro-inflammatory macrophages in a subject in need thereof comprising administering to said subject an effective amount of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells.

In an embodiment, the invention also relates to the use of:
  a modified anti-SIRPa antibody or antigen-binding fragment thereof as defined above, or
  a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, in the manufacture of a medicament for the treatment of any condition susceptible of being improved or prevented by modifying macrophage polarization to pro-inflammatory macrophages.

Modifying the polarization of macrophages to favor pro-inflammatory cells can be useful in a number of pathologies or situations. As described above, this modification is particularly useful in the context of cancers, to restore an anti-tumor activity of macrophages and/or prevent the pro-tumoral activity of M2-type macrophages. Inappropriate immune responses due to an excess of M2-type macrophage polarization also occur in infectious diseases, fibrosis, vaccination, trauma and chronic inflammatory diseases.

Thus, according to a particular embodiment, a modified anti-SIRPa antibody of the invention can be used to treat an individual who has a cancer selected from the group consisting of lung cancers, mesothelioma cancers, ovary cancers, liver cancers, bladder cancers, brain cancers, breast cancers, colon cancers, sarcomas, pancreas cancers, head and neck cancers, kidney cancers, thymomas, gliomas, melanomas and hematologic cancers such as lymphomas (Hodgkin's lymphoma and non-Hodgkin's lymphoma), leukemias such as T and B Acute or Chronic Lymphoblastic Leukemia (ALL or CLL) or Acute or Chronic myeloid leukemia (AML or CML) and Myelomas.

In an embodiment, the invention relates to:
  a modified anti-SIRPa antibody or antigen-binding fragment thereof as defined above, or
  a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, for use in the treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction.

In an embodiment, the invention relates to a method of treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction in a subject in need thereof comprising administering to said subject an effective amount of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, In an embodiment, the invention relates to the use of:
- a modified anti-SIRPa antibody or antigen-binding fragment thereof as defined above, or
- a modified anti-SIRPa antibody or antigen-binding fragment thereof, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in the manufacture of a medicament for the treatment of a pathology selected from the group consisting of a cancer (in particular inflammatory cancers and cancers with infiltrated myeloid cells particularly with infiltrated MDSCs and/or TAM cells), an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction.

In an embodiment, the invention relates to a modified anti-human SIRPa antibody or antigen-binding fragment thereof as defined above, for its uses as defined above, wherein said modified anti-human SIRPa antibody or antigen-binding fragment thereof of the invention is administered to a patient presenting a SIRPa-positive tumor.

In an embodiment, the invention relates to:
- a modified anti-SIRPa antibody or antigen-binding fragment thereof as defined above, or
- a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells,
for use in vaccination.

In an embodiment, the invention relates to a method of vaccination of a subject comprising administering to said subject an effective amount of:
a modified anti-SIRPa antibody or antigen-binding fragment thereof as defined above, or
a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells.

In an embodiment, the invention relates to the use of:
a modified anti-SIRPa antibody or antigen-binding fragment thereof as defined above, or
a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells,
in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells,
for the manufacture of a vaccine.

Suppressive myeloid cells limit the effectiveness of vaccination, especially in young children. Thus, an anti-SIRPa/g would limit the benefit provided by an anti-SIRPa on the vaccine response, preventing T lymphocytes from responding to vaccination.

The modified antibody or antigen-binding fragment thereof of the invention can be administered in a variety of suitable routes, e.g. intravenously (IV), subcutaneously (SC), or, intramuscularly (IM) to the subject.

The modified antibody or antigen-binding fragment thereof can be administered alone or in combination with another therapeutic agent, e.g. a second human monoclonal antibody or antigen binding fragment thereof. In another example, the antibody is administered together with another agent, for example, an immunosuppressive agent, an erythropoiesis-stimulating agent (ESA), in combination with therapeutic cell compositions, and the like.

In an embodiment, the invention relates to a modified anti-SIRPa antibody or antigen-binding fragment thereof for its use as defined above, wherein the anti-SIRPa antibody or antigen-binding fragment is combined with a second therapeutic agent.

In particular, anti-SIRPa antibodies of the present invention can be combined with some other potential strategies for overcoming tumor immune evasion mechanisms with agents in clinical development or already on the market (see table 1 from Antonia et al. Immuno-oncology combinations: a review of clinical experience and future prospects. Clin. Cancer Res. Off. J. Am. Assoc. Cancer Res. 20, 6258-6268, 2014):

1—Reversing the inhibition of adaptive immunity (blocking T-cell checkpoint pathways), for example by using an anti-CTLA4, an anti-PD1 or an anti-PD-L1 molecule;

2—Switching on adaptive immunity (promoting T-cell costimulatory receptor signaling using agonist molecules, in particular antibodies), for example by targeting CD137 (4-1BB) using agonist molecules including agonist anti-CD137 (anti-4-1BB) antibodies or CD137 (4-1BB) ligands;

3—Improving the function of innate immune cells;

4—Activating the immune system (potentiating immune-cell effector function), for example through vaccine-based strategies.

The administration of the second therapeutic agent can be simultaneous or not with the administration of the anti-SIRPa antibody. Depending on the nature of the second agent, a co-administration can be prepared in the form of a combination drug (product), also known as a "combo". A combo is a fixed-dose combination that includes two or more active pharmaceutical ingredients combined in a single dosage form, which is manufactured and distributed in fixed doses. But the dose regimen and/or the administration route can also differ.

In a preferred embodiment, this second therapeutic agent is selected from the group consisting of chemotherapeutic agents, radiotherapy agents, immunotherapeutic agents, cell therapy agents (such as CAR-T cells), antibiotics and probiotics. Said immunotherapeutic agent can also be an antibody targeting tumoral antigen, particularly selected from the group consisting of anti-Her2, anti-EGFR, anti-CD20, anti-CD19, anti-CD52.

The modified antibody may be provided at an effective dose from about 1 ng/kg body weight to about 30 mg/kg body weight, or more. In specific embodiments, the dosage may range from 1 µg/kg to about 20 mg/kg, optionally from 10 µg/kg up to 10 mg/kg or from 100 µg/kg up to 5 mg/kg.

The term "effective dose" or "effective dosage" or "effective amount" is defined as an amount sufficient to achieve or at least partially achieve the desired effect. The term "effective dose" is meant to encompass an amount sufficient to cure or at least partially arrest the disease and its complications in a patient already suffering from the disease. Amounts or doses effective for this use will depend on the condition to be treated, the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted such that it can be administered to the patient once or over a series of administrations, and in order to obtain the optimal therapeutic effect.

Dosing for such purposes may be repeated as required, e.g. daily, semi-weekly, weekly, semi-monthly, monthly, or as required during relapses.

In an aspect, the invention also relates to:
a modified anti-SIRPa antibody or antigen-binding fragment thereof as defined above, or
a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells,
in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells,
for use in a diagnostic test, particularly in personalized medicine, more particularly in a companion diagnostic test.

In an embodiment, the invention relates to a method of diagnostic, particularly in personalized medicine, more particularly in a companion diagnostic test, using:
a modified anti-SIRPa antibody or antigen-binding fragment thereof as defined above, or
a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells,
in particular which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, In an embodiment, the invention relates to the use of:
a modified anti-SIRPa antibody or antigen-binding fragment thereof as defined above, or
a modified anti-SIRPa antibody or antigen-binding fragment thereof which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and/or which does not inhibit, preferably which increases, the proliferation of T-cells and/or which does not inhibit the binding of CD47 to SIRPg and/or which increases the secretion of TNFa by PBMC and T-cells and/or which increases the secretion of IFNg by PBMC and/or which increases the secretion of MIP1a by macrophages and/or which increases the activation of human T cells, in particular, which comprises a heavy chain constant domain or a fragment thereof linked to an immunotherapeutic agent, said immunotherapeutic agent comprising or consisting of a protein selected from the group consisting of human PD1, human PDL1, human CD80, human 4-1BBL, immunotherapeutic agent variants thereof and immunotherapeutic agent fragments thereof, preferably the extracellular domain thereof, and which inhibits the binding of CD47 to SIRPa and which does not bind specifically to SIRPg and which does not inhibit, preferably which increases, the proliferation of T-cells and which does not inhibit the binding of CD47 to SIRPg and which increases the secretion of TNFa by PBMC and T-cells and which increases the secretion of IFNg by PBMC and which increases the secretion of MIP1a by macrophages and which increases the activation of human T cells, in the manufacture of a medicament for a diagnostic test, particularly in personalized medicine, more particularly in a companion diagnostic test.

In an aspect, the invention also relates to an in vitro or ex vivo method of diagnosis, in particular a method of diagnostic suitable for use in personalized medicine, more particularly in a companion diagnosis, wherein a modified anti-SIRPa antibody or an antigen-binding fragment thereof of the invention is used for the detection of SIRPa+ cells in a sample previously obtained from a subject and optionally for the quantification of the expression of SIRPa.

In an aspect, the invention also relates to the use of a modified anti-SIRPa antibody or an antigen-binding fragment thereof of the invention, in the manufacture of a medicament suitable for use in a diagnostic test, in particular for use in personalized medicine, or in a companion diagnostic test.

In an aspect, the invention also relates to the use of at least one modified anti-human SIRPa antibody or antigen-binding fragment thereof of the invention, as a means for determination of the expression and/or level of expression of SIRPa in a biological sample previously obtained from an individual.

In an aspect, the invention also relates to an in vitro or ex vivo method to determine a SIRPa positive cells in a subject from a biological sample previously obtained from said subject, comprising:
i) determining in vitro the expression and/or the level of expression of SIRPa, in a biological sample previously obtained from said subject using the modified anti-human SIRPa antibody or antigen-binding fragment thereof of the invention.

In an aspect, the invention also relates to the use, in particular in vitro or ex vivo, of at least one modified anti-human SIRPa antibody or antigen-binding fragment thereof of the invention in a method wherein SIRPa is used as a biomarker that is predictive for the response to a treatment in a subject, in particular in a cancer subject.

In an aspect, the invention also relates to an in vitro or ex vivo method of predicting the response of a cancer subject to a treatment, in particular with a modified anti-human SIRPa antibody or antigen-binding fragment thereof of the invention, comprising:
determining the expression level of SIRPa in a tumour sample previously obtained from a subject, in particular with a modified anti-human SIRPa antibody or antigen-binding fragment thereof of the invention, and
comparing the expression level of SIRPa to a value representative of an expression level of SIRPa in a non-responding subject population, wherein a higher expression level of SIRPa in the tumour sample of the subject is indicative for a subject who will respond to the treatment.

In an aspect, the invention also relates to a method of in vitro or ex vivo determining the presence of SIRPa+ cells in a sample previously obtained from a subject which comprises determining presence of SIRPa as a biomarker that is predictive for the response of a subject to a treatment, in particular a response of a subject diagnosed with a cancer, wherein said method comprises:
determining the expression level of SIRPa in a tumor sample previously obtained from a subject, in particular with any modified anti-human SIRPa antibody or antigen-binding fragment thereof as defined here above, and
comparing the expression level of SIRPa to a value representative of an expression level of SIRPa in a non-responding subject population, wherein a higher expression level of SIRPa in the tumor sample of the subject is indicative for a patient who will respond to the treatment.

Compositions

In another aspect, the invention relates to a pharmaceutical composition comprising a modified antibody or antigen-binding fragment thereof as defined above and/or an isolated nucleic acid molecule or a group of isolated nucleic acid molecules of the invention and a pharmaceutically acceptable carrier.

As used herein, a "pharmaceutical composition" is meant to encompass a composition suitable for administration to a subject or patient, such as a mammal, especially a human. In general, a "pharmaceutical composition" is sterile and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, a "pharmaceutically acceptable carrier" is meant to encompass an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable carrier" as used herein includes both one and more than one such excipient, diluent, carrier, and adjuvant.

In particular, the invention relates to a pharmaceutical composition which comprises as an active ingredient a modified antibody or antigen-binding fragment thereof as defined above and a pharmaceutically acceptable carrier.

Combination Products

In another aspect, the invention relates to a therapeutic means, in particular a combination product means, which comprises as active ingredients: a modified anti-SIRPa antibody or antigen-binding fragment thereof as defined above and/or an isolated nucleic acid molecule or a group of isolated nucleic acid molecules of the invention and a second therapeutic agent, wherein said active ingredients are formulated for separate, sequential or combined therapy, in particular for combined or sequential use.

In particular, the invention relates to a combination product comprising a modified anti-SIRPa antibody or antigen-binding fragment thereof as defined above and/or an isolated nucleic acid molecule or a group of isolated nucleic acid molecules of the invention and a second therapeutic agent for simultaneous, separate or sequential use a medicament.

In an embodiment, the invention relates to a combination product as defined above, wherein the second therapeutic agent is selected from the group consisting of chemotherapeutic agents, radiotherapy agents, cell therapy agents, immunotherapeutic agents, antibiotics and probiotics.

In an embodiment, the invention relates to a combination product as defined above, wherein said immunotherapeutic agent is selected from the group consisting of therapeutic vaccines, immune checkpoint blockers or activators, in particular of adaptive immune cells (T and B lymphocytes) and antibody-drug conjugates.

In an embodiment, the invention relates to a combination product as defined above, wherein said immune checkpoint blocker or activator of adaptive immune cells (T and B lymphocytes) is selected from the group consisting of anti-PDL1, anti-PD1, anti-CTLA4, anti-CD137, anti-CD2, anti-CD28, anti-CD40, anti-HVEM, anti-BTLA, anti-CD160, anti-TIGIT, anti-TIM-1/3, anti-LAG-3, anti-2B4, and anti-OX40, anti-CD40 agonist, CD40-L, TLR agonists, anti-ICOS, ICOS-L and B-cell receptor agonists, in particular selected from the group consisting of anti-PDL1, anti-PD1 and anti-CD137.

In one embodiment, said immunotherapeutic agent is an antibody targeting tumoral antigen, particularly selected from the group consisting of anti-Her2, anti-EGFR, anti-CD20, anti-CD19, anti-CD52.

In an aspect, the invention relates to a combination product as defined above, for simultaneous, separate or sequential use in the treatment of any condition susceptible of being improved or prevented by differentiating myeloid-derived suppressor cells (MDSC) into differentiated MDSC, in particular into differentiated MDSC expressing at least one human marker selected from the group consisting of CD80, CD86 and CD103, in particular at least two human markers selected from the group consisting of CD80, CD86 and CD103, and more particularly into cells expressing human markers CD80, CD86 and CD103; and/or into differentiated MDSC expressing CD11b.

In an embodiment, the invention relates to a method of treatment of any condition susceptible of being improved or prevented by differentiating myeloid-derived suppressor cells (MDSC) into differentiated MDSC in a subject in need thereof comprising administering simultaneously, separately or sequentially to said subject an effective amount of a combination product as defined above.

In an embodiment, the invention relates to the use of a combination product as defined above in the manufacture of a medicament for the treatment any condition susceptible of being improved or prevented by differentiating myeloid-derived suppressor cells (MDSC) into differentiated MDSC.

In an aspect, the invention relates to a combination product as defined above, for simultaneous, separate or sequential use in the treatment of any condition susceptible of being improved or prevented by modifying macrophage polarization to pro-inflammatory macrophages.

In an embodiment, the invention relates to a method of treatment of any condition susceptible of being improved or prevented by modifying macrophage polarization to pro-inflammatory macrophages in a subject in need thereof comprising administering simultaneously, separately or sequentially to said subject an effective amount of a combination product as defined above.

In an embodiment, the invention relates to the use of a combination product as defined above in the manufacture of a medicament for the treatment any condition susceptible of being improved or prevented by modifying macrophage polarization to pro-inflammatory macrophages.

In an aspect, the invention relates to a combination product as defined above, for simultaneous, separate or sequential use in the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction or for use in vaccination.

In an embodiment, the invention relates to a method of treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction of a subject in need thereof comprising administering simultaneously, separately or sequentially to said subject an effective amount of a combination product as defined above.

In an embodiment, the invention relates to the use of a combination product as defined above, in the manufacture of a medicament for the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction or for use in vaccination.

Nucleic Acids

In another aspect, the invention relates to an isolated nucleic acid molecule or a group of isolated nucleic acid molecules encoding a modified antibody or antigen-binding fragment thereof as defined above.

As used herein, a nucleic acid molecule can be double stranded and single stranded, linear and circular. It is preferably comprised in a vector which is preferably comprised in a host cell.

In an embodiment, the invention relates to an isolated nucleic acid molecule or a group of isolated nucleic acid molecules encoding a modified antibody or antigen-binding fragment thereof as defined above, said nucleic acid molecule comprising or consisting of at least one sequence selected from SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68 and SEQ ID NO: 69, and at least one sequence encoding an immunotherapeutic agent, in particular PDL1, PD1, CD80, CD86, OX40L, 4-1BBL, ICOSL and their variants and fragments thereof, more particularly PD1, PDL1, CD80, 4-1BBL and their variants and fragments thereof.

In embodiment, the invention relates to an isolated nucleic acid molecule or a group of isolated nucleic acid molecules encoding an antibody or antigen-binding fragment thereof as defined above, said nucleic acid molecules comprising:

a sequence encoding the heavy chain variable domain of said antibody, preferably comprising:
SEQ ID NO: 58, SEQ ID NO: 59 or SEQ ID NO: 60,
SEQ ID NO: 61 or SEQ ID NO: 62, and
SEQ ID NO: 63, SEQ ID NO: 64, SEQ ID NO: 65 or SEQ ID NO: 66, and/or a sequence encoding the light chain variable domain of said antibody, preferably comprising:
SEQ ID NO: 67,
SEQ ID NO: 68, and
SEQ ID NO: 69, and at least one sequence encoding an immunotherapeutic agent, in particular PDL1, PD1, CD80, CD86, OX40L, 4-1BBL, ICOSL and their variants, more particularly PD1, PDL1, CD80, 4-1BBL and their variants.

TABLE 12

Sequences coding the CDRs of the heavy chain variable domains and the CDRs of the light chain variable domains of antibodies according to the invention.

| | | |
|---|---|---|
| Nucleic acid sequences coding the HCDR1 (corresponding to the amino acid sequence SEQ ID NO: 14) | AGCTATTGGGTGCAC<br>TCTTATTGGGTGCAC<br>TCCTATTGGGTGCAC | SEQ ID NO: 58<br>SEQ ID NO: 59<br>SEQ ID NO: 60 |
| Nucleic acid sequence coding the HCDR2 (corresponding to the amino acid sequence SEQ ID NO: 15) | AACATCGACCCCAGCGACTCTGATACC<br>CATTACAATCAGAAGTTTAAGGAC | SEQ ID NO: 61 |
| Nucleic acid sequence coding the HCDR2 (corresponding to the amino acid sequence SEQ ID NO: 16) | AACATCGACCCCAGCGACTCTGATACA<br>CACTACTCCCCTAGCTTTCAGGGC | SEQ ID NO: 62 |
| Nucleic acid sequence coding the HCDR3 (corresponding to the amino acid sequence SEQ ID NO: 17) | GGAGGAACCGGAACAATGGCTTGGTT<br>TGCTTAC | SEQ ID NO: 63 |
| Nucleic acid sequence coding the HCDR3 (corresponding to the amino acid sequence SEQ ID NO: 18) | GGAGGAACCGGCACACTGGCTTGGTT<br>CGCTTAC | SEQ ID NO: 64 |
| Nucleic acid sequence coding the HCDR3 (corresponding to the amino acid sequence SEQ ID NO: 19) | GGAGGAACCGGAACAATGGCTTACTT<br>CGCTTAT | SEQ ID NO: 65 |
| Nucleic acid sequence coding the HCDR3 (corresponding to the amino acid sequence SEQ ID NO: 20) | GGAGGAACCGGCACACTGGCTTACTT<br>CGCTTAT | SEQ ID NO: 66 |
| Nucleic acid sequence coding the LCDR1 (corresponding to the amino acid sequence SEQ ID NO: 21) | AGGTCCAGCCAGTCCCTGGTGCACAG<br>CTATGGCAACACATACCTGTAT | SEQ ID NO: 67 |
| Nucleic acid sequence coding the LCDR2 (corresponding to the amino acid sequence SEQ ID NO: 22) | AGGGTGTCTAATCGGTTCTCC | SEQ ID NO: 68 |
| Nucleic acid sequence coding the LCDR3 (corresponding to the amino acid sequence SEQ ID NO: 23) | TTTCAGGGCACCCATGTGCCATACACA | SEQ ID NO: 69 |

In particular, the invention relates to a nucleic acid molecule comprising or consisting of a sequence selected from SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54 and SEQ ID NO: 55, and of at least one sequence encoding an immunotherapeutic agent, in particular selected from PDL1, PD1, CD80, CD86, OX40L, 4-1BBL, ICOSL, their variants and fragments thereof, more particularly from PD1, PDL1, CD80, 4-1BBL their variants and fragments thereof.

TABLE 13

Sequences coding the heavy chain variable domains and the light chain variable domains of antibodies according to the invention.

| | | |
|---|---|---|
| Nucleic acid sequence coding the heavy chain variable domain of the wild-type antibody | CAGGTGCAGCTGCAGCAGCCAGGAGCTGAGCTGGTGAG<br>GCCTGGCTCCAGCGTGAAGCTGTCCTGCAAGGCTAGCGG<br>CTACACCTTCACAAGCTATTGGGTGCACTGGGTGAAGCA<br>GCGGCCAATCCAGGGCCTGGAGTGGATCGGCAACATCG | SEQ ID NO: 46 |

TABLE 13-continued

Sequences coding the heavy chain variable domains and the light chain variable domains of antibodies according to the invention.

| | | |
|---|---|---|
| (chimeric and mouse 18D5) | ACCCCAGCGACTCTGATACCCATTACAATCAGAAGTTTAA GGACAAGGCCTCTCTGACCGTGGATAAGTCTTCCAGCAC AGCTTATATGCAGCTGTCTTCCCTGACATTCGAGGATTCC GCCGTGTACTATTGCGTGAGGGGAGGAACCGGAACAAT GGCTTGGTTTGCTTACTGGGGCCAGGGCACCCTGGTGAC AGTGTCTGCT | |
| Nucleic acid sequence coding the heavy chain variable domain of humanized variant (HA) | GAGGTGCAGCTGGTGCAGAGCGGAGCTGAGGTGAAGA AGCCAGGCGAGTCTCTGAGGATCTCCTGCAAGGCTAGCG GCTACACCTTCACATCTTATTGGGTGCACTGGGTGCGGC AGATGCCAGGCAAGGGCCTGGAGTGGATCGGCAACATC GACCCTAGCGACTCTGATACCCACTACAATCAGAAGTTTA AGGACCATGTGACCCTGTCTGTGGATAAGTCCATCAGCA CAGCCTATCTGCAGCTGTCCAGCCTGAAGGCCTCCGATAC AGCTATGTACTATTGCGTGAGGGGAGGAACCGGAACAA TGGCTTGGTTCGCTTACTGGGGCCAGGGCACCCTGGTGA CAGTGTCTTCC | SEQ ID NO: 47 |
| Nucleic acid sequence coding the heavy chain variable domain of humanized variant (HB) | GAGGTGCAGCTGGTGCAGTCCGGAGCTGAGGTGAAGAA GCCAGGCGAGTCTCTGAGGATCTCCTGCAAGGCTTCTGG CTACTCCTTCACCAGCTATTGGGTGCACTGGGTGCGGCA GATGCCAGGCAAGGGCCTGGAGTGGATGGGCAACATCG ACCCTAGCGACTCTGATACACACTACAATCAGAAGTTTAA GGACCATGTGACCCTGAGCGTGGATAAGTCCATCAGCAC AGCCTATCTGCAGCTGTCCAGCCTGAAGGCCTCTGATACC GCTATGTACTATTGCGTGAGGGGAGGAACCGGAACAAT GGCTTGGTTCGCTTACTGGGGCCAGGGCACCCTGGTGAC AGTGTCTTCC | SEQ ID NO: 48 |
| Nucleic acid sequence coding the heavy chain variable domain of humanized variant (HC) | GAGGTGCAGCTGGTGCAGTCTGGCGCCGAGGTGAAGAA GCCAGGCGAGAGCCTGAGGATCTCTTGCAAGGCTAGCG GCTACTCTTTCACCTCCTATTGGGTGCACTGGGTGCGGCA GATGCCAGGCAAGGGCCTGGAGTGGATGGGCAACATCG ACCCCAGCGACTCTGATACACACTACTCCCCTAGCTTTCA GGGCCATGTGACCCTGTCCGTGGACAAGTCTATCTCCAC AGCCTATCTGCAGCTGTCCAGCCTGAAGGCCAGCGATAC CGCTATGTACTATTGCGTGAGGGGAGGAACCGGAACAAT GGCTTGGTTCGCTTACTGGGGCCAGGGCACCCTGGTGAC AGTGTCTTCC | SEQ ID NO: 49 |
| Nucleic acid sequence coding the heavy chain variable domain of humanized variant (HE) | GAGGTGCAGCTGGTGCAGTCTGGCGCCGAGGTGAAGAA GCCAGGCGAGAGCCTGAGGATCTCTTGCAAGGCTAGCG GCTACTCTTTCACCTCCTATTGGGTGCACTGGGTGCGGCA GATGCCAGGCAAGGGCCTGGAGTGGATGGGCAACATCG ACCCCAGCGACTCTGATACACACTACTCCCCTAGCTTTCA GGGCCATGTGACCCTGTCCGTGGACAAGTCTATCTCCAC AGCCTATCTGCAGCTGTCCAGCCTGAAGGCCAGCGATAC CGCTATGTACTATTGCGTGAGGGGAGGAACCGGCACACT GGCTTGGTTCGCTTACTGGGGCCAGGGCACCCTGGTGAC AGTGTCTTCC | SEQ ID NO: 50 |
| Nucleic acid sequence coding the heavy chain variable domain of humanized variant (HF) | GAGGTGCAGCTGGTGCAGTCTGGCGCCGAGGTGAAGAA GCCAGGCGAGAGCCTGAGGATCTCTTGCAAGGCTAGCG GCTACTCTTTCACCTCCTATTGGGTGCACTGGGTGCGGCA GATGCCAGGCAAGGGCCTGGAGTGGATGGGCAACATCG ACCCCAGCGACTCTGATACACACTACTCCCCTAGCTTTCA GGGCCATGTGACCCTGTCCGTGGACAAGTCTATCTCCAC AGCCTATCTGCAGCTGTCCAGCCTGAAGGCCAGCGATAC CGCTATGTACTATTGCGTGAGGGGAGGAACCGGAACAAT GGCTTACTTCGCTTATTGGGGCCAGGGCACCCTGGTGAC AGTGTCTTCC | SEQ ID NO: 51 |
| Nucleic acid sequence coding the heavy chain variable domain of humanized variant (HEF) | GAGGTGCAGCTGGTGCAGTCTGGCGCCGAGGTGAAGAA GCCAGGCGAGAGCCTGAGGATCTCTTGCAAGGCTAGCG GCTACTCTTTCACCTCCTATTGGGTGCACTGGGTGCGGCA GATGCCAGGCAAGGGCCTGGAGTGGATGGGCAACATCG ACCCCAGCGACTCTGATACACACTACTCCCCTAGCTTTCA GGGCCATGTGACCCTGTCCGTGGACAAGTCTATCTCCAC AGCCTATCTGCAGCTGTCCAGCCTGAAGGCCAGCGATAC CGCTATGTACTATTGCGTGAGGGGAGGAACCGGCACACT GGCTTACTTCGCTTATTGGGGCCAGGGCACCCTGGTGAC AGTGTCTTCC | SEQ ID NO: 52 |
| Nucleic acid sequence coding the light chain of the wild-type antibody (chimeric and mouse | GACGTGGTCATGACCCAGACACCACTGAGCCTGCCCGTG TCCCTGGGCGATCAGGCCTCTATCTCCTGCAGGTCCAGCC AGTCCCTGGTGCACAGCTATGGCAACACATACCTGTATTG GTACCTGCAGAAGCCAGGCCAGTCCCCCAAGCTGCTGAT | SEQ ID NO: 53 |

TABLE 13-continued

Sequences coding the heavy chain variable domains and the light chain variable domains of antibodies according to the invention.

| | | |
|---|---|---|
| 18D5) | CTACAGGGTGTCTAATCGGTTCTCCGGCGTGCCTGACAG<br>GTTCTCCGGCTCTGGCTCCGGCACCGATTTCACACTGAAG<br>ATCAGCAGGGTGGAGGCTGAGGACCTGGGCGTGTATTT<br>CTGTTTTCAGGGCACCCATGTGCCATACACATTTGGCTCT<br>GGCACCAAGCTGGAGATCAAG | |
| Nucleic acid sequence coding the light chain variable domain of humanized variant A (LA) | GACGTGGTCATGACACAGAGCCCACTGTCTCTGCCTGTG<br>ACCCTGGGACAGCCAGCCTCTATCTCCTGCAGGTCCAGCC<br>AGTCCCTGGTGCACAGCTATGGCAACACATACCTGTATTG<br>GTACCAGCAGAGGCCCGGACAGAGCCCAAGGCTGCTGA<br>TCTACAGGGTGTCTAATCGGTTCTCCGGCGTGCCTGACA<br>GGTTTAGCGGCTCTGGCTCCGGCACCGATTTCACACTGA<br>AGATCTCTAGAGTGGAGGCTGAGGATGTGGGCGTGTAT<br>TTCTGTTTTCAGGGCACCCATGTGCCATACACATTTGGCG<br>GCGGCACCAAGGTGGAGATCAAG | SEQ ID NO: 54 |
| Nucleic acid sequence coding the light chain variable domain of humanized variant (LB) | GACGTGGTCATGACACAGAGCCCACTGTCTCTGCCTGTG<br>ACCCTGGGACAGCCAGCCTCTATCTCCTGCAGGTCCAGCC<br>AGTCCCTGGTGCACAGCTACGGCAACACATACCTGTATT<br>GGTTCCAGCAGAGGCCCGGACAGAGCCCAAGGCTGCTG<br>ATCTATAGGGTGTCTAATCGGTTCTCCGGCGTGCCTGACA<br>GGTTTAGCGGATCTGGATCCGGAACCGACTTCACCCTGA<br>AGATCTCTAGAGTGGAGGCTGAGGATGTGGGCGTGTAC<br>TATTGTTTCCAGGGCACCCATGTGCCATACACATTTGGCG<br>GCGGCACCAAGGTGGAGATCAAG | SEQ ID NO: 55 |

In particular, the invention relates to a nucleic acid molecule comprising or consisting of a sequence encoding an amino acid sequence selected from the group consisting of: SEQ ID NO: SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 12, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184 and SEQ ID NO: 185.

In particular, the invention relates to a nucleic acid molecule comprising or consisting of:
   a sequence encoding an amino acid sequence selected from the group consisting of: SEQ ID NO: 143, SEQ ID NO: 144, SEQ ID NO: 145, SEQ ID NO: 146, SEQ ID NO: 147, SEQ ID NO: 148, SEQ ID NO: 149, and SEQ ID NO: 185, and
   a sequence SEQ ID NO: 55.

In particular, the invention relates to a nucleic acid molecule comprising or consisting of:
   a sequence SEQ ID NO: 52, and
   a sequence encoding an amino acid sequence selected from the group consisting of: SEQ ID NO: 171, SEQ ID NO: 172, SEQ ID NO: 173, SEQ ID NO: 174, SEQ ID NO: 175, SEQ ID NO: 176 and SEQ ID NO: 177.

Vectors

In another aspect, the invention relates to a vector comprising the nucleic acid molecule as defined above.

As used herein, a "vector" is a nucleic acid molecule used as a vehicle to transfer genetic material into a cell. The term "vector" encompasses plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

Host Cells

In another aspect, the invention relates to an isolated host cell comprising a vector as defined above and/or an isolated nucleic acid molecule or a group of isolated nucleic acid molecules of the invention. As used herein, the term "host cell" is intended to include any individual cell or cell culture that can be or has been recipient of vectors, exogenous nucleic acid molecules, and polynucleotides encoding the antibody construct of the present invention; and/or recipients of the antibody construct itself. The introduction of the respective material into the cell can be carried out by way of transformation, transfection and the like. The term "host cell" is also intended to include progeny or potential progeny of a single cell. Suitable host cells include prokaryotic or eukaryotic cells, and also include but are not limited to bacteria, yeast cells, fungi cells, plant cells, and animal cells such as insect cells and mammalian cells, e.g., murine, rat, rabbit, macaque or human.

Kits

In another aspect, the invention relates to a kit comprising:
- a modified antibody or antigen-binding fragment thereof as defined above,
- a nucleic acid molecule coding said modified antibody or antigen-binding fragment thereof,
- a vector comprising said nucleic acid molecule, and/or
- a cell comprising said vector.

As a matter of convenience, the modified antibody of the present invention can be provided in a kit, i.e. a packaged combination of reagents.

In the context of the present invention, the term "kit" means two or more components (one of which corresponding to the antibody or antigen-binding thereof, the nucleic acid molecule, the vector or the cell of the invention) packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material containing the modified antibody construct of the present invention in an appropriate dosage for administration. The kit may additionally contain directions for use (e.g. in the form of a leaflet or instruction manual), means for administering the modified antibody construct of the present invention such as a syringe, pump, infuser or the like, means for reconstituting the antibody construct of the invention and/or means for diluting the antibody construct of the invention.

In an embodiment, the invention relates to a kit as defined above for a single-dose administration unit. The kit of the invention may also contain a first recipient comprising a dried/lyophilized modified antibody construct and a second recipient comprising an aqueous formulation. In certain embodiments of this invention, kits containing single-chambered and multi-chambered pre-filled syringes (e.g., liquid syringes and lysosyringes) are provided.

Method of Manufacturing an Antibody

In an aspect, the invention also relates to a method of manufacturing an antibody, in particular an antibody of the invention, comprising immunizing a non-human animal, in particular a non-human mammal, against at least one antigen as defined above, and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequence of human SIRPa consisting of SEQ ID NO: 3 (KFRKGSPD[DV]/[T]E), and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequence of human SIRPa consisting of SEQ ID NO: 3 (KFRKGSPD[DV]/[T]E) and at least one epitope sequence of human SIRPa selected from the group consisting of SEQ ID NO: 1 (SLIPVGP), SEQ ID NO: 2 (G/ARELIYNQKEGH), SEQ ID NO: 4 (QHTVSFTCESHGFSPRDITLKWF), SEQ ID NO: 5 (ICEVAHVTLQG) or SEQ ID NO: 6 (YPQRLQLTWLE), and in particular collecting the resulting serum from said immunised non-human animal to obtain antibodies directed against said antigen.

In particular, the invention also relates to a method of manufacturing an antibody comprising immunizing a non-human animal against an antigen comprising or consisting of the epitope sequences of human SIRPa consisting of SEQ ID NO: 1 (SLIPVGP), SEQ ID NO: 2 (G/ARELIYNQKEGH), SEQ ID NO: 3 (KFRKGSPD[DV]/[T]E), SEQ ID NO: 4 (QHTVSFTCESHGFSPRDITLKWF), SEQ ID NO: 5 (ICEVAHVTLQG) and SEQ ID NO: 6 (YPQRLQLTWLE), and in particular collecting the resulting serum from said immunised non-human animal to obtain antibodies directed against said antigen.

In particular, the invention also relates to a method of manufacturing an antibody as defined above comprising a step wherein the antibody is linked to an immunotherapeutic agent as defined previously.

Method of Selecting a Modified Antibody

In an aspect, the invention relates to a method of selecting a modified antibody of the invention or an antigen-binding fragment of such an antibody, comprising or consisting of at least one of the following steps:

a. testing (e.g. according to a method describing in the Examples 1, 2 and 3) the ability of a modified antibody or an antigen-binding fragment of such an antibody to bind to SIRPa, in particular to an antigen as defined above, b. testing (e.g. according to a method describing in the Examples 7 and 8) the ability of a modified antibody or an antigen-binding fragment of such an antibody to bind to SIRPb, c. testing (e.g. according to a method describing in the Examples 9 and 10) the ability of a modified antibody or an antigen-binding fragment of such an antibody to bind to SIRPg, d. testing (e.g. according to a method describing in the Examples 4 and 5) the ability of a modified antibody or an antigen-binding fragment of such an antibody to inhibit the binding of human CD47 to human SIRPa;

e. testing (e.g. according to a method describing in the Example 12) the ability of a modified antibody or an antigen-binding fragment of such an antibody to bind to T cells;

f. testing (e.g. according to a method describing in the Example 13) the ability of a modified antibody, or an antigen-binding fragment of such an antibody not to inhibit the T cells proliferation, preferably the ability to increase the proliferation of T cells;

g. testing (e.g. according to a method describing in the Example 11) the ability of a modified antibody or an antigen-binding fragment of such an antibody to inhibit the binding of human CD47 to human SIRPg;

h. testing (e.g. according to a method describing in the Examples 28 or 31) the ability of a modified antibody or an antigen-binding fragment of such an antibody to increase the secretion of TNFa by human PBMC and/or by human T-lymphocytes;

i. testing (e.g. according to a method describing in the Example 29) the ability of a modified antibody or an antigen-binding fragment of such an antibody to increase the secretion of IFNg by human PBMC;

j. testing (e.g. according to a method described in example 35) the ability of a modified antibody or an antigen-binding fragment of such antibody to increase the activation of human T cells;

and optionally comprising the following step:

> selecting a modified antibody or an antigen-binding fragment of such an antibody which specifically binds to SIRPa, in particular to an antigen as defined above, and which significantly inhibits the binding of CD47 to SIRPa, and which does not bind specifically to human SIRPg, and/or which does not bind specifically to human T-cells, and/or which does not significantly inhibit, preferably which increases, the proliferation of human T-cells, and/or which does not significantly inhibit the binding of human CD47 to human SIRPg and/or which increases the secretion of TNFa by human PBMC and/or by human T-lymphocytes and/or which increases the secretion of IFNg by human PBMC and/or which increases the activation of human T cells; more particularly which specifically binds to SIRPa, in particular to an antigen as defined above, and which significantly inhibits the binding of CD47 to SIRPa, and which does not bind specifically to human SIRPg, and which does not bind specifically to human T-cells, and which does not significantly inhibit, preferably which increases, the proliferation of human T-cells, and which does not significantly inhibit the binding of human CD47 to human SIRPg and which increases the secretion of TNFa by human PBMC and/or by human T-lymphocytes and which increases the secretion of IFNg by human PBMC and which increases the activation of human T cells, in particular human T lymphocytes.

The method of selecting a modified antibody of the invention can advantageously be performed further to the method of manufacturing an antibody according to the invention.

The following Figures and Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

FIGURE LEGENDS

FIG. 1. Binding analyses of anti-SIRPa antibodies by ELISA assay (human SIRPa-His coating and anti-human kappa detection).
Assessment by ELISA on immobilized SIRPa-His of chimeric (♦), HALA (□), HFLA (*), HFLB (+), HEFLA (▲), HEFLB (■), SIRP29 (Δ), Kwar23 (○) on Figure A; of HCLA (•), HCLB (x), HELA (◇), HELB (–) on Figure B; of HALB (–), HBLA (_), HBLB (■) on Figure C. Revelation was performed with a donkey anti-human antibody and revealed by colorimetry at 450 nm using TMB substrate. ED50 is the concentration of the indicated antibody to reach 50% of the signal in this assay. Binding of m18D5 clone (■) (n=4), SE5A5 commercial clone (▲) (n=7), 6G10 clone (▼) (n=3) and 12D7 clone (□) (n=4) on Figure D.

FIG. 2. Affinity analysis by Biacore of anti-SIRP antibodies on human SIRPa recombinant protein. SIRPa-His recombinant protein was immobilized onto a CM5 chip at 5 µg/ml (500 RU) and the indicated antibodies were added at different concentration. Values were measured after an association period (ka) of 3 min followed by a dissociation period of 10 min (kd) to determine affinity constant (KD).

FIG. 3. Binding analyses of anti-SIRPa antibodies on human monocytes (homozygote for SIRPa variant 1 (v1/v1)).
(A, B) Assessment by cytofluorometry on human monocytes v1/v1 (previously stained with human Fc Receptor Binding Inhibitor antibody) of chimeric (♦), HALA (□), HFLA (*), HFLB (+), HEFLA (▲), HEFLB (■), SIRP29 (Δ), Kwar23 (○). Revelation was performed with a PE labeled mouse anti-human Fc mAb on Canto II cytometer, values corresponding to percentage of stained monocytes. ED50 is the concentration of the indicated antibody to reach 50% of the signal in this assay. Figure A corresponds to the percentage of monocytes v1/v1 stained. Figure B corresponds to the mean of fluorescence intensity (MFI) of monocytes v1/v1.
(C, D) Binding study of SIRPa antibodies on human monocytes by Flow cytometry (FACS): different anti-SIRPa antibodies were tested: m18D5 (■) (n=1), SE7C2 (▲)(n=2), 12D7 (□)(n=2), 6G10 (♦) (n=4): Figure C represents the Mean Fluorescence Intensity (MFI) of the different antibodies over a dose response. Figure D represents the percentage of stained monocytes over antibody dose response. Statistical analysis were performed when it was possible.
(E, F, G) SIRPa variants binding in the population by anti-h SIRPa antibodies: The capacity of different anti-hSIRPa antibodies to bind SIRPa variants in the 32 volunteers was measured by FACS with a PE-anti mouse IgG. All clones were tested at 10 µg/ml: m18D5 (■), 12D7 (▼), 6G10 (♦) and commercial antibodies SE5A5 (□), SE7C2 (Δ). Figure E represents the homozygote Variant 1 volunteers (n=16). Figure F represents the homozygote variant 2 volunteers (n=8). Figure G represents the heterozygote V1/V2 volunteers (n=8).

FIG. 4. Competition of anti-SIRPa antibodies with CD47 on SIRPa.
(A) Assessment by ELISA on immobilized SIRPa-His of chimeric (♦), HFLA (*), HFLB (+), HEFLA (▲), HEFLB (■), SIRP29 (Δ), Kwar23 (○) at different concentrations incubated with constant concentration of biotinylated CD47-Fc (6 µg/ml). Revelation was performed with streptavidin peroxidase to detect CD47 molecule and revealed by colorimetry at 450 nm using TMB substrate. The results of a second experiment are given with the IC50 values. IC50 is the concentration of the indicated antibody to inhibit 50% of the signal in this assay.
(B) Antagonist activity study of anti-SIRPa antibodies on SIRPa-CD47 interaction by ELISA: The different anti-SIRPa antibodies were tested over a dose response: m18D5 clone (■)(n=1), commercial antibody SE5A5 (▲)(n=2) and m12D7 (□)(n=2). The figure represents the percentage of CD47 positive SIRPa-CD47 interactions measured by ELISA during a dose response of anti-hSIRPa antibodies.

FIG. 5. Competition of anti-SIRPa antibodies with CD47 on human monocytes.
(A, B) Assessment by cytometry on human monocytes (v1/v1) of chimeric (♦), HFLA (*), HFLB (+), HEFLA (▲), HEFLB (■) at different concentrations incubated with constant concentration of biotinylated CD47-Fc (10 µg/ml). Revelation was performed with PhycoErythrin-streptavidin to detect CD47 molecule and revealed by Canto II cytometer. IC50 is the concentration of the indicated antibody to inhibit 50% of the signal in this assay. Figure A corresponds to the percentage of positive cells. Figure B corresponds to the mean of fluorescence intensity.
(C) Antagonist activity study of anti-SIRPa antibodies on Sirpa-CD47 interaction by FACS: The different anti-SIRPa antibodies were tested over a dose response: m18D5 clone (■)(n=1), commercial antibody SE7C2 (▲) (n=2) and m12D7 (□)(n=2). Figure C represents the percentage of CD47 positive cells measured by FACS after competition with anti-hSIRPa antibodies.

FIG. 6. (A) Affinity analysis by Blitz of anti-SIRP antibody on human SIRPa recombinant protein pre-incubated or not with SP-D ligand. SIRPa-His recombinant protein was immobilized onto a NINTA biosensor at 10 μg/ml and the SP-D ligand was added at 100 μg/ml (saturating concentration). Then anti-SIRPa antibody was added at 20 μg/ml and affinity values were deduced after an association period (ka) of 120 sec followed by a dissociation period of 120 sec (kd) to determine affinity constant (KD). (B) Affinity analysis by Blitz of anti-SIRP antibody on human SIRPa recombinant protein pre-incubated with mouse 18D5 antibody. SIRPa-His recombinant protein was immobilized onto a NINTA biosensor at 10 μg/ml and the anti-SIRPa antibody was added at 20 μg/ml (saturating concentration). Then SP-D ligand was added at 100 μg/ml and affinity values were deduced after an association period (ka) of 120 sec followed by a dissociation period of 120 sec (kd) to determine affinity constant (KD).

FIG. 7. (A) Affinity analysis by Blitz of anti-SIRP antibodies on human SIRPb recombinant protein. SIRPb-His recombinant protein was immobilized onto a NINTA biosensor and the indicated antibodies were added at 20 μg/ml. Values were deduced after an association period (ka) of 120 sec followed by a dissociation period of 120 sec (kd) to determine affinity constant (KD). (B) Binding analysis of anti-SIRP antibodies (human SIRPb-His coating and anti-human kappa detection). Assessment by ELISA on immobilized SIRPb-His of HEFLB (■), SIRP29 (Δ), Kwar23 (○), B4B6 (♦) and IgG4 Ab control (■) Revelation was performed with a donkey anti-human antibody with the exception of B4B6 revealed with a mouse antibody and revealed by colorimetry at 450 nm using TMB substrate.

FIG. 8. (A) Affinity analysis by Blitz of anti-SIRP antibodies on human SIRPg recombinant protein. SIRPg-His recombinant protein was immobilized onto a NINTA biosensor and the indicated antibodies were added at 10 μg/ml. Values were deduced after an association period (ka) of 120 sec followed by a dissociation period of 120 sec (kd) to determine affinity constant (KD). (B) Binding analysis by ELISA assay of anti-SIRP antibodies on SIRPg (human SIRPg-His coating and anti-human kappa detection). Assessment by ELISA on immobilized SIRPg-His of HEFLB (■), SIRP29 (Δ), Kwar23 (○), LSB2-20 (•) and IgG4 Ab control (■). Revelation was performed with a donkey anti-human antibody and revealed by colorimetry at 450 nm using TMB substrate.

FIG. 9. Affinity analysis by Blitz of CD47 on human SIRPg recombinant protein pre-incubated with anti-SIRP antibodies. SIRPg-His recombinant protein was immobilized onto a NINTA biosensor at 10 μg/ml and the indicated antibodies were added at 20 μg/ml (saturating concentration). Then, CD47Fc was added at 100 μg/ml and affinity values were deduced after an association period (ka) of 120 sec followed by a dissociation period of 120 sec (kd) to determine affinity constant (KD).

FIG. 10. Geometric mean fluorescence intensity measured by flow cytometry on (A) peripheral human CD3+ T cells, (B) red blood cells or (C) platelets after staining with different monoclonal antibodies and revealing with secondary anti-IgG fluorescent antibody.

FIG. 11. Percentage of positive peripheral human CD3+ T cells after staining with different monoclonal antibodies. The table indicates the value of % of positive cells in duplicate experiments.

FIG. 12. Human T cells isolated from peripheral blood mononuclear cells from healthy volunteers were stimulated with (A) (C) anti-CD3+ anti-CD28 beads at a 1:1 ratio for 3 days or (B) (D) with allogeneic dendritic cells (DC) at a 5 T cell: 1 DC ratio for 5 days or (E) with different concentrations of tuberculin unpurified protein derivative (PPD) for 5 days. Antibodies were added at day 0 of the culture. Proliferation was measured by incorporation of $H^3$-thymidine during the last 12 h of culture.

Figure 13:
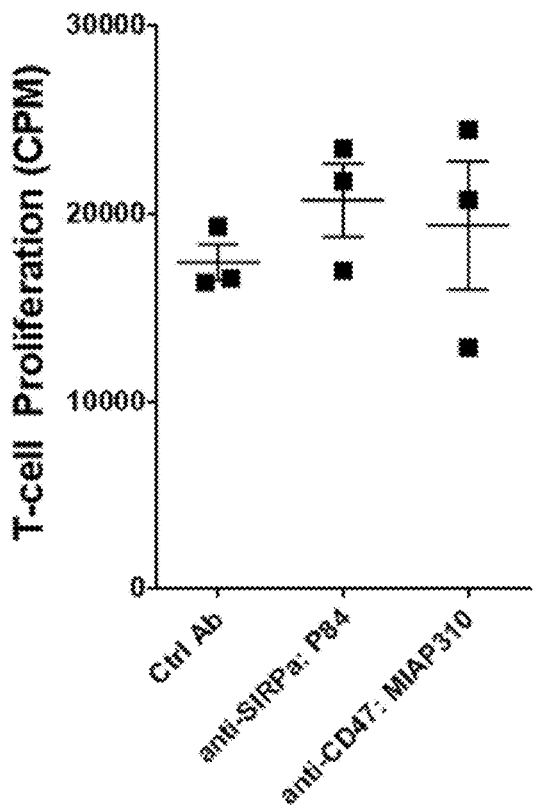

FIG. 13. Mouse CD8+ T cells were isolated from splenocytes of naive mice. CD8 T cells were stimulated with anti-CD3+ anti-CD28 beads at a 1:1 ratio for 3 days. Antibodies were added at day 0 of the culture. Proliferation was measured by incorporation of $H^3$-thymidine during the last 12 h of culture.

FIG. 14. Human T cells isolated from peripheral blood mononuclear cells from healthy volunteers were stimulated with allogeneic dendritic cells (DC) at a 5 T cell: 1 DC ratio for 5 days. Antibodies were added at day 0 of the culture. Proliferation was measured by incorporation of $H^3$-thymidine during the last 12 h of culture.

Figure 15A:
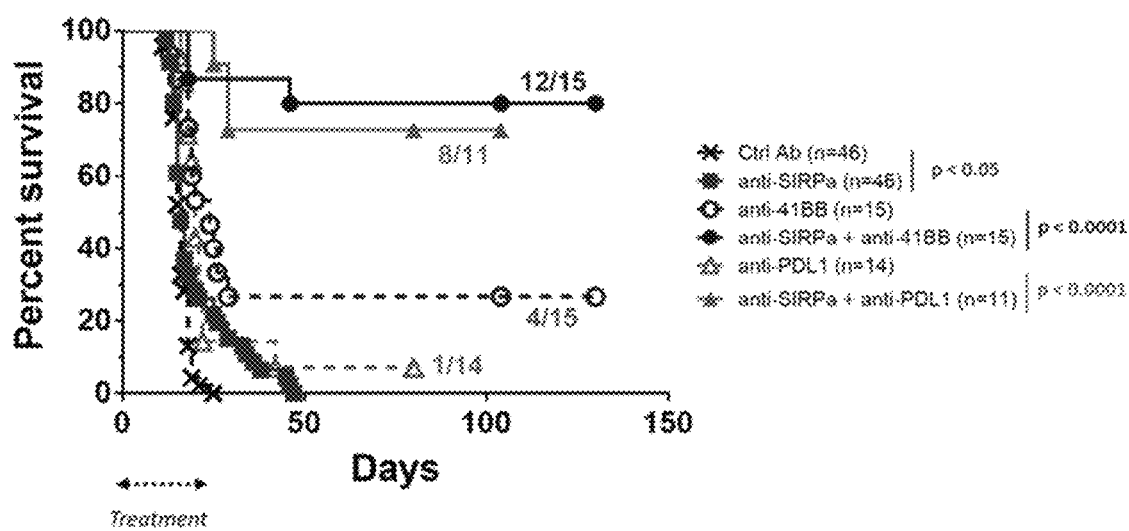
Figure 15C:
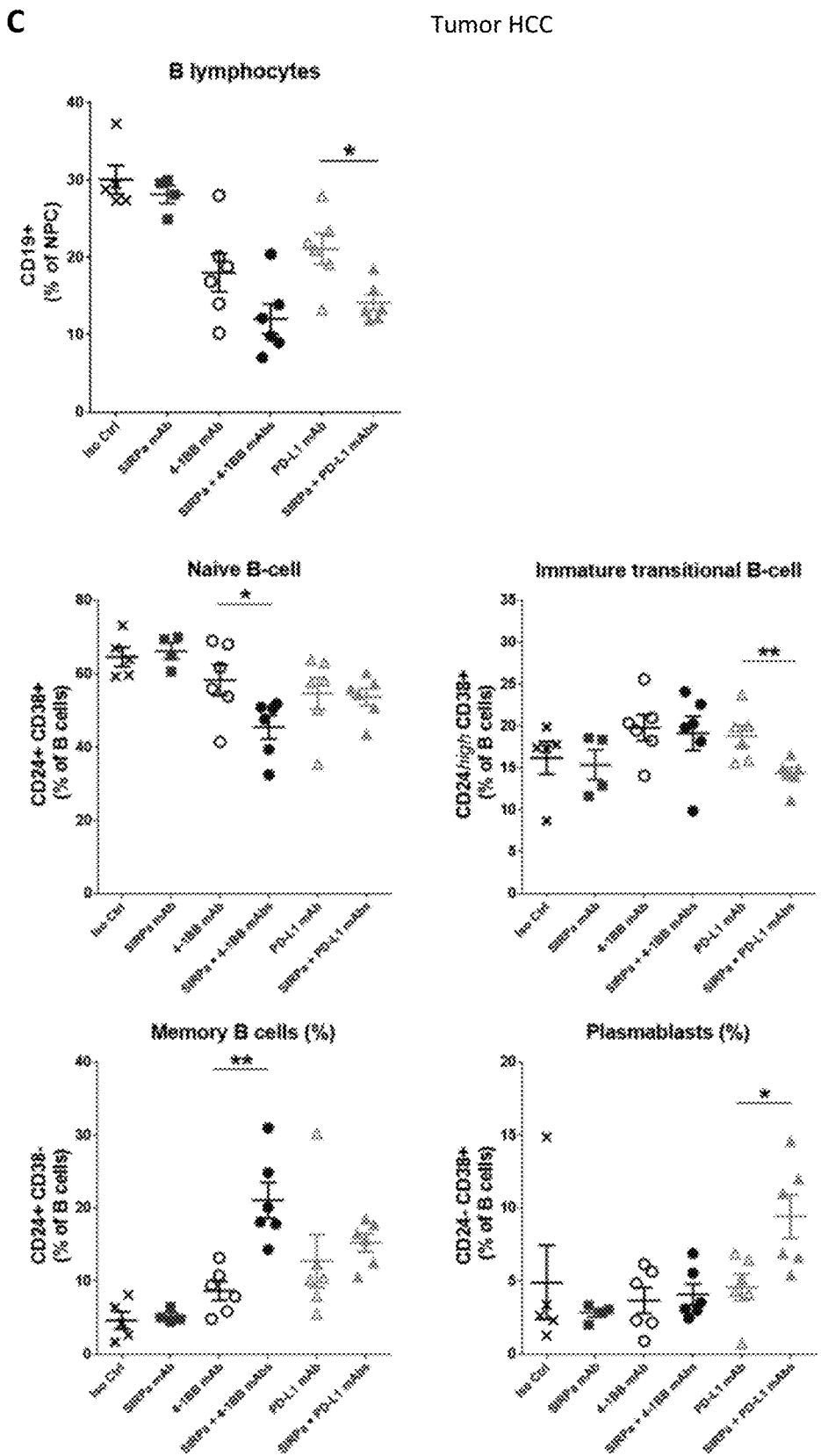
Figure 15C:
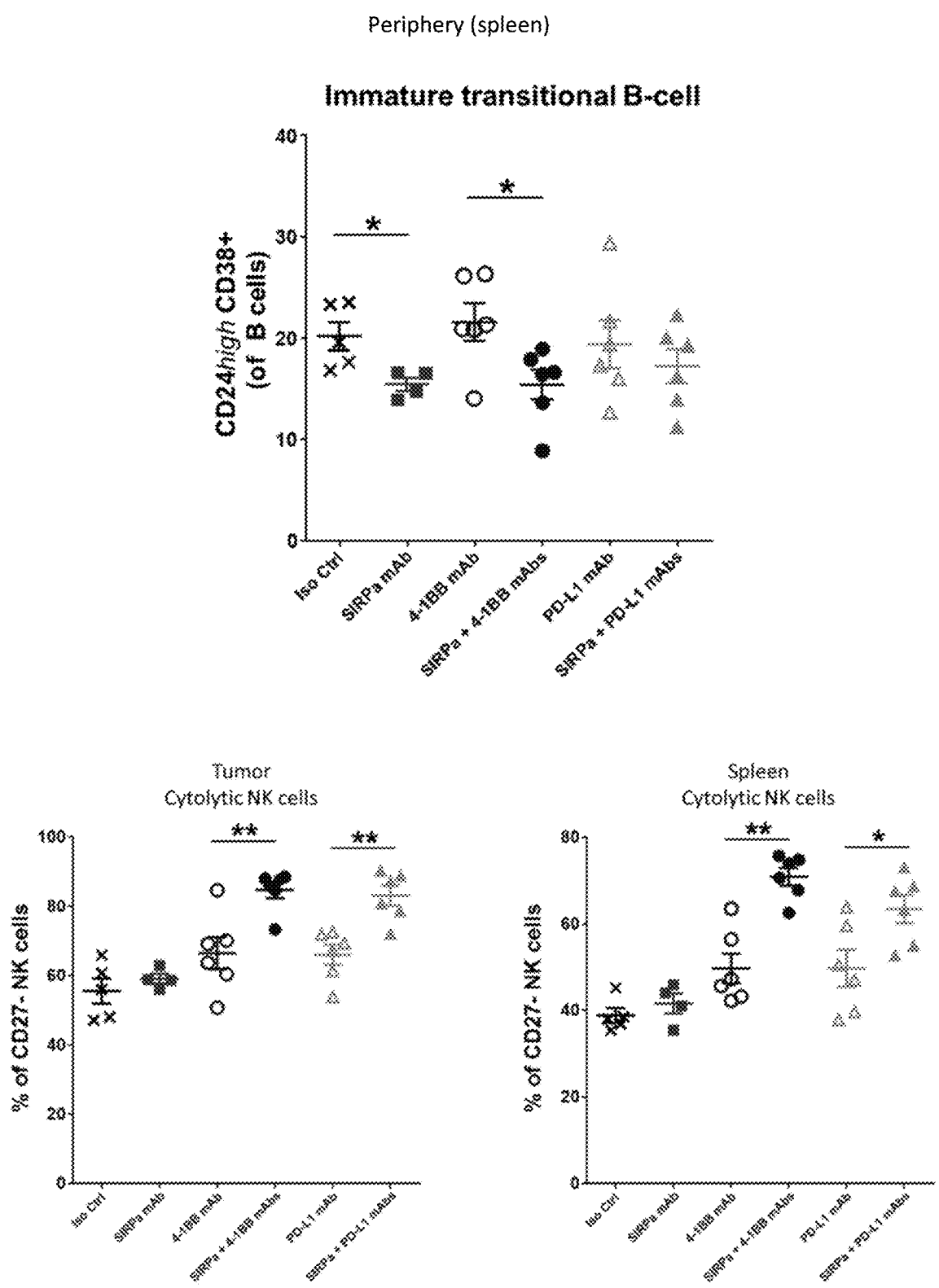

FIG. 15. (A) Anti-tumor effect of anti-SIRPa (P84 clone) i.p. administration three times a week for 4 weeks (300 μg/injection) in combination or not with two injections (day 4 & 8) of anti-4-1-BB mAb (3H3 clone, 100 μg/injection) or with injections (twice a week) of anti-PDL-1 (10F.9G2 clone, 200 μg/injection, treatment during 4 weeks) in an orthotropic model of murine hepatoma (2.5.10^6 of Hepa 1.6 cells injected through the portal vein on day 0). Mice were considered cured when they survived three times longer than the time necessary to all control mice died. (B) Tumor infiltrating cells were analyzed at day 13 after tumor inoculation. (C) Tumor infiltrating cells and spleen cells were analyzed at day 13 after tumor inoculation. (D) Mice previously cured in the hepatoma model by anti-SIRPa+ anti-4-1BB injection or SIRPa mutant mice treated with anti-4-1BB were rechallenged by Hepa 1.6 cells injection in the spleen (2.5.10^6 cells/mouse). Naive mice were injected in parallel in the same route in order to compare tumor development with rechallenged mice. Mice were then left untreated. (E) Mice previously cured in the hepatoma model by anti-SIRPa+ anti-4-1BB were rechallenged by Hepa 1.6 cells injection in the spleen (2.5.10^6 cells/mouse) and their spleen was harvested 30 days after rechallenge. Splenocytes and T-cell splenocytes were isolated. Naive mice were injected intravenously with vehicle, whole splenocytes (10.10^6/mouse) or T-cell purified from splenocytes (2.5.10^6/mouse) and all received Hepa1.6 cell injection in the spleen (2.5.10^6 cells/mouse). Mice were then left untreated and considered cured when they survived three times longer than the time necessary to all control mice died.

Figure 16:
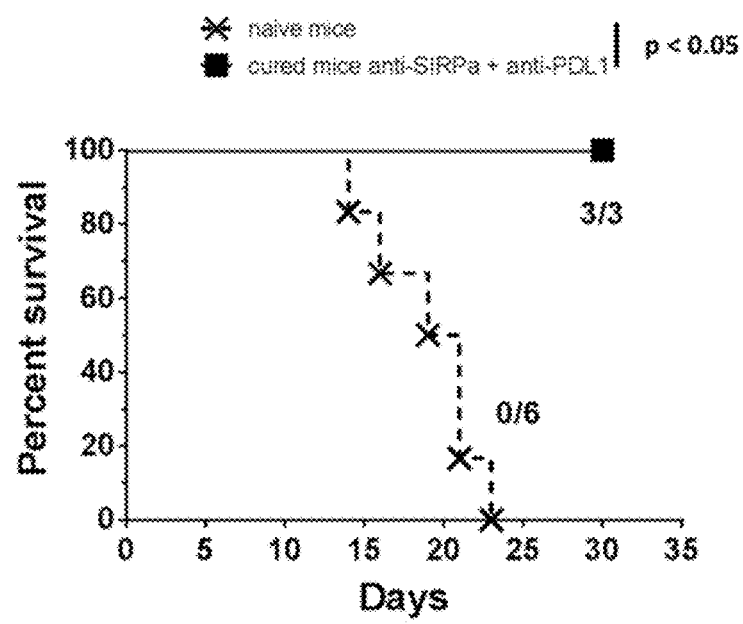

FIG. 16. Mice previously cured in the hepatoma model by anti-SIRPa+ anti-PDL1 injection were rechallenged by Hepa 1.6 cells injection in the spleen (2.5.10^6 cells/mouse). Naive mice were injected in parallel in the same route in order to compare tumor development with rechallenged mice. Mice were then left untreated.

Figure 17:
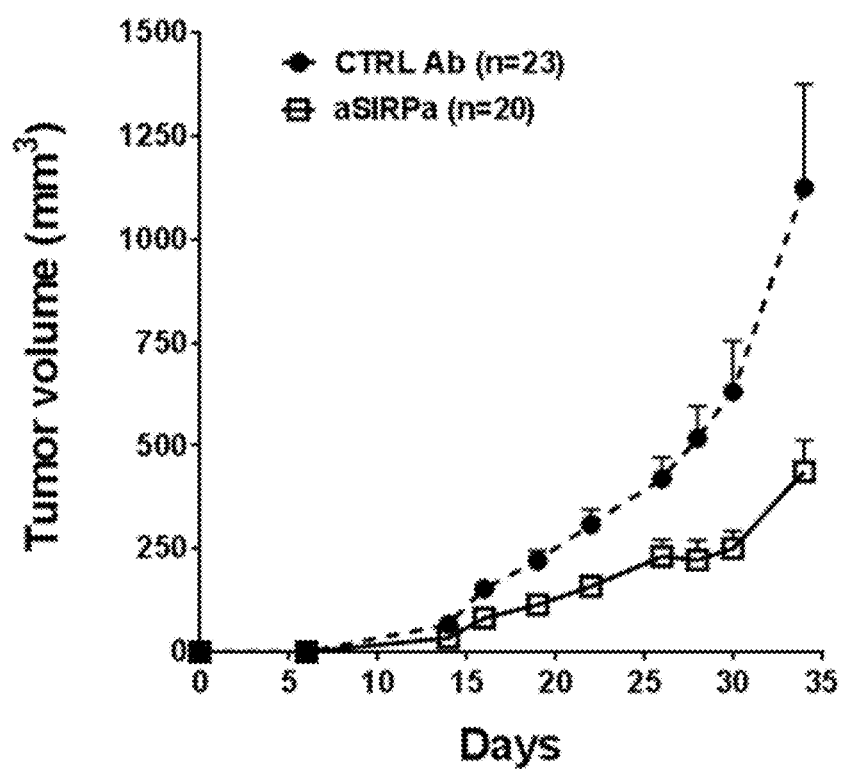

FIG. 17. Anti-tumor effect of anti-SIRPa (P84 clone) i.p. administration three times a week for 4 weeks (200 μg/injection) in an orthotopic model of murine mammary carcinoma (0.25.10^6 of 4T1 cells injected in the mammary gland). The tumor development was evaluated by measuring the diameter of the tumor and calculated according to the formula: =(0.52*($d^2$))^1.5. Mice were euthanized when tumor development was nearly 1000 mm³ according to the ethical guidelines.

Figure 18:
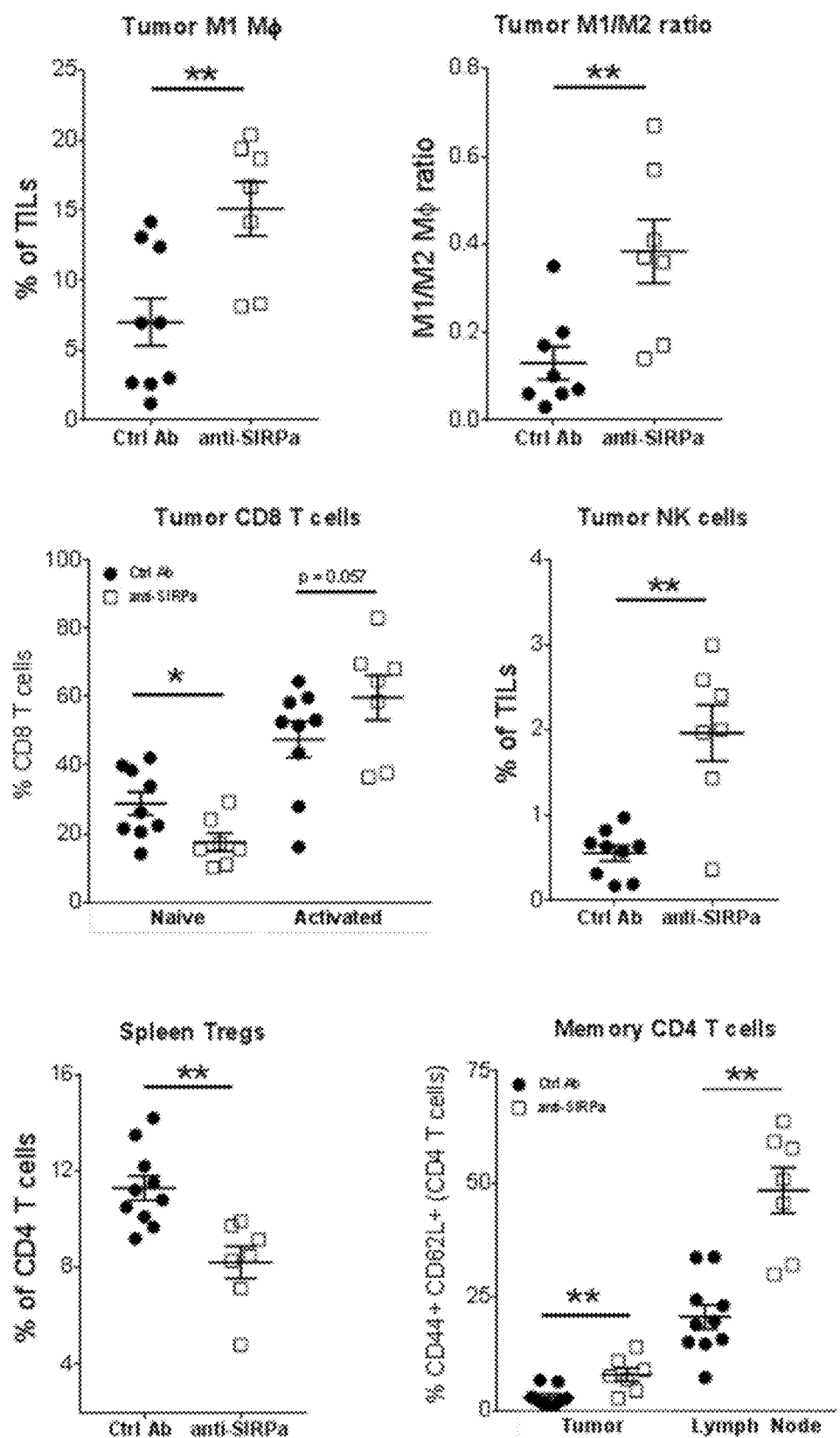

FIG. 18. Immune cells phenotype analysis in spleen, tumor and lymph nodes of mice treated with anti-SIRPa (P84 clone) or ctrl mAb i.p. three times a week for two weeks (200 µg/injection) in an orthotropic model of murine mammary carcinoma (0.25.10^6 of 4T1 cells injected in the mammary gland). Immune cell analysis were performed two weeks after tumor inoculation.

Figure 19:
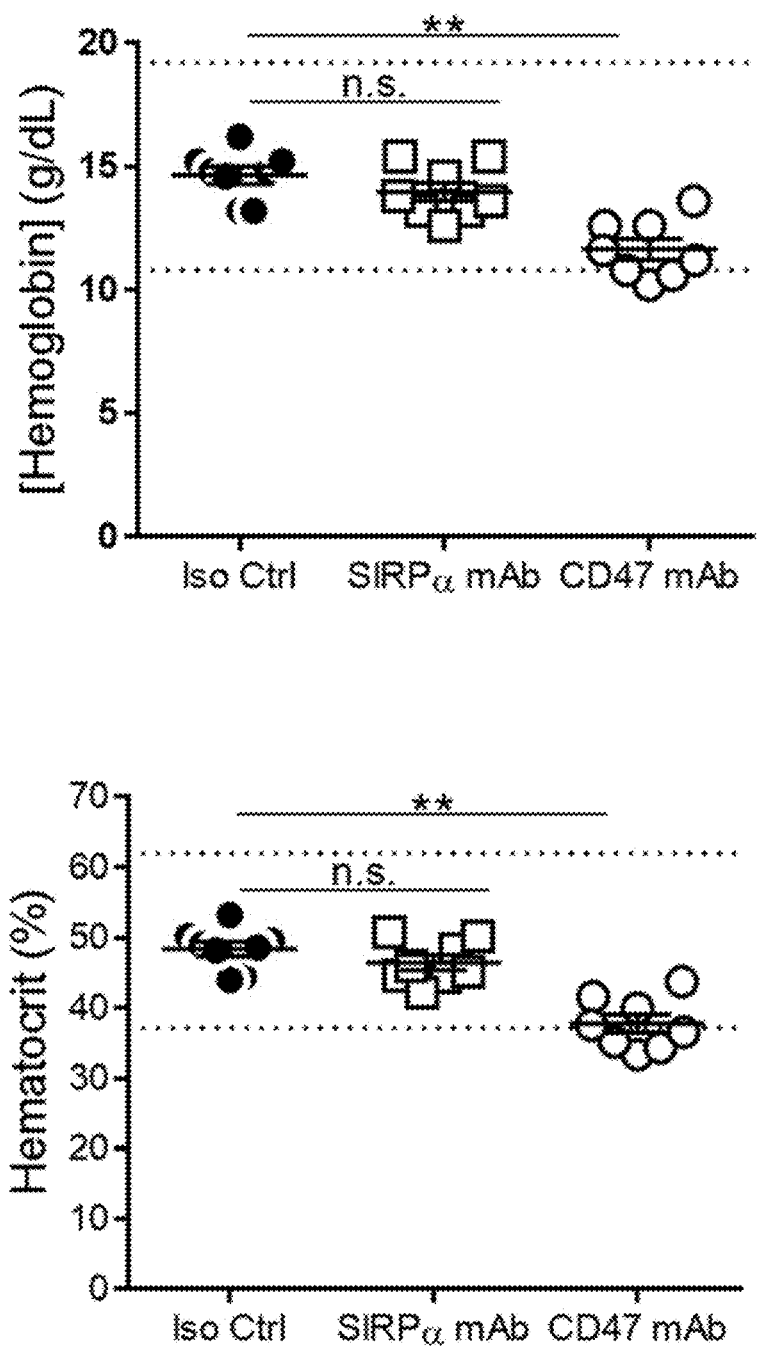

FIG. 19. Anti-SIRPa (P84 clone), anti-CD47 (MIAP410 clone) and irrelevant isotype control were administered intraperitoneally at day 0 and day 2 at 12 mg/kg in C57Bl/6 mice. Blood samples were collected at day 0 and day 3 in EDTA containing tubes and blood count was performed with a XS-800i hematology analyzer (Sysmex). The level of hemoglobin (left) and the percentage of hematocrit (right) were evaluated at day 3. The dotted-lines represent normal range values in the C57Bl/6 mice for each parameter.

Figure 20:
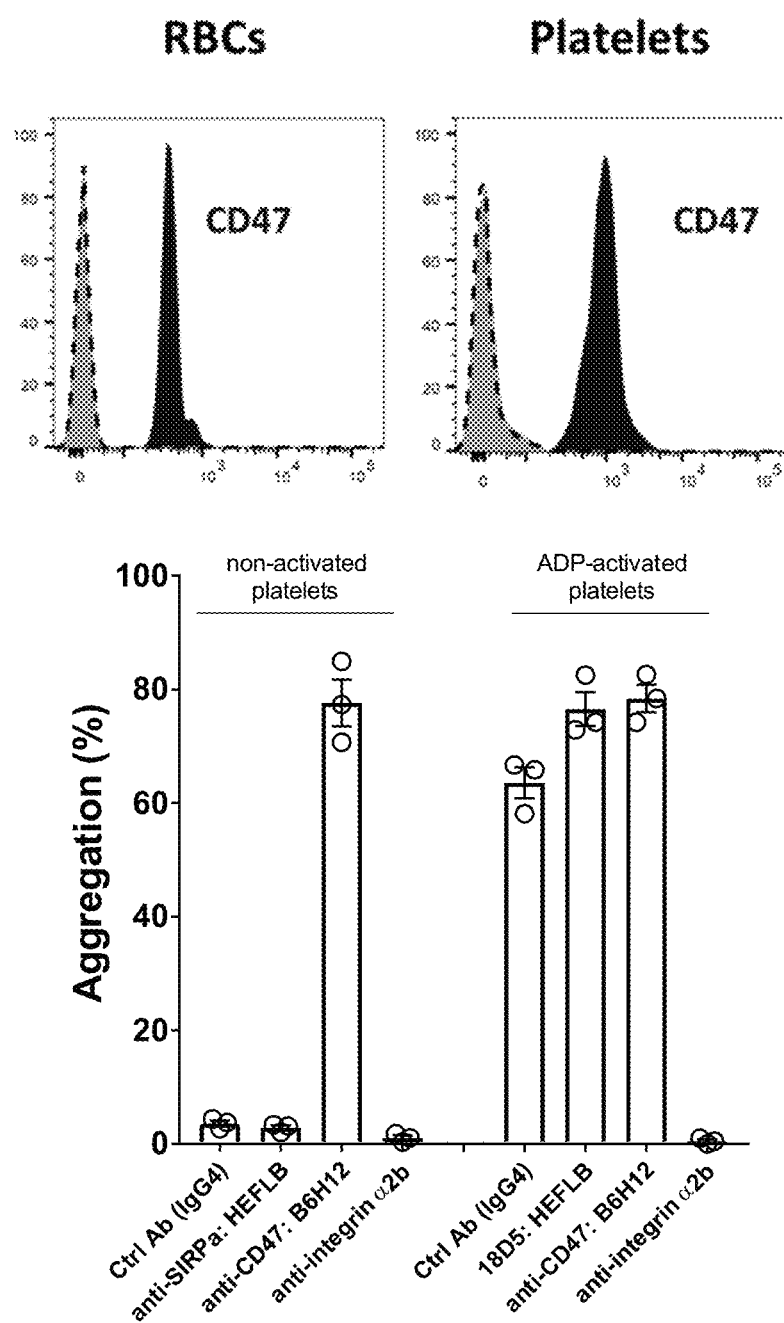

FIG. 20. (Up) Flow cytometry analysis of anti-SIRPa (HEFLB, grey) and anti-CD47 (B6H12, black) mAb as compared to a control mAb (dotted line) on human platelets freshly isolated from the blood of healthy donors. (Bottom) Human platelet aggregation measurement using optical aggregometer in the presence of a 50 µg/ml of control mAb, anti-SIRPa (HEFLB), anti-CD47 (B6H12) or anti-integrin αIIb as positive control of inhibitor of aggregation. Antibodies were evaluated on non-activated and ADP-activated platelets.

Figure 21:
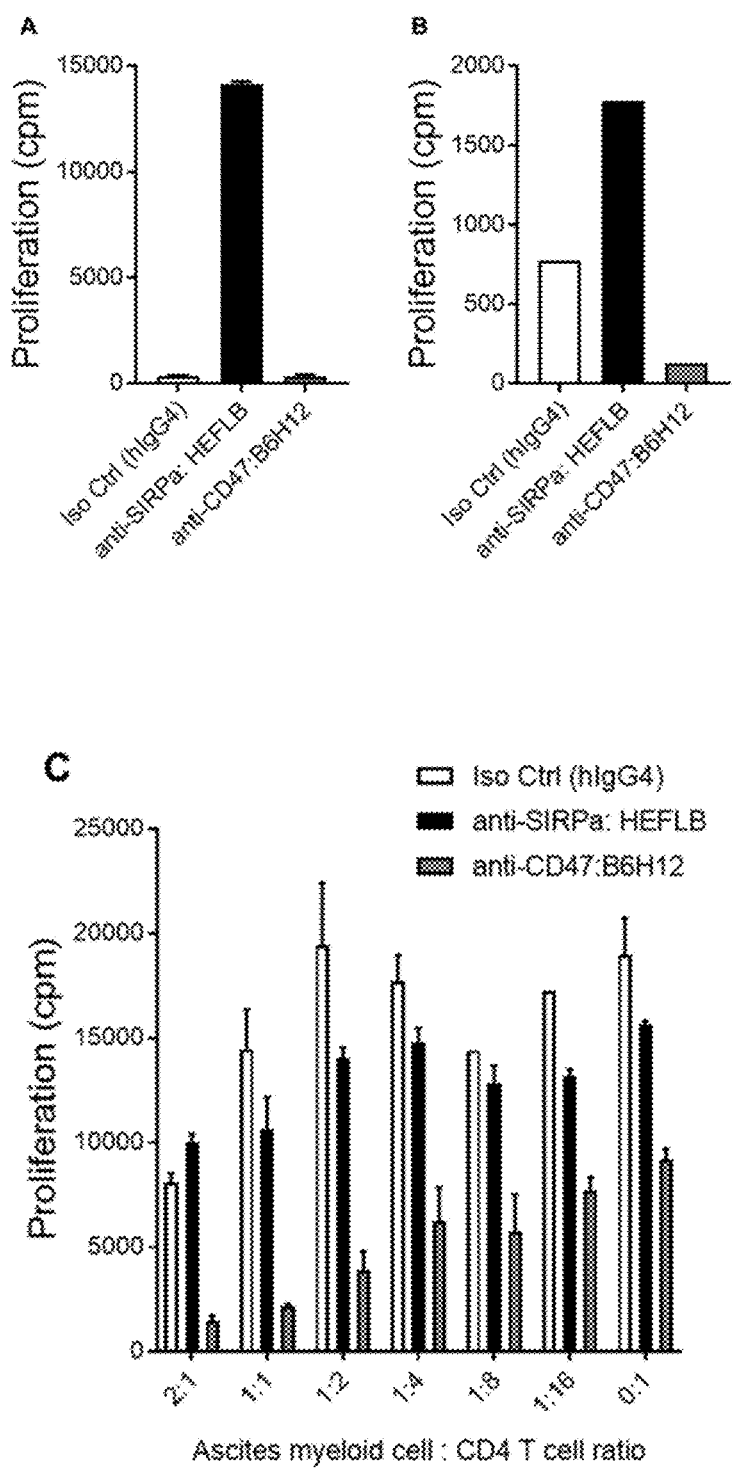

FIG. 21. Allogeneic CD4+ T cells were cultured in a 1:1 ratio with CD14+ myeloid cells extracted from (A) fresh or (B) frozen ovarian cancer ascites with 10 µg/ml of control antibody (white), anti-SIRPa HEFLB (black) or anti-CD47 mAb (grey). Proliferation was measured at day 5 by ³H-thymidine incorporation. (C) Alternatively, allogeneic T cells were cultured in a 5:1 ratio with allogeneic dendritic cells and different ratio of CD14+ myeloid cells extracted from ovarian cancer ascites in the presence of 10 µg/ml of antibody as in (A).

Figure 22:
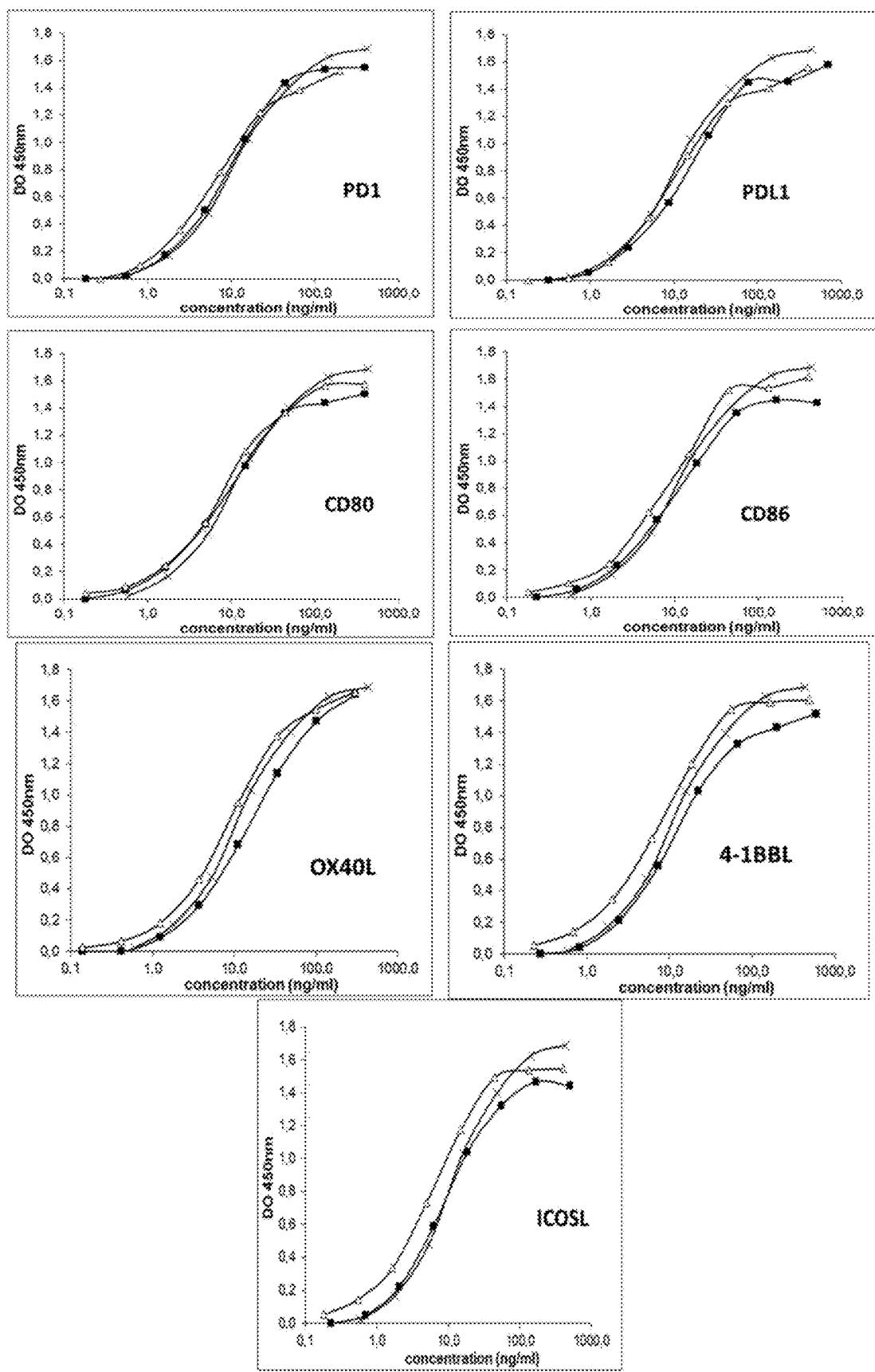

FIG. 22. SIRPa ELISA binding Assay of modified antibodies. Assessment by ELISA on immobilized SIRPa-His of the unmodified anti-SIRPa antibody (HEFLB) and different modified anti-SIRPa HEFLB antibodies with polypeptide linked on heavy chain (VHprot+VL (■)) or linked on light chain (VH+ VLprot (Δ)). The results are obtained with modified anti-SIRPa antibodies conjugated to the extracellular domain (ECD) of PD1, PDL1, CD80, CD86, OX40L, 4-1BBL or ICOSL.

Figure 23:
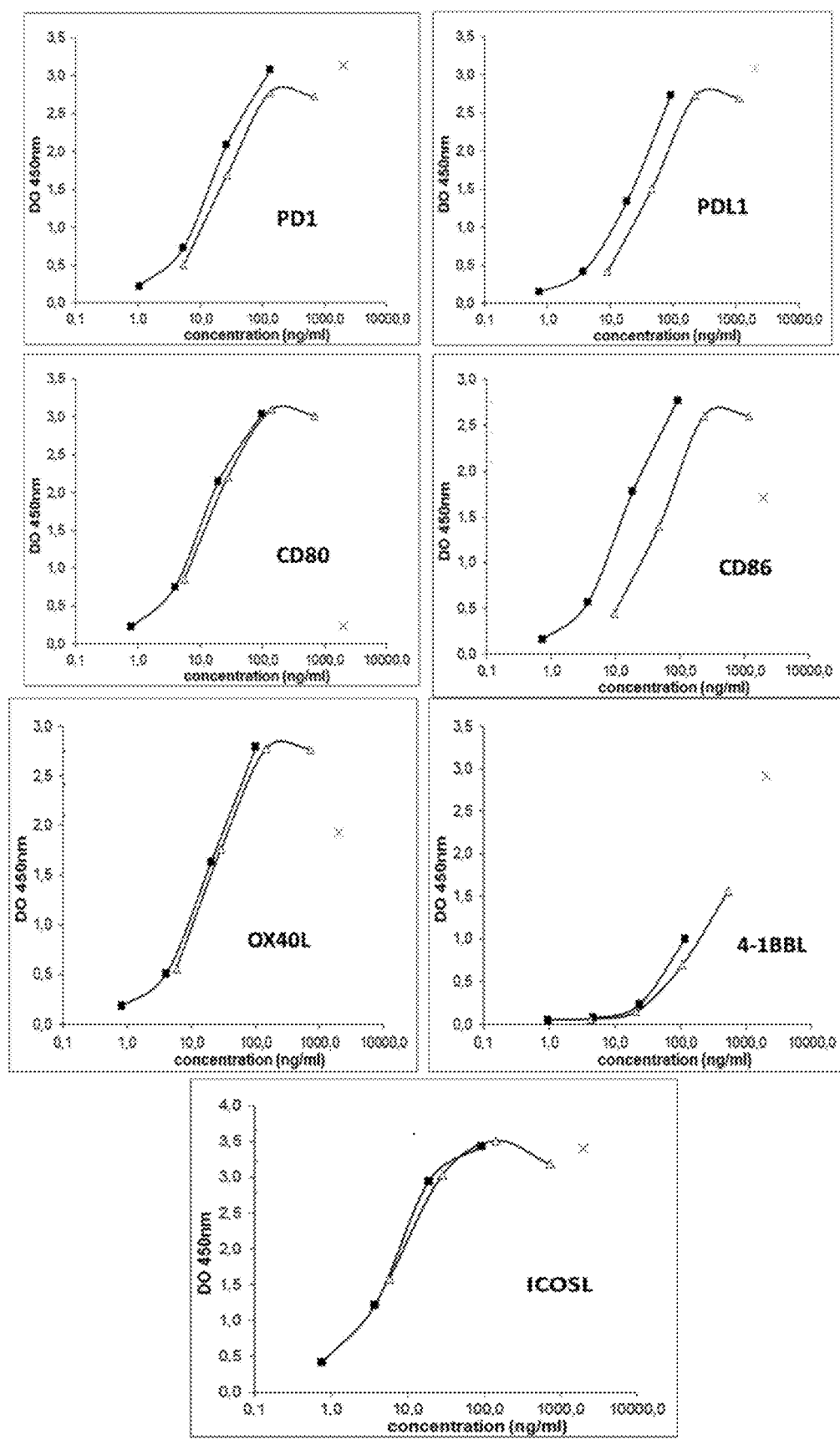

FIG. 23. Detection of the ECD of the fused protein on modified anti-SIRPa antibodies by ELISA. Assessment by ELISA on immobilized SIRPa-His of the anti-SIRPa antibody (HEFLB) and different modified anti-SIRPa HEFLB antibodies with fused protein on the heavy chain (VHprot+VL (■)) or linked on the light chain (VH+ VLprot (Δ)). The results are obtained with modified anti-SIRPa antibodies conjugated to the extracellular domain (ECD) of PD1, PDL1, CD80, CD86, OX40L, 4-1BBL or ICOSL.

Figure 24:
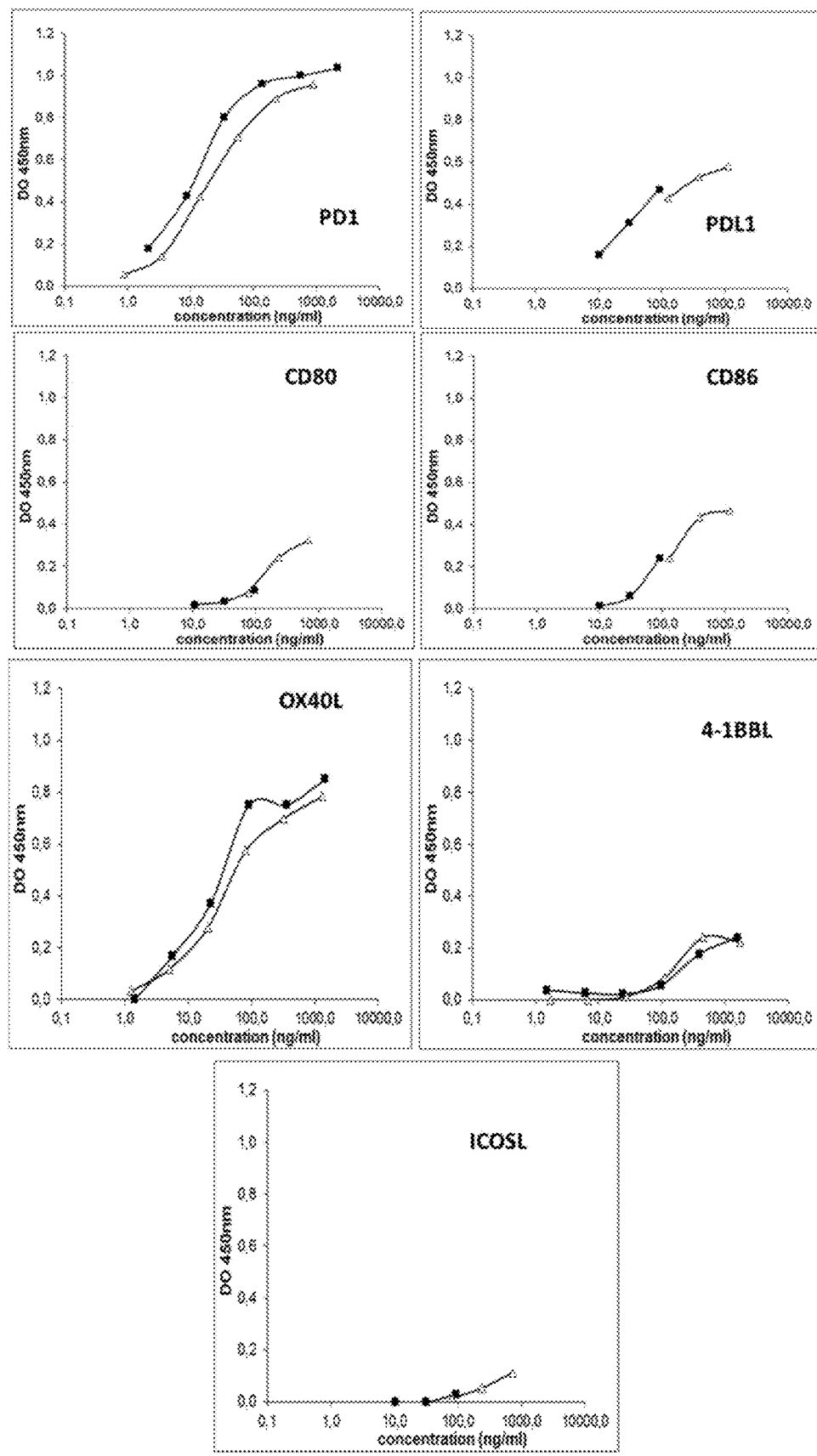

FIG. 24. Ligand binding assay with the different modified anti-SIRPa antibodies by ELISA. Assessment by ELISA on immobilized SIRPa-His of different modified anti-SIRPa antibodies with fused protein linked to the heavy chain (VHprot+VL (■)) or linked to the light chain (VH+ VLprot (Δ)). Detection was performed with specific ligand of the different fused conjugates: PDL1Fc (for PD1), PD1His (for PDL1), CTLA4-Fc (for CD80 and CD86), OX40Fc (for OX40L), 4-1BBFcHis (for 4-1BBL), CD28Fc (for ICOSL) and revealed respectively by mouse anti-human PDL1, mouse anti-His, mouse anti-human CTLA4Fc, mouse anti-human OX40, mouse anti-human His, mouse anti-human CD28 then with peroxidase labelled anti-mouse IgG then by colorimetry at 450 nm using TMB substrate.

Figure 25:
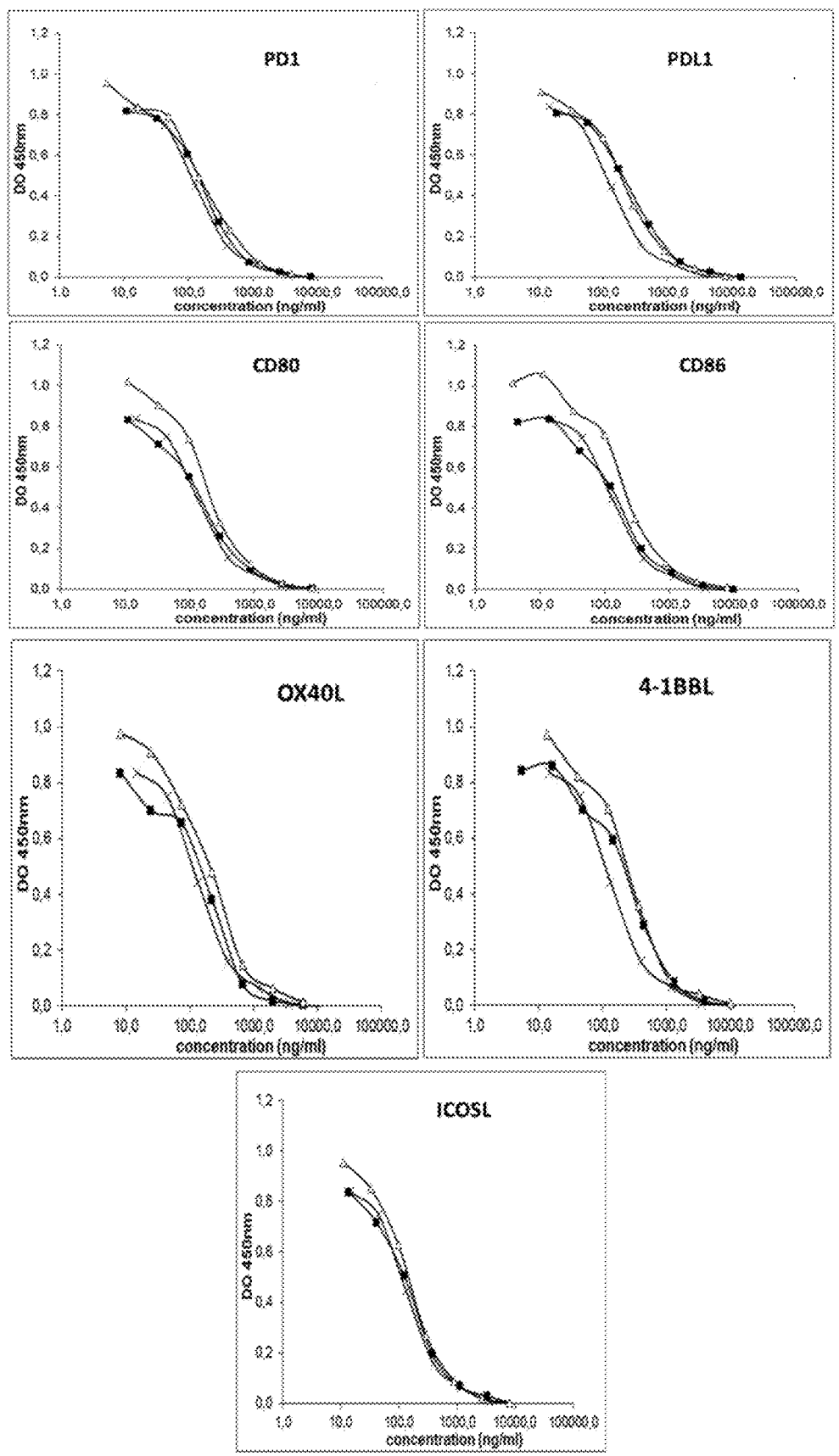

FIG. 25. Competition assay on the SIRPa-CD47 interaction with different modified anti-SIRPa antibodies by ELISA. Antagonist activity measurement of the different modified anti-SIRPa antibodies. Assessment by ELISA on coated SIRPa-His of anti-SIRPa alone (HEFLB (x)), different modified anti-SIRPa HEFLB antibodies with fused protein linked to the heavy chain (VHprot+VL (■)) or linked to the light chain (VH+ VLprot (Δ)) at different concentrations and incubated with constant concentration of biotinylated CD47-Fc (6 µg/ml). The results are obtained with modified anti-SIRPa antibodies conjugated to the extracellular domain (ECD) of PD1, PDL1, CD80, CD86, OX40L, 4-1BBL or ICOSL.

Figure 26:
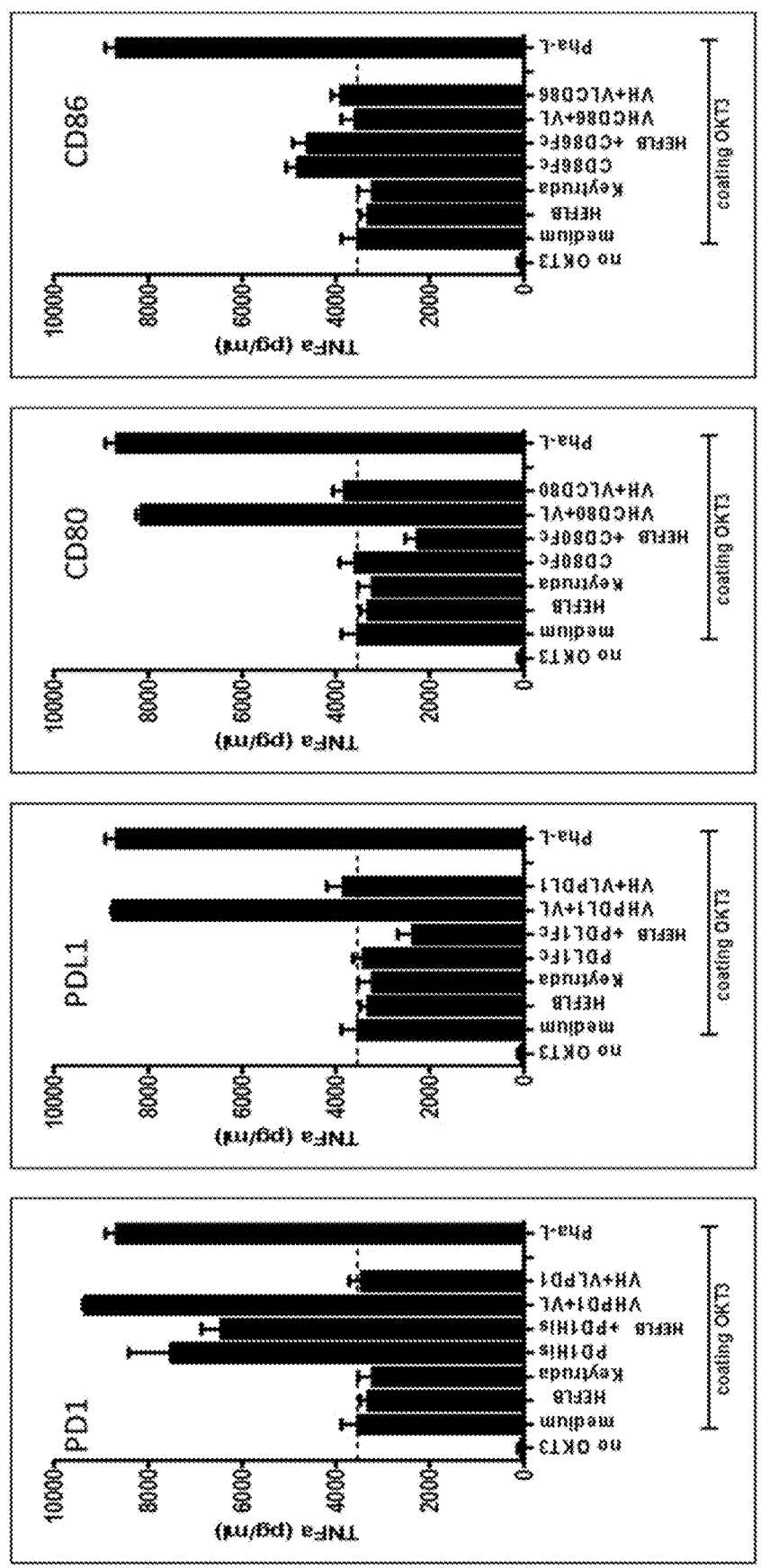
Figure 26:
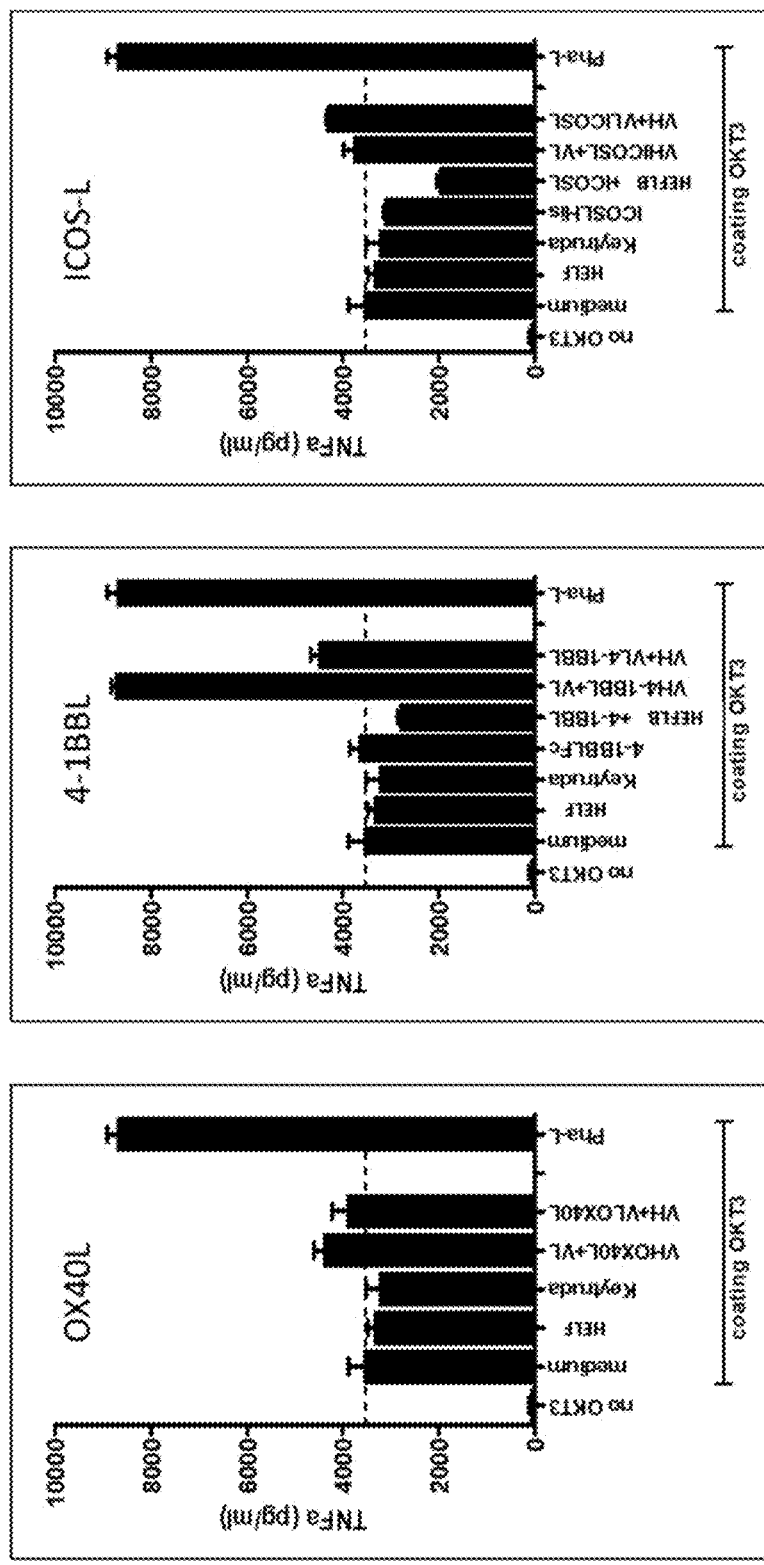

FIG. 26. TNFa secretion assay on PBMC with soluble modified anti-SIRPa antibodies. Assessment by ELISA of the TNFa secretion by PBMC activated by OKT3 (1 µg/ml) and soluble anti-SIRPa HELFB antibody, anti-PD1 (Keytruda mAb), HEFLB+recombinant protein (not fused), modified anti-SIRPa HEFLB antibodies with fused protein on the heavy chain (VHprot+VL) or on the light chain (VH+ VLprot) of the antibody at 10 µg/ml or Pha-L as a positive control for 2 days at 37° C., 5% CO2. The results are obtained with modified anti-SIRPa HEFLB antibodies fused to PD1, PDL1, CD80, CD86, OX40L, 4-1BBL or ICOSL. Results are representative of 3 different donors.

Figure 27:
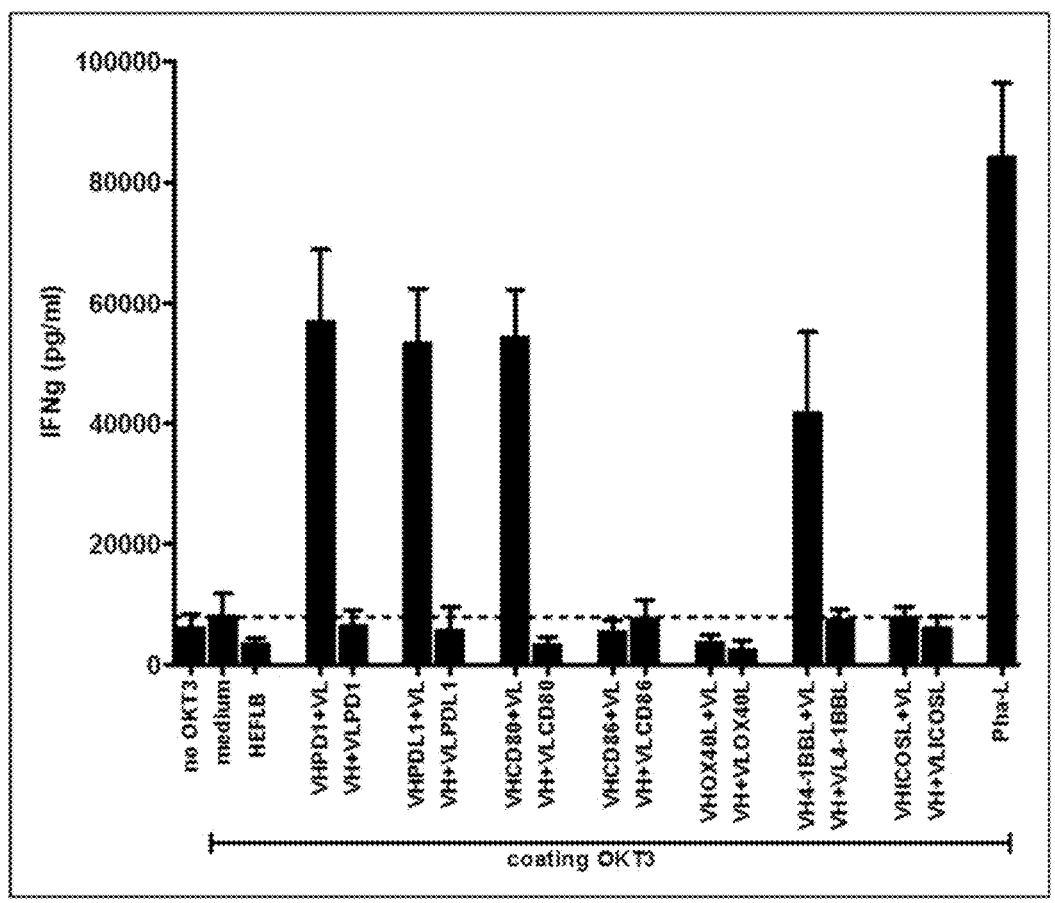

FIG. 27. IFNg secretion assay by PBMC (n=3) with soluble modified anti-SIRPa antibodies. Assessment by ELISA of IFNg secretion by PBMC activated by OKT3 (1 µg/ml) and soluble anti-SIRPa HELFB antibody, anti-PD1 (Keytruda mAb), HEFLB+recombinant protein (not fused), modified anti-SIRPa HEFLB antibodies with fused protein on the heavy chain VHprot+VL or on the light chain VH+ VLprot of the antibody at 10 µg/ml or Pha-L as a positive control for 2 days at 37° C., 5% CO2. The results are obtained with modified anti-SIRPa HEFLB antibodies fused to PD1, PDL1, CD80, CD86, OX40L, 4-1BBL or ICOL.

Figure 28:
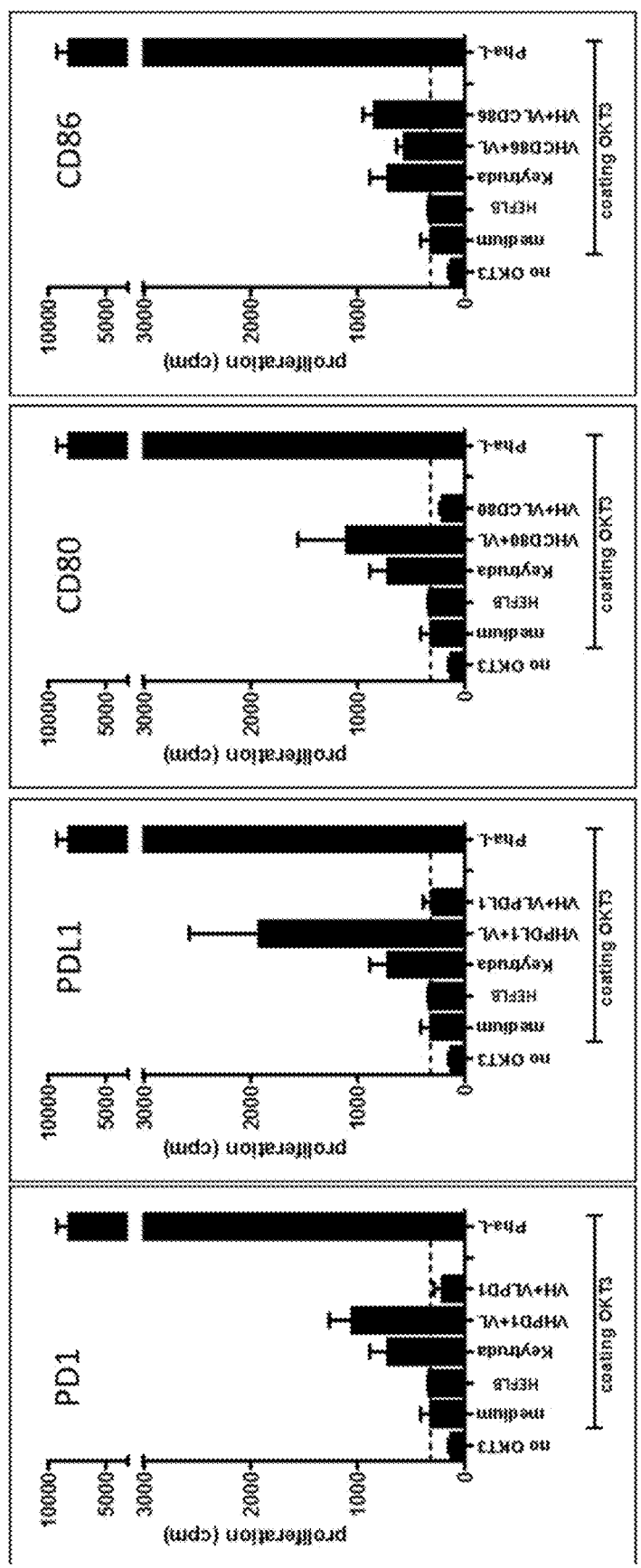
Figure 28:
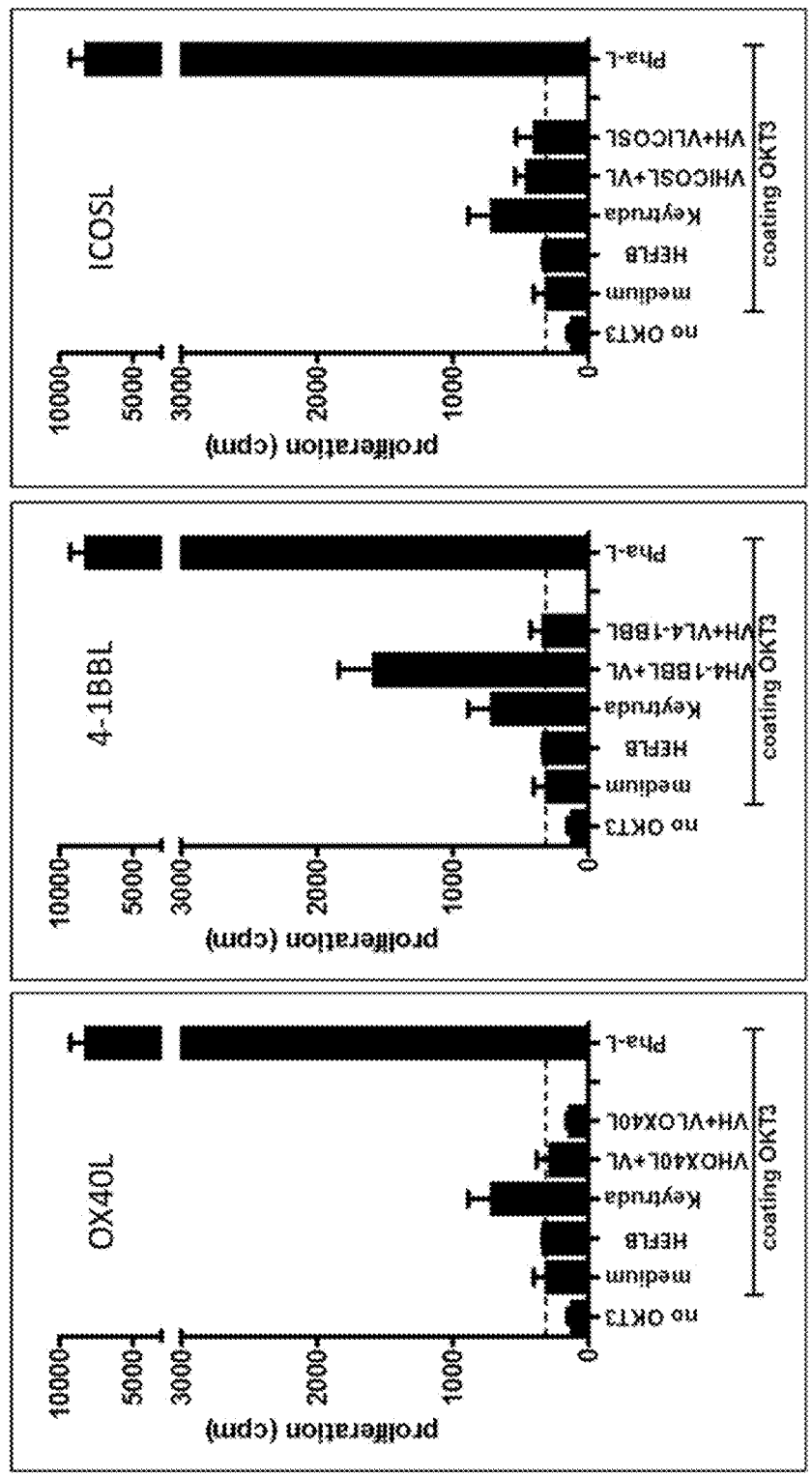

FIG. 28. Proliferation assay of human isolated T-lymphocytes with soluble modified anti-SIRPa antibodies. Assessment of T-cell proliferation on coated OKT3 (1 µg/ml) with soluble different proteins: anti-SIRPa HEFLB antibody, anti-PD1 Keytruda mAb, recombinant protein, HEFLB+ recombinant protein, or modified anti-SIRPa HEFLB antibodies fused to a protein on heavy chain VHprot+VL or on light chain VH+ VLprot at 10 µg/ml or Pha-L positive control for 3 days at 37° C., 5% CO2. ³H thymidine was incorporated 8 hours before measurement, and results were expressed in cpm to determine the level of proliferation. The results are obtained with modified anti-SIRPa HEFLB antibodies fused to PD1, PDL1, CD80, CD86, OX40L, 4-1BBL or ICOSL.

Figure 29:
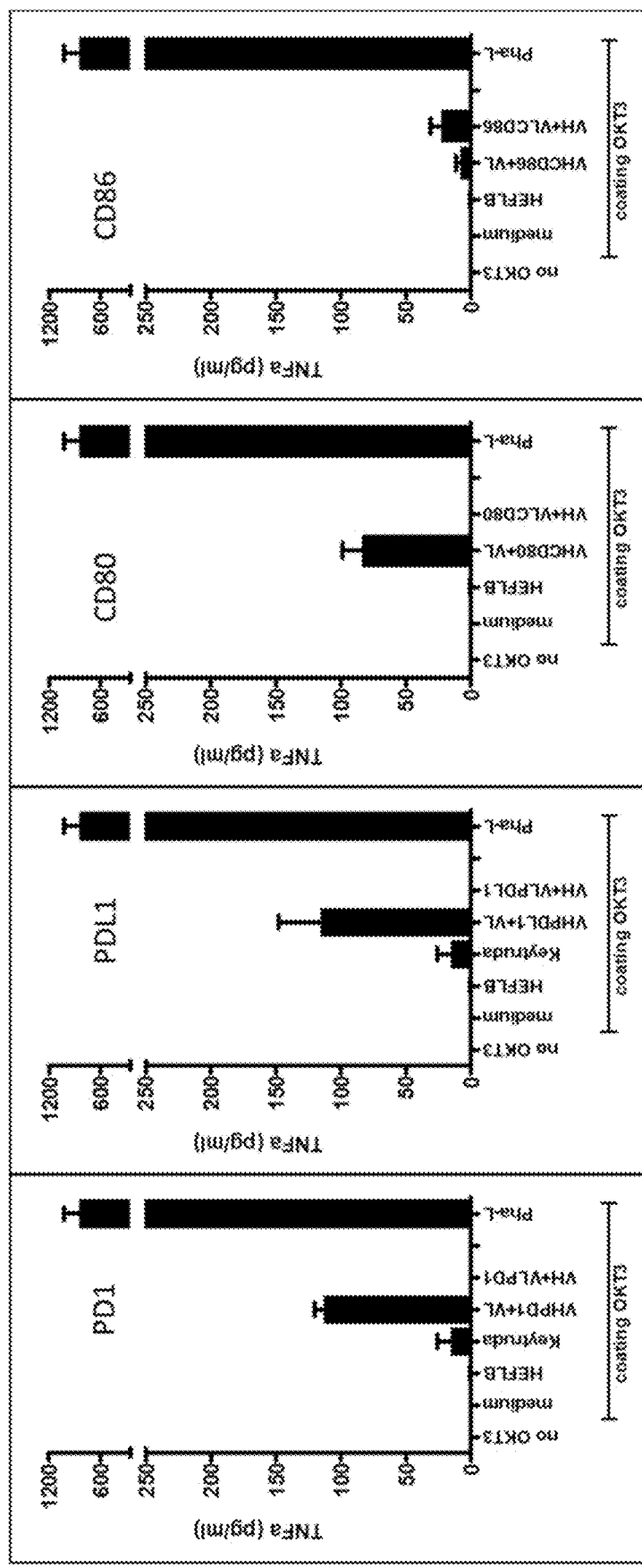
Figure 29:
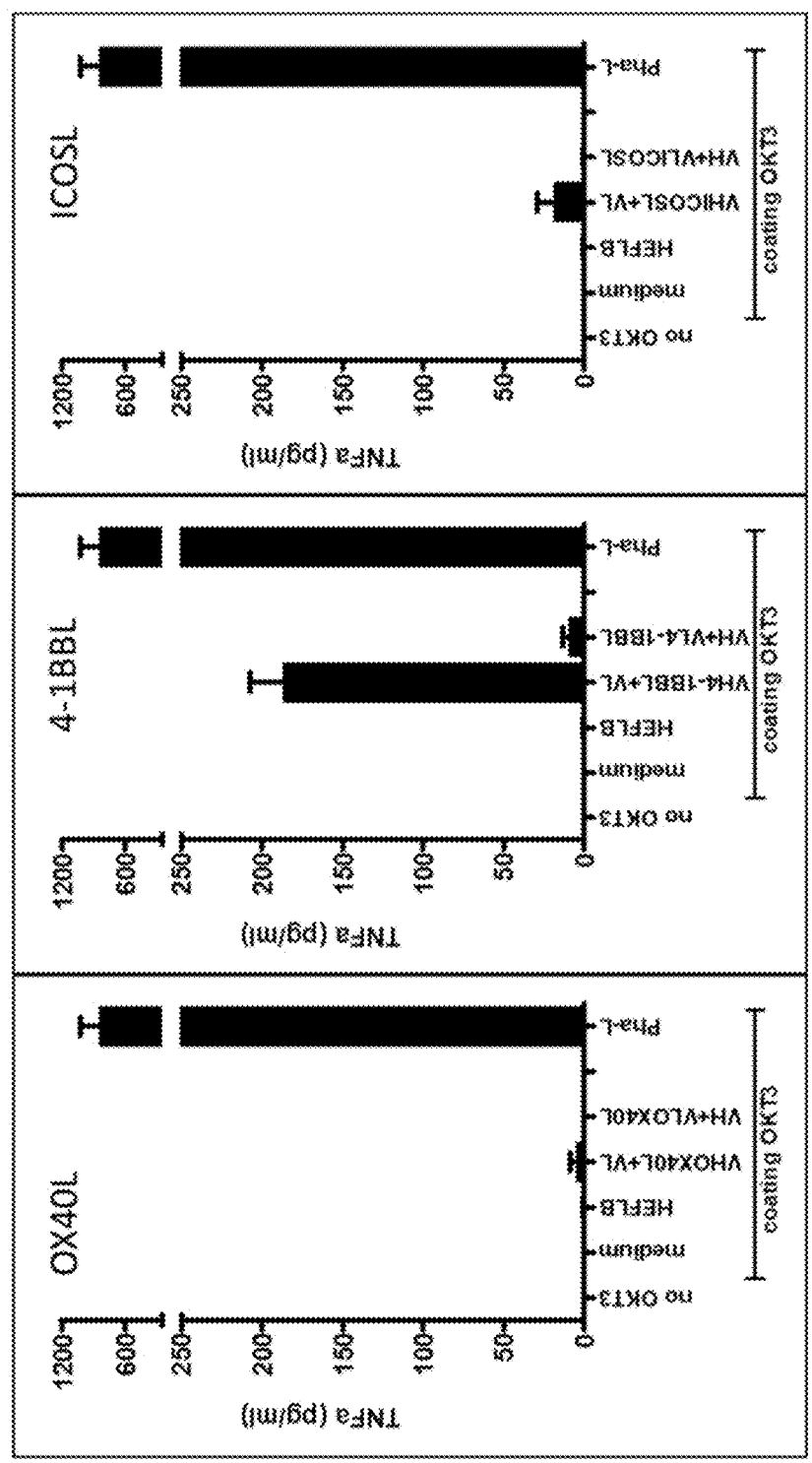

FIG. 29. TNFa secretion assay by human isolated T-lymphocytes with soluble modified anti-SIRPa antibodies. Assessment by ELISA of TNFa secretion by OKT3 coated T cells (1 µg/ml) with soluble different proteins: anti-SIRPa HEFLB antibody, anti-PD1 Keytruda mAb, recombinant protein, HEFLB antibodies plus recombinant protein (not fusioned), or modified anti-SIRPa HEFLB antibodies fused to a protein on heavy chain VHprot+VL or on light chain VH+ VLprot at 10 µg/ml for 2 days at 37° C., 5% CO2. The results are obtained with modified anti-SIRPa HEFLB antibodies fused to PD1, PDL1, CD80, CD86, OX40L, 4-1BBL or ICOSL.

Figure 30:
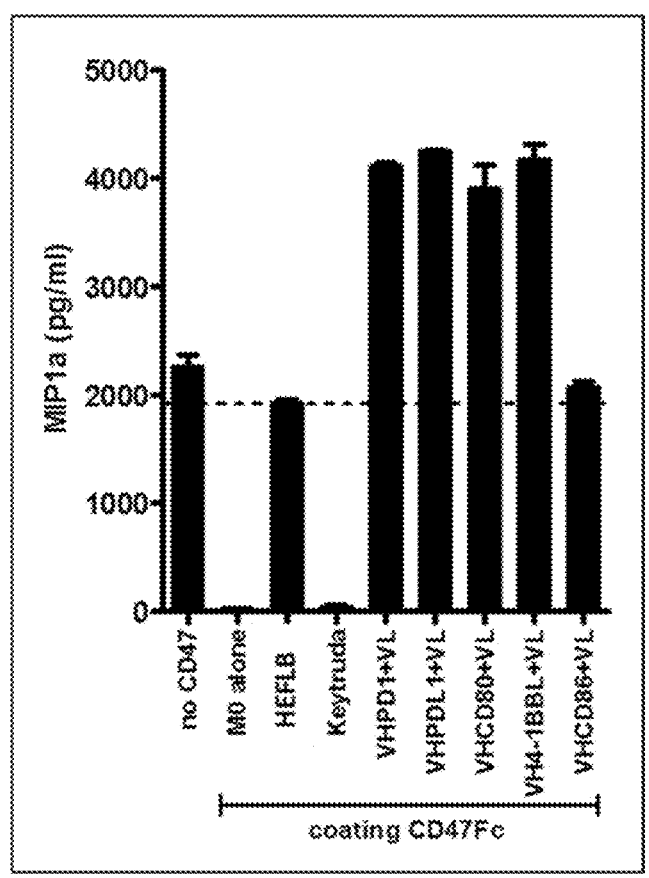

FIG. 30. MIP1a (CCL3) secretion assay by ELISA on immature human macrophages. Immature macrophages were cultured with CD47Fc then soluble protein was added: anti-SIRPa HEFLB antibody, anti-PD1 Keytruda mAb, or modified anti-SIRPa HEFLB antibodies (fused to PD1, PDL1, CD80 or 4-1BBL) on the heavy chain VHprot+VL at 10 µg/ml for 24 h at 37° C., 5% CO2. Supernatants were collected and MIP1a secretion was measured by ELISA. The results are obtained with modified anti-SIRPa HEFLB antibodies fused to PD1, PDL1, CD80, CD86, OX40L, 4-1BBL or ICOSL.

Figure 31:
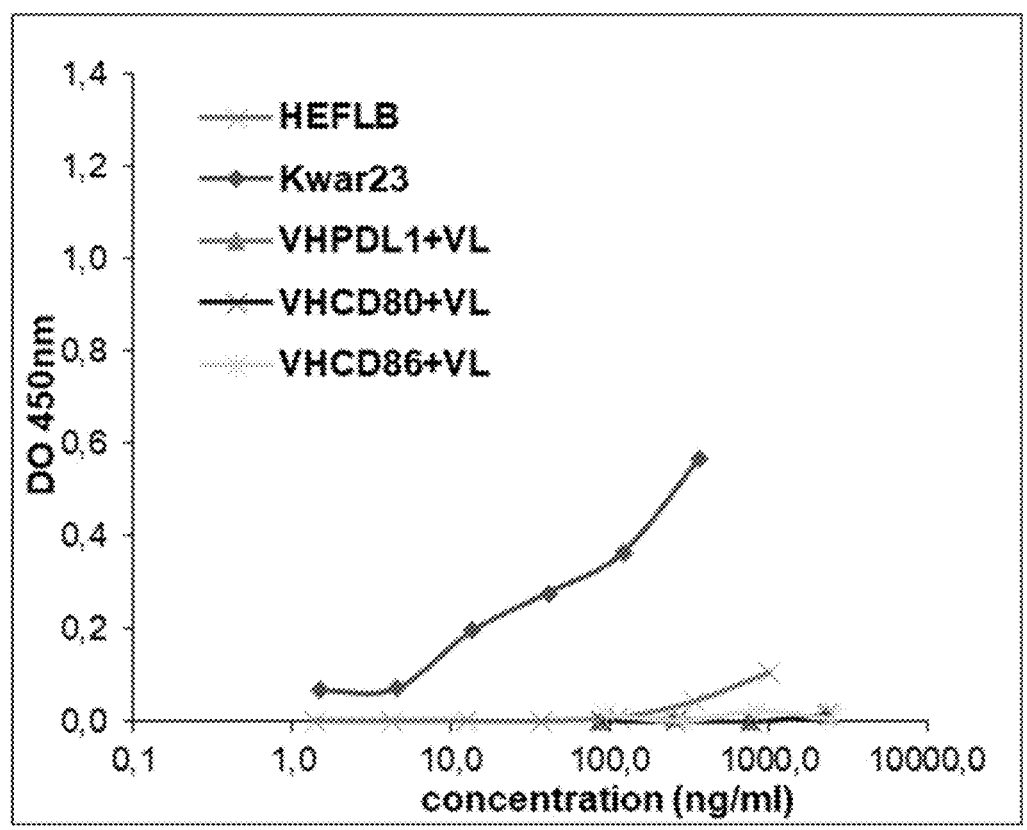

FIG. 31. Modified anti-SIRPa antibodies and Binding anti-SIRPg ELISA assay. Assessment by ELISA on immobilized human SIRPg-His of HEFLB antibody, modified anti-SIRPa antibodies fused on the VH chain to PDL1, CD80 or CD86, or Kwar23 antibody. Revelation was performed with a peroxidase labelled anti-human IgG-Fc and revealed by colorimetry at 450 nm using TMB substrate.

FIG. 32. Modified anti-SIRPa antibodies effects on MIP1a, TNFa and IFNg secretion in macrophages and T cells bioassays. Culture of CD47-coated (1 µg/ml) immature macrophages (human monocytes with GM-CSF at 10 ng/ml for 2 days), addition of different antibodies described below at 10 µg/ml for 24 h at 37° C., 5% $CO_2$ and addition of OKT3 pre-activated T cells.
Soluble HEFLB antibody alone or combined with recombinant proteins (PDL1Fc, 4-1BBL1Fc, CD80His or CD86His), anti-B12-4 fused to PDL1 or 4-1BBL1 or CD80 or CD86 as bifunctional Isotype control antibodies or modified anti-SIRPa antibodies fused to PDL1, 4-1BBL, CD80 or CD86 on heavy chain (VHprot+VL) were tested.
A. MIP1a (CCL3) secretion assay by immature macrophages with soluble modified anti-SIRPa antibodies. Supernatants were collected and MIP1a secretion was measured by ELISA.
B. Assessment by ELISA of TNFa secretion in presence of different soluble proteins as described above at 10 µg/ml at 37° C., 5% $CO_2$.
C. Assessment by ELISA of IFNg secretion in presence of different soluble proteins as described above at 10 µg/ml at 37° C., 5% $CO_2$.

Figure 33:
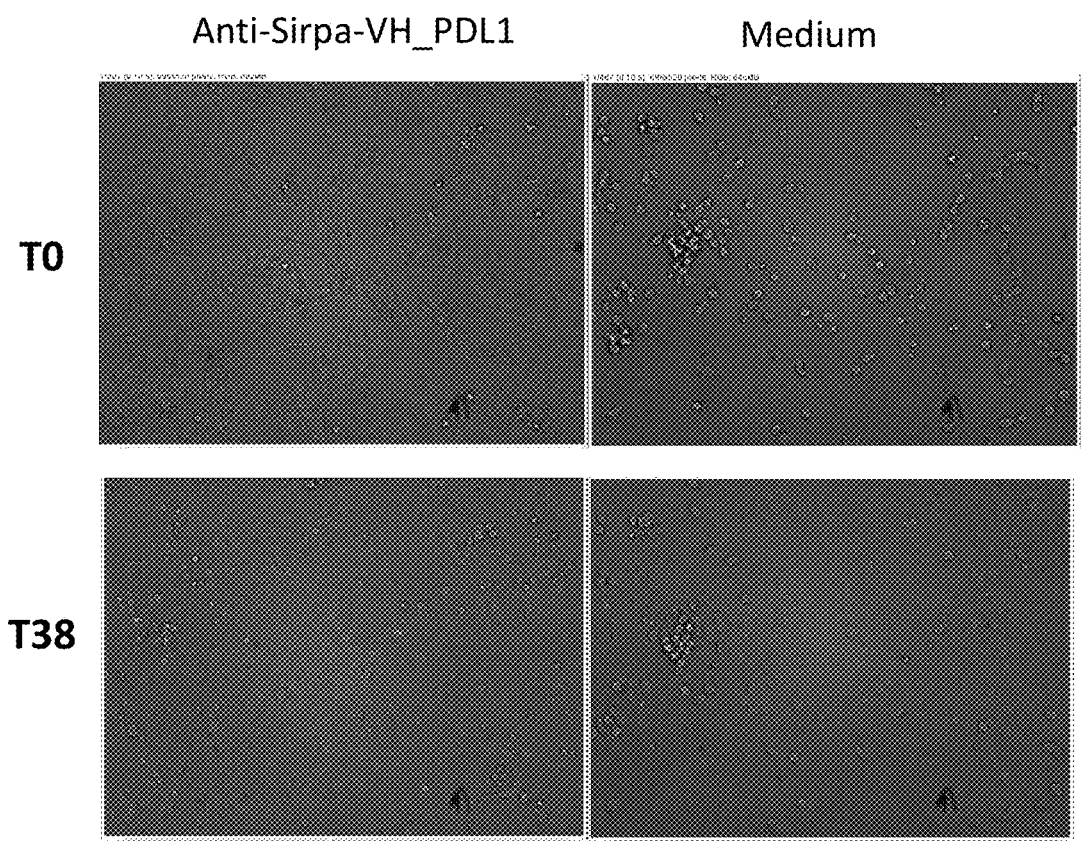

FIG. 33. T cell activation measurement using calcium intracellular Time-Lapse Assay. CD47 Pre-coated immature macrophages for 24 h were cocultured with Fura-OKT3 stained T cells in presence of modified anti-SIRPa antibody with PDL1 fused on the VH chain. Calcium activity was measured at T0 and T38 minutes after adding T cells.

EXAMPLES

In the following Examples, the antibody "18D5" (or "m18D5") corresponds to the mouse antibody 18D5, the "chimeric" antibody corresponds to the chimeric mouse/human 18D5 antibody, and the antibodies "HALA, HALB, HBLA, HBLB, HCLA, HCLB, HELA, HELB, HFLA, HFLB, HEFLA and HEFLB" correspond to specific humanized 18D5 variants. The antibodies 6G10 and 12D7 belong to the Applicant; these antibodies have been obtained by the same method than m18D5 and are used as control. These control antibodies are IgG2a mouse monoclonal anti-human SIRPa antibodies.
In addition, commercial antibodies were used for comparison. The first one is an anti-SIRPa antibody, named SE7C2 (Santa Cruz sc-23863); the second antibody is an antibody able to recognize both SIRP α/β and is named SE5A5 (BioLegend BLE323802); and the third one is an anti-human SIRPa antibody named Kwar23 (Creative Biolabs). An anti-human SIRPa antibody named SIRP29 from University of Toronto described in the PCT application WO2013056352 was also used for comparison.

To create modified anti-SIRPa antibodies, the sequence of the humanized anti-SIRPa antibody IgG4m (HEFLB), heavy or light chain has been coupled to the extracellular domain (ECD) of co-stimulatory or co-inhibitory immune checkpoint proteins in the C-terminal extremity of the heavy chain or light chain of the antibody. For fusion of each different protein on the HEFLB heavy chain, extracellular domains of PD1, PDL1, CD80, CD86, OX40L, 4-1BBL or ICOSL were synthetized and cloned by NsiI in VH-pFuseCHIg-hG4m expression plasmid containing humanized heavy chain of HEFLB and Fc of human IgG4 mutated (S228P) to stabilize hinge region (pFuseCHIg-hG4m vector from Invivogen, Toulouse). For fusion of each different protein on the light chain of HEFLB, extracellular domains of PD1, PDL1, CD80, CD86, OX40L, 4-1BBL or ICOSL were synthetized and cloned by AccI/NheI in VL-pFuse2CLIg-hk expression plasmid containing humanized light chain of HEFLB and human CLkappa (pFuse2CLIg-hk from Invivogen, Toulouse).
In HEK 293 Freestyle cells, plasmids containing VHhFcG4 wild-type or fused with protein have been co-transfected, by lipofectamine method, with plasmids containing VL-CLk wt (VHprot+VL); and VHhFcG4 wild-type has been co-transfected with plasmid containing VL-CLk wild-type or fused with one of the proteins (VH+ VLprot). After 48-72 h incubation, supernatant was recovered and purified by affinity on Protein A chromatography (HiTrap, GeHealthcare) with citric acid 0.1M pH 3 elution buffer. Purified antibodies were dialyzed in PBS and concentrated. Each antibody was quantified by sandwich ELISA and tested in activity assay against SIRPa or ligand like antigen.

Examples 1 to 23 show experimental results obtained with the unmodified anti-SIRPa 18D5 variants (FIGS. 1 to 21).
Examples 24 to 32 show experimental results obtained with the modified HEFLB variant linked in C-ter, on its heavy chain or on its light chain, to different immunotherapeutic agents (FIGS. 22 to 30).

Example 1. Binding Analyses of the Anti-SIRPa Antibodies on SIRPa by ELISA

Method: The binding activity of the anti-SIRPa antibodies was assessed by ELISA. For the ELISA assay with the chimeric antibody, the humanized antibodies, SIRP29 and Kwar23, a recombinant hSIRPa (Sino Biologicals, Beijing, China; reference 11612-H08H) was immobilized on plastic at 0.5 µg/ml in carbonate buffer (pH9.2) and the purified antibody was added to measure binding. After incubation and washing, peroxidase-labeled donkey anti-human IgG (Jackson Immunoresearch; USA; reference 709-035-149) was added and revealed by conventional methods.

For the ELISA assay with the mouse antibodies, a recombinant hSIRPa (Sino Biologicals, Beijing, China; reference 10975-H08H) was immobilized on plastic at 0.5 µg/ml in carbonate buffer (pH9.2) and the purified antibody was added to measure binding. After incubation and washing, peroxidase-labeled goat anti-mouse Fc chain (Jackson Immunoresearch; reference 115-036-071) was added and revealed by conventional methods.

Results: As shown in FIGS. 1A, 1B and 1C, the binding activity of the different anti-SIRPa antibodies on SIRPa as measured by ELISA showed effective concentrations (EC50) of 2.9 ng/ml for the chimeric antibody, 3.9 ng/ml for HALA, 5.1 ng/ml for HFLA, 4.0 ng/ml for HFLB, 7.1 ng/ml for HEFLA, 4.4 ng/ml HEFLB in a first experiment, 4.06 ng/ml for the chimeric antibody, 5.60 ng/ml for HCLA, 5.59 ng/ml for HCLB, 4.61 ng/ml for HFLA, 4.13 ng/ml for HELB in a second experiment, and 2.74 ng/ml for the chimeric antibody, 2.53 ng/ml for HALB, 2.68 ng/ml for HBLA, 2.95 ng/ml for HBLB in a third experiment. Those results indicate that the antibodies of the invention tested are good SIRPa binders by ELISA as compared to other known anti-SIRPa antibodies SIRP29 (3.7 ng/ml) and Kwar23 (3.3 ng/ml). Those results indicate that the epitope recognized by all the antibodies of the invention is accessible when SIRPa is coated on a plastic well.

As shown in FIG. 1D, the binding activity of different anti-SIRPa antibodies on SIRPa as measured by ELISA showed an effective dose (ED50) of 0.16 nM (24 ng/ml) for SE5A5 and 0.06 nM (9 ng/ml) for the clone m18D5. The clones 6G10 and 12D7 did not seem to bind SIRPa by ELISA assay. Those results indicate that the clone m18D5 is a good SIRPa binder by ELISA compared to a commercial antibody and indicate that the epitope recognized by this clone is accessible when SIRPa is coated on a plastic well compared to clones 6G10 and 12D7.

Example 2. Biosensor Affinity Measurement of the Anti-SIRPa Antibodies for SIRPa Method: Recombinant hSIRPa (Sino Biologicals, Beijing, China; reference 11612-H08H) was immobilized into a CM5 sensor chip (GeHealthcare; France) at 5 μg/ml (500 RU) and antibodies were applied at different concentrations with a flow rate of 40 μl/min. Analysis was performed with a BIAcore 3000 (Biacore, GeHealthcare). Values were measured after an association period (ka) of 3 min followed by a dissociation period of 10 min (kd) to determine affinity constant (KD).

Results: As shown in FIG. 2, the antibodies of the invention have a strong affinity (KD) for SIRPa (from 1.93e-10 M to 3.67e-10 M), which is equivalent to the affinity of the known anti-SIRPa antibodies SIRP29 and Kwar23 and better than the affinity of the commercial anti-SIRPa antibodies SE7C2 and SE5A5.

Example 3. SIRPa Binding Assay on Human Monocytes by Cytofluorometry

Method: To measure the binding of the anti-SIRPa antibodies on human monocytes, human Fc Receptor Binding Inhibitor (BD pharmingen; USA; reference 564220) was first added for 30 min at room-temperature to block human Fc receptors on human monocytes to reduce background. Then, an antibody was incubated for 30 min at 4° C., and washed before stained 30 min at 4° C. with PE-labelled anti-human IgG Fc (Biolegend; USA; reference 409303). For the mouse antibodies, a PE-labelled anti-mouseIgG (Jackson Immunoresearch; reference 715-116-151) was used. Samples were analyzed on BD LSRII or Canto II cytofluorometer.

Results: As shown in FIG. 3, the results indicate a strong binding of the anti-SIRPa antibodies of the invention on human monocytes and a binder binding (as measured with the MFI (Median Fluorescent Intensity)) that the known anti-SIRPa antibodies Kwar23, SE7C2 and SE5A5.

Example 4. Competitive Analysis Between CD47 and the Anti-SIRPa Antibodies by Antagonist ELISA Assay Method: For competitive ELISA assay, recombinant hSIRPa (Sino Biologicals, Beijing, China; reference 11612-H08H) was immobilized on plastic at 0.5 μg/ml in carbonate buffer (pH9.2). For the chimeric antibody, the humanized antibodies, SIRP29 and Kwar23, a purified antibody (at different concentrations) was mixed with 6 μg/ml final (fix concentration) of biotinylated Human CD47Fc (AcroBiosystems interchim; France; reference: #CD7-H82F6) to measure competitive binding for 2 h at 37° C. After incubation and washing, peroxidase-labeled streptavidin (Vector laboratoring; USA; reference SA-5004) was added to detect Biotin-CD47Fc binding and revealed by conventional methods. For the mouse antibodies, a purified antibody (at different concentrations) was mixed with 0.04 μg/ml of CD47Fc (Sino Biologicals, Beijing, China; reference 12283-H02H) to measure competitive binding for 2 h at 37° C. After incubation and washing, peroxidase-labeled donkey anti-human Fc chain (Jackson Immunoresearch; reference 709-035-149) was added to detect CD47Fc binding and revealed by conventional methods.

Results: As shown in FIG. 4, the antibodies of the invention have an antagonist activity on the SIRPa-CD47 interaction. In particular, it is observed that the chimeric antibody, HFLA, HFLB, HEFLA and HEFLB have a better antagonist activity as compared to the antagonist activity of SIRP29 and the commercial anti-SIRPa antibody SE5A5.

Example 5. Competitive Analysis Between CD47 and the Humanized Anti-SIRPa Antibodies on Human Monocytes by Antagonist Cytofluorometry Assay Method: To measure the competition between CD47 and the humanized anti-SIRPa antibodies on human monocytes, a purified antibody was added on monocytes for 15 min at 4° C., then mixed with 5 μg/ml final of biotinylated Human CD47Fc (AcroBiosystems interchim; France; reference: #CD7-H82F6) and incubated for 30 min at 4° C. to measure competitive binding antibody. After incubation and washing, PE-labelled streptavidin (BDBiosciences; USA; reference 554061) was added for 15 min at 4° C. to detect Biotin-CD47Fc binding and analyzed on BD LSRII or Canto II cytofluorometer.

To measure the competition between CD47 and the mouse anti-hSIRPa antibodies on human monocytes, a purified antibody was added on monocytes for 15 min at 4° C., then mixed with 5 μg/ml final of CD47Fc (Sino Biologicals, Beijing, China; reference 12283-H02H) and incubated for 15 min at 4° C. to measure competitive binding antibody. After incubation and washing, FITC-labelled anti-human Fc (Beckman Coulter; reference IM1627) was added for 15 min at 4° C. to detect CD47Fc binding and analyzed on BD LSRII or Canto II cytofluorometer.

Results: As shown in FIG. 5, the antibodies of the invention have an antagonist activity on SIRPa-CD47 interaction on human monocytes.

Example 6. Blitz Method Competition with SP-D

Method: This method was performed with a Blitz (Forte Bio; USA; reference C22-2 No 61010-1).
Condition A: SIRPa+Anti-SIRPa antibody+Surfactant Protein D (SP-D). In a first step, SIRPa (His) recombinant protein (Sino Biologicals, Beijing, China; reference 11612-H08H) was immobilized at 10 µg/ml by histidine tail into a Ni-NTA biosensor (Forte Bio; USA; reference 18-0029) for 30 seconds. In a second step, anti-SIRPa antibodies were added at 20 µg/mL (saturating concentration) for 120 seconds. Then, human SP-D (R et D Systems; USA; reference 1920-SP-050) was associated at 100 µg/mL, in competition with anti-SIRPa antibodies, for 120 seconds. The dissociation of SP-D was made in kinetics buffer for 120 seconds. Analysis of data was made with the Blitz pro 1.2 software, which calculated association constant (ka) and dissociation constant (kd) and determined the affinity constant KD (ka/kd).

Condition B: SIRPa+Surfactant Protein D (SP-D)+Anti-SIRPa antibody. In a first step, Sirp-a (His) recombinant protein (Sino Biologicals, Beijing, China; reference 11612-H08H) was immobilized at 10 µg/ml by histidine tail into a Ni-NTA biosensor (Forte Bio; USA; reference 18-0029) for 30 seconds. In a second step, human SP-D (R et D Systems; USA; reference 1920-SP-050) was added at 100 µg/mL for 120 seconds. Then, anti-SIRPa antibodies were associated at 20 µg/mL (saturating concentration) for 120 seconds. The dissociation of anti-SIRPa antibody was made in kinetics buffer for 120 seconds. Analysis data was made with the Blitz pro 1.2 software, which calculated association constant (ka) and dissociation constant (kd) and determined the affinity constant KD (ka/kd).

Results: As shown in FIG. 6, the binding of the anti-SIRPa antibody 18D5 does not block the binding of SP-D to SIRPa and the binding of SP-D does not block the binding of 18D5 to SIRPa. Thus, the antibody of the invention does not inhibit the interaction between SIRPa and SP-D.

Example 7. Affinity of the Anti-SIRPa Antibodies for SIRPb by Blitz Method

Method: This method was performed with a Blitz (Forte Bio; USA; reference C22-2 No 61010-1). Recombinant hSIRPb-His (Antibodies-online; USA; reference ABIN3077231) was immobilized at 10 µg/ml by histidine tail into a Ni-NTA biosensor (Forte Bio; USA; reference 18-0029) for 30 seconds. Then, an anti-SIRPa antibody was associated at 20 µg/mL for 120 seconds. The dissociation of anti-SIRPa antibody was made in kinetics buffer for 120 seconds. Analysis of data was made with the Blitz pro 1.2 software, which calculated association constant (ka) and dissociation constant (kd) and determined the affinity constant KD (ka/kd).

Results: As shown in FIG. 7A, the antibodies of the invention have a lower affinity for SIRPb as compared to SIRPa. In particular, it is noted that the chimeric antibody, HFLA, HFLB, HEFLA, HEFLB have a reduced affinity for SIRPb as compared to SIRP29 and Kwar23.

Example 8. ELISA Binding of Anti-SIRP Antibodies on SIRPb

Method: For activity ELISA assay, recombinant hSIRPb-His (Antibodies-online; USA; reference ABIN1466557) was immobilized on plastic at 1 µg/ml in carbonate buffer (pH9.2) and a purified antibody was added to measure binding. After incubation and washing, peroxidase-labeled donkey anti-human IgG (Jackson Immunoresearch; USA; reference 709-035-149) was added and revealed by conventional methods.

Results: As shown in FIG. 7B, the anti-SIRPa antibodies have a low affinity for SIRPb. It must be indicated that the revelation was performed with a donkey anti-human antibody for all antibodies except for B4B6 (revealed with a mouse antibody), which may explain that the signal obtained for the anti-SIRPb antibody B4B6 is lower than the signal obtained for the anti-SIRPa antibodies.

Example 9. Affinity Analysis of the Anti-SIRPa Antibodies for SIRPg by Blitz Method Method: This method was performed with a Blitz (Forte Bio; USA; reference C22-2 No 61010-1). Recombinant hSIRPg-His (Sino Biologicals, Beijing, China; reference 11828-H08H) was immobilized at 10 µg/ml by histidine tail into a Ni-NTA biosensor (Forte Bio; USA; reference 18-0029) for 30 seconds. Then, an anti-SIRPa antibody was associated at 20 µg/mL for 120 seconds. The dissociation of anti-SIRPa antibody was made in kinetics buffer for 120 seconds. Analysis of data was made with the Blitz pro 1.2 software, which calculated association constant (ka) and dissociation constant (kd) and determined the affinity constant KD (ka/kd).

Results: As shown in FIG. 8A, the anti-SIRPa antibodies of the invention have a low affinity for SIRPg. This affinity is slightly weaker than the affinity of the known anti-SIRPa antibodies SIRP29 and Kwar23. However, the kinetics properties differ between anti-SIRPa antibodies, SIRP29 and Kwar23, with a high dissociation rate constant (Kd) for anti-SIRPa antibodies as compared to SIRP29 and Kwar23. In particular, HFLB has the lowest affinity for SIRPg with a KD value of 1.036e-7 M that equals to a 2-log difference as compared to the KD values of SIRP29 and Kwar23.

Example 10. ELISA Binding of the Anti-SIRP Antibodies on SIRPg

Method: For activity ELISA assay, hSIRPg-His (Sino Biologicals, Beijing, China; reference 11828-H08H) was immobilized on plastic at 1 µg/ml in carbonate buffer (pH9.2) and purified antibody were added to measure binding. After incubation and washing, peroxidase-labeled donkey anti-human IgG (Jackson Immunoresearch; USA; reference 709-035-149) was added and revealed by conventional methods.

Results: As shown in FIG. 8B, the anti-SIRPa antibody HEFLB does not bind SIRPg while the known anti-SIRPa antibodies SIRP29 and Kwar23 show a significant binding to SIRPg.

Example 11. Blitz Method Competition with CD47 for SIRPg: SIRPg+Anti-SIRPa Antibody+CD47

Method: This method was performed with a Blitz (Forte Bio; USA; reference C22-2 No 61010-1). In a first step, hSIRPg-His (Sino Biologicals, Beijing, China; reference 11828-H08H) was immobilized at 10 µg/ml by histidine tail into a Ni-NTA biosensor (Forte Bio; USA; reference 18-0029) for 30 seconds. In a second step, an anti-SIRPa antibody was added at 20 µg/mL (saturating concentration) for 120 seconds. Then, human CD47Fc ((Sino Biologicals, Beijing, China; reference 12283-H02H) was associated at 100 µg/mL, in competition with anti-SIRPa antibodies, for 120 seconds. The dissociation of CD47Fc was made in kinetics buffer for 120 seconds. Analysis data was made with the Blitz pro 1.2 software, which calculated association constant (ka) and dissociation constant (kd) and determined the affinity constant KD (ka/kd).

Results: As shown in FIG. 9, the anti-SIRPa HEFLB of the invention does not compete with the binding of CD47 to SIRPg. At the opposite, the other known antibodies SIRP29 and, in particular, kwar23 compete with the binding of CD47 to SIRPg.

Example 12. Binding to Blood Cells by Flow Cytometry

Method: The experiment was realized to analyze the binding of the anti-SIRPa antibodies on human blood cells. CD3-positive T lymphocytes, red blood cells and platelets were extracted from purified blood from healthy volunteers. Cells were then stained for 30 min at 4° C. with 10 micrograms/ml of each tested antibody, washed and then stained with a secondary fluorescent anti-IgG antibody for another 30 min at 4° C. After washes, cells were analyzed on a CANTO II (BD Bioscience) flow cytometer.

Results: As shown in FIG. 10, the T cells, the red blood cells and the platelets are positive for CD47, which is expressed ubiquitously, and they were stained with the B6H12 antibody. The SIRP29 and the Kwar23 antibodies, like LSB2.20 (specific anti-SIRPγ antibody), bind to T cells that are known to express SIRPγ. However, the anti-SIRPa humanized 18D5 antibody does not bind to the T cells (same results obtained with four different 18D5 humanized variants tested). Red blood cells and platelets do not express SIRPa and, thus, they were not revealed with the humanized 18D5 antibody and the other anti-SIRPa antibodies. This result shows the specificity of the humanized 18D5 antibody for SIRPa on live cells as compared to the known anti-SIRPa antibodies.

As shown in FIG. 11, the T-cells are not stained by the humanized 18D5 antibody (same results obtained with five different 18D5 humanized variants tested) and with the chimeric 18D5 (data not shown) whereas more than 70% of T cells are stained by SIRP29 and Kwar23.

Example 13. Human CD3+ T Cell Proliferation

Method: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (LifeTechnologies) at a 1 bead for 1 T cell ratio during three days, or allogeneic mature dendritic cells generated in vitro at a 5 T cell for 1 mDC during 5 days or with different concentrations of tuberculin unpurified protein derivative (PPD) for 5 days. Antibodies targeting the SIRPa/CD47 pathway were added from the beginning of the proliferation test at a saturating concentration (10 µg/mL). Proliferation was measured by incorporation of $H^3$-thymidine during the last 12 h of culture.

Results: As shown in FIG. 12, the anti-SIRPa antibody HALA and HEFLB variants do not inhibit the T cell proliferation when T cells are stimulated with anti-CD3+ anti-CD28 beads (A) (C) or with allogenic dendritic cells (B) (D) or with PPD (E), whereas the anti-SIRPa Kwar23 inhibits T cell proliferation when T cells are stimulated with allogenic dendritic cells. As expected, the anti-CD47 antibodies and the anti-SIRPg antibody are inhibitors of the T cell proliferation.

Example 14. Mouse CD8+ T Cell Proliferation

Method: Splenocytes were isolated from naive mice. CD8 T cells were selected by positive selection using an AutoMACS (Miltenyi) and plated in 96-round well plate (50 000 cells/well). The proliferative signals were provided by anti-CD3/anti-CD28 coated microbeads (LifeTechnologies) at a 1 bead for 1 T cell ratio during three days. A mouse anti-SIRPa antibody (P84) and an anti-CD47 antibody (MIAP310) targeting the SIRPa/CD47 pathway were added from the beginning of the proliferation test at a saturating concentration (10 µg/mL). Proliferation was measured by incorporation of $H^3$-thymidine during the last 12 h of culture.

Results: As shown in FIG. 13, there is no inhibition of the anti-SIRPa or anti-CD47 antibody on the proliferation of mouse T cells. This result is explained by the fact that mice does not express the SIRPg gene. Thus, mice can be used as a model to predict the in vivo effects of a specific anti-SIRPa antibody that does not bind SIRPg. In contrast, anti-CD47 or non-selective anti-SIRPa antibodies in vivo preclinical efficacy, in particular on adaptive immunity and generation of memory T lymphocytes, is not predictive of human situation.

Example 15. Human T Cell Proliferation

Method: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (LifeTechnologies) at a 1 bead for 1 T cell ratio during three days, or allogeneic mature dendritic cells generated in vitro at a 5 T cell for 1 mDC during 5 days. Antibodies were added from the beginning of the proliferation test at a saturating concentration (5 µg/mL for anti-CD47 and anti-SIRPa antibodies and 2.5 µg/mL for the anti-PD-1/PD-L1 antibodies and the recombinant 4-1BBL). Proliferation was measured by incorporation of $H^3$-thymidine during the last 12 h of culture.

Results: As shown in FIG. 14, the anti-PD-1/PD-L1 antibodies and the recombinant 4-1BBL have a boost effect on the proliferation of human T cells, while anti-CD47 has a negative effect on the proliferation of human T cells. In particular, the anti-CD47 antibody prevents the human T-cell immunostimulatory efficacy of anti-PD-1/PD-L1 or 4-1BB agonist agents. The anti-SIRPa HEFLB has no significant effect on the proliferation of T cells.

Example 16. Anti-Tumor Effects in Mice

Method: Mice were anesthetized with a cocktail of xylazine/ketamine. After a laparotomy, tumoral Hepa 1.6 cells were injected through the portal vein ($2.5.10^6$ cells/100 µL) in PBS. The treatment was started 4 days after tumor injection. The agonistic anti-4-1BB monoclonal antibody (3H3) was injected two times at d4 and d8 after Hepa 1.6 cells (Hepatocarninoma cells, HCC) injection intraperitoneally in PBS (100 µg/injection). The anti-PDL1 monoclonal antibody was injected twice a week during 4 weeks intraperitoneally in PBS (200 µg/injection). The antagonistic anti-SIRPa antibody (P84) was injected three time a week during four weeks intraperitoneally in PBS (300 µg/injection).

The anti-tumor response was evaluated in the orthotopic model of HCC thirteen days after the tumor inoculation. At this time, the tumor and the spleen were collected in order to phenotype the immune cells that infiltrated the tumor or in the systemic way. Splenocytes and non-parenchymal cells (NPC) of the liver which are the infiltrating immune cells were stained with four different mixes for flow cytometry acquisition.

Results: As shown in FIG. 15A, the anti-SIRPa antibody alone significantly prolongs survival in a fraction of mice (28%). In combination with anti-4-1BB or anti-PDL1 antibodies, anti-SIRPa antibody allows a very high response rate of mice surviving even after treatment withdrawal.

As shown in FIG. 15B, the combination of anti-SIRPa with a co-stimulatory agent (e.g. anti-4-1BB) or T-cell checkpoint inhibitor (e.g. anti-PDL1) modifies the tumor microenvironment by decreasing the regulatory and immunosuppressive immune cells (Tregs, Mo-MDSC) while increasing accumulation of effector memory CD8+ T cells in combination with anti-4-1BB. The Mo-MDSC are characterized by a high expression of Ly6C and no Ly6G among the CD11b positive- and MHC class II negative-population. As shown in FIG. 15C, the combination of anti-SIRPa with a co-stimulatory agent (e.g. anti-4-1BB) or T-cell checkpoint inhibitor (e.g. anti-PDL1) modifies the cell composition of the tumor microenvironment and in periphery in the spleen, by decreasing the frequency of immature and naïve B cells while increasing accumulation of memory and plasmablast cells. Similarly, accumulation of cytolytic (CD27-negative) NK cells is induced the tumor and periphery by the anti-SIRPa combination with anti-41BB or anti-PDL1.

Altogether, anti-SIRPa modifies the tumor and peripheral immunity in particular adaptive (T-cell, Tregs, B-cells) and innate (MDSC, Macrophages, NK cells) immune cells contributing to tumor elimination and long-term protection.

Example 17. Anti-Tumor Effects in Mice Previously Cured

Method: Mice previously cured in the hepatoma model by anti-SIRPa+ anti-4-1BB injection or SIRPa mutant mice treated with anti-4-1BB were rechallenged by Hepa 1.6 cells injection in the spleen (2.5.10^6 cells/mouse). Mice were anesthetized with 3% of isoflurane in the air. After incision on the flank of the mice and isolation of the spleen, tumoral Hepa 1.6 cells were injected into the spleen (2.5.10$^6$ cells/504) in PBS. Naive mice were injected in parallel in the same route in order to compare tumor development with rechallenged mice.

Results: As shown in FIG. 15D, all the cured mice survived when rechallenged and, at the opposite, all naïve mice died. This result demonstrates that memory T cells were induced under anti-SIRPa therapy or absence of SIRPa signals (SIRPa mutant mice) and still persist on the long-term in cured mice.

Example 18. Anti-Tumor Effects of T-Cell Splenocytes or Whole Splenocytes Collected from Mice Previously Cured Method: Cured anti-SIRPa+ anti-4-1BB rechallenged mice were euthanized and the spleen was collected. After red blood cell lysis, splenocytes were extracted and CD3 positive T cells were isolated from a part of splenocytes with an AutoMACS. After anesthesia, mice were injected with either T-cell splenocytes (2.5.10$^6$ cells/100 µL) or whole splenocytes (10.10$^6$ cells/100 µL) or excipient alone (PBS) intravenously. All mice received Hepa 1.6 cells through the portal vein as described previously (2.5.10$^6$ cells/100 µL).

Results: As shown in FIG. 15E, the splenocytes and isolated T lymphocytes collected from cured mices has a high positive effect on the survival of mice. This results indicate that memory T cells are present in the splenocytes of the cured mice after treatment of the hepatoma and are responsible on the long-term adaptive immune memory.

Example 19. Anti-Tumor Effects in Mice Previously Cured

Method: Mice previously cured in the hepatoma model by anti-SIRPa+ anti-PDL-1 injection were rechallenged by Hepa 1.6 cells injection in the spleen (2.5.10^6 cells/mouse). Mice were anesthetized with 3% of isoflurane in the air. After incision on the flank of the mice and isolation of the spleen, tumoral Hepa 1.6 cells were injected into the spleen (2.5.10$^6$ cells/504) in PBS. Naive mice were injected in parallel in the same route in order to compare tumor development with rechallenged mice.

Results: As shown in FIG. 16, all the cured mice survived when rechallenged and, at the opposite, all naïve mice died. This result suggests that memory T cells are still present in cured mice. This result demonstrates that memory T cells were induced under anti-SIRPa therapy and still persist on the long-term in cured mice.

Example 20. Effects of the Growth of a Tumor in a Mammary Carcinoma Model

Method: Mice were anesthetized with 3% of isoflurane in the air. Mice were shaved on the abdomen and 4T1 cells were injected in the mammary gland with an insulinic syringe (30 Gauges) in 50 µL of PBS. The antagonistic anti-SIRPa antibody (P84) or a control antibody was injected three time a week during four weeks intraperitoneally in PBS (200 µg/injection).

Results: As shown in FIG. 17, the anti-SIRPa antibody significantly ($p<0.01$) reduces the growth of the tumor in the mammary carcinoma model as compared to a control antibody.

FIG. 18 shows the immune cell analysis two weeks after inoculation. Anti-SIRPa has a positive effect on myeloid and non-myeloid cells (T and NK cells) both in tumor and in periphery (spleen) with a dramatic decrease of Tregs and accumulation of memory T cells.

Example 21. Effects of SIRPa Antibodies on the Concentration of Hemoglobin and on the Hematocrit Method: Anti-SIRPa (P84 clone), anti-CD47 (MIAP410 clone) and irrelevant isotype control were administered intraperitoneally at day 0 and day 2 at 12 mg/kg in C57Bl/6 mice. Blood samples were collected at day 0 and day 3 in EDTA containing tubes and blood count was performed with a XS-800i haematology analyzer (Sysmex). The level of hemoglobin (left) and the percentage of hematocrit (right) were evaluated at day 3.

Results: As shown in FIG. 19, the anti-SIRPa antibody has no toxic effect on the concentration of hemoglobin and on the hematocrit. At the opposite, the anti-CD47 antibody induces a decrease of the concentration of hemoglobin and of the hematocrit in accordance with anemia observed during phase 1 in man.

Example 22. Platelet Aggregation

Method: Blood was collected from healthy donor volunteers into Vacuette collection tubes (Greiner Bio-One) buffered with sodium citrate. Platelet rich plasma (PRP) and platelet poor plasma (PPP) were obtained by centrifugation for 10 minutes at 200 g and 15 minutes at 3 500 g, respectively. The working PRP was adjusted to $3.10^8$ platelets·$L^{-1}$. Inhibition Assays: mAb were pre-incubated with PRP for a final concentration of 40 or 50 µg·$mL^{-1}$ test antibodies. After 3 minutes without stirring, platelet aggregation was initiated with ADP 5 µM addition. Aggregation was determined by measuring the transmission of light through the sample at 37° C. with continuous stirring using a standard optical aggregometer (TA-8V Thrombo-Aggregometer, SD Innovation SAS, Frouard, France). The transmission of PPP was set as 100%. Aggregation was recorded under stirring for a total of 5 minutes. Induction Assays: Platelet aggregation was directly initiated by mAb addition (50 µg·$mL^{-1}$). Aggregation was recorded under stirring for a total of max. 10 minutes.

Results: As shown in FIG. 20, in contrast to anti-CD47 antibodies, anti-SIRPa antibodies does not bind to human red blood cells or platelets. Consequently, anti-CD47 induces in vitro human platelets aggregation while anti-SIRPa antibodies does not. Similarly, anti-SIRPa antibodies does not disturb reversible ADP-induced human platelets aggregation while anti-integrin alpha 2b completely abrogates it.

Example 23. Proliferation of Allogeneic T Cells by SIRPa-Blocking CD14+ Cells from a Cancer Ovarian Ascitis Method: Allogeneic CD4 T cells were isolated by positive selection using an AutoMACS (Miltenyi) from hPBMC of a buffy coat of a healthy volunteer. CD4 were plated in 96-round well plate (50 000 cells/well). CD14+ cells were isolated by the same method from the ascitis of a cancer ovarian patient. The CD14+ cells were plated with the allogeneic CD4 T cells at a 1:1 ratio for 5 days. In some conditions, human LPS-matured allogeneic monocyte-derived dendritic cells (moDC) were added at a 1:5 ratio to stimulate T cells and analyzed the immunosuppressive action of different ratio of CD14+MDSC purified from the ascite. Antibodies targeting the SIRPa/CD47 pathway were added from the beginning of the proliferation test at a saturating concentration (10 µg/mL). Proliferation was measured by incorporation of $H^3$-thymidine during the last 12 h of culture.

Results: As shown in FIGS. 21A and 21B, Fresh and frozen human myeloid cells (TAM) purified from ovarian cancer ascites are hypo-stimulating allogeneic human T lymphocytes. In contrast to anti-CD47 antibodies, anti-SIRPa antibodies modifies myeloid cells properties allowing human T-cell activation and proliferation.

As shown in FIG. 21C, human myeloid cells (MDSC) purified from ovarian cancer ascites can suppress human T-cell proliferation induced by allogeneic moDC at 1:1 and 2:1 myeloid to T-cell ratio. In contrast to anti-CD47 antibodies, anti-SIRPa antibodies does not potentiates the immunosuppression induced by human MDSC.

Example 24. SIRPa ELISA Binding Assay with Modified Antibodies by ELISA

Method: For ELISA assay, recombinant hSIRPa (Sino Biologicals, Beijing, China; reference 11612-H08H) was immobilized on plastic at 0.5 µg/ml in carbonate buffer (pH9.2) and different modified anti-SIRPa antibodies were added to measure binding to SIRPa. After incubation and washing, peroxidase-labeled donkey anti-human IgG (Jackson Immunoresearch; USA; reference 709-035-149) was added and revealed by conventional methods. Revelation was performed with a peroxidase labelled anti-human IgG-Fc and revealed by colorimetry at 450 nm using TMB substrate. ED50 was then measured as the concentration of the indicated antibody to reach 50% of the signal in this assay.

Results: FIG. 22 shows that all modified anti-SIRPa antibodies comprising immunotherapeutic agents functionally bind to SIRPa with a good concentration compared to the parental antibody (HEFLB) used as a positive control.

Example 25. Detection of the ECD of the Fused Protein on Modified Antibodies by ELISA Method: Recombinant hSIRPa (Sino Biologicals, Beijing, China; reference 11612-H08H) was immobilized on plastic at 0.5 µg/ml in carbonate buffer (pH9.2) and modified antibodies were added. Detection of the fused protein on the modified anti-SIRPa antibodies was performed with a mouse anti-human PD1 (eBiosciences; reference 12-2799-41), mouse anti-human PDL1 (BD biosciences; reference 558065), mouse anti-human CD80 (BD biosciences; reference 557226), mouse anti-human CD86 (BD biosciences; reference 555658), mouse anti-human OX40L (R&Dsystems; reference MAB10541), mouse anti-human 4-1BBL (BD biosciences; reference 559446) or mouse anti-human ICOSL (BD biosciences; reference 552502). After incubation and washing, peroxidase labelled anti-mouse IgG (Jackson Immunoresearch; USA; reference 715-036-151) was added and revealed by conventional methods.

Results: FIG. 23 shows that every ECD of the fused protein of the modified anti-SIRPa antibodies are well recognized by specific monoclonal antibodies when linked to the heavy chain or to the light chain.

Example 26. Ligand Binding Assay with the Different Modified Anti-SIRPa Antibodies Method: Assessment by ELISA on immobilized SIRPa-His of different modified anti-SIRPa antibodies with fused protein linked to the heavy chain (VHprot+VL (■)) or linked to the light chain (VH+ VLprot (∆)). Detection was performed with specific ligand of the different fused conjugates: PDL1Fc (for PD1), PD1His (for PDL1), CTLA4-Fc (for CD80 and CD86) and Figure B—OX40Fc (for OX40L), 4-1BBFcHis (for 4-1BBL), CD28Fc (for ICOSL) and revealed respectively by mouse anti-human PDL1, mouse anti-His, mouse anti-human CTLA4Fc, mouse anti-human OX40, mouse anti-human His, mouse anti-human CD28 then with peroxidase labelled anti-mouse IgG then by colorimetry at 450 nm using TMB substrate.

Results: FIG. 24 show that modified anti-SIRPa antibody comprising PD1, PDL1, CD80, CD86, OX40L, 4-1BBL and ICOSL can bind to the specific ligand of the fused protein independently that is linked on the heavy or the light chain of the antibody.

Example 27. Competition Assay on SIRPa-CD47 Interaction with Different Modified Anti-SIRPa Antibodies by ELISA Method: For competitive ELISA assay, recombinant hSIRPa (Sino Biologicals, Beijing, China; reference 11612-H08H) was immobilized on plastic at 0.5 µg/ml in carbonate buffer (pH9.2). Each purified antibody (at different concentrations) were mixed with 6 µg/ml final (fix concentration) of biotinylated Human CD47Fc (AcroBiosystems interchim; France; reference: #CD7-H82F6) to measure competitive binding for 2 h at 37° C. After incubation and washing, peroxidase-labeled streptavidin (Vector laboratory; USA; reference SA-5004) was added to detect Biotin-CD47Fc binding and revealed by conventional methods.

Results: FIG. 25 shows that all modified anti-SIRPa antibodies comprising immunotherapeutic agents are able to compete with CD47 for the binding to SIRPa. No significant differences are observed between modified antibodies comprising the protein fused on heavy or light chain and parental anti-SIRPa antibody alone (HEFLB). All constructs conserved their antagonistic activity against CD47-SIRPa interaction compared to the anti-SIRPa alone (HEFLB) used as a positive control.

Example 28. TNFa Secretion Assay by ELISA on Human PBMC

Method: Polypropylene P96-plate was coated with OKT3 at 1 µg/ml (anti-CD3 antibody). After washing with PBS, human PBMC (100000 cells/w) were added with 10 µg/ml of soluble HELFB antibody, anti-PD1 Keytruda mAb, recombinant protein, OSE172+recombinant protein (PD1-His; PDL1-Fc; CD80-Fc; CD86-Fc; 4-1BBL-Fc or ICOSL-his) as a control for each fused protein (ratio 1:1), modified anti-SIRPa antibodies or Pha-L as a positive control in complete medium (with 2% human SAB) for 3 days at 37° C., 5% CO2. 3H thymidine was incorporated 8 hours before measurement, and results were expressed in cpm to determine the level of proliferation. After 48 h of stimulation (24 h before 3H incorporation), 25 µl/well of supernatant was recovered to measure concentration of cytokine secretion. TNFa was measured by ELISA with human TNFa kit (BD biosciences; reference 555212). Results were expressed in pg/ml of cytokine in supernatant.

Results: FIG. 26 does not show differences in TNFa secretion when cells are incubated with anti-SIRPa antibody (HEFLB) or anti-PD1 keytruda or non-fused immunotherapeutic agent, excepted PD1His or CD86-Fc alone which induce over-secretions of TNFa. These over-secretions were not modified when cells were incubated in combination with anti-SIRPa (HEFLB) and recombinant protein PD1His or CD86-Fc. Similarly other combination of anti-SIRPa HEFLB and non-fused recombinant protein does not increase TNFa secretion.

Interestingly, the modified anti-SIRPa antibodies comprising PD1, PDL1, CD80 or 4-1BBL induce important secretions of TNFa when the immunotherapeutic agent is on the C-terminal domain of the heavy chain. All together, these results show a potent positive effect of the modified anti-SIRPa antibodies comprising PD1, PDL1, CD80 or 4-1BBL on the heavy chain on the proinflammatory cytokine TN Fa secretion.

Example 29. IFNg Secretion Assay by ELISA on Human PBMC

Method: Polypropylene P96-plate was coated with OKT3 at 1 µg/ml (anti-CD3 antibody). After washing with PBS, human PBMC (100000 cells/w) were added with 10 µg/ml of soluble HELFB antibody, anti-PD1 Keytruda mAb, recombinant protein, OSE172+recombinant protein (PD1-His; PDL1-Fc; CD80-Fc; CD86-Fc; 4-1BBL-Fc or ICOSL-his) as a control for each fused protein (ratio 1:1), modified anti-SIRPa antibodies or Pha-L as a positive control in complete medium (with 2% human SAB) for 3 days at 37° C., 5% CO2. 3H thymidine was incorporated 8 hours before measurement, and results were expressed in cpm to determine the level of proliferation. After 48 h of stimulation (24 h before 3H incorporation), 25 µl/well of supernatant was recovered to measure concentration of cytokine secretion. IFNg was measured by ELISA with human IFNg kit (BD biosciences; reference 555142). Results were expressed in pg/ml of cytokine in supernatant.

Results: FIG. 27 confirms the above results observed for TNFa secretion, since the proinflammatory IFNg cytokines secretion (a T-cell specific cytokine) is strongly increased with modified anti-SIRPa antibodies comprising PD1, PDL1, CD80 or 4-1BBL on the C-terminal domain of the heavy chain.

Example 30. Proliferation Assay with Human T-Lymphocytes

Method: Human T-lymphocytes (LT) were sorted with Pan T cell isolation kit (Miltenyi Biotec; reference 130-096-535) from human PBMC, and incubated overnight at 37° C., 5% CO2 in TexMaCS medium (Miltenyi Biotec; reference 130-097-196). The next day, polypropylene P96-plate was coated with OKT3 at 1 µg/ml (pre activation signal). After washing with PBS, human LT (100000 cells/w) was added with 10 µg/ml of soluble HEFLB, anti-PD1 Keytruda mAb, recombinant protein (PD1-His; PDL1-Fc; CD80-Fc; CD86-Fc; 4-1BBL-Fc or ICOSL-his) as a control for each fused protein, HELFB+recombinant protein (ratio 1:1), each different modified anti-SIRPa antibodies or Pha-L as a positive control in complete medium (with 2% human SAB) for 3 days at 37° C., 5% CO2. 3H thymidine was incorporated 8 hours before measurement, and results were expressed in cpm to determine the level of proliferation.

Results: FIG. 28 shows that human T cells proliferation induced with anti-CD3 is not significantly modified with anti-SIRPa antibody alone (HEFLB). Modified anti-SIRPa antibodies comprising PD1, PDL1, CD80, CD86 or 4-1BBL on the heavy chain increase the proliferation of human isolated T cells. No effect is observed with the same bi-functional anti-SIRPa antibodies when the protein is fused to the light chain or when fused to OX40L or ICOSL (heavy or light chain).

Example 31. TNFa Secretion Assay by ELISA on Human Isolated T Lymphocytes

Method: Human T-lymphocytes (LT) were sorted with Pan T cell isolation kit (Miltenyi Biotec; reference 130-096-535) from human PBMC, and incubated overnight at 37° C., 5% CO2 in TexMaCS medium (Miltenyi Biotec; reference 130-097-196). The next day, polypropylene P96-plate was coated with OKT3 at 1 µg/ml (pre activation signal). After washing with PBS, human LT (100000 cells/w) was added with 10 µg/ml of soluble HEFLB, anti-PD1 Keytruda mAb, recombinant protein (PD1-His; PDL1-Fc; CD80-Fc; CD86-Fc; 4-1BBL-Fc or ICOSL-his) as a control for each fused protein, HELFB+recombinant protein (ratio 1:1), each different modified anti-SIRPa antibodies or Pha-L as a positive control in complete medium (with 2% human SAB) for 3 days at 37° C., 5% CO2. 3H thymidine was incorporated 8 hours before measurement, and results were expressed in cpm to determine the level of proliferation. After 48 h of stimulation (24 h before 3H incorporation), 25µl/well of supernatant was recovered to measure concentration of cytokine secretion. TNFa was measured by ELISA with human TNFa kit (BD biosciences; reference 555212), and IFNg was measured by ELISA with human IFNg kit (BD biosciences; reference 555142). Results were expressed in pg/ml of cytokine in supernatant.

Results: Similarly to T-cell proliferation study, TNFa secretion described in FIG. 29 shows that T-cells do not secrete significant amount of TNFa when stimulated with anti-CD3 (OKT3), even when adding with anti-SIRPa HEFLB mAb. In contrast, TNFa secretion is induced with modified anti-SIRPa antibodies comprising PD1, PDL1, CD80 or 4-1BBL to the heavy chain. These results are comparable of the results presented on TNFa secreted by PBMC (see Example 28) and confirm the functional activity of the fused protein on their specific T cell pathway.

Example 32. MIP1a Secretion Assay by ELISA on Human Macrophages

Method: Human immature macrophages were generated using human monocytes elutriated from PBMC (UTCG plateform, Nantes), which were incubated 2 days with GM-CSF (CellGenix; reference 1412-050) at 10 ng/ml in complete medium (with 10% SVF) for 2 days at 37° C., 5% CO2. Polypropylene P96-plate was coated with CD47Fc (Sino Biologicals, Beijing, China; reference 12283-H02H) at 10 µg/ml in PBS. After washing with PBS, human immature macrophages (scrapped and washed) (100000 cells/w) were added with 10 µg/ml of soluble HEFLB antibody, anti-PD1 Keytruda mAb or modified anti-SIRPa antibodies for 24 h at 37° C., 5% CO2. Supernatants were recovered to measure concentration of MIP1a (CCL3) secretion. MIP1a was measured by ELISA with human MIP1a/CCL3 kit (R&Dsystems; reference DY270). Results were expressed in pg/ml of cytokine in supernatant.

Results: In order to confirm the functional SIRPa antagonist activity of the different modified antibodies comprising immunotherapeutic agents, a test on MIP1a, a potential target inhibited by the CD47-Sirpa interaction, has been performed. As shown FIG. 30, macrophages secrete MIP1a in a basal state (no CD47). The secretion was strongly inhibited when macrophages are incubated with CD47Fc demonstrating that the activation of SIRPa inhibitory signals by CD47 induces immunosuppression and inhibits MIP1a secretion. The blocking of the interaction with the anti-SIRPa HEFLB antibody restores this secretion to the basal MIP1a secretion level. This confirms the good antagonist activity of the anti-SIRPa antibody on the CD47-SIRPa interaction. As shown in FIG. 30, the modified anti-SIRPa antibodies comprising PD1, PDL1, CD80 or 4-1BBL induce higher secretion of MIP1a by human macrophages than anti-SIRPa antibody alone. These results show that the modified antibodies have an increased SIRPa antagonist property since they are capable to generate higher levels of MIP1a secretion than the anti-SIRPa HEFLB antibody non-fused to protein. Again, the modified antibody comprising CD86 presents the same results as the anti-SIRPa antibody alone.

Inventors showed that bi-functional anti-SIRPa antibodies referred in examples as modified anti-SIRPa antibodies were able to bind both SIRPa and the ligand of the immunotherapeutic agent referred as fused protein (the ligand of the fused proteins are PD1, PDL1, PDL2, CD28, CTLA4, 4-1BB, ICOS or OX40). The immunotherapeutic agents on the bi-functional anti-SIRPa antibodies were well recognized by a specific antibody indicating the good expression of the ECD of each immunotherapeutic agent of the bi-functional anti-SIRPa antibodies.

In a surprising manner, bifunctional anti-SIRPa antibodies comprising ECD of PD1, PDL1, CD80 or 4-1BBL as immunotherapeutic agents on the heavy chain, were functional regarding their capacity to inhibit the interaction of SIRPa to CD47 inducing an over secretion of MIP1a and were functional regarding their capacity of inducing or not inhibiting T-cell activation and proliferation. Bi-functional anti-SIRPa antibodies comprising ECD of PD1, PDL1, CD80 or 4-1BBL on the heavy chain presented a synergic efficacy on TNFa and IFNg secretion (proinflammatory cytokines) by PBMC underlying their potency in inducing a proinflammatory tumor environment compare to the immunotherapeutic agent alone or combined with an anti-SIRPa antibody.

Example 33. Binding Analyses of the Modified Anti-SIRPa Antibodies on SIRPg by ELISA Method. For activity ELISA assay, hSIRPg-His (Sino Biologicals, Beijing, China; reference 11828-H08H) was immobilized on plastic at 1 µg/ml in carbonate buffer (pH9.2) and purified antibodies were added to measure binding of the humanized anti-SIRPa antibody HEFLB, the anti-SIRPa Kwar antibody and the modified anti-SIRPa antibodies fused to the ECD of PDL1, CD80, CD86 or 4-1BBL. After incubation and washing, peroxidase-labeled donkey anti-human IgG (Jackson Immunoresearch; USA; reference 709-035-149) was added and revealed by conventional methods.

Results. As shown on FIG. 31, Kwar antibody is able to bind SIRPg. However, the bifunctional form of the anti-SIRPa antibodies of the invention fused with any immunotherapeutic agents does not bind SIRPg such as the HEFLB parental antibody underlying the specificity of the bifunctional anti-SIRPa antibodies against SIRPa-CD47 interaction.

Example 34. MIP1a, TNFa and IFNg Secretion Assay by ELISA on Co-Culture of Human Macrophages with Human T Lymphocytes Method. Human immature macrophages were generated using human monocytes elutriated from PBMC (UTCG platform, Nantes), which were incubated 2 days with GM-CSF (CellGenix; reference 1412-050) at 10 ng/ml in complete medium (with 10% SVF) at 37° C., 5% CO2. Polypropylene P96-plate was coated with CD47Fc (Sino Biologicals, Beijing, China; reference 12283-H02H) at 10 µg/ml in PBS. After washing with PBS, human immature macrophages (scrapped and washed) (100000 cells/w) were added with 10 µg/ml of soluble HEFLB antibody or modified anti-SIRPa antibodies (VH-PDL1, VH-4-1BBL, VH-CD80 or VH-CD86) for 24 h at 37° C., 5% CO2. Then we added human T lymphocytes pre-activated with OKT3 (T lymphocytes were isolated according to the method described in example 31). Supernatants were recovered to measure concentration of MIP1a (CCL3) (kit R&Dsystems; reference DY270), TNFa (kit BD biosciences; reference 555212) or IFNg secretion (kit BD biosciences; reference 555142).

Results. In a co-cultured system allowing in the same assay the measurement of the inhibition of the SIRPa-CD47 interaction and the T cell activation, we observed in an interesting but unexpected manner that the bifunctional anti-SIRPa antibodies fused to PDL1, CD80 or 4-1BBL are able to induce a higher secretion of M1Pa (A), TNFa (B) and IFNg (C), as compared to the anti-SIRPa antibodies alone or in separate combinations with the recombinant PDL1 or CD80 or 4-1BBL (FIG. 32). Furthermore, the functional efficacy of the bifunctional anti-SIRPa is observed when the immunotherapeutic agent is fused on the C-terminal portion of the VH chain of the anti-SIRPa antibody (as shown FIGS. 26 and 27). This functional effect is not observed for the bifunctional anti-SIRPa when fused on the light chain or when the immunotherapeutic agents is CD86, ICOS-L or OX40L (data not shown). These results show that the modified anti-SIRPa antibodies coupled with PDL1, CD80 and 4-1BBL have a stronger inhibitory effect on the SIRPa-CD47 interaction and a better efficacy on T cell activation than the anti-SIRPa antibody alone or combined separately with the recombinant immunotherapeutic agents or than an irrelevant bifunctional antibody such as B12-PDL1, or B12-CD80 or B12-4-1BBL. The bifunctional molecules as presented herein are capable of inducing T cells activation through inhibition of the PD1/PDL1 or CTLA-4/80 or CD80/PDL1 axis as well as potentializing the 4-1BB/4-1BBL or CD80/CD28 signals (to induce potent adaptative immune response, in particular anti-tumor response and/or inducing long-live memory T cells).

Example 35. Time-Lapse T Cells Activation

Methods. Human immature macrophages were generated using human monocytes elutriated from PBMC (UTCG plateform, Nantes), which were incubated with GM-CSF (CellGenix; reference 1412-050) at 10 ng/ml in complete medium (with 10% SVF) for 24 h at 37° C., 5% CO2. IBIDI chambers 8 wells (IBIDI; Germany; reference 80826) was coated with CD47Fc (Sino Biologicals, Beijing, China; reference 12283-H02H) at 10 µg/ml in PBS. After washing with PBS, human immature macrophages (scrapped and washed) (300000 cells/w) were added with 10 µg/ml of soluble HEFLB and bifunctional anti-Sirpa-PDL1 in IBIDI chambers for 24 h at 37° C., 5% CO2. Supernatants were recovered to measure concentration of MIP1a (CCL3) secretion. Then, T lymphocytes from another healthy donor were separated after Ficoll with Pan T cell isolation kit (Miltenyi Biotec; reference 130-096-535) and stained with FURA-2 calcium indicator (Invitrogen; reference F1221). Fura-2 labelled T-cells (300000 cells/well) were added to wells containing immature macrophage and antibodies and stimulated with addition of agonist anti-CD3 at 3 µg/ml final (Inserm U1064; Nantes, clone OKT3). Time-lapse on each well was performed with Nikon microscopy. Fura-2 indicator appeared blue in non-stimulated T-cells and became more and more red with T-cell activation.

Results. As shown in FIG. 33, the bifunctional anti-SIRPa-PDL1 antibody elicits a strong T cells activation due to the inhibition of the interaction between SIRPa and CD47 and the inhibition of the endogenous PDL1-PD1 interaction in a co-culture assay. Such a blocking of the endogenous PD1/PDL1 interaction is reflected by the presence into the cells of a higher quantity of calcium (orange/red cells) as compared to the control on the right side of FIG. 33. This assay confirms that the bi-functional anti-SIRPa-PDL1 is capable to activate T cells.

The invention claimed is:

1. A bifunctional anti-human signal regulatory protein alpha (SIRPa) antibody or antigen-binding fragment thereof, which comprises:
   a) a heavy chain variable domain comprising HCDR1, HCDR2 and HCDR3, and
   b) a light chain variable domain comprising LCDR1, LCDR2 and LCDR3,
   wherein:
   HCDR1 comprises the amino acid sequence set forth in SEQ ID NO: 14,
   HCDR2 comprises the amino acid sequence set forth in SEQ ID NO: 15 or SEQ ID NO: 16,
   HCDR3 comprises the amino acid sequence set forth in SEQ ID NO: 17, SEQ ID NO: 18, SEQ ID NO: 19, or SEQ ID NO: 20,
   LCDR1 comprises the amino acid sequence set forth in SEQ ID NO: 21,
   LCDR2 comprises the amino acid sequence set forth in SEQ ID NO: 22, and
   LCDR3 comprises the amino acid sequence set forth in SEQ ID NO: 23,
   and which comprises a heavy chain constant domain or a fragment thereof, said heavy chain constant domain or fragment thereof being linked to an immunotherapeutic agent, said immunotherapeutic agent comprising a protein selected from the group consisting of human PD1, human PDL1, human CD80, human 4-1BBL, immunotherapeutic agent variants thereof and immunotherapeutic agent fragments thereof.

2. The bifunctional anti-human SIRPa antibody or antigen-binding fragment thereof according to claim 1, which is an antagonist of SIRPa and which inhibits the binding of human CD47 to human SIRPa.

3. The bifunctional anti-human SIRPa antibody or antigen-binding fragment thereof according to claim 1, which does not specifically bind to human SIRPg.

4. The bifunctional anti-human SIRPa antibody or antigen-binding fragment thereof according to claim 1, which comprises:
   a heavy chain variable domain comprising the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30, and
   a light chain variable domain comprising the amino acid sequence selected from the group consisting of SEQ ID NO: 31, SEQ ID NO: 32 and SEQ ID NO: 33.

5. The bifunctional anti-human SIRPa antibody or antigen-binding fragment thereof according to claim 1, which comprises:
   a heavy chain variable domain comprising the amino acid sequence set forth in SEQ ID NO: 24, and
   a light chain variable domain comprising the amino acid sequence set forth in SEQ ID NO: 31,
   or
   a heavy chain variable domain comprising the amino acid sequence set forth in SEQ ID NO: 25, and
   a light chain variable domain comprising the amino acid sequence set forth in SEQ ID NO: 32,
   or
   a heavy chain variable domain comprising the amino acid sequence set forth in SEQ ID NO: 25, and
   a light chain variable domain comprising the amino acid sequence set forth in SEQ ID NO: 33,
   or
   a heavy chain variable domain comprising the amino acid sequence set forth in SEQ ID NO: 26, and
   a light chain variable domain comprising the amino acid sequence set forth in SEQ ID NO: 32,
   or
   a heavy chain variable domain comprising the amino acid sequence set forth in SEQ ID NO: 26, and
   a light chain variable domain comprising the amino acid sequence set forth in SEQ ID NO: 33,
   or
   a heavy chain variable domain comprising the amino acid sequence set forth in SEQ ID NO: 27, and
   a light chain variable domain comprising the amino acid sequence set forth in SEQ ID NO: 32, or
a heavy chain variable domain comprising the amino acid sequence set forth in SEQ ID NO: 27, and
a light chain variable domain comprising the amino acid sequence set forth in SEQ ID NO: 33,
or
a heavy chain variable domain comprising the amino acid sequence set forth in SEQ ID NO: 28, and
a light chain variable domain comprising the amino acid sequence set forth in SEQ ID NO: 32,
or
a heavy chain variable domain comprising the amino acid sequence set forth in SEQ ID NO: 28, and
a light chain variable domain comprising the amino acid sequence set forth in SEQ ID NO: 33,
or
a heavy chain variable domain comprising the amino acid sequence set forth in SEQ ID NO: 29, and
a light chain variable domain comprising the amino acid sequence set forth in SEQ ID NO: 32,
or
a heavy chain variable domain comprising the amino acid sequence set forth in SEQ ID NO: 29, and
a light chain variable domain comprising the amino acid sequence set forth in SEQ ID NO: 33,
or
a heavy chain variable domain comprising the amino acid sequence set forth in SEQ ID NO: 30, and
a light chain variable domain comprising the amino acid sequence set forth in SEQ ID NO: 32,
or
a heavy chain variable domain comprising the amino acid sequence set forth in SEQ ID NO: 30, and
a light chain variable domain comprising the amino acid sequence set forth in SEQ ID NO: 33.

6. The bifunctional anti-human SIRPa antibody or antigen-binding fragment thereof according to claim 1, wherein the immunotherapeutic agent is a protein comprising a sequence selected from the group consisting of: SEQ ID NO: 81, SEQ ID NO: 82, SEQ ID NO: 83, SEQ ID NO: 85 and SEQ ID NO: 88.

7. The bifunctional anti-human SIRPa antibody or antigen-binding fragment thereof according to claim 1, wherein the heavy chain is linked to the immunotherapeutic agent by a linker sequence.

8. The bifunctional anti-human SIRPa antibody or antigen-binding fragment thereof according to claim 1, wherein the immunotherapeutic agent is linked to the C-terminal extremity of the heavy chain constant domain or fragment thereof of said antibody or antigen-binding fragment thereof.

9. The bifunctional anti-human SIRPa antibody or antigen-binding fragment thereof according to claim 1, wherein said bifunctional antibody is a humanized monoclonal antibody.

10. The bifunctional anti-human SIRPa antibody or antigen-binding fragment thereof according to claim 1, that comprises:
a heavy chain comprising the amino acid sequence SEQ ID NO: 56 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 57,
or
a heavy chain comprising the amino acid sequence SEQ ID NO: 36 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 43,
or
a heavy chain comprising the amino acid sequence SEQ ID NO: 37 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 44,
or
a heavy chain comprising the amino acid sequence SEQ ID NO: 37 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 45,
or
a heavy chain comprising the amino acid sequence SEQ ID NO: 38 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 44,
or
a heavy chain comprising the amino acid sequence SEQ ID NO: 38 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 45,
or
a heavy chain comprising the amino acid sequence SEQ ID NO: 39 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 44,
or
a heavy chain comprising the amino acid sequence SEQ ID NO: 39 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 45,
or
a heavy chain comprising the amino acid sequence SEQ ID NO: 40 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and
a light chain comprising the amino acid sequence SEQ ID NO: 44,
or
a heavy chain comprising the amino acid sequence SEQ ID NO: 40 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and a light chain comprising the amino acid sequence SEQ ID NO: 45, or a heavy chain comprising the amino acid sequence SEQ ID NO: 41 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and a light chain comprising the amino acid sequence SEQ ID NO: 44, or a heavy chain comprising the amino acid sequence SEQ ID NO: 41 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and a light chain comprising the amino acid sequence SEQ ID NO: 45, or a heavy chain comprising the amino acid sequence SEQ ID NO: 42 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and a light chain comprising the amino acid sequence SEQ ID NO: 44, or a heavy chain comprising the amino acid sequence SEQ ID NO: 42 linked at its C-terminal extremity to a protein comprising a sequence selected from the group consisting of SEQ ID NO: 81, SEQ ID NO: 82, SEQ ID NO: 83, SEQ ID NO: 85, and SEQ ID NO: 88, and a light chain comprising the amino acid sequence SEQ ID NO: 45.

11. The bifunctional anti-human SIRPa antibody or antigen-binding fragment thereof according to claim 1, that comprises:

a heavy chain comprising the amino acid sequence selected from the group consisting of SEQ ID NO: 94, SEQ ID NO: 95, SEQ ID NO: 96, SEQ ID NO: 98, and SEQ ID NO: 178, and a light chain comprising the amino acid sequence SEQ ID NO: 57, or a heavy chain comprising the amino acid sequence selected from the group consisting of SEQ ID NO: 101, SEQ ID NO: 102, SEQ ID NO: 103, SEQ ID NO: 105, and SEQ ID NO: 179, and a light chain comprising the amino acid sequence SEQ ID NO: 43, or a heavy chain comprising the amino acid sequence selected from the group consisting of SEQ ID NO: 108, SEQ ID NO: 109, SEQ ID NO: 110, SEQ ID NO: 112, and SEQ ID NO: 180, and a light chain comprising the amino acid sequence SEQ ID NO: 44, or a heavy chain comprising the amino acid sequence selected from the group consisting of SEQ ID NO: 108, SEQ ID NO: 109, SEQ ID NO: 110, SEQ ID NO: 112, and SEQ ID NO: 180, and a light chain comprising the amino acid sequence SEQ ID NO: 45, or a heavy chain comprising the amino acid sequence selected from the group consisting of SEQ ID NO: 115, SEQ ID NO: 116, SEQ ID NO: 117, SEQ ID NO: 119, and SEQ ID NO: 181, and a light chain comprising the amino acid sequence SEQ ID NO: 44, or a heavy chain comprising the amino acid sequence selected from the group consisting of SEQ ID NO: 115, SEQ ID NO: 116, SEQ ID NO: 117, SEQ ID NO: 119, and SEQ ID NO: 181, and a light chain comprising the amino acid sequence SEQ ID NO: 45, or a heavy chain comprising the amino acid sequence selected from the group consisting of SEQ ID NO: 122, SEQ ID NO: 123, SEQ ID NO: 124, SEQ ID NO: 126, and SEQ ID NO: 182, and a light chain comprising the amino acid sequence SEQ ID NO: 44, or a heavy chain comprising the amino acid sequence selected from the group consisting of SEQ ID NO: 122, SEQ ID NO: 123, SEQ ID NO: 124, SEQ ID NO: 126, and SEQ ID NO: 182, and a light chain comprising the amino acid sequence SEQ ID NO: 45, or a heavy chain comprising the amino acid sequence selected from the group consisting of SEQ ID NO: 129, SEQ ID NO: 130, SEQ ID NO: 131, SEQ ID NO: 133, and SEQ ID NO: 183, and a light chain comprising the amino acid sequence SEQ ID NO: 44, or a heavy chain comprising the amino acid sequence selected from the group consisting of SEQ ID NO: 129, SEQ ID NO: 130, SEQ ID NO: 131, SEQ ID NO: 133, and SEQ ID NO: 183, and a light chain comprising the amino acid sequence SEQ ID NO: 45, or a heavy chain comprising the amino acid sequence selected from the group consisting of SEQ ID NO: 136, SEQ ID NO: 137, SEQ ID NO: 138, SEQ ID NO: 140, and SEQ ID NO: 184, and a light chain comprising the amino acid sequence SEQ ID NO: 44, or a heavy chain comprising the amino acid sequence selected from the group consisting of SEQ ID NO: 136, SEQ ID NO: 137, SEQ ID NO: 138, SEQ ID NO: 140, and SEQ ID NO: 184, and a light chain comprising the amino acid sequence SEQ ID NO: 45, or a heavy chain comprising the amino acid sequence selected from the group consisting of: SEQ ID NO: 143, SEQ ID NO: 144, SEQ ID NO: 145, SEQ ID NO: 147, and SEQ ID NO: 185, and a light chain comprising the amino acid sequence SEQ ID NO: 44, or a heavy chain comprising the amino acid sequence selected from the group consisting of SEQ ID NO: 143, SEQ ID NO: 144, SEQ ID NO: 145, SEQ ID NO: 147, and SEQ ID NO: 185, and a light chain comprising the amino acid sequence SEQ ID NO: 45.

12. The bifunctional anti-human SIRPa antibody or antigen-binding fragment thereof according to claim 1, wherein the immunotherapeutic agent fragment consists of 50 to 300 amino acid residues.

13. The bifunctional anti-human SIRPa antibody or antigen-binding fragment thereof according to claim 1, which does not inhibit the binding of human CD47 to human SIRPg.

14. The bifunctional anti-human SIRPa antibody or antigen-binding fragment thereof according to claim 1, which does not inhibit the proliferation and/or activation of human T-cells.

15. The bifunctional anti-human SIRPa antibody or antigen-binding fragment thereof according to claim 9, wherein the antibody light chain constant domain is derived from a human kappa light chain constant domain or comprises the sequence of SEQ ID NO: 35.

16. The bifunctional anti-human SIRPa antibody or antigen-binding fragment thereof according to claim 9, wherein the antibody heavy chain constant domain is derived from a human IgG1, IgG2, IgG3, or IgG4 heavy chain constant domain or comprises the sequence of SEQ ID NO: 34.

17. The bifunctional anti-human SIRPa antibody or antigen-binding fragment thereof according to claim 1, wherein said immunotherapeutic agent comprises the extracellular domain of a protein selected from the group consisting of human PD1, human PDL1, human CD80, human 4-1BBL, immunotherapeutic agent variants thereof and immunotherapeutic agent fragments thereof, and wherein the immunotherapeutic agent variant is selected from the group consisting of PD1, PDL1, CD80 and 4-1BBL variants sharing at least 70% identity with one amino acid sequence selected from the group consisting of SEQ ID NO: 81, SEQ NO: 82, SEQ ID NO: 83, SEQ ID NO: 85 and SEQ ID NO: 88.

18. The bifunctional anti-human SIRPa antibody or antigen-binding fragment thereof according to claim 4, which comprises:
    a light chain variable domain comprising the amino acid sequence set forth in SEQ ID NO: 33, and
    a heavy chain variable domain comprising the amino acid sequence selected from the group consisting of SEQ ID NO: 24, SEQ ID NO: 25, SEQ ID NO: 26, SEQ ID NO: 27, SEQ ID NO: 28, SEQ ID NO: 29 and SEQ ID NO: 30.

19. The bifunctional anti-human SIRPa antibody or antigen-binding fragment thereof according to claim 18, which comprises a heavy chain variable domain comprising SEQ ID NO: 29 or SEQ ID NO: 30.

20. The bifunctional anti-human SIRPa antibody or antigen-binding fragment thereof according to claim 19, which comprises a heavy chain variable domain comprising SEQ ID NO: 30.

21. The bifunctional anti-human SIRPa antibody or antigen-binding fragment thereof according to claim 7, wherein the heavy chain is linked to the immunotherapeutic agent by a linker sequence selected from the group consisting of SEQ ID NO: 89, SEQ ID NO: 90, SEQ ID NO: 91, SEQ ID NO: 92, GGG, GGS and SEQ ID NO: 93.

22. A combination product comprising: at least one bifunctional anti-human SIRPa antibody or antigen-binding fragment thereof according to claim 1;
    a second therapeutic agent selected from the group consisting of chemotherapeutic agents, radiotherapy agents, cell therapy agents, immunotherapeutic agents, antibiotics, probiotics, therapeutic vaccines, immune checkpoint blockers or activators, and antibody-drug conjugates.

23. The combination product according to claim 22, wherein the bifunctional anti-human SIRPa antagonist antibody or antigen-binding fragment thereof and the second therapeutic agent are formulated for separate, sequential or combined therapy.

24. The combination product according to claim 22, wherein the immune checkpoint blockers or activators are of adaptive immune cells.

25. The combination product according to claim 24, wherein the adaptive immune cells are T or B lymphocytes.

26. The combination product according to claim 23, wherein the bifunctional anti-human SIRPa antagonist antibody or antigen-binding fragment thereof or the isolated nucleic acid molecule or the group of isolated nucleic acid molecules or the vector or the cell and the second therapeutic agent are formulated for combined or sequential use.

27. A pharmaceutical composition comprising at least one bifunctional anti-human SIRPa antibody or antigen-binding fragment thereof according to claim 1;
    a pharmaceutically acceptable carrier.

28. The pharmaceutical composition according to claim 27, wherein said bifunctional anti-human SIRPa antagonist antibody or antigen-binding fragment thereof:
    does not inhibit the proliferation of human T-cells;
    does not inhibit the binding of human CD47 to human SIRPg;
    increases the secretion of TNFa by human PBMC;
    increases the secretion of TNFa by human T-cells;
    increases the secretion of IFNg by human PBMC; and/or
    increases the secretion of MIP1a by human macrophages.

29. The pharmaceutical composition according to claim 28, wherein said bifunctional anti-human SIRPa antagonist antibody or antigen-binding fragment thereof does not inhibit the proliferation of human T-cells and increases the proliferation of human T-cells.

30. The pharmaceutical composition according to claim 22, wherein said bifunctional anti-human SIRPa antagonist antibody or antigen-binding fragment thereof:
    does not inhibit the proliferation of human T-cells;
    does not inhibit the binding of human CD47 to human SIRPg;
    increases the secretion of TNFa by human PBMC;
    increases the secretion of TNFa by human T-cells;
    increases the secretion of IFNg by human PBMC; and/or
    increases the secretion of MIP1a by human macrophages.

31. The pharmaceutical composition according to claim 30, wherein said bifunctional anti-human SIRPa antagonist antibody or antigen-binding fragment thereof does not inhibit the proliferation of human T-cells and increases the proliferation of human T-cells.

32. An isolated nucleic acid molecule, a group of isolated nucleic acid molecules, or a vector encoding a bifunctional antibody or antigen-binding fragment thereof according to claim 1.

33. An isolated host cell comprising the nucleic acid molecule, the group of isolated nucleic acid molecules, or the vector according to claim 32.

34. A method for treating a patient having a cancer, comprising the administration of the bifunctional anti-human SIRPa antibody or antigen-binding fragment thereof according to claim 1.

* * * * *